US009655960B2

(12) United States Patent
Lee et al.

(10) Patent No.: US 9,655,960 B2
(45) Date of Patent: May 23, 2017

(54) HIGH YIELD YELLOW FEVER VIRUS STRAIN WITH INCREASED PROPAGATION IN CELLS

(71) Applicant: GE HEALTHCARE BIO-SCIENCES CORP., Piscataway, NJ (US)

(72) Inventors: Cynthia K. Lee, Needham, MA (US); Thomas P. Monath, Harvard, MA (US); Patrick M. Guertin, Mendon, MA (US); Edward G. Hayman, Hanover, NH (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 61 days.

(21) Appl. No.: 14/267,942

(22) Filed: May 2, 2014

(65) Prior Publication Data

US 2014/0322270 A1 Oct. 30, 2014

Related U.S. Application Data

(60) Division of application No. 13/012,917, filed on Jan. 25, 2011, now Pat. No. 8,741,312, which is a continuation-in-part of application No. PCT/US2010/043010, filed on Jul. 23, 2010.

(60) Provisional application No. 61/230,483, filed on Jul. 31, 2009.

(51) Int. Cl.
*A61K 39/12* (2006.01)
*C12N 7/01* (2006.01)
*C12N 7/00* (2006.01)
*A61K 39/00* (2006.01)

(52) U.S. Cl.
CPC ............... *A61K 39/12* (2013.01); *C12N 7/00* (2013.01); *A61K 2039/5252* (2013.01); *A61K 2039/55505* (2013.01); *A61K 2039/55566* (2013.01); *C12N 2770/24121* (2013.01); *C12N 2770/24134* (2013.01)

(58) Field of Classification Search
None
See application file for complete search history.

(56) References Cited

U.S. PATENT DOCUMENTS

| 4,810,492 | A | 3/1989 | Fujita .................. A61K 37/02 |
| 6,432,411 | B1 | 8/2002 | Ivy .................... A61K 39/12 |
| 6,589,531 | B1 | 7/2003 | Andino-Pavlovsky .......... A61K 39/12 |
| 6,893,643 | B2 | 5/2005 | Andino-Pavlovsky .......... A61K 39/12 |
| 6,962,708 | B1 | 11/2005 | Chambers ............... C12N 7/01 |
| 7,049,428 | B1 | 5/2006 | Rice .................. C07H 21/00 |
| 7,060,280 | B2 | 6/2006 | Lee .................... A61K 39/00 |
| 7,227,011 | B2 | 6/2007 | Chang ................. C07H 21/04 |
| 7,417,136 | B1 | 8/2008 | Chang ................. C07H 21/04 |
| 7,521,177 | B2 | 4/2009 | Chang ................. C12Q 1/70 |
| 7,632,510 | B2 | 12/2009 | Chang ................. A61K 39/12 |
| 7,662,394 | B2 | 2/2010 | Chang ................. A61K 39/12 |
| 2005/0002968 | A1 | 1/2005 | Monath et al. |
| 2007/0031451 | A1 | 2/2007 | Slifka ................. A61K 39/12 |
| 2007/0269458 | A1 | 11/2007 | Guirakhoo et al. |
| 2008/0241186 | A1 | 10/2008 | Chang ................. A61K 39/00 |
| 2008/0248064 | A1 | 10/2008 | Chang ................. A61K 39/12 |
| 2009/0263470 | A1 | 10/2009 | Coller ................ A61K 9/127 |
| 2010/0003273 | A1 | 1/2010 | Chang ................ A61K 39/193 |
| 2010/0040643 | A1 | 2/2010 | Chang ................. A61K 39/12 |
| 2010/0158938 | A1 | 6/2010 | Guirakhoo ............ A61K 3/295 |

FOREIGN PATENT DOCUMENTS

| EP | WO 03054174 | 7/2003 |
| EP | 1 894 998 A1 | 5/2008 |
| WO | WO 2004/009764 | 1/2004 |
| WO | WO2011/014416 | 2/2011 |

OTHER PUBLICATIONS

Beasley et al., Virus Research, 2013, 176:280-284.*
Souza, M., et al., Vaccine, vol. 27, No. 46, 2009, p. 6420-6423.
Monath, T., Vaccine, vol. 28, No. 22, 2010, p. 3827-3840.
Beasley, D., et al., Virus Research, vol. 176, No. 1-2, 2013, p. 280-284.
Monath, T., et al., American Journal of Tropical Medicine and Hygiene, vol. 83, No. 5, Suppl. S, 2010, p. 16.
Extended European Search Report dated Jan. 2, 2014 issued on corresponding EP application No. 11809985.2.
Search Report and Written Opinion from corresponding EP Application No. 10804909.9-1405 dated Feb. 11, 2013.
Chang, G. J. et al., "Nucleotide sequence variation of the envelope protein gene identifies two distinct genotypes of yellow fever virus.", Journal of Virology, vol. 69, No. 9, pp. 5773-5780, Jan. 1, 1995.
Database UniProt [Online], "SubName: Full=Envelope glycoprotein; Flags: Fragment;" Dec. 15, 2009.
International Preliminary Report on Patentability, dated Feb. 9, 2012, for PCT/US2010/043010 (the parent case, 8 pages (in English).
Kessler, N., et al, "Suitability of MDCK Cells Grown in a Serum-Free Medium for Influenza Virus Production." Brown F. Robertson JS, Schild GC, Wood JM (eds): Inactivated Influenza Vaccines Prepared in Cell Culture, Dev Biol Stand, Basel karger, 1999, vol. 98, pp. 13-21.
Merten, O-W., et al. "Production of Influenza Virus in Serum-Free Mammalian Cell Cultures." Brown F, Robertson JS, Schild GC, Wood JM (eds): Inactivated Influenza Vaccines Prepared in Cell Culture, Dev Biol Stand, Basel, Karger, 1999, vol. 98, pp. 23-37.

(Continued)

*Primary Examiner* — Stacy B Chen
(74) *Attorney, Agent, or Firm* — Grogan, Tuccillo & Vanderleeden, LLP

(57) ABSTRACT

The invention provides a an inactive, non-replicating vaccine comprising whole virion, chemically inactivated Yellow Fever virus which is inactivated using a method that ensures preservation of critical, neutralizing epitopes. The Yellow Fever virus has been adapted to propagate in cells to higher yields than the unadapted virus. The invention also provides methods for preventing Yellow Fever viral infection.

6 Claims, 73 Drawing Sheets

(56) References Cited

OTHER PUBLICATIONS

Rourou, Samia, et al. "A microcarrier cell culture process for propagating rabies virus in Vero cells grown in a stirred bioreactor under fully animal component free conditions." Elsevier Ltd.—Vaccine 25 (2007) 3879-3889.
Caij, A., et al. "High titre Hog Cholera virus production on Cytodex 3® microcarrier cultures." Archives of Virology © by Springer-Verlag 1989 Arch Virol (1989) 105: 113-118.
Berry, J.M., et al. "Production of Reovirus Type-1 and Type-3 from Vero Cells Grown on Solid and Macroporous Microcarriers." Biotechnology and Bioengineering, vol. 62, No. 1, Jan. 5, 1999, pp. 12-19.
Yokomizo, A.Y., et al. "Rabies Virus Production in High Vero Cell Density Cultures on Macroporous Microcarriers." Biotechnology and Bioengineering, vol. 85, No. 5, Mar. 5, 2004, pp. 506-515.
Sheets, Rebecca, "History and Characterization of the Vero Cell Line," A report prepared by CDR Rebecca Sheets, Ph.D., USPHS CBER/OVRR/DVRPA/VVB for the Vaccines and related Biological Products Advisory Committee Meeting to be held on May 12, 2000. Time Stamped: May 8, 2000.
International Search Report and Written Opinion, dated Aug. 18, 2011, for PCT/US2011/022347 (the parent case), 13 pages (in English).
Search History by International Searching Authority mail date Aug. 18, 2011, for PCT/US2011/022347 (the parent case), 3 pages (in English).
Wang, Eryu, et al. "Comparison of the genomes of the wild-type French viscerotropic strain of yellow fever virus with its vaccine derivative French neurotropic vaccine." *Journal of General Virology*, (1995) 76, 2749-2755.
International Search Report and Written Opinion, dated Mar. 2, 2011, for PCT/US2010/043010 (the parent case), 12 pages (in English).
Search History by International Searching Authority mail date Mar. 2, 2011, for PCT/US2010/043010 (the parent case), 7 pages (in English).
Schlesinger, Jacob J., et al. "Replication of yellow fever virus in the mouse central nervous system: comparison of neuroadapted and non-neuroadaped virus and partial sequence analysis of the neuroadapted strain," *Journal of General Virology*, 77, 1277-1285 (1996).
Lee, Eva, et al. "E Protein Domain III Determinants of Yellow Fever Virus 17D Vaccine Strain Enhance Binding to Glycosaminoglycans, Impede Virus Spread, and Attenuate Virulence," *Journal of Virology*, 6024-6033 (Jun. 2008).
Monath, Thomas P., et al. "Single Mutation in the Flavivirus Envelope Protein Hinge Region Increases Neurovirulence for Mice and Monkeys but Decreases Viscerotropism for Monkeys: Relevance to Development and Safety Testing of Live, Attenuated Vaccines," *Journal of Virology*, 1932-1943 (Feb. 2002).

\* cited by examiner

```
Vero MWCB ──▶ Thaw one vial Vero MWCB
              Passage 143
              Subculture on Day 4-7
                     │
                     ▼
              Seed into new T75
              Passage 144
              Subculture on Day 3-6
                     │
                     ▼
              Seed into new T75
              Passage 145
              Subculture on Day 3-6
                     │
                     ▼
              Expand to T150
              Passage 146
              Subculture on Day 3-6
                     │
                     ▼
              Expand to 10 T225s ──────▶ Expand to T225
              for production              Passage 148
              Passage 147                      │
                     │                         ▼
Yellow Fever 17D ──▶ Cells @ >80% confluency  Seed into new T225
Pre-Master Virus     Infect @ MOI ~0.01        Passage 149
                     │                         │
                     ▼                         ▼
              CPE > 80%                 Expand to 10 T225s
              Harvest supernatant       For production
              Add sorbitol to 7%        Passage 150
                     │                         │
                     ▼                         ▼
              Fill 2 mL / cryovial      Cells @ >80% confluency
              Store ≤ -60°C             Infect @ MOI ~0.01
                     │                         │
                     ▼                         ▼
              Yellow Fever 17D          CPE > 80%
              Master Virus Seed         Harvest supernatant
              (MVS)                     Add sorbitol to 7%
                                               │
                                               ▼
                                        Fill 2 mL / cryovial
                                        Store ≤ -60°C
                                               │
                                               ▼
                                        Yellow Fever 17D
                                        Working Virus Seed
                                        (WVS)
```

MVS QC Testing:
Mycoplasma
Mycobacterium tuberculosis
Retrovirus (F-PERT)
In vitro adventitious virus with neutralization
In vivo adventitious virus with neutralization, if feasible
Sterility
Infectivity - plaque assay
Identity – 2E10 monoclonal ELISA
2E10 Epitope Titer - 2E10 Monoclonal ELISA

WVS QC Testing:
Mycoplasma
Mycobacterium tuberculosis
Retrovirus (F-PERT)
In vitro adventitious virus with neutralization
In vivo adventitious virus with neutralization, if feasible
Sterility
Infectivity - plaque assay
Identity – 2E10 monoclonal ELISA
2E10 Epitope Titer - 2E10 Monoclonal ELISA

YF-VAX virus replication Curve for passage one and passage 11

```
(SEQ ID NO:1) P1_cons   : AGTAAATCCTGTGTGCTAATTGAGGTGCATTGGTCTGCAAATCGAGTTGCTAGGCAATAACACATTTGGATTAA :  75
(SEQ ID NO:2) P11_cons  : AGTAAATCCTGTGTGCTAATTGAGGTGCATTGGTCTGCAAATCGAGTTGCTAGGCAATAACACATTTGGATTAA :  75

(SEQ ID NO:1) P1_cons   : TTTTAATCGTTCGTTGAGCGATTAGCAGAGAACTGACCAGAACATGTCTGGTCGTAAAGCTCAGGGAAAAACCCT : 150
(SEQ ID NO:2) P11_cons  : TTTTAATCGTTCGTTGAGCGATTAGCAGAGAACTGACCAGAACATGTCTGGTCGTAAAGCTCAGGGAAAAACCCT : 150

(SEQ ID NO:1) P1_cons   : GGGCGTCAATATGGTACGACGAGGAGTTCGCTCCTTGTCAAACAAAATAAACAAAAACAAAAACAAATTGGAAA  : 225
(SEQ ID NO:2) P11_cons  : GGGCGTCAATATGGTACGACGAGGAGTTCGCTCCTTGTCAAACAAAATAAACAAAAACAAAAACAAATTGGAAA  : 225

(SEQ ID NO:1) P1_cons   : CAGACCTGGACCTTCAAGAGAGGTTGTTGGAAAATGCTGGACCAAGACAAGGCTTGGCTGTTCTAAGGAAAGTCAAGAG : 300
(SEQ ID NO:2) P11_cons  : CAGACCTGGACCTTCAAGAGAGGTTGTTCAAGAGGATTTATCTTTTTCTTTTTTGTTCAACATTTTGACTGAAAAAAGAT : 300

(SEQ ID NO:1) P1_cons   : CACAGCCCACCTAAAGAGGATTGTGGAAAATGCTGGACCAAGACAAGGCTTGGCTGTTCTAAGGAAAGTCAAGAG : 375
(SEQ ID NO:2) P11_cons  : CACAGCCCACCTAAAGAGGATTGTGGAAAATGCTGGACCAAGACAAGGCTTGGCTGTTCTAAGGAAAGTCAAGAG : 375

(SEQ ID NO:1) P1_cons   : AGTGGTGGCCAGTTTGATGAGAGGATTGTCCTCAAGGAAAACGCCCGTTCCCATGATGTTCTGACTGTGCAATTCCT : 450
(SEQ ID NO:2) P11_cons  : AGTGGTGGCCAGTTTGATGAGAGGATTGTCCTCAAGGAAAACGCCCGTTCCCATGATGTTCTGACTGTGCAATTCCT : 450

(SEQ ID NO:1) P1_cons   : AATTTTGGGAATGCTGTTGATGACGGGTGGAGTGACCTTGGTGCGGAAAAACAGATGGTTGCTCCTAAATGTGAC : 525
(SEQ ID NO:2) P11_cons  : AATTTTGGGAATGCTGTTGATGACGGGTGGAGTGACCTTGGTGCGGAAAAACAGATGGTTGCTCCTAAATGTGAC : 525
```

FIG. 4A

```
(SEQ ID NO:1) P1_cons   : ATCTGAGGACCTCGGGAAAAACATTCTCTGTGGGCACAGGCAACTGCACACAACATTTTGGAAGCCAAGTACTG : 600
(SEQ ID NO:2) P11_cons  : ATCTGAGGACCTCGGGAAAAACATTCTCTGTGGGCACAGGCAACTGCACACAACATTTTGGAAGCCAAGTACTG : 600

(SEQ ID NO:1) P1_cons   : GTGCCCAGACTCAATGGAATACAACTGTCCCAATCTCAGTCCAAGAGAGGAGCCAGATGACATTGATTGCTGGTG : 675
(SEQ ID NO:2) P11_cons  : GTGCCCAGACTCAATGGAATACAACTGTCCCAATCTCAGTCCAAGAGAGGAGCCAGATGACATTGATTGCTGGTG : 675

(SEQ ID NO:1) P1_cons   : CTATGGGGTGGAAAAACGTTAGAGTCGCATATGGTAAGTGTGACTCAGCAGGCAGGTCTAGGAGGTCAAGAAGGGC : 750
(SEQ ID NO:2) P11_cons  : CTATGGGGTGGAAAAACGTTAGAGTCGCATATGGTAAGTGTGACTCAGCAGGCAGGTCTAGGAGGTCAAGAAGGGC : 750

(SEQ ID NO:1) P1_cons   : CATTGACTTGCCTACGCATGAAAAACCATGGTTTGAAGACCCGGCAAGAAAAATGGATGACTGGAAGAATGGGTGA : 825
(SEQ ID NO:2) P11_cons  : CATTGACTTGCCTACGCATGAAAAACCATGGTTTGAAGACCCGGCAAGAAAAATGGATGACTGGAAGAATGGGTGA : 825

(SEQ ID NO:1) P1_cons   : AAGGCAACTCCAAAAGATTGAGAGATGGTTCGTGAGGAACCCCTTTTTTGCAGTGACGGCTCTGACCATTGCCTA : 900
(SEQ ID NO:2) P11_cons  : AAGGCAACTCCAAAAGATTGAGAGATGGTTCGTGAGGAACCCCTTTTTTGCAGTGACGGCTCTGACCATTGCCTA : 900

(SEQ ID NO:1) P1_cons   : CCTTGTGGGAAGCAACATGACGCAACGAGTCGTGATTGCCCTGTGTTGGTCCGGCCTACTCAGC : 975
(SEQ ID NO:2) P11_cons  : CCTTGTGGGAAGCAACATGACGCAACGAGTCGTGATTGCCCTGTGTTGGTCCGGCCTACTCAGC : 975

(SEQ ID NO:1) P1_cons   : TCACTGCATTGGAATTACTGACAGGGATTTCATTGAGGGGTGCATGGAGGAACTTGGGTTTCAGCTACCCTGGA : 1050
(SEQ ID NO:2) P11_cons  : TCACTGCATTGGAATTACTGACAGGGATTTCATTGAGGGGTGCATGGAGGAACTTGGGTTTCAGCTACCCTGGA : 1050
```

FIG. 4B

```
(SEQ ID NO:1) P1_cons  : GCAAGACAAGTGTGTCACTGTTATGGCCCCTGACAAGCCTTCATTGGACATCTCACTAGAGACAGTAGCCATTGA : 1125
(SEQ ID NO:2) P11_cons : GCAAGACAAGTGTGTCACTGTTATGGCCCCTGACAAGCCTTCATTGGACATCTCACTAGAGACAGTAGCCATTGA : 1125

(SEQ ID NO:1) P1_cons  : TAGACCTGCTGAGGTGAGGAAAGTGTGTTACAGTTCTCACTCATGTGAAGATTAATGACAAGTGCCCCAG : 1200
(SEQ ID NO:2) P11_cons : TAGACCTGCTGAGGTGAGGAAAGTGTGTTACAGTTCTCACTCATGTGAAGATTAATGACAAGTGCCCCAG : 1200

(SEQ ID NO:1) P1_cons  : CACTGGAGAGGGCCCACCTAGCTGAAGAGAACGAAGGGACAATGCGTGCAAGCGCACTTATTCTGATAGAGGCTG : 1275
(SEQ ID NO:2) P11_cons : CACTGGAGAGGGCCCACCTAGCTGAAGAGAACGAAGGGACAATGCGTGCAAGCGCACTTATTCTGATAGAGGCTG : 1275

(SEQ ID NO:1) P1_cons  : GGGCAATGGCTGTGCCTATTTGGGAAAGGGAGCATTGTGGCGCCAAATTCACTTGTGCCAAATCCATGAG : 1350
(SEQ ID NO:2) P11_cons : GGGCAATGGCTGTGCCTATTTGGGAAAGGGAGCATTGTGGCGCCAAATTCACTTGTGCCAAATCCATGAG : 1350

(SEQ ID NO:1) P1_cons  : TTTGTTTGAGGTTGATCAGACCAAATTCAGTATGTCATCAGAGCACAATTGCATGTAGGGGCCAAGCAGGAAAA : 1425
(SEQ ID NO:2) P11_cons : TTTGTTTGAGGTTGATCAGACCAAATTCAGTATGTCATCAGAGCACAATTGCATGTAGGGGCCAAGCAGGAAAA : 1425

(SEQ ID NO:1) P1_cons  : TTGGACTACCGACATTAAGACTCTCAAGTTTGATGCCCTGTCAGGCTCCCAGGAAGTCGAGTTCATTGGGTATGG : 1500
(SEQ ID NO:2) P11_cons : TTGGACTACCGACATTAAGACTCTCAAGTTTGATGCCCTGTCAGGCTCCCAGGAAGTCGAGTTCATTGGGTATGG : 1500

(SEQ ID NO:1) P1_cons  : AAAAGCTACACTGGAATGCCAGGTGCAAACTGCGGTGGACTTTGGTAACAGTTACATCGCTGAGATGGAAACAGA : 1575
(SEQ ID NO:2) P11_cons : AAAAGCTACACTGGAATGCCAGGTGCAAACTGCGGTGGACTTTGGTAACAGTTACATCGCTGAGATGGAAACAGA : 1575
```

FIG. 4C

```
(SEQ ID NO: 1) P1_cons   : GAGCTGGATAGTGGACAGACAGTGGGCCCAGGACTTGACCCTGCCATGGCAGAGTGGAAGTGGCGGGGTGTGGAG : 1650
(SEQ ID NO: 2) P11_cons  : GAGCTGGATAGTGGACAGACAGTGGGCCCAGGACTTGACCCTGCCATGGCAGAGTGGAAGTGGCGGGGTGTGGAG : 1650
                                  1580      *      1600       *      1620       *      1640       *

(SEQ ID NO: 1) P1_cons   : AGAGATGCATCATCTTTGTCGAATTTGAACCTCCGCATGCCGCCACTATCAGAGTACTGGCCCTGGGAAACCAGGA : 1725
(SEQ ID NO: 2) P11_cons  : AGAGATGCATCATCTTTGTCGAATTTGAACCTCCGCATGCCGCCACTATCAGAGTACTGGCCCTGGGAAACCAGGA : 1725
                                  1660      *      1680       *      1700       *      1720

(SEQ ID NO: 1) P1_cons   : AGGCTCCTTGAAAACAGCTCTTACTGGCGCAATGAGGGTTACAAAGGACACAAATGACAACAACCTTTACAAACT : 1800
(SEQ ID NO: 2) P11_cons  : AGGCTCCTTGAAAACAGCTCTTACTGGCGCAATGAGGGTTACAAAGGACACAAATGACAACAACCTTTACAAACT : 1800
                            *      1740       *      1760       *      1780       *     1800

(SEQ ID NO: 1) P1_cons   : ACATGGTGGACATGTTTCTTGCAGAGTGAAATTGTCACACTCAAGGGGACATCCTACAAAATATGCAC : 1875
(SEQ ID NO: 2) P11_cons  : ACATGGTGGACATGTTTCTTGCAGAGTGAAATTGTCACACTCAAGGGGACATCCTACAAAATATGCAC : 1875
                                  *      1820       *      1840       *      1860       *

(SEQ ID NO: 1) P1_cons   : TGACAAAAATGTTTTTTTGTCAAGAACCCAACTGACACTGGCCATGGCACTGTTGTGATGCAGGTGAAAGTGTCAAA : 1950
(SEQ ID NO: 2) P11_cons  : TGACAAAAATGTTTTTTTGTCAAGAACCCAACTGACACTGGCCATGGCACTGTTGTGATGCAGGTGAAAGTGTCAAA : 1950
                             1880       *      1900       *      1920       *      1940

(SEQ ID NO: 1) P1_cons   : AGGAGCCCCCTGCAGGATTCCAGTGATAGTAGCTGATGATCTTACAGCGGCAATCAATAAAGGCATTTTGGTTAC : 2025
(SEQ ID NO: 2) P11_cons  : AGGAGCCCCCTGCAGGATTCCAGTGATAGTAGCTGATGATCTTACAGCGGCAATCAATAAAGGCATTTTGGTTAC : 2025
                                  *      1960       *      1980       *      2000       *      2020

(SEQ ID NO: 1) P1_cons   : AGTTAACCCCATCGCCTCAACCAATGATGATGAAGTGCTGATTGAGGTGAACCCACCTTTTGGAGACAGCTACAT : 2100
(SEQ ID NO: 2) P11_cons  : AGTTAACCCCATCGCCTCAACCAATGATGATGAAGTGCTGATTGAGGTGAACCCACCTTTTGGAGACAGCTACAT : 2100
                                  *      2040       *      2060       *      2080       *      2100
```

FIG. 4D

| | | |
|---|---|---|
| (SEQ ID NO: 1) P1_cons : | TATCGTTGGGAGAGGAGATTCACGTCTCACTTACCAGTGGCACAAAGAGGGAAGCTCAATAGGAAAGTTGTTCAC | 2175 |
| (SEQ ID NO: 2) P11_cons : | TATCGTTGGGAGAGGAGATTCACGTCTCACTTACCAGTGGCACAAAGAGGGAAGCTCAATAGGAAAGTTGTTCAC | 2175 |
| (SEQ ID NO: 1) P1_cons : | TCAGACCATGAAAGGCGTGGAACGCCTGGCCGTCATGGGAGAACACCGCCTGGGATTTCAGCTCCGCTGGAGGGTT | 2250 |
| (SEQ ID NO: 2) P11_cons : | TCAGACCATGAAAGGCGTGGAACGCCTGGCCGTCATGGGAGAACACCGCCTGGGATTTCAGCTCCGCTGGAGGGTT | 2250 |
| (SEQ ID NO: 1) P1_cons : | CTTCACTTCGGTTGGGAAAGGAATTCATACGGTGTTTGCCTCTGCCTTTCAGGGGCTATTTGCGGCTTGAACTG | 2325 |
| (SEQ ID NO: 2) P11_cons : | CTTCACTTCGGTTGGGAAAGGAATTCATACGGTGTTTGCCTCTGCCTTTCAGGGGCTATTTGCGGCTTGAACTG | 2325 |
| (SEQ ID NO: 1) P1_cons : | GATAACAAAGGTCATCATGGGGGCGGTACTTATATGGGTTGGCATCAACACAAGAAACATGACAATGTCCATGAG | 2400 |
| (SEQ ID NO: 2) P11_cons : | GATAACAAAGGTCATCATGGGGGCGGTACTTATATGGGTTGGCATCAACACAAGAAACATGACAATGTCCATGAG | 2400 |
| (SEQ ID NO: 1) P1_cons : | CATGATCTTGGTAGGAGTGATCATGATGTTTTTGTCTCTAGGAGTTGGGGCGGATCAAGGATGCGCCATCAACTT | 2475 |
| (SEQ ID NO: 2) P11_cons : | CATGATCTTGGTAGGAGTGATCATGATGTTTTTGTCTCTAGGAGTTGGGGCGGATCAAGGATGCGCCATCAACTT | 2475 |
| (SEQ ID NO: 1) P1_cons : | TGGCAAGAGAGAGCTCAAGTGCGGAGATGGTATCTTCATATTTAGAGACTCTGATGACTGGCTGAACAAGTACTC | 2550 |
| (SEQ ID NO: 2) P11_cons : | TGGCAAGAGAGAGCTCAAGTGCGGAGATGGTATCTTCATATTTAGAGACTCTGATGACTGGCTGAACAAGTACTC | 2550 |
| (SEQ ID NO: 1) P1_cons : | ATACTATCCAGAAGATCCTGTGAAGCTTGCATCAATAGTGAAAGCCTCTTTTGAAGAAGGGAAGTGTGGCCTAAA | 2625 |
| (SEQ ID NO: 2) P11_cons : | ATACTATCCAGAAGATCCTGTGAAGCTTGCATCAATAGTGAAAGCCTCTTTTGAAGAAGGGAAGTGTGGCCTAAA | 2625 |

FIG. 4E

```
                                 2640           *           2660            *           2680          *            2700
(SEQ ID NO:1) P1_cons  : TTCAGTTGACTCCCTTGAGCATGAGATGTGGAGAAGCAGGCAGATGAGATGAGATCAATGCCATTTTTGAGGAAAAACGA : 2700
(SEQ ID NO:2) P11_cons : TTCAGTTGACTCCCTTGAGCATGAGATGTGGAGAAGCAGGCAGATGAGATGAGATCAATGCCATTTTTGAGGAAAAACGA : 2700

*           2720           *           2740            *           2760           *
(SEQ ID NO:1) P1_cons  : GGTGGACATTTCTGTTGTCGTGCAGGATCCAAAGAATGTTTACCAGAGAGAACTCATCCATTTTCCAGAATTCG : 2775
(SEQ ID NO:2) P11_cons : GGTGGACATTTCTGTTGTCGTGCAGGATCCAAAGAATGTTTACCAGAGAGAACTCATCCATTTTCCAGAATTCG : 2775

2780          *            2800           *           2820           *            2840          *
(SEQ ID NO:1) P1_cons  : GGATGGTCTGCAGTATGGTTGGAAGACTTGGGGTAAGAACCTTGTGTTCTCCCCAGGGAGGAAGAATGGAAGCTT : 2850
(SEQ ID NO:2) P11_cons : GGATGGTCTGCAGTATGGTTGGAAGACTTGGGGTAAGAACCTTGTGTTCTCCCCAGGGAGGAAGAATGGAAGCTT : 2850

*           2860           *           2880           *            2900          *            2920
(SEQ ID NO:1) P1_cons  : CATCATAGATGGAAAGTCCAGGAAAGAATGCCCGTTTTCAAACCGGGTCTGGAATTCTTTCCAGATAGAGGAGTT : 2925
(SEQ ID NO:2) P11_cons : CATCATAGATGGAAAGTCCAGGAAAGAATGCCCGTTTTCAAACCGGGTCTGGAATTCTTTCCAGATAGAGGAGTT : 2925

*           2940           *           2960           *            2980          *            3000
(SEQ ID NO:1) P1_cons  : TGGGACGGGAGTGTTCACCACACGCGTGTACATGGACGCAGTCTTTGAATACACCATAGACTGCGATGGATCTAT : 3000
(SEQ ID NO:2) P11_cons : TGGGACGGGAGTGTTCACCACACGCGTGTACATGGACGCAGTCTTTGAATACACCATAGACTGCGATGGATCTAT : 3000

*           3020           *           3040           *            3060          *
(SEQ ID NO:1) P1_cons  : CTTGGGTGCAGCGGTGAACGGTGAAAAAAAAGAGTGCCCATGCCTCTCCAACATTTTGGATGGAAGTCATGAAGTAAA : 3075
(SEQ ID NO:2) P11_cons : CTTGGGTGCAGCGGTGAACGGTGAAAAAAAAGAGTGCCCATGCCTCTCCAACATTTTGGATGGAAGTCATGAAGTAAA : 3075

3080          *            3100           *           3120           *            3140          *
(SEQ ID NO:1) P1_cons  : TGGGACATGGATGATCCACACCTTGGAGGCATTAGATTACAAGGAGTGTGAGTGGCCACTGACACATACGATTGG : 3150
(SEQ ID NO:2) P11_cons : TGGGACATGGATGATCCACACCTTGGAGGCATTAGATTACAAGGAGTGTGAGTGGCCACTGACACATACGATTGG : 3150
```

FIG. 4F

```
                             3180              3200             3220
                      *       |        *        |        *        |
(SEQ ID NO:1)  P1_cons  : AACATCAGTTGAAGAGAGTGAAATGTTCATGCCGAGATCAATGGGAGGCCCAGTTAGCTCTCACAATCATATCCC : 3225
(SEQ ID NO:2)  P11_cons : AACATCAGTTGAAGAGAGTGAAATGTTCATGCCGAGATCAATGGGAGGCCCAGTTAGCTCTCACAATCATATCCC : 3225

3240              3260             3280            3300
                   *       |        *        |        *        |        *      |
(SEQ ID NO:1)  P1_cons  : TGGATACAAGGTTCAGACGAACGGACCTTGGATGCAGGTACCACTAGAAGTGAAGAGAGAAGCTTGCCCAGGGAC : 3300
(SEQ ID NO:2)  P11_cons : TGGATACAAGGTTCAGACGAACGGACCTTGGATGCAGGTACCACTAGAAGTGAAGAGAGAAGCTTGCCCAGGGAC : 3300

3320             3340              3360
                       *       |        *        |        *        |        *
(SEQ ID NO:1)  P1_cons  : TAGCGTGATCATTGATGCAACTGTGATGGACGGGAAAATCAACCAGATCCACCACGGATAGCGGGAAAGTTAT : 3375
(SEQ ID NO:2)  P11_cons : TAGCGTGATCATTGATGCAACTGTGATGGACGGGAAAATCAACCAGATCCACCACGGATAGCGGGAAAGTTAT : 3375

3380             3400              3420             3440
                   *       |        *        |        *        |        *        |
(SEQ ID NO:1)  P1_cons  : TCCTGAATGGTGTTGCCGCTCCTGCACAATGCCGCCTGTGAGCTTCCATGGTAGTGATGGGTGTTGGTATCCCAT : 3450
(SEQ ID NO:2)  P11_cons : TCCTGAATGGTGTTGCCGCTCCTGCACAATGCCGCCTGTGAGCTTCCATGGTAGTGATGGGTGTTGGTATCCCAT : 3450

3460              3480             3500            3520
                      *       |        *        |        *        |        *      |
(SEQ ID NO:1)  P1_cons  : GGAAATTAGGCCAAGGAAAACGCATGAAAGCCATCTGGTGCGCCTCCTGGGTTACAGCTGGAGAAATACATGCTGT : 3525
(SEQ ID NO:2)  P11_cons : GGAAATTAGGCCAAGGAAAACGCATGAAAGCCATCTGGTGCGCCTCCTGGGTTACAGCTGGAGAAATACATGCTGT : 3525

3540             3560              3580           3600
                       *       |        *        |        *        |        *      |
(SEQ ID NO:1)  P1_cons  : CCCTTTTGGTTTGGTGAGCATGAGCAATGATGATAGCAAGTGGTCCTAAGGAAAAGACAGGGACCAAAGCAAATGTT : 3600
(SEQ ID NO:2)  P11_cons : CCCTTTTGGTTTGGTGAGCATGAGCAATGATGATAGCAAGTGGTCCTAAGGAAAAGACAGGGACCAAAGCAAATGTT : 3600

3620              3640             3660
                   *       |        *        |        *        |        *
(SEQ ID NO:1)  P1_cons  : GGTTGGAGGAGTAGTGCTCTTGGGAGCAAGTAACTCTCCTTGATTTGCTGAAACTCACAGT : 3675
(SEQ ID NO:2)  P11_cons : GGTTGGAGGAGTAGTGCTCTTGGGAGCAAGTAACTCTCCTTGATTTGCTGAAACTCACAGT : 3675
```

FIG. 4G

```
                            3680            3700            3720            3740
                              *               *               *               *
(SEQ ID NO:1) P1_cons  : GGCTGTGGGATTGCATTTCCATGAGATGAACAATGGAGGAGACGCCATGTATATGGCGTTGATTGCTGCCTTTTC : 3750
(SEQ ID NO:2) P11_cons : GGCTGTGGGATTGCATTTCCATGAGATGAACAATGGAGGAGACGCCATGTATATGGCGTTGATTGCTGCCTTTTC : 3750

3760            3780            3800            3820
                              *               *               *               *
(SEQ ID NO:1) P1_cons  : AATCAGACCAGGGCTGCTCATCGGCTTTGGGCTCAGGACCCTCGGGAACGCCCTTGTGCTGACCCT : 3825
(SEQ ID NO:2) P11_cons : AATCAGACCAGGGCTGCTCATCGGCTTTGGGCTCAGGACCCTCGGGAACGCCCTTGTGCTGACCCT : 3825

3840            3860            3880            3900
                              *               *               *               *
(SEQ ID NO:1) P1_cons  : AGGAGCAGCCATGGTGGAGATTGCCTTGGGTGGCGTGATGGGCGGCCTGTGAAGTATCTAAATGCAGTTTCTCT : 3900
(SEQ ID NO:2) P11_cons : AGGAGCAGCCATGGTGGAGATTGCCTTGGGTGGCGTGATGGGCGGCCTGTGAAGTATCTAAATGCAGTTTCTCT : 3900

3920            3940            3960
                              *               *               *
(SEQ ID NO:1) P1_cons  : CTGCATCCTGACAATAAATGCTGTTGCTTCTAGGAAAGCATCAAATACCATCTTGCCCCTCATGGCTCTGTTGAC : 3975
(SEQ ID NO:2) P11_cons : CTGCATCCTGACAATAAATGCTGTTGCTTCTAGGAAAGCATCAAATACCATCTTGCCCCTCATGGCTCTGTTGAC : 3975

3980            4000            4020            4040
                              *               *               *               *
(SEQ ID NO:1) P1_cons  : ACCTGTCACTATGGCTGAGGTGAGACTTGCCGCAATGTTCTTTTGTGCCGTGGTTATCATAGGGGTCCTTCACCA : 4050
(SEQ ID NO:2) P11_cons : ACCTGTCACTATGGCTGAGGTGAGACTTGCCGCAATGTTCTTTTGTGCCGTGGTTATCATAGGGGTCCTTCACCA : 4050

4060            4080            4100            4120
                              *               *               *               *
(SEQ ID NO:1) P1_cons  : GAATTTCAAGGACACCTCCATGCAGAAGACTATACCTCTGGTGGCCCTCACACTCACATCTTACCTGGGCTTGAC : 4125
(SEQ ID NO:2) P11_cons : GAATTTCAAGGACACCTCCATGCAGAAGACTATACCTCTGGTGGCCCTCACACTCACATCTTACCTGGGCTTGAC : 4125

4140            4160            4180            4200
                              *               *               *               *
(SEQ ID NO:1) P1_cons  : ACAACCTTTTTTGGGCCTGTGTGCATTTCTGCCAACCCGCATATTTGGGCAAGGAGTATCCCAGTGAATGAGGC : 4200
(SEQ ID NO:2) P11_cons : ACAACCTTTTTTGGGCCTGTGTGCATTTCTGCCAACCCGCATATTTGGGCAAGGAGTATCCCAGTGAATGAGGC : 4200
```

FIG. 4H

```
(SEQ ID NO:1) P1_cons   : ACTCGCAGCAGCTGGTCTAGTGGGAGTGCTGGCAGGACTGGCTTTTCAGGAGATGGAGAACTTCCTTGGTCCGAT : 4275
(SEQ ID NO:2) P11_cons  : ACTCGCAGCAGCTGGTCTAGTGGGAGTGCTGGCAGGACTGGCTTTTCAGGAGATGGAGAACTTCCTTGGTCCGAT : 4275
                                  4220      4240      4260      *

(SEQ ID NO:1) P1_cons   : TGCAGTTGGAGGACTCCTGATGATGCTGGTTAGCGTGGCTGGAGGGTGGATGGGCTAGAGCTCAAGAAGCTTGG : 4350
(SEQ ID NO:2) P11_cons  : TGCAGTTGGAGGACTCCTGATGATGCTGGTTAGCGTGGCTGGAGGGTGGATGGGCTAGAGCTCAAGAAGCTTGG : 4350
                                  4300      *         4320      *         4340

(SEQ ID NO:1) P1_cons   : TGAAGTTTCATGGGAAGAGAGGCGGAGATCAGCGGGAGTTCCGCCCGCTATGATGTGGCACTCAGTGAACAAGG : 4425
(SEQ ID NO:2) P11_cons  : TGAAGTTTCATGGGAAGAGAGGCGGAGATCAGCGGGAGTTCCGCCCGCTATGATGTGGCACTCAGTGAACAAGG : 4425
                                  4360      *         4380      *         4400      *         4420

(SEQ ID NO:1) P1_cons   : GGAGTTCAAGCTGCTGCTTTCTGAAGAGAAAGTGCCATGGGACCAGTTGTGATGACCTCGCTGGCCTTGGTTGGGGC : 4500
(SEQ ID NO:2) P11_cons  : GGAGTTCAAGCTGCTGCTTTCTGAAGAGAAAGTGCCATGGGACCAGTTGTGATGACCTCGCTGGCCTTGGTTGGGGC : 4500
                                  4440      *         4460      *         4480      *         4500

(SEQ ID NO:1) P1_cons   : TGCCCTCCATCCATTTGCTCTTCTGCTCTTGCTGGTCCTTGCTGTTTCATGTCAGGGGAGCTAGGAGAAGTGG : 4575
(SEQ ID NO:2) P11_cons  : TGCCCTCCATCCATTTGCTCTTCTGCTCTTGCTGGTCCTTGCTGTTTCATGTCAGGGGAGCTAGGAGAAGTGG : 4575
                                  4520      *         4540      *         4560      *

(SEQ ID NO:1) P1_cons   : GGATGTCTTGTGGGATATTCCCACTCCTAAGATCATCGAGGAATGTGAACATCTGGAGGATGGGATTTATGGCAT : 4650
(SEQ ID NO:2) P11_cons  : GGATGTCTTGTGGGATATTCCCACTCCTAAGATCATCGAGGAATGTGAACATCTGGAGGATGGGATTTATGGCAT : 4650
                                  4580      *         4600      *         4620      *         4640

(SEQ ID NO:1) P1_cons   : ATTCCAGTCAACCTTCTTGGGGCCCTCCCAGCGAGGAGTGGGAGTGGCACAGGAGGGGTGTTCCACACAATGTG : 4725
(SEQ ID NO:2) P11_cons  : ATTCCAGTCAACCTTCTTGGGGCCCTCCCAGCGAGGAGTGGGAGTGGCACAGGAGGGGTGTTCCACACAATGTG : 4725
                                  4660      *         4680      *         4700      *         4720
```

FIG. 4I

```
                          *        4740         *        4760         *        4780         *        4800
(SEQ ID NO:1) P1_cons  : GCATGTCACAAGAGGAGCTTTCCTTGTCAGGAATGGCAAGAAGTTGATTCCATCTTGGGCTTCAGTAAAGGAAGA : 4800
(SEQ ID NO:2) P11_cons : GCATGTCACAAGAGGAGCTTTCCTTGTCAGGAATGGCAAGAAGTTGATTCCATCTTGGGCTTCAGTAAAGGAAGA : 4800

*        4820         *        4840         *        4860         *
(SEQ ID NO:1) P1_cons  : CCTTGTCGCCTATGGTGGCTCATGGAAGTTGGAGAGGAAGAGGTCCAGTTGATCGCGGC : 4875
(SEQ ID NO:2) P11_cons : CCTTGTCGCCTATGGTGGCTCATGGAAGTTGGAGAGGAAGAGGTCCAGTTGATCGCGGC : 4875

4880         *        4900         *        4920         *        4940         *
(SEQ ID NO:1) P1_cons  : TGTTCCAGGAAAAGAACGTGGTCAACGTCCAGACAAAAACCGAGCTTGTTCAAAGTGAGGAATGGGGGAGAAATCGG : 4950
(SEQ ID NO:2) P11_cons : TGTTCCAGGAAAAGAACGTGGTCAACGTCCAGACAAAAACCGAGCTTGTTCAAAGTGAGGAATGGGGGAGAAATCGG : 4950

*        4960         *        4980         *        5000         *        5020
(SEQ ID NO:1) P1_cons  : GGCTGTCGCTCTTGACTATCCGAGTGGCACTTCAGGATCTCCTATTGTTAACAGGAACGGAGAGGTGATTGGGCT : 5025
(SEQ ID NO:2) P11_cons : GGCTGTCGCTCTTGACTATCCGAGTGGCACTTCAGGATCTCCTATTGTTAACAGGAACGGAGAGGTGATTGGGCT : 5025

*        5040         *        5060         *        5080         *        5100
(SEQ ID NO:1) P1_cons  : GTACGGCAATGGCATCCTTGTCGTGGTGACAACTCCTTCGTCCGCCATATCCCAGACTGAGGTGAAGGAAGAAGG : 5100
(SEQ ID NO:2) P11_cons : GTACGGCAATGGCATCCTTGTCGTGGTGACAACTCCTTCGTCCGCCATATCCCAGACTGAGGTGAAGGAAGAAGG : 5100

*        5120         *        5140         *        5160         *
(SEQ ID NO:1) P1_cons  : AAAGGAGGAGCTCCAAGAGATCCCGACAATGCTAAAGAAAGGAATGACAACTGTCCTTGATTTTCATCCTGGAGC : 5175
(SEQ ID NO:2) P11_cons : AAAGGAGGAGCTCCAAGAGATCCCGACAATGCTAAAGAAAGGAATGACAACTGTCCTTGATTTTCATCCTGGAGC : 5175

5180         *        5200         *        5220         *        5240         *
(SEQ ID NO:1) P1_cons  : TGGGAAGACAAGACGTTTCCTCCCACAGATCTTGGCCGAGTGCGCACGGAGACGCTTGCGCACTCTTGTGTTGGC : 5250
(SEQ ID NO:2) P11_cons : TGGGAAGACAAGACGTTTCCTCCCACAGATCTTGGCCGAGTGCGCACGGAGACGCTTGCGCACTCTTGTGTTGGC : 5250
```

FIG. 4J

```
(SEQ ID NO:1) P1_cons  : CCCCACCAGGGTTGTTCTTTCTGAAATGAAGGAGGCTTTTCACGGCCTGGACGTGAAATTCCACACACAGGCTTT : 5325
(SEQ ID NO:2) P11_cons : CCCCACCAGGGTTGTTCTTTCTGAAATGAAGGAGGCTTTTCACGGCCTGGACGTGAAATTCCACACACAGGCTTT : 5325

(SEQ ID NO:1) P1_cons  : TTCCGCTCACGGCAGCGGGAGAGAAGTCATTGATGCTATGTGCCATGCCACCCTAACTTACAGGATGTTGAACC : 5400
(SEQ ID NO:2) P11_cons : TTCCGCTCACGGCAGCGGGAGAGAAGTCATTGATGCTATGTGCCATGCCACCCTAACTTACAGGATGTTGAACC : 5400

(SEQ ID NO:1) P1_cons  : AACTAGGGTTGTTAACTGGGAAGTGATCATTATGGATGAAGCCCATTTTTGGATCCAGCTAGCATAGCCGCTAG : 5475
(SEQ ID NO:2) P11_cons : AACTAGGGTTGTTAACTGGGAAGTGATCATTATGGATGAAGCCCATTTTTGGATCCAGCTAGCATAGCCGCTAG : 5475

(SEQ ID NO:1) P1_cons  : AGGTTGGGCAGCGCACAGAGAGCTAGGGCAAATGAAAGTGCAACAATCTTGATGACAGCCACACCGCCTGGACTAG : 5550
(SEQ ID NO:2) P11_cons : AGGTTGGGCAGCGCACAGAGAGCTAGGGCAAATGAAAGTGCAACAATCTTGATGACAGCCACACCGCCTGGACTAG : 5550

(SEQ ID NO:1) P1_cons  : TGATGAATTTCCACATTCAAATGGTGAAATAGAAGATGTTCAAACGGACATACCCAGTGAGCCCTGGAACACAGG : 5625
(SEQ ID NO:2) P11_cons : TGATGAATTTCCACATTCAAATGGTGAAATAGAAGATGTTCAAACGGACATACCCAGTGAGCCCTGGAACACAGG : 5625

(SEQ ID NO:1) P1_cons  : GCATGACTGGATCCTGGCTGACAAAAGGCCCACGGCATGGTTCCTTCCATCCATCAGAGCTGCAAATGTCATGGC : 5700
(SEQ ID NO:2) P11_cons : GCATGACTGGATCCTGGCTGACAAAAGGCCCACGGCATGGTTCCTTCCATCCATCAGAGCTGCAAATGTCATGGC : 5700

(SEQ ID NO:1) P1_cons  : TGCCTCTTTGCGTAAGGCTGGAAAGAGTGTGGTCCTGAACAGGAAAACCTTTGAGAGAGAATACCCCACGAT : 5775
(SEQ ID NO:2) P11_cons : TGCCTCTTTGCGTAAGGCTGGAAAGAGTGTGGTCCTGAACAGGAAAACCTTTGAGAGAGAATACCCCACGAT : 5775
```

FIG. 4K

```
(SEQ ID NO:1) P1_cons  : AAAGCAGAAGAAACCTGACTTTATATTGGCCACTGACATAGCTGAAATGGGAGCCAACCTTTGCGTGGAGCGAGT : 5850
(SEQ ID NO:2) P11_cons : AAAGCAGAAGAAACCTGACTTTATATTGGCCACTGACATAGCTGAAATGGGAGCCAACCTTTGCGTGGAGCGAGT : 5850
                                 5780           *          5800           *          5820           *          5840

(SEQ ID NO:1) P1_cons  : GCTGGATTGCAGGACGGCTTTTAAGCCTGTGCTTGTGGATGAAGGGAGGAAGGTGGCAATAAAAAGGGCCACTTCG : 5925
(SEQ ID NO:2) P11_cons : GCTGGATTGCAGGACGGCTTTTAAGCCTGTGCTTGTGGATGAAGGGAGGAAGGTGGCAATAAAAAGGGCCACTTCG : 5925
                                 5860           *          5880           *          5900           *          5920

(SEQ ID NO:1) P1_cons  : TATCTCCGCATCCTCTGCTCTCAAAGGAGGGGGCGCATTGGGAGAGAAATCCCAACAGAGATGGAGACTCATACTA : 6000
(SEQ ID NO:2) P11_cons : TATCTCCGCATCCTCTGCTCTCAAAGGAGGGGGCGCATTGGGAGAGAAATCCCAACAGAGATGGAGACTCATACTA : 6000
                                  *            5940           *          5960           *          5980           *           6000

(SEQ ID NO:1) P1_cons  : CTATTCTGAGCCTACAAGTGAAAATAATGCCCACCACGTCTGCTGGTTGGAGGCCTCAATGCTCTCTTGGACAACAT : 6075
(SEQ ID NO:2) P11_cons : CTATTCTGAGCCTACAAGTGAAAATAATGCCCACCACGTCTGCTGGTTGGAGGCCTCAATGCTCTCTTGGACAACAT : 6075
                                 6020           *          6040           *          6060           *

(SEQ ID NO:1) P1_cons  : GGAGGTGAGGGTGGAATGGTCGCCCCCACTCTATGGCGTTGAAGGAACTAAAACACCAGTTTCCCCTGGTGAAAT : 6150
(SEQ ID NO:2) P11_cons : GGAGGTGAGGGTGGAATGGTCGCCCCCACTCTATGGCGTTGAAGGAACTAAAACACCAGTTTCCCCTGGTGAAAT : 6150
                                 6080           *          6100           *          6120           *          6140

(SEQ ID NO:1) P1_cons  : GAGACTGAGGGATGACCAGAGGAGAAAGTCTTCAGAGAACTAGTGAGGAATTGTGACCTGCCCGTTTGGCTTTCGTG : 6225
(SEQ ID NO:2) P11_cons : GAGACTGAGGGATGACCAGAGGAGAAAGTCTTCAGAGAACTAGTGAGGAATTGTGACCTGCCCGTTTGGCTTTCGTG : 6225
                                 6160           *          6180           *          6200           *          6220

(SEQ ID NO:1) P1_cons  : GCAAGTGGCCAAGGCTGGTTTGAAGACGAATGATCGTAAGTGGTGTTTTGAAGGCCCTGAGGAACATGAGATCTT : 6300
(SEQ ID NO:2) P11_cons : GCAAGTGGCCAAGGCTGGTTTGAAGACGAATGATCGTAAGTGGTGTTTTGAAGGCCCTGAGGAACATGAGATCTT : 6300
                                 6240           *          6260           *          6280           *          6300
```

FIG. 4L

```
(SEQ ID NO:3) P1_transla : MSGRKAQGKTLGVNMVRGVRSLSNKIKQKTKQIGNRPGPSRGVQGFIFFFLFNILTGKKITAHLKRLWKMLD :  73
(SEQ ID NO:4) P1l_transl : MSGRKAQGKTLGVNMVRGVRSLSNKIKQKTKQIGNRPGPSRGVQGFIFFFLFNILTGKKITAHLKRLWKMLD :  73
(SEQ ID NO:5) B-P1_prM-E : ---------------------------------------------------------------------- :   -
(SEQ ID NO:6) B3-P11_prM : ---------------------------------------------------------------------- :   -

(SEQ ID NO:3) P1_transla : PRQGLAVLRKVKRVVASLMRGLSSRKRRSHDVLITVQFLILGMLLMTGGVTLVRKNRWLLLNVTSEDLGKTFSV : 146
(SEQ ID NO:4) P1l_transl : PRQGLAVLRKVKRVVASLMRGLSSRKRRSHDVLITVQFLILGMLLMTGGVTLVRKNRWLLLNVTSEDLGKTFSV : 146
(SEQ ID NO:5) B-P1_prM-E : -------------------------------ILGMLLMTGGVTLVRKNRWLLLNVTSEDLGKTFSV :  35
(SEQ ID NO:6) B3-P11_prM : --------------------------------GMLLMTGGVTLVRKNRWLLLNVTSEDLGKTFSV :  33

(SEQ ID NO:3) P1_transla : GTGNCTTNILEAKYWCPDSMEYNCPNLSPREEPDDICWCYGVENVRVAYGKCDSAGRSRRSRRAIDLPTHEN : 219
(SEQ ID NO:4) P1l_transl : GTGNCTTNILEAKYWCPDSMEYNCPNLSPREEPDDICWCYGVENVRVAYGKCDSAGRSRRSRRAIDLPTHEN : 219
(SEQ ID NO:5) B-P1_prM-E : GTGNCTTNILEAKYWCPDSMEYNCPNLSPREEPDDICWCYGVENVRVAYGKCDSAGRSRRSRRAIDLPTHEN : 108
(SEQ ID NO:6) B3-P11_prM : GTGNCTTNILEAKYWCPDSMEYNCPNLSPREEPDDICWCYGVENVRVAYGKCDSAGRSRRSRRAIDLPTHEN : 106

(SEQ ID NO:3) P1_transla : HGLKTRQEKWMTGRMGERQLQKIERWFVRNPFFAVTALTIAYLIVGSNMTQRVVIALLVLAVGPAYSAHCIGIT : 292
(SEQ ID NO:4) P1l_transl : HGLKTRQEKWMTGRMGERQLQKIERWFVRNPFFAVTALTIAYLIVGSNMTQRVVIALLVLAVGPAYSAHCIGIT : 292
(SEQ ID NO:5) B-P1_prM-E : HGLKTRQEKWMTGRMGERQLQKIERWFVRNPFFAVTALTIAYLIVGSNMTQRVVIALLVLAVGPAYSAHCIGIT : 181
(SEQ ID NO:6) B3-P11_prM : HGLKTRQEKWMTGRMGERQLQKIERWFVRNPFFAVTALTIAYLIVGSNMTQRVVIALLVLAVGPAYSAHCIGIT : 179

(SEQ ID NO:3) P1_transla : DRDFIEGVHGGTWVSATLEQDKCVTVMAPDKPSLDISLETVAIDRPAEVRKVCYNAVLTHVKINDKCPSTGEA : 365
(SEQ ID NO:4) P1l_transl : DRDFIEGVHGGTWVSATLEQDKCVTVMAPDKPSLDISLETVAIDRPAEVRKVCYNAVLTHVKINDKCPSTGEA : 365
(SEQ ID NO:5) B-P1_prM-E : DRDFIEGVHGGTWVSATLEQDKCVTVMAPDKPSLDISLETVAIDRPAEVRKVCYNAVLTHVKINDKCPSTGEA : 254
(SEQ ID NO:6) B3-P11_prM : DRDFIEGVHGGTWVSATLEQDKCVTVMAPDKPSLDISLETVAIDRPAEVRKVCYNAVLTHVKINDKCPSTGEA : 252
```

FIG. 5A

```
                              *         380         *         400         *         420         *         4
(SEQ ID NO: 3) P1_transla : HLAEENEGDNACKRTYSDRGWGNGCGLFGKGSIVACAKFTCAKSMSLFEVDQTKIQYVIRAQLHVGAKQENWT : 438
(SEQ ID NO: 4) P11_transl : HLAEENEGDNACKRTYSDRGWGNGCGLFGKGSIVACAKFTCAKSMSLFEVDQTKIQYVIRAQLHVGAKQENWT : 438
(SEQ ID NO: 5) B-P1_prM-E : HLAEENEGDNACKRTYSDRGWGNGCGLFGKGSIVACAKFTCAKSMSLFEVDQTKIQYVIRAQLHVGAKQENWT : 327
(SEQ ID NO: 6) B3-P11_prM : HLAEENEGDNACKRTYSDRGWGNGCGLFGKGSIVACAKFTCAKSMSLFEVDQTKIQYVIRAQLHVGAKQENWT : 325

40          *         460         *         480         *         500         *
(SEQ ID NO: 3) P1_transla : TDIKTLKFDALSGSQEVEFIGYKATLECQVQTAVDFGNSYIAEMETESWIVDRQWAQDLTLPWQSGSGGVWR : 511
(SEQ ID NO: 4) P11_transl : TDIKTLKFDALSGSQEVEFIGYKATLECQVQTAVDFGNSYIAEMETESWIVDRQWAQDLTLPWQSGSGGVWR : 511
(SEQ ID NO: 5) B-P1_prM-E : TDIKTLKFDALSGSQEVEFIGYKATLECQVQTAVDFGNSYIAEMETESWIVDRQWAQDLTLPWQSGSGGVWR : 400
(SEQ ID NO: 6) B3-P11_prM : TDIKTLKFDALSGSQEVEFIGYKATLECQVQTAVDFGNSYIAEMETESWIVDRQWAQDLTLPWQSGSGGVWR : 398

520         *         540         *         560         *         580         *
(SEQ ID NO: 3) P1_transla : EMHHLVEFEPPHAATIRVLALGNQEGSLKTALTGAMRVTKDTNDNNLYKLHGGHVSCRVKLSALTLKGTSYKI : 584
(SEQ ID NO: 4) P11_transl : EMHHLVEFEPPHAATIRVLALGNQEGSLKTALTGAMRVTKDTNDNNLYKLHGGHVSCRVKLSALTLKGTSYKI : 584
(SEQ ID NO: 5) B-P1_prM-E : EMHHLVEFEPPHAATIRVLALGNQEGSLKTALTGAMRVTKDTNDNNLYKLHGGHVSCRVKLSALTLKGTSYKI : 473
(SEQ ID NO: 6) B3-P11_prM : EMHHLVEFEPPHAATIRVLALGNQEGSLKTALTGAMRVTKDTNDNNLYKLHGGHVSCRVKLSALTLKGTSYKI : 471

*         600         *         620         *         640         *
(SEQ ID NO: 3) P1_transla : CTDKMFFVKNPTDTGHGTVVMQVKVSKGAPCRIPVIVADDLTAAINKGILVTVNPIASTNDDEVLIEVNPPFG : 657
(SEQ ID NO: 4) P11_transl : CTDKMFFVKNPTDTGHGTVVMQVKVSKGAPCRIPVIVADDLTAAINKGILVTVNPIASTNDDEVLIEVNPPFG : 657
(SEQ ID NO: 5) B-P1_prM-E : CTDKMFFVKNPTDTGHGTVVMQVKVSKGAPCRIPVIVADDLTAAINKGILVTVNPIASTNDDEVLIEVNPPFG : 546
(SEQ ID NO: 6) B3-P11_prM : CTDKMFFVKNPTDTGHGTVVMQVKVSKGAPCRIPVIVADDLTAAINKGILVTVNPIASTNDDEVLIEVNPPFG : 544

660         *         680         *         700         *         720         *
(SEQ ID NO: 3) P1_transla : DSYIIVGRGDSRLTYQWHKEGSSIGKLFTQTMKGVERLAVMGDTAWDFSSAGGFFTSVGKGIHTVFGSAFQGL : 730
(SEQ ID NO: 4) P11_transl : DSYIIVGRGDSRLTYQWHKEGSSIGKLFTQTMKGVERLAVMGDTAWDFSSAGGFFTSVGKGIHTVFGSAFQGL : 730
(SEQ ID NO: 5) B-P1_prM-E : DSYIIVGRGDSRLTYQWHKEGSSIGKLFTQTMKGVERLAVMGDTAWDFSSAGGFFTSVGKGIHTVFGSAFQGL : 619
(SEQ ID NO: 6) B3-P11_prM : DSYIIVGRGDSRLTYQWHKEGSSIGKLFTQTMKGVERLAVMGDTAWDFSSAGGFFTSVGKGIHTVFGSAFQGL : 617
```

FIG. 5B

```
(SEQ ID NO:3) P1_transla  : FGGLNWITKVIMGAVLIWGINTRNMTMSMSMILVGVIMMFLSLGVGADQGCAINFGKRELKCGDGIFIFRDS : 803
(SEQ ID NO:4) P11_transl  : FGGLNWITKVIMGAVLIWGINTRNMTMSMSMILVGVIMMFLSLGVGADQGCAINFGKRELKCGDGIFIFRDS : 803
(SEQ ID NO:5) B-P1_prM-E  : FGGLNWITKVIMGAVLIWGINTRNMTMSMSMILVGVIMMFLSLGVGADQGCAINFGKRELKCGD------- : 684
(SEQ ID NO:6) B3-P11_prM  : FGGLNWITKVIMGAVLIWGINTRNMTMSMSMILVGVIMMFLSLGVGADQGCAINFGKREL----------- : 678
                                    740       *        760       *        780       *        800

(SEQ ID NO:3) P1_transla  : DDWLNKYSYPEDPVKLASIVKASFEEGKCGLNSVDSLEHEMWRSRADEINAIFEENEVDISVVVQDPKNVYQ : 876
(SEQ ID NO:4) P11_transl  : DDWLNKYSYPEDPVKLASIVKASFEEGKCGLNSVDSLEHEMWRSRADEINAIFEENEVDISVVVQDPKNVYQ : 876
(SEQ ID NO:5) B-P1_prM-E  : ---------------------------------------------------------------------- : -
(SEQ ID NO:6) B3-P11_prM  : ---------------------------------------------------------------------- : -
                                    *        820       *        840       *        860       *

(SEQ ID NO:3) P1_transla  : RGTHPFSRIRDGLQYGWKTWGKNLVFSPGRKNGSFIIDGKSRKECPFSNRVWNSFQIEEFGTGVFTTRVYMDA : 949
(SEQ ID NO:4) P11_transl  : RGTHPFSRIRDGLQYGWKTWGKNLVFSPGRKNGSFIIDGKSRKECPFSNRVWNSFQIEEFGTGVFTTRVYMDA : 949
(SEQ ID NO:5) B-P1_prM-E  : ----------------------------------------------------------------------- : -
(SEQ ID NO:6) B3-P11_prM  : ----------------------------------------------------------------------- : -
                                   880       *        900       *        920       *        940

(SEQ ID NO:3) P1_transla  : VFEYTIDCDGSILGAAVNGKKSAHGSPTFWMGSHEVNGTWMIHTLEALDYKECEWPLTHTIGTSVEESEMFMP : 1022
(SEQ ID NO:4) P11_transl  : VFEYTIDCDGSILGAAVNGKKSAHGSPTFWMGSHEVNGTWMIHTLEALDYKECEWPLTHTIGTSVEESEMFMP : 1022
(SEQ ID NO:5) B-P1_prM-E  : ----------------------------------------------------------------------- : -
(SEQ ID NO:6) B3-P11_prM  : ----------------------------------------------------------------------- : -
                                    *        960       *        980       *       1000       *       1020

(SEQ ID NO:3) P1_transla  : RSIGGPVSSHNHIPGYKVQTNGPWMQVPLEVKREACPGTSVIIDGNCDGRGKSTRSTTDSGKVIPEWCCRSCT : 1095
(SEQ ID NO:4) P11_transl  : RSIGGPVSSHNHIPGYKVQTNGPWMQVPLEVKREACPGTSVIIDGNCDGRGKSTRSTTDSGKVIPEWCCRSCT : 1095
(SEQ ID NO:5) B-P1_prM-E  : ----------------------------------------------------------------------- : -
(SEQ ID NO:6) B3-P11_prM  : ----------------------------------------------------------------------- : -
                                   1040       *       1060       *       1080       *
```

FIG. 5C

```
(SEQ ID NO:3) P1_transla  :          1100         *        1120         *        1140         *        1160
(SEQ ID NO:3) P1_transla  : MPPVSFHGSDGCWYPMEIRPRKTHESHLVRSWVTAGEIHAVPFGLVSMMIAMEVVLRKRQGPKQMLVGGVVLL : 1168
(SEQ ID NO:4) P11_transl  : MPPVSFHGSDGCWYPMEIRPRKTHESHLVRSWVTAGEIHAVPFGLVSMMIAMEVVLRKRQGPKQMLVGGVVLL : 1168
(SEQ ID NO:5) B-P1_prM-E  : ---------------------------------------------------------------------- : -
(SEQ ID NO:6) B3-P11_prM  : ---------------------------------------------------------------------- : -

*        1180         *        1200         *        1220         *        1240
(SEQ ID NO:3) P1_transla  : GAMLVGQVTLLDLLKLTVAVGLHFHEMNNGGDAMYMALIAAFSIRPGLLIGFGLRTLWSPRERLVLTLGAAMV : 1241
(SEQ ID NO:4) P11_transl  : GAMLVGQVTLLDLLKLTVAVGLHFHEMNNGGDAMYMALIAAFSIRPGLLIGFGLRTLWSPRERLVLTLGAAMV : 1241
(SEQ ID NO:5) B-P1_prM-E  : ---------------------------------------------------------------------- : -
(SEQ ID NO:6) B3-P11_prM  : ---------------------------------------------------------------------- : -

*        1260         *        1280         *        1300         *
(SEQ ID NO:3) P1_transla  : EIALGGVMGGLMKYLNAVSLCILITINAVASRKASNTILPLMALLTPVTMAEVRLAAMFFCAVVIIGVLHQNFK : 1314
(SEQ ID NO:4) P11_transl  : EIALGGVMGGLMKYLNAVSLCILITINAVASRKASNTILPLMALLTPVTMAEVRLAAMFFCAVVIIGVLHQNFK : 1314
(SEQ ID NO:5) B-P1_prM-E  : ---------------------------------------------------------------------- : -
(SEQ ID NO:6) B3-P11_prM  : ---------------------------------------------------------------------- : -

1320         *        1340         *        1360         *        1380
(SEQ ID NO:3) P1_transla  : DTSMQKTIPIVALTLTSYLGLTQPFLGLCAFLATRIFGRRSIPVNEALAAAGLVGVLAGLAFQEMENFLGPIA : 1387
(SEQ ID NO:4) P11_transl  : DTSMQKTIPIVALTLTSYLGLTQPFLGLCAFLATRIFGRRSIPVNEALAAAGLVGVLAGLAFQEMENFLGPIA : 1387
(SEQ ID NO:5) B-P1_prM-E  : ---------------------------------------------------------------------- : -
(SEQ ID NO:6) B3-P11_prM  : ---------------------------------------------------------------------- : -

*        1400         *        1420         *        1440         *        1460
(SEQ ID NO:3) P1_transla  : VGGLLMMLVSVAGRVDGLELKKLGEVSWEEEAEISGSSARYDVALSEQGEFKLLSEEKVPWDQVVMTSLALVG : 1460
(SEQ ID NO:4) P11_transl  : VGGLLMMLVSVAGRVDGLELKKLGEVSWEEEAEISGSSARYDVALSEQGEFKLLSEEKVPWDQVVMTSLALVG : 1460
(SEQ ID NO:5) B-P1_prM-E  : ---------------------------------------------------------------------- : -
(SEQ ID NO:6) B3-P11_prM  : ---------------------------------------------------------------------- : -
```

FIG. 5D

```
(SEQ ID NO:3) P1_transla  : AALHPFALLLVLAGWLFHVRGARRSGDVLWDIPTPKIIEECEHLEDGIYGIFQSTFLGASQRGVGVAQGGVFH : 1533
(SEQ ID NO:4) P11_transl  : AALHPFALLLVLAGWLFHVRGARRSGDVLWDIPTPKIIEECEHLEDGIYGIFQSTFLGASQRGVGVAQGGVFH : 1533
(SEQ ID NO:5) B-P1_prM-E  : ------------------------------------------------------------------------ : -
(SEQ ID NO:6) B3-P11_prM  : ------------------------------------------------------------------------ : -

(SEQ ID NO:3) P1_transla  : TMWHVTRGAFLVRNGKKLIPSWASVKEDLVAYGGSWKLEGRWDGEEEVQLIAAVPGKNVVNVQTKPSLFKVRN : 1606
(SEQ ID NO:4) P11_transl  : TMWHVTRGAFLVRNGKKLIPSWASVKEDLVAYGGSWKLEGRWDGEEEVQLIAAVPGKNVVNVQTKPSLFKVRN : 1606
(SEQ ID NO:5) B-P1_prM-E  : ------------------------------------------------------------------------ : -
(SEQ ID NO:6) B3-P11_prM  : ------------------------------------------------------------------------ : -

(SEQ ID NO:3) P1_transla  : GGEIGAVALDYPSGTSGSPIVNRNGEVIGLYGNGILVGDNSFVSAISQTEVKEEGKEELQEIPTMLKKGMTTV : 1679
(SEQ ID NO:4) P11_transl  : GGEIGAVALDYPSGTSGSPIVNRNGEVIGLYGNGILVGDNSFVSAISQTEVKEEGKEELQEIPTMLKKGMTTV : 1679
(SEQ ID NO:5) B-P1_prM-E  : ------------------------------------------------------------------------ : -
(SEQ ID NO:6) B3-P11_prM  : ------------------------------------------------------------------------ : -

(SEQ ID NO:3) P1_transla  : LDFHPGAGKTRRFLPQILAECARRRLRTLVLAPTRVVLSEMKEAFHGLDVKFHTQAFSAHGSGREVIDAMCHA : 1752
(SEQ ID NO:4) P11_transl  : LDFHPGAGKTRRFLPQILAECARRRLRTLVLAPTRVVLSEMKEAFHGLDVKFHTQAFSAHGSGREVIDAMCHA : 1752
(SEQ ID NO:5) B-P1_prM-E  : ------------------------------------------------------------------------ : -
(SEQ ID NO:6) B3-P11_prM  : ------------------------------------------------------------------------ : -

(SEQ ID NO:3) P1_transla  : TLTYRMLEPTRVVNWEVIIMDEAHFLDPASIAARGWAAHRARANESATILMTATPPGTSDEFPHSNGEIEDVQ : 1825
(SEQ ID NO:4) P11_transl  : TLTYRMLEPTRVVNWEVIIMDEAHFLDPASIAARGWAAHRARANESATILMTATPPGTSDEFPHSNGEIEDVQ : 1825
(SEQ ID NO:5) B-P1_prM-E  : ------------------------------------------------------------------------ : -
(SEQ ID NO:6) B3-P11_prM  : ------------------------------------------------------------------------ : -
```

FIG. 5E

| | | |
|---|---|---|
| (SEQ ID NO:3) P1_transla | : TDIPSEPWNTGHDWILADKRPTAWFLPSIRAANVMAASLRKAGKSVVVLNRKTFEREYPTIKQKKPDFILATD | : 1898 |
| (SEQ ID NO:4) P11_transl | : TDIPSEPWNTGHDWILADKRPTAWFLPSIRAANVMAASLRKAGKSVVVLNRKTFEREYPTIKQKKPDFILATD | : 1898 |
| (SEQ ID NO:5) B-P1_prM-E | : ------------------------------------------------------------------------ | : -- |
| (SEQ ID NO:6) B3-P11_prM | : ------------------------------------------------------------------------ | : -- |

| | | |
|---|---|---|
| (SEQ ID NO:3) P1_transla | : IAEMGANLCVERVLDCRTAFKPVLVDEGRKVAIKGPLRISASSAAQRRGRIGRNPNRDGDSYYYSEPTSENNA | : 1971 |
| (SEQ ID NO:4) P11_transl | : IAEMGANLCVERVLDCRTAFKPVLVDEGRKVAIKGPLRISASSAAQRRGRIGRNPNRDGDSYYYSEPTSENNA | : 1971 |
| (SEQ ID NO:5) B-P1_prM-E | : ------------------------------------------------------------------------ | : -- |
| (SEQ ID NO:6) B3-P11_prM | : ------------------------------------------------------------------------ | : -- |

| | | |
|---|---|---|
| (SEQ ID NO:3) P1_transla | : HHVCWLEASMLLDNMEVRGGMVAPLYGVEGTKTPVSPGEMRLRDDQRKVFRELVRNCDLPVWLSWQVAKAGLK | : 2044 |
| (SEQ ID NO:4) P11_transl | : HHVCWLEASMLLDNMEVRGGMVAPLYGVEGTKTPVSPGEMRLRDDQRKVFRELVRNCDLPVWLSWQVAKAGLK | : 2044 |
| (SEQ ID NO:5) B-P1_prM-E | : ------------------------------------------------------------------------ | : -- |
| (SEQ ID NO:6) B3-P11_prM | : ------------------------------------------------------------------------ | : -- |

| | | |
|---|---|---|
| (SEQ ID NO:3) P1_transla | : TNDRKWCFEGPEEHEILNDSGETVKCRAPGGAKKPLRPRWCDERVSSDQSALSEFIKFAEGRRGAAEVLVVLS | : 2117 |
| (SEQ ID NO:4) P11_transl | : TNDRKWCFEGPEEHEILNDSGETVKCRAPGGAKKPLRPRWCDERVSSDQSALSEFIKFAEGRRGAAEVLVVLS | : 2117 |
| (SEQ ID NO:5) B-P1_prM-E | : ------------------------------------------------------------------------ | : -- |
| (SEQ ID NO:6) B3-P11_prM | : ------------------------------------------------------------------------ | : -- |

| | | |
|---|---|---|
| (SEQ ID NO:3) P1_transla | : ELPDFLAKKGGEAMDTISVFLHSEEGSRAYRNALSMMPEAMTIVMLFILAGLLTSGMVIFFMSPKGISRMSMA | : 2190 |
| (SEQ ID NO:4) P11_transl | : ELPDFLAKKGGEAMDTISVFLHSEEGSRAYRNALSMMPEAMTIVMLFILAGLLTSGMVIFFMSPKGISRMSMA | : 2190 |
| (SEQ ID NO:5) B-P1_prM-E | : ------------------------------------------------------------------------ | : -- |
| (SEQ ID NO:6) B3-P11_prM | : ------------------------------------------------------------------------ | : -- |

FIG. 5F

```
(SEQ ID NO:3) P1_transla  :  MGTMAGCGYLMFLGGVKPTHISYIMLIFFVLMVVVIPEPGQQRSIQDNQVAYLIIGILTLVSAVAANELGMLE  : 2263
(SEQ ID NO:4) P11_transl  :  MGTMAGCGYLMFLGGVKPTHISYIMLIFFVLMVVVIPEPGQQRSIQDNQVAYLIIGILTLVSAVAANELGMLE  : 2263
(SEQ ID NO:5) B-P1_prM-E  :  ---------------------------------------------------------------------  :    -
(SEQ ID NO:6) B3-P11_prM  :  ---------------------------------------------------------------------  :    -

(SEQ ID NO:3) P1_transla  :  KTKEDLFGKKNLIPSSASPWSWPDLDLKPGAAWTVYYGIVTMLSPMLHHWIKVEYGNLSLSGIAQSASVLSFM  : 2336
(SEQ ID NO:4) P11_transl  :  KTKEDLFGKKNLIPSSASPWSWPDLDLKPGAAWTVYYGIVTMLSPMLHHWIKVEYGNLSLSGIAQSASVLSFM  : 2336
(SEQ ID NO:5) B-P1_prM-E  :  ---------------------------------------------------------------------  :    -
(SEQ ID NO:6) B3-P11_prM  :  ---------------------------------------------------------------------  :    -

(SEQ ID NO:3) P1_transla  :  DKGIPFMKMNISVIMLLVSGWNSITVMPLLCGIGCAMLHWSLILPGIKAQQSKLAQRRVFHGVAKNPVVDGNP  : 2409
(SEQ ID NO:4) P11_transl  :  DKGIPFMKMNISVIMLLVSGWNSITVMPLLCGIGCAMLHWSLILPGIKAQQSKLAQRRVFHGVAKNPVVDGNP  : 2409
(SEQ ID NO:5) B-P1_prM-E  :  ---------------------------------------------------------------------  :    -
(SEQ ID NO:6) B3-P11_prM  :  ---------------------------------------------------------------------  :    -

(SEQ ID NO:3) P1_transla  :  TVDIEEAPEMPALYEKKLALYLLLALSLASVAMCRTPFSLAEGIVLASAALGPLIEGNTSLLWNGPMAVSMTG  : 2482
(SEQ ID NO:4) P11_transl  :  TVDIEEAPEMPALYEKKLALYLLLALSLASVAMCRTPFSLAEGIVLASAALGPLIEGNTSLLWNGPMAVSMTG  : 2482
(SEQ ID NO:5) B-P1_prM-E  :  ---------------------------------------------------------------------  :    -
(SEQ ID NO:6) B3-P11_prM  :  ---------------------------------------------------------------------  :    -

(SEQ ID NO:3) P1_transla  :  VMRGNHYAFVGVMYNLWKMKTGRRGSANGKTLGEVWKRELNLLDKRQFELYKRTDIVEVDRDTARRHLAEGKV  : 2555
(SEQ ID NO:4) P11_transl  :  VMRGNHYAFVGVMYNLWKMKTGRRGSANGKTLGEVWKRELNLLDKRQFELYKRTDIVEVDRDTARRHLAEGKV  : 2555
(SEQ ID NO:5) B-P1_prM-E  :  ---------------------------------------------------------------------  :    -
(SEQ ID NO:6) B3-P11_prM  :  ---------------------------------------------------------------------  :    -
```

FIG. 5G

```
(SEQ ID NO:3) P1_transla : DTGVAVSRGTAKLRWFHERGYVKLEGRVIDLGCGRGGWCYYAAAQKEVSGVKGFTLGRDGHEKPMNVQSLGWN : 2628
(SEQ ID NO:4) P11_transl : DTGVAVSRGTAKLRWFHERGYVKLEGRVIDLGCGRGGWCYYAAAQKEVSGVKGFTLGRDGHEKPMNVQSLGWN : 2628
(SEQ ID NO:5) B-P1_prM-E : ------------------------------------------------------------------------ : -
(SEQ ID NO:6) B3-P11_prM : ------------------------------------------------------------------------ : -
                             2560      *        2580       *        2600       *        2620

(SEQ ID NO:3) P1_transla : IITFKDKTDIHRLEPVKCDTLLCDIGESSSSSVTEGERTVRVLDTVEKWLACGVDNFCVKVLAPYMPDVLEKL : 2701
(SEQ ID NO:4) P11_transl : IITFKDKTDIHRLEPVKCDTLLCDIGESSSSSVTEGERTVRVLDTVEKWLACGVDNFCVKVLAPYMPDVLEKL : 2701
(SEQ ID NO:5) B-P1_prM-E : ------------------------------------------------------------------------ : -
(SEQ ID NO:6) B3-P11_prM : ------------------------------------------------------------------------ : -
                              *        2640       *        2660       *        2680       *  2700

(SEQ ID NO:3) P1_transla : ELLQRRFGGTVIRNPLSRNSTHEMYYVSGARSNVTFTVNQTSRLLMRRMRRPTGKVTLEADVILPIGTRSVET : 2774
(SEQ ID NO:4) P11_transl : ELLQRRFGGTVIRNPLSRNSTHEMYYVSGARSNVTFTVNQTSRLLMRRMRRPTGKVTLEADVILPIGTRSVET : 2774
(SEQ ID NO:5) B-P1_prM-E : ------------------------------------------------------------------------ : -
(SEQ ID NO:6) B3-P11_prM : ------------------------------------------------------------------------ : -
                             2720       *        2740       *        2760       *

(SEQ ID NO:3) P1_transla : DKGPLDKEAIEERVERIKSEYMTSWFYDNDNPYRTWHYCGSYVTKTSGSAASMVNGVIKILTYPWDRIEEVTR : 2847
(SEQ ID NO:4) P11_transl : DKGPLDKEAIEERVERIKSEYMTSWFYDNDNPYRTWHYCGSYVTKTSGSAASMVNGVIKILTYPWDRIEEVTR : 2847
(SEQ ID NO:5) B-P1_prM-E : ------------------------------------------------------------------------ : -
(SEQ ID NO:6) B3-P11_prM : ------------------------------------------------------------------------ : -
                             2780       *        2800       *        2820       *        2840

(SEQ ID NO:3) P1_transla : MAMTDTTPFGQQRVFKEKVDTRAKDPPAGTRKIMKVVNRWLFRHLAREKNPRLCTKEEFIAKVRSHAAIGAYL : 2920
(SEQ ID NO:4) P11_transl : MAMTDTTPFGQQRVFKEKVDTRAKDPPAGTRKIMKVVNRWLFRHLAREKNPRLCTKEEFIAKVRSHAAIGAYL : 2920
(SEQ ID NO:5) B-P1_prM-E : ------------------------------------------------------------------------ : -
(SEQ ID NO:6) B3-P11_prM : ------------------------------------------------------------------------ : -
                              *        2860       *        2880       *        2900       *  2920
```

FIG. 5H

|                          |                                                                                              |        |
|--------------------------|----------------------------------------------------------------------------------------------|--------|
|                          | *       2940            *       2960            *       2980            *                   |        |
| (SEQ ID NO:3) P1_transla | : EEQEQWKTANEAVQDPKFWELVDEERKLHQQGRCRTCVYNMMGKREKKLSEFGKAKGSRAIWYMLGARYLEF                    | : 2993 |
| (SEQ ID NO:4) P11_transl | : EEQEQWKTANEAVQDPKFWELVDEERKLHQQGRCRTCVYNMMGKREKKLSEFGKAKGSRAIWYMLGARYLEF                    | : 2993 |
| (SEQ ID NO:5) B-P1_prM-E | : ------------------------------------------------------------------------                   | : -    |
| (SEQ ID NO:6) B3-P11_prM | : ------------------------------------------------------------------------                   | : -    |
|                          |                                                                                              |        |
|                          | 3000            *       3020            *       3040            *       3060                |        |
| (SEQ ID NO:3) P1_transla | : EALGFLNEDHWASRENSGGGVEGIGLQYLGYVIRDLAAMDGGGFYADDTAGWDTRITEADLDDEQEILNYMSP                   | : 3066 |
| (SEQ ID NO:4) P11_transl | : EALGFLNEDHWASRENSGGGVEGIGLQYLGYVIRDLAAMDGGGFYADDTAGWDTRITEADLDDEQEILNYMSP                   | : 3066 |
| (SEQ ID NO:5) B-P1_prM-E | : ------------------------------------------------------------------------                   | : -    |
| (SEQ ID NO:6) B3-P11_prM | : ------------------------------------------------------------------------                   | : -    |
|                          |                                                                                              |        |
|                          | *       3080            *       3100            *       3120            *       314          |        |
| (SEQ ID NO:3) P1_transla | : HHKKLAQAVMEMTYKNKVVKVLRPAPGGKAYMDVISRRDQRGSGQVVTYALNTITNLKVQLIRMAEAEMVIHH                   | : 3139 |
| (SEQ ID NO:4) P11_transl | : HHKKLAQAVMEMTYKNKVVKVLRPAPGGKAYMDVISRRDQRGSGQVVTYALNTITNLKVQLIRMAEAEMVIHH                   | : 3139 |
| (SEQ ID NO:5) B-P1_prM-E | : ------------------------------------------------------------------------                   | : -    |
| (SEQ ID NO:6) B3-P11_prM | : ------------------------------------------------------------------------                   | : -    |
|                          |                                                                                              |        |
|                          | 0            *       3160            *       3180            *       3200            *      |        |
| (SEQ ID NO:3) P1_transla | : QHVQDCDESVLTRLEAWLTEHGCNRLKRMAVSGDDCVVRPIDDRFGLALSHLNAMSKVRKDISEWQPSKGWND                   | : 3212 |
| (SEQ ID NO:4) P11_transl | : QHVQDCDESVLTRLEAWLTEHGCNRLKRMAVSGDDCVVRPIDDRFGLALSHLNAMSKVRKDISEWQPSKGWND                   | : 3212 |
| (SEQ ID NO:5) B-P1_prM-E | : ------------------------------------------------------------------------                   | : -    |
| (SEQ ID NO:6) B3-P11_prM | : ------------------------------------------------------------------------                   | : -    |
|                          |                                                                                              |        |
|                          | 3220            *       3240            *       3260            *       3280                |        |
| (SEQ ID NO:3) P1_transla | : WENVPFCSHHFHELQLKDGRRIVVPCREQDELIGRGRVSPGNGWMIKETACLSKAYANMWSLMYFHKRDMRLL                   | : 3285 |
| (SEQ ID NO:4) P11_transl | : WENVPFCSHHFHELQLKDGRRIVVPCREQDELIGRGRVSPGNGWMIKETACLSKAYANMWSLMYFHKRDMRLL                   | : 3285 |
| (SEQ ID NO:5) B-P1_prM-E | : ------------------------------------------------------------------------                   | : -    |
| (SEQ ID NO:6) B3-P11_prM | : ------------------------------------------------------------------------                   | : -    |

FIG. 5I

|                              |   |                                                                      |        |
|------------------------------|---|----------------------------------------------------------------------|--------|
|                              |   | *         3300        *         3320        *         3340        * |        |
| (SEQ ID NO:3) P1_transla     | : | SLAVSSAVPTSWVPQGRTTWSIHGKGEWMTTEDMLEVWNRVWITNNPHMQDKTMVKKWRDVPYLTKRQDKLCG | : 3358 |
| (SEQ ID NO:4) P11_transl     | : | SLAVSSAVPTSWVPQGRTTWSIHGKGEWMTTEDMLEVWNRVWITNNPHMQDKTMVKKWRDVPYLTKRQDKLCG | : 3358 |
| (SEQ ID NO:5) B-P1_prM-E     | : | ------------------------------------------------------------------------ | : --   |
| (SEQ ID NO:6) B3-P11_prM     | : | ------------------------------------------------------------------

```
P1_consens : TGACAAGCCTTCATTGGACACATCTCACTAGAGACACAGTAGCCATTGATAGACCTGCTGAGGTGAGGAAAAGTGTG : 1152
B-P1_conse : TGACAAGCCTTCATTGGACACATCTCACTAGAGACACAGTAGCCATTGATAGACCTGCTGAGGTGAGGAAAAGTGTG : 1113
C-P1_genom : TGACAAGCCTTCATTGGACACATCTCACTAGAGACACAGTAGCCATTGATAGACCTGCTGAGGTGAGGAAAAGTGTG : 1113
B3-P11_con : TGACAAGCCTTCATTGGACACATCTCACTAGAGACACAGTAGCCATTGATAGACCTGCTGAGGTGAGGAAAAGTGTG : 1127
C1-P11_con : TGACAAGCCTTCATTGGACACATCTCACTAGAGACACAGTAGCCATTGATAGACCTGCTGAGGTGAGGAAAAGTGTG : 1111

P1_consens : TTACAATGCAGTTCTCACTCATGTGAAGATTAATGACAAGTGCCCCAGCACTGAGAGAGGCCCACCTAGCTGA : 1224
B-P1_conse : TTACAATGCAGTTCTCACTCATGTGAAGATTAATGACAAGTGCCCCAGCACTGAGAGAGGCCCACCTAGCTGA : 1185
C-P1_genom : TTACAATGCAGTTCTCACTCATGTGAAGATTAATGACAAGTGCCCCAGCACTGAGAGAGGCCCACCTAGCTGA : 1185
B3-P11_con : TTACAATGCAGTTCTCACTCATGTGAAGATTAATGACAAGTGCCCCAGCACTGAGAGAGGCCCACCTAGCTGA : 1199
C1-P11_con : TTACAATGCAGTTCTCACTCATGTGAAGATTAATGACAAGTGCCCCAGCACTGAGAGAGGCCCACCTAGCTGA : 1183

P1_consens : AGAGAACGAAGGGACAATGCGTGCAAGCGCACTTATTCTGATAGAGGCTGGGGCAATGCTGTGTGGCCTATT : 1296
B-P1_conse : AGAGAACGAAGGGACAATGCGTGCAAGCGCACTTATTCTGATAGAGGCTGGGGCAATGCTGTGTGGCCTATT : 1257
C-P1_genom : AGAGAACGAAGGGACAATGCGTGCAAGCGCACTTATTCTGATAGAGGCTGGGGCAATGCTGTGTGGCCTATT : 1257
B3-P11_con : AGAGAACGAAGGGACAATGCGTGCAAGCGCACTTATTCTGATAGAGGCTGGGGCAATGCTGTGTGGCCTATT : 1271
C1-P11_con : AGAGAACGAAGGGACAATGCGTGCAAGCGCACTTATTCTGATAGAGGCTGGGGCAATGCTGTGTGGCCTATT : 1255

P1_consens : TGGGAAAGGGAGCATGCGCCATGTGCCAAATCCACTTGTGCCAAATCCATGAGTTTGTTGAGGTTGATCA : 1368
B-P1_conse : TGGGAAAGGGAGCATGCGCCATGTGCCAAATCCACTTGTGCCAAATCCATGAGTTTGTTGAGGTTGATCA : 1329
C-P1_genom : TGGGAAAGGGAGCATGCGCCATGTGCCAAATCCACTTGTGCCAAATCCATGAGTTTGTTGAGGTTGATCA : 1329
B3-P11_con : TGGGAAAGGGAGCATGCGCCATGTGCCAAATCCACTTGTGCCAAATCCATGAGTTTGTTGAGGTTGATCA : 1343
C1-P11_con : TGGGAAAGGGAGCATGCGCCATGTGCCAAATCCACTTGTGCCAAATCCATGAGTTTGTTGAGGTTGATCA : 1327

P1_consens : GACCAAAATTCAGTATGTCATCAGAGACAATTGCATGTAGGGCCAAGCAGGAAAATTGGACTACCGACAT : 1440
B-P1_conse : GACCAAAATTCAGTATGTCATCAGAGACAATTGCATGTAGGGCCAAGCAGGAAAATTGGACTACCGACAT : 1401
C-P1_genom : GACCAAAATTCAGTATGTCATCAGAGACAATTGCATGTAGGGCCAAGCAGGAAAATTGGACTACCGACAT : 1401
B3-P11_con : GACCAAAATTCAGTATGTCATCAGAGACAATTGCATGTAGGGCCAAGCAGGAAAATTGGACTACCGACAT : 1415
C1-P11_con : GACCAAAATTCAGTATGTCATCAGAGACAATTGCATGTAGGGCCAAGCAGGAAAATTGGACTACCGACAT : 1399
```

FIG. 8D

```
P1_consens  : TAAGACTCTCAAGTTTGATGCCCTGTCAGGCTCCCAGGAAGTCGAGTTCATTGGGTATGGAAAAGCTACACT : 1512
B-P1_conse  : TAAGACTCTCAAGTTTGATGCCCTGTCAGGCTCCCAGGAAGTCGAGTTCATTGGGTATGGAAAAGCTACACT : 1473
C-P1_genom  : TAAGACTCTCAAGTTTGATGCCCTGTCAGGCTCCCAGGAAGTCGAGTTCATTGGGTATGGAAAAGCTACACT : 1473
B3-P11_con  : TAAGACTCTCA##TTTGATGCCCTGTCAGGCTCCCAGGAAGTCGAGTTCATTGGGTATGGAAAAGCTACACT : 1487
C1-P11_con  : TAAGACTCTCAAGTTTGATGCCCTGTCAGGCTCCCAGGAAGTCGAGTTCATTGGGTATGGAAAAGC##ACACT : 1471

1520            *            1540            *            1560            *            1580

P1_consens  : GGAATGCCAGGTGCAAACTGCGGTGGACTTTGGTAACAGTTACATCGCTGAGATGGAAACAGAGAGCTGGAT : 1584
B-P1_conse  : GGAATGCCAGGTGCAAACTGCGGTGGACTTTGGTAACAGTTACATCGCTGAGATGGAAACAGAGAGCTGGAT : 1545
C-P1_genom  : GGAATGCCAGGTGCAAACTGCGGTGGACTTTGGTAACAGTTACATCGCTGAGATGGAAACAGAGAGCTGGAT : 1545
B3-P11_con  : GGAATGCCAGGTGCAAACTGCGGTGGACTTTGGTAACAGTTACATCGCTGAGATGGAAACAGAGAGCTGGAT : 1559
C1-P11_con  : GGAATGCCAGGTGCAAACTGCGGTGGACTTTGGTAACAGTTACATCGCTGAGATGGAAACAGAGAGCTGGAT : 1543

*            1600            *            1620            *            1640            *

P1_consens  : AGTGGACAGAACAGTGGGCCCAGGACTTGAACCTCCGCATGGCCAGAGTGGAAGTGGCGGGGTGTGGAGAGAT : 1656
B-P1_conse  : AGTGGACAGAACAGTGGGCCCAGGACTTGAACCTCCGCATGGCCAGAGTGGAAGTGGCGGGGTGTGGAGAGAT : 1617
C-P1_genom  : AGTGGACAGAACAGTGGGCCCAGGACTTGAACCTCCGCATGGCCAGAGTGGAAGTGGCGGGGTGTGGAGAGAT : 1617
B3-P11_con  : AGTGGACAGAACAGTGGGCCCAGGACTTGAACCTCCGCATGGCCAGAGTGGAAGTGGCGGGGTGTGGAGAGAT : 1631
C1-P11_con  : AGTGGACAGAACAGTGGGCCCAGGACTTGAACCTCCGCATGGCCAGAGTGGAAGTGGCGGGGTGTGGAGAGAT : 1615

1660            *            1680            *            1700            *            1720            *

P1_consens  : GCATCATCTTGTCGAATTTGAACCTCCGCCACTCAGAGTACTGGCCCTGGGAAACCAGGAAGG : 1728
B-P1_conse  : GCATCATCTTGTCGAATTTGAACCTCCGCCACTCAGAGTACTGGCCCTGGGAAACCAGGAAGG : 1689
C-P1_genom  : GCATCATCTTGTCGAATTTGAACCTCCGCCACTCAGAGTACTGGCCCTGGGAAACCAGGAAGG : 1689
B3-P11_con  : GCATCATCTTGTCGAATTTGAACCTCCGCCACTCAGAGTACTGGCCCTGGGAAACCAGGAAGG : 1703
C1-P11_con  : GCATCATCTTGTCGAATTTGAACCTCCGCCACTCAGAGTACTGGCCCTGGGAAACCAGGAAGG : 1687

*            1740            *            1760            *            1780            *            1800

P1_consens  : CTCCTTGAAAACAGCTCTTACTGGCCAATGAGGGTTACAAAGGACACAAATGACAACAACCTTTACAAACT : 1800
B-P1_conse  : CTCCTTGAAAACAGCTCTTACTGGCCAATGAGGGTTACAAAGGACACAAATGACAACAACCTTTACAAACT : 1761
C-P1_genom  : CTCCTTGAAAACAGCTCTTACTGGCCAATGAGGGTTACAAAGGACACAAATGACAACAACCTTTACAAACT : 1761
B3-P11_con  : CTCCTTGAAAACAGCTCTTACTGGCCAATGAGGGTTACAAAGGACACAAATGACAACAACCTTTACAAACT : 1775
C1-P11_con  : CTCCTTGAAAACAGCTCTTACTGGCCAATGAGGGTTACAAAGGACACAAATGACAACAACCTTTACAAACT : 1759
```

FIG. 8E

```
                        *        1820         *        1840         *        1860         *
P1_consens : ACATGGTGGACATGTTTCTTCTGCAGAGTGAAATTGTCAGCTTTGACACTCCAAGGGACATCCTACAAAATATG : 1872
B-P1_conse : ACATGGTGGACATGTTTCTTCTGCAGAGTGAAATTGTCAGCTTTGACACTCCAAGGGACATCCTACAAAATATG : 1833
C-P1_genom : ACATGGTGGACATGTTTCTTCTGCAGAGTGAAATTGTCAGCTTTGACACTCCAAGGGACATCCTACAAAATATG : 1833
B3-P11_con : ACATGGTGGACATGTTTCTTCTGCAGAGTGAAATTGTCAGCTTTGACACTCCAAGGGACATCCTACAAAATATG : 1847
C1-P11_con : ACATGGTGGACATGTTTCTTCTGCAGAGTGAAATTGTCAGCTTTGACACTCCAAGGGACATCCTACAAAATATG : 1831

1880          *        1900         *        1920         *       1940
P1_consens : CACTGACAAAATGTTTTTTGTCAAGAACCCAACTGACACTGGCCATGGCACTGTTGTGATGCAGGTGAAAGT : 1944
B-P1_conse : CACTGACAAAATGTTTTTTGTCAAGAACCCAACTGACACTGGCCATGGCACTGTTGTGATGCAGGTGAAAGT : 1905
C-P1_genom : CACTGACAAAATGTTTTTTGTCAAGAACCCAACTGACACTGGCCATGGCACTGTTGTGATGCAGGTGAAAGT : 1905
B3-P11_con : CACTGACAAAATGTTTTTTGTCAAGAACCCAACTGACACTGGCCATGGCACTGTTGTGATGCAGGTGAAAGT : 1919
C1-P11_con : CACTGACAAAATGTTTTTTGTCAAGAACCCAACTGACACTGGCCATGGCACTGTTGTGATGCAGGTGAAAGT : 1903

*        1960         *        1980         *        2000         *
P1_consens : GTCAAAAGGAGCCCCCTGCAGGATTCCAGTGATAGTAGCTGATGATCTTACAGCGCAATCAATAAAGGCAT : 2016
B-P1_conse : GTCAAAAGGAGCCCCCTGCAGGATTCCAGTGATAGTAGCTGATGATCTTACAGCGCAATCAATAAAGGCAT : 1977
C-P1_genom : GTCAAAAGGAGCCCCCTGCAGGATTCCAGTGATAGTAGCTGATGATCTTACAGCGCAATCAATAAAGGCAT : 1977
B3-P11_con : GTCAAAAGGAGCCCCCTGCAGGATTCCAGTGATAGTAGCTGATGATCTTACAGCGCAATCAATAAAGGCAT : 1991
C1-P11_con : GTCAAAAGGAGCCCCCTGCAGGATTCCAGTGATAGTAGCTGATGATCTTACAGCGCAATCAATAAAGGCAT : 1975

2020         *        2040         *        2060         *        2080
P1_consens : TTTGGTTACAGTTAACCCCATGCCCTCAACCAATGATGATGAAGTGCTGATTGAGGTGAACCCACCTTTTGG : 2088
B-P1_conse : TTTGGTTACAGTTAACCCCATGCCCTCAACCAATGATGATGAAGTGCTGATTGAGGTGAACCCACCTTTTGG : 2049
C-P1_genom : TTTGGTTACAGTTAACCCCATGCCCTCAACCAATGATGATGAAGTGCTGATTGAGGTGAACCCACCTTTTGG : 2049
B3-P11_con : TTTGGTTACAGTTAACCCCATGCCCTCAACCAATGATGATGAAGTGCTGATTGAGGTGAACCCACCTTTTGG : 2063
C1-P11_con : TTTGGTTACAGTTAACCCCATGCCCTCAACCAATGATGATGAAGTGCTGATTGAGGTGAACCCACCTTTTGG : 2047

*        2100         *        2120         *        2140         *        2160
P1_consens : AGACAGCTACATTATCGTTGGGAGAGAGATTCACGTCTCACTTACCAGTGGCACAAAGAGGAAGCTCAAT : 2160
B-P1_conse : AGACAGCTACATTATCGTTGGGAGAGAGATTCACGTCTCACTTACCAGTGGCACAAAGAGGAAGCTCAAT : 2121
C-P1_genom : AGACAGCTACATTATCGTTGGGAGAGAGATTCACGTCTCACTTACCAGTGGCACAAAGAGGAAGCTCAAT : 2121
B3-P11_con : AGACAGCTACATTATCGTTGGGAGAGAGATTCACGTCTCACTTACCAGTGGCACAAAGAGGAAGCTCAAT : 2135
C1-P11_con : AGACAGCTACATTATCGTTGGGAGAGAGATTCACGTCTCACTTACCAGTGGCACAAAGAGGAAGCTCAAT : 2119
```

FIG. 8F

```
                              *      2180         *      2200         *      2220         *
(SEQ ID NO: 15) P1_consens  : AGGAAAGTTGTCACTCAGACCATGAGAACCTGAACGCGTGAACGCCTGGCCGTCATGGGAGACACCGCCTGGATTT : 2232
(SEQ ID NO: 9)  B-P1_conse  : AGGAAAGTTGTCACTCAGACCATGAGAACCTGAACGCGTGAACGCCTGGCCGTCATGGGAGACACCGCCTGGATTT : 2193
(SEQ ID NO: 10) C-P1_genom  : AGGAAAGTTGTCACTCAGACCATGAGAACCTGAACGCGTGAACGCCTGGCCGTCATGGGAGACACCGCCTGGATTT : 2193
(SEQ ID NO: 11) B3-P11_con  : AGGAAAGTTGTCACTCAGACCATGAGAACCTGAACGCGTGAACGCCTGGCCGTCATGGGAGACACCGCCTGGATTT : 2207
(SEQ ID NO: 12) C1-P11_con  : AGGAAAGTTGTCACTCAGACCATGAGAACCTGAACGCGTGAACGCCTGGCCGTCATGGGAGACACCGCCTGGATTT : 2191

2240         *      2260         *      2280         *      2300
(SEQ ID NO: 15) P1_consens  : CAGCTCCGCTGGAGGGTTCTTCACTTCGGTTGGGAAAGGAATTCATACGGTGTTTGGCTCTGCCTTTCAGGG : 2304
(SEQ ID NO: 9)  B-P1_conse  : CAGCTCCGCTGGAGGGTTCTTCACTTCGGTTGGGAAAGGAATTCATACGGTGTTTGGCTCTGCCTTTCAGGG : 2265
(SEQ ID NO: 10) C-P1_genom  : CAGCTCCGCTGGAGGGTTCTTCACTTCGGTTGGGAAAGGAATTCATACGGTGTTTGGCTCTGCCTTTCAGGG : 2265
(SEQ ID NO: 11) B3-P11_con  : CAGCTCCGCTGGAGGGTTCTTCACTTCGGTTGGGAAAGGAATTCATACGGTGTTTGGCTCTGCCTTTCAGGG : 2279
(SEQ ID NO: 12) C1-P11_con  : CAGCTCCGCTGGAGGGTTCTTCACTTCGGTTGGGAAAGGAATTCATACGGTGTTTGGCTCTGCCTTTCAGGG : 2263

*      2320         *      2340         *      2360         *
(SEQ ID NO: 15) P1_consens  : GCTATTTGGCGGCCTTGAACTGGATAACAAAGTCATCATGGGGCCGGTACTTATATGGGTTGGCATCAACAC : 2376
(SEQ ID NO: 9)  B-P1_conse  : GCTATTTGGCGGCCTTGAACTGGATAACAAAGTCATCATGGGGCCGGTACTTATATGGGTTGGCATCAACAC : 2337
(SEQ ID NO: 10) C-P1_genom  : GCTATTTGGCGGCCTTGAACTGGATAACAAAGTCATCATGGGGCCGGTACTTATATGGGTTGGCATCAACAC : 2337
(SEQ ID NO: 11) B3-P11_con  : GCTATTTGGCGGCCTTGAACTGGATAACAAAGTCATCATGGGGCCGGTACTTATATGGGTTGGCATCAACAC : 2351
(SEQ ID NO: 12) C1-P11_con  : GCTATTTGGCGGCCTTGAACTGGATAACAAAGTCATCATGGGGCCGGTACTTATATGGGTTGGCATCAACAC : 2335

2380         *      2400         *      2420         *      2440
(SEQ ID NO: 15) P1_consens  : AAGAAACATGACAATGTCCATGAGCATGATCTTGGTAGGAGTGATCATGATGTTTTTGTCTCTAGGAGTTGG : 2448
(SEQ ID NO: 9)  B-P1_conse  : AAGAAACATGACAATGTCCATGAGCATGATCTTGGTAGGAGTGATCATGATGTTTTTGTCTCTAGGAGTTGG : 2409
(SEQ ID NO: 10) C-P1_genom  : AAGAAACATGACAATGTCCATGAGCATGATCTTGGTAGGAGTGATCATGATGTTTTTGTCTCTAGGAGTTGG : 2409
(SEQ ID NO: 11) B3-P11_con  : AAGAAACATGACAATGTCCATGAGCATGATCTTGGTAGGAGTGATCATGATGTTTTTGTCTCTAGGAGTTGG : 2423
(SEQ ID NO: 12) C1-P11_con  : AAGAAACATGACAATGTCCATGAGCATGATCTTGGTAGGAGTGATCATGATGTTTTTGTCTCTAGGAGTTGG : 2407

*      2460         *      2480         *      2500         *      2520
(SEQ ID NO: 15) P1_consens  : GGCGGATCAAGGAGATGCCGCCATCAACTTGGCAAGAGAGAGAGCTCAAGTGCGAGATGGTATCTTCATATTTAG : 2520
(SEQ ID NO: 9)  B-P1_conse  : GGCGGATCAAGGAGATGCCGCCATCAACTTGGCAAGAGAGAGAGCTCAAGTGCGAGATGGTATCTTCATATTTAG : 2481
(SEQ ID NO: 10) C-P1_genom  : GGCGGATCAAGGAGATGCCGCCATCAACTTGGCAAGAGAGAGAGCTCAAGTGCGAGATGGTATCTTCATATTTAG : 2481
(SEQ ID NO: 11) B3-P11_con  : GGCGGATCAAGGAGATGCCGCCATCAACTTGGCAAGAGAGAGAGCTCAAGTGCGAGATGGTATCTTCATATTTAG : 2495
(SEQ ID NO: 12) C1-P11_con  : GGCGGATCAAGGAGATGCCGCCATCAACTTGGCAAGAGAGAGAGCTCAAGTGCGAGATGGTATCTTCATATTTAG : 2479
```

FIG. 8G

| | | | |
|---|---|---|---|
| (SEQ ID NO: 15) | P1_consens | : AGACTCTGATGACTGGCTGAACAAGTACTCATACTATCCAGAAGATCCTGTGAAGCTTGCATCAATAGTGAA : | 2592 |
| (SEQ ID NO: 9) | B-P1_conse | : AGACTCTGATGACTGGCTGAACAAGTACTCATACTATCCAGAAGATCCTGTGAAGCTTGCATCAATAGTGAA : | 2553 |
| (SEQ ID NO: 10) | C-P1_genom | : AGACTCTGATGACTGGCTGAACAAGTACTCATACTATCCAGAAGATCCTGTGAAGCTTGCATCAATAGTGAA : | 2553 |
| (SEQ ID NO: 11) | B3-P1_con | : AGACTCTGATGACTGGCTGAACAAGTACTCATACTATCCAGAAGATCCTGTGAAGCTTGCATCAATAGTGAA : | 2567 |
| (SEQ ID NO: 12) | C1-P11_con | : AGACTCTGATGACTGGCTGAACAAGTACTCATACTATCCAGAAGATCCTGTGAAGCTTGCATCAATAGTGAA : | 2551 |
| (SEQ ID NO: 15) | P1_consens | : AGCCTCTTTTGAAGAAGGGAAGTGTGGCCTAAATTCAGTTGACTCCCTTGAGCATGAGATGTGGAGAAGCAG : | 2664 |
| (SEQ ID NO: 9) | B-P1_conse | : AGCCTCTTTTGAAGAAGGGAAGTGTGGCCTAAATTCAGTTGACTCCCTTGAGCATGAGATGTGGAGAAGCAG : | 2625 |
| (SEQ ID NO: 10) | C-P1_genom | : AGCCTCTTTTGAAGAAGGGAAGTGTGGCCTAAATTCAGTTGACTCCCTTGAGCATGAGATGTGGAGAAGCAG : | 2625 |
| (SEQ ID NO: 11) | B3-P1_con | : AGCCTCTTTTGAAGAAGGGAAGTGTGGCCTAAATTCAGTTGACTCCCTTGAGCATGAGATGTGGAGAAGCAG : | 2639 |
| (SEQ ID NO: 12) | C1-P11_con | : AGCCTCTTTTGAAGAAGGGAAGTGTGGCCTAAATTCAGTTGACTCCCTTGAGCATGAGATGTGGAGAAGCAG : | 2623 |
| (SEQ ID NO: 15) | P1_consens | : GGCAGAGATGAGATCAATGCCATTTTGAGGAAAACAGAGTGGACATTCTGTGTCGTCGTGCAGGATCCAAAGAA : | 2736 |
| (SEQ ID NO: 9) | B-P1_conse | : GGCAGAGATGAGATCAATGCCATTTTGAGGAAAACAGAGTGGACATTCTGTGTCGTCGTGCAGGATCCAAAGAA : | 2697 |
| (SEQ ID NO: 10) | C-P1_genom | : GGCAGAGATGAGATCAATGCCATTTTGAGGAAAACAGAGTGGACATTCTGTGTCGTCGTGCAGGATCCAAAGAA : | 2697 |
| (SEQ ID NO: 11) | B3-P1_con | : GGCAGAGATGAGATCAATGCCATTTTGAGGAAAACAGAGTGGACATTCTGTGTCGTCGTGCAGGATCCAAAGAA : | 2711 |
| (SEQ ID NO: 12) | C1-P11_con | : GGCAGAGATGAGATCAATGCCATTTTGAGGAAAACAGAGTGGACATTCTGTGTCGTCGTGCAGGATCCAAAGAA : | 2695 |
| (SEQ ID NO: 15) | P1_consens | : TGTTTACCAGAGAGAGAGAACTCATCCATTTTCCAGAATTCGGGATGGTCTGCAGTATGGTTGGAAGACTTGGGG : | 2808 |
| (SEQ ID NO: 9) | B-P1_conse | : TGTTTACCAGAGAGAGAGAACTCATCCATTTTCCAGAATTCGGGATGGTCTGCAGTATGGTTGGAAGACTTGGGG : | 2769 |
| (SEQ ID NO: 10) | C-P1_genom | : TGTTTACCAGAGAGAGAGAACTCATCCATTTTCCAGAATTCGGGATGGTCTGCAGTATGGTTGGAAGACTTGGGG : | 2769 |
| (SEQ ID NO: 11) | B3-P1_con | : TGTTTACCAGAGAGAGAGAACTCATCCATTTTCCAGAATTCGGGATGGTCTGCAGTATGGTTGGAAGACTTGGGG : | 2783 |
| (SEQ ID NO: 12) | C1-P11_con | : TGTTTACCAGAGAGAGAGAACTCATCCATTTTCCAGAATTCGGGATGGTCTGCAGTATGGTTGGAAGACTTGGGG : | 2767 |
| (SEQ ID NO: 15) | P1_consens | : TAAGAACCTTGTCTCCCCAGGGAGGAGGAGAATGAAGCTTCATCATAGATGAAGATCCAGGAAAGAATG : | 2880 |
| (SEQ ID NO: 9) | B-P1_conse | : TAAGAACCTTGTCTCCCCAGGGAGGAGGAGAATGAAGCTTCATCATAGATGAAGATCCAGGAAAGAATG : | 2841 |
| (SEQ ID NO: 10) | C-P1_genom | : TAAGAACCTTGTCTCCCCAGGGAGGAGGAGAATGAAGCTTCATCATAGATGAAGATCCAGGAAAGAATG : | 2841 |
| (SEQ ID NO: 11) | B3-P1_con | : TAAGAACCTTGTCTCCCCAGGGAGGAGGAGAATGAAGCTTCATCATAGATGAAGATCCAGGAAAGAATG : | 2855 |
| (SEQ ID NO: 12) | C1-P11_con | : TAAGAACCTTGTCTCCCCAGGGAGGAGGAGAATGAAGCTTCATCATAGATGAAGATCCAGGAAAGAATG : | 2839 |

```
                                                  *      3260       *      3280       *      3300       *
(SEQ ID NO: 15) P1_consens  : GACGAACGGACCTTGGATGCAGTTGGATGCAGTTACCACTAGAAGTGAAGAGAGAAGCTTGCCCAGGGACTAGCGTGATCAT : 3312
(SEQ ID NO: 9)  B-P1_conse  : GACGAACGGACCTTGGATGCAGTTGGATGCAGTTACCACTAGAAGTGAAGAGAGAAGCTTGCCCAGGGACTAGCGTGATCAT : 3273
(SEQ ID NO: 10) C-P1_genom  : GACGAACGGACCTTGGATGCAGTTGGATGCAGTTACCACTAGAAGTGAAGAGAGAAGCTTGCCCAGGGACTAGCGTGATCAT : 3273
(SEQ ID NO: 11) B3-P11_con  : GACGAACGGACCTTGGATGCAGTTGGATGCAGTTACCACTAGAAGTGAAGAGAGAAGCTTGCCCAGGGACTAGCGTGATCAT : 3287
(SEQ ID NO: 12) C1-P11_con  : GACGAACGGACCTTGGATGCAGTTGGATGCAGTTACCACTAGAAGTGAAGAGAGAAGCTTGCCCAGGGACTAGCGTGATCAT : 3271

*      3340       *      3360       *      3380       *
(SEQ ID NO: 15) P1_consens  : TGATGGCAACTGTGATGGACGCGGGAGCGGGGAAAATCAACCAGATCCACCACGGAAAGTTATTCCTGAATG : 3384
(SEQ ID NO: 9)  B-P1_conse  : TGATGGCAACTGTGATGGACGCGGGAGCGGGGAAAATCAACCAGATCCACCACGGAAAGTTATTCCTGAATG : 3345
(SEQ ID NO: 10) C-P1_genom  : TGATGGCAACTGTGATGGACGCGGGAGCGGGGAAAATCAACCAGATCCACCACGGAAAGTTATTCCTGAATG : 3345
(SEQ ID NO: 11) B3-P11_con  : TGATGGCAACTGTGATGGACGCGGGAGCGGGGAAAATCAACCAGATCCACCACGGAAAGTTATTCCTGAATG : 3359
(SEQ ID NO: 12) C1-P11_con  : TGATGGCAACTGTGATGGACGCGGGAGCGGGGAAAATCAACCAGATCCACCACGGAAAGTTATTCCTGAATG : 3343

*      3400       *      3420       *      3440       *
(SEQ ID NO: 15) P1_consens  : GTGTTGCGCTCCTGCACAATGCCGCCTGAGCTTCCATGGTAGTGATGGGGTGTTGGTATCCCATGGAAAT : 3456
(SEQ ID NO: 9)  B-P1_conse  : GTGTTGCGCTCCTGCACAATGCCGCCTGAGCTTCCATGGTAGTGATGGGGTGTTGGTATCCCATGGAAAT : 3417
(SEQ ID NO: 10) C-P1_genom  : GTGTTGCGCTCCTGCACAATGCCGCCTGAGCTTCCATGGTAGTGATGGGGTGTTGGTATCCCATGGAAAT : 3417
(SEQ ID NO: 11) B3-P11_con  : GTGTTGCGCTCCTGCACAATGCCGCCTGAGCTTCCATGGTAGTGATGGGGTGTTGGTATCCCATGGAAAT : 3431
(SEQ ID NO: 12) C1-P11_con  : GTGTTGCGCTCCTGCACAATGCCGCCTGAGCTTCCATGGTAGTGATGGGGTGTTGGTATCCCATGGAAAT : 3415

3460       *      3480       *      3500       *      3520
(SEQ ID NO: 15) P1_consens  : TAGGCCAAGGAAAACGCATGAAAAGCCATCTGGTGCGCGCTCCTGGGTTACAGCTGGAGAAATACATGCTGTCCC : 3528
(SEQ ID NO: 9)  B-P1_conse  : TAGGCCAAGGAAAACGCATGAAAAGCCATCTGGTGCGCGCTCCTGGGTTACAGCTGGAGAAATACATGCTGTCCC : 3489
(SEQ ID NO: 10) C-P1_genom  : TAGGCCAAGGAAAACGCATGAAAAGCCATCTGGTGCGCGCTCCTGGGTTACAGCTGGAGAAATACATGCTGTCCC : 3489
(SEQ ID NO: 11) B3-P11_con  : TAGGCCAAGGAAAACGCATGAAAAGCCATCTGGTGCGCGCTCCTGGGTTACAGCTGGAGAAATACATGCTGTCCC : 3503
(SEQ ID NO: 12) C1-P11_con  : TAGGCCAAGGAAAACGCATGAAAAGCCATCTGGTGCGCGCTCCTGGGTTACAGCTGGAGAAATACATGCTGTCCC : 3487

*      3540       *      3560       *      3580       *      3600
(SEQ ID NO: 15) P1_consens  : TTTTGGTTTGGTGAGCATGATGATAGCAATGGAAGTGGTCCTAAGGAAAAGACAGGGAAAAAGACAGGGACCAAAAGCAAATGTT : 3600
(SEQ ID NO: 9)  B-P1_conse  : TTTTGGTTTGGTGAGCATGATGATAGCAATGGAAGTGGTCCTAAGGAAAAGACAGGGAAAAAGACAGGGACCAAAAGCAAATGTT : 3561
(SEQ ID NO: 10) C-P1_genom  : TTTTGGTTTGGTGAGCATGATGATAGCAATGGAAGTGGTCCTAAGGAAAAGACAGGGAAAAAGACAGGGACCAAAAGCAAATGTT : 3561
(SEQ ID NO: 11) B3-P11_con  : TTTTGGTTTGGTGAGCATGATGATAGCAATGGAAGTGGTCCTAAGGAAAAGACAGGGAAAAAGACAGGGACCAAAAGCAAATGTT : 3575
(SEQ ID NO: 12) C1-P11_con  : TTTTGGTTTGGTGAGCATGATGATAGCAATGGAAGTGGTCCTAAGGAAAAGACAGGGAAAAAGACAGGGACCAAAAGCAAATGTT : 3559
```

```
(SEQ ID NO:15)  P1_consens  : CATGGCTCTCTGTTGACACCTGTCACTATGGCTGAGGTGAGACTTGCCGCCAATGTTCTTTTGTGCCGTGGTTAT : 4032
(SEQ ID NO:9)   B-P1_conse  : CATGGCTCTCTGTTGACACCTGTCACTATGGCTGAGGTGAGACTTGCCGCCAATGTTCTTTTGTGCCGTGGTTAT : 3993
(SEQ ID NO:10)  C-P1_genom  : CATGGCTCTCTGTTGACACCTGTCACTATGGCTGAGGTGAGACTTGCCGCCAATGTTCTTTTGTGCCGTGGTTAT : 3993
(SEQ ID NO:11)  B3-P11_con  : CATGGCTCTCTGTTGACACCTGTCACTATGGCTGAGGTGAGACTTGCCGCCAATGTTCTTTGTGCCGTGGTTAT : 4007
(SEQ ID NO:12)  C1-P11_con  : CATGGCTCTCTGTTGACACCTGTCACTATGGCTGAGGTGAGACTTGCCGCCAATGTTCTTTTGTGCCGTGGTTAT : 3991

(SEQ ID NO:15)  P1_consens  : CATAGGGGTCCTTCACCAGAATTTCAAGGACACCTCTGGTGGCCCTCACACT : 4104
(SEQ ID NO:9)   B-P1_conse  : CATAGGGGTCCTTCACCAGAATTTCAAGGACACCTCTGGTGGCCCTCACACT : 4065
(SEQ ID NO:10)  C-P1_genom  : CATAGGGGTCCTTCACCAGAATTTCAAGGACACCTCTGGTGGCCCTCACACT : 4065
(SEQ ID NO:11)  B3-P11_con  : CATAGGGGTCCTTCACCAGAATTTCAAGGACACCTCTGGTGGCCCTCACACT : 4079
(SEQ ID NO:12)  C1-P11_con  : CATAGGGGTCCTTCACCAGAATTTCAAGGACACCTCTGGTGGCCCTCACACT : 4063

(SEQ ID NO:15)  P1_consens  : CACATCTTACCTGGGCTTGACACAACCTTTTTGGGCCTGTGCATTTCTGGCAACCCGCATATTTGGGCG : 4176
(SEQ ID NO:9)   B-P1_conse  : CACATCTTACCTGGGCTTGACACAACCTTTTTGGGCCTGTGCATTTCTGGCAACCCGCATATTTGGGCG : 4137
(SEQ ID NO:10)  C-P1_genom  : CACATCTTACCTGGGCTTGACACAACCTTTTTGGGCCTGTGCATTTCTGGCAACCCGCATATTTGGGCG : 4137
(SEQ ID NO:11)  B3-P11_con  : CACATCTTACCTGGGCTTGACACAACCTTTTTGGGCCTGTGCATTTCTGGCAACCCGCATATTTGGGCG : 4151
(SEQ ID NO:12)  C1-P11_con  : CACATCTTACCTGGGCTTGACACAACCTTTTTGGGCCTGTGCATTTCTGGCAACCCGCATATTTGGGCG : 4135

(SEQ ID NO:15)  P1_consens  : AAGGAGTATCCCAGTGAATGAGGAGCACTCGCAGCAGCTGGTCTAGTGGAGTGCTGGCAGGACTGGCTTTTCA : 4248
(SEQ ID NO:9)   B-P1_conse  : AAGGAGTATCCCAGTGAATGAGGAGCACTCGCAGCAGCTGGTCTAGTGGAGTGCTGGCAGGACTGGCTTTTCA : 4209
(SEQ ID NO:10)  C-P1_genom  : AAGGAGTATCCCAGTGAATGAGGAGCACTCGCAGCAGCTGGTCTAGTGGAGTGCTGGCAGGACTGGCTTTTCA : 4209
(SEQ ID NO:11)  B3-P11_con  : AAGGAGTATCCCAGTGAATGAGGAGCACTCGCAGCAGCTGGTCTAGTGGAGTGCTGGCAGGACTGGCTTTTCA : 4223
(SEQ ID NO:12)  C1-P11_con  : AAGGAGTATCCCAGTGAATGAGGAGCACTCGCAGCAGCTGGTCTAGTGGAGTGCTGGCAGGACTGGCTTTTCA : 4207

(SEQ ID NO:15)  P1_consens  : GGAGATGGAGAACTTCCTTGGTCCGATTGCAGTTGGAGGACTCCTGATGATGCTGGTTAGCGTTGGCTGGGAG : 4320
(SEQ ID NO:9)   B-P1_conse  : GGAGATGGAGAACTTCCTTGGTCCGATTGCAGTTGGAGGACTCCTGATGATGCTGGTTAGCGTTGGCTGGGAG : 4281
(SEQ ID NO:10)  C-P1_genom  : GGAGATGGAGAACTTCCTTGGTCCGATTGCAGTTGGAGGACTCCTGATGATGCTGGTTAGCGTTGGCTGGGAG : 4281
(SEQ ID NO:11)  B3-P11_con  : GGAGATGGAGAACTTCCTTGGTCCGATTGCAGTTGGAGGACTCCTGATGATGCTGGTTAGCGTTGGCTGGGAG : 4295
(SEQ ID NO:12)  C1-P11_con  : GGAGATGGAGAACTTCCTTGGTCCGATTGCAGTTGGAGGACTCCTGATGATGCTGGTTAGCGTTGGCTGGGAG : 4279
```

| | | |
|---|---|---|
| (SEQ ID NO: 15) P1_consens : | GCGAGGAGTGGGAGTGGCACAGGAGGAGGGGTGTTCCACAATGTGGCATGTCACAAGAGGAGCTTTCCTTGT | 4752 |
| (SEQ ID NO: 9) B-P1_conse : | GCGAGGAGTGGGAGTGGCACAGGAGGAGGGGTGTTCCACAATGTGGCATGTCACAAGAGGAGCTTTCCTTGT | 4713 |
| (SEQ ID NO: 10) C-P1_genom : | GCGAGGAGTGGGAGTGGCACAGGAGGAGGGGTGTTCCACAATGTGGCATGTCACAAGAGGAGCTTTCCTTGT | 4713 |
| (SEQ ID NO: 11) B3-P11_con : | GCGAGGAGTGGGAGTGGCACAGGAGGAGGGGTGTTCCACAATGTGGCATGTCACAAGAGGAGCTTTCCTTGT | 4727 |
| (SEQ ID NO: 12) C1-P11_con : | GCGAGGAGTGGGAGTGGCACAGGAGGAGGGGTGTTCCACAATGTGGCATGTCACAAGAGGAGCTTTCCTTGT | 4711 |
| (SEQ ID NO: 15) P1_consens : | CAGGAATGGCAAGAAGTTGATTCCATCTTGGGCTTCAGTAAAGAAGACCTTGTCGCCTATGGTGGCTCATG | 4824 |
| (SEQ ID NO: 9) B-P1_conse : | CAGGAATGGCAAGAAGTTGATTCCATCTTGGGCTTCAGTAAAGAAGACCTTGTCGCCTATGGTGGCTCATG | 4785 |
| (SEQ ID NO: 10) C-P1_genom : | CAGGAATGGCAAGAAGTTGATTCCATCTTGGGCTTCAGTAAAGAAGACCTTGTCGCCTATGGTGGCTCATG | 4785 |
| (SEQ ID NO: 11) B3-P11_con : | CAGGAATGGCAAGAAGTTGATTCCATCTTGGGCTTCAGTAAAGAAGACCTTGTCGCCTATGGTGGCTCATG | 4799 |
| (SEQ ID NO: 12) C1-P11_con : | CAGGAATGGCAAGAAGTTGATTCCATCTTGGGCTTCAGTAAAGAAGACCTTGTCGCCTATGGTGGCTCATG | 4783 |
| (SEQ ID NO: 15) P1_consens : | GAAGTTGGAAGGCAGATGGGATGGAGAGGAAGAGGTCCAGTTGATCGCGGCTGTTCCAGGAAAGAACGTGGT | 4896 |
| (SEQ ID NO: 9) B-P1_conse : | GAAGTTGGAAGGCAGATGGGATGGAGAGGAAGAGGTCCAGTTGATCGCGGCTGTTCCAGGAAAGAACGTGGT | 4857 |
| (SEQ ID NO: 10) C-P1_genom : | GAAGTTGGAAGGCAGATGGGATGGAGAGGAAGAGGTCCAGTTGATCGCGGCTGTTCCAGGAAAGAACGTGGT | 4857 |
| (SEQ ID NO: 11) B3-P11_con : | GAAGTTGGAAGGCAGATGGGATGGAGAGGAAGAGGTCCAGTTGATCGCGGCTGTTCCAGGAAAGAACGTGGT | 4871 |
| (SEQ ID NO: 12) C1-P11_con : | GAAGTTGGAAGGCAGATGGGATGGAGAGGAAGAGGTCCAGTTGATCGCGGCTGTTCCAGGAAAGAACGTGGT | 4855 |
| (SEQ ID NO: 15) P1_consens : | CAACGTCCAGACAAAACCGAGCTTGTTCAAAGTGAGGAATGGGGGAGAAATCGGGGCTGTCGCTCTTGACTA | 4968 |
| (SEQ ID NO: 9) B-P1_conse : | CAACGTCCAGACAAAACCGAGCTTGTTCAAAGTGAGGAATGGGGGAGAAATCGGGGCTGTCGCTCTTGACTA | 4929 |
| (SEQ ID NO: 10) C-P1_genom : | CAACGTCCAGACAAAACCGAGCTTGTTCAAAGTGAGGAATGGGGGAGAAATCGGGGCTGTCGCTCTTGACTA | 4929 |
| (SEQ ID NO: 11) B3-P11_con : | CAACGTCCAGACAAAACCGAGCTTGTTCAAAGTGAGGAATGGGGGAGAAATCGGGGCTGTCGCTCTTGACTA | 4943 |
| (SEQ ID NO: 12) C1-P11_con : | CAACGTCCAGACAAAACCGAGCTTGTTCAAAGTGAGGAATGGGGGAGAAATCGGGGCTGTCGCTCTTGACTA | 4927 |
| (SEQ ID NO: 15) P1_consens : | TCCGAGTGGCACTTCAGATCTCCTATTGTTAACAGGAACGGAGAGGTGATTGGCTACGGCAATGGCAT | 5040 |
| (SEQ ID NO: 9) B-P1_conse : | TCCGAGTGGCACTTCAGATCTCCTATTGTTAACAGGAACGGAGAGGTGATTGGCTACGGCAATGGCAT | 5001 |
| (SEQ ID NO: 10) C-P1_genom : | TCCGAGTGGCACTTCAGATCTCCTATTGTTAACAGGAACGGAGAGGTGATTGGCTACGGCAATGGCAT | 5001 |
| (SEQ ID NO: 11) B3-P11_con : | TCCGAGTGGCACTTCAGATCTCCTATTGTTAACAGGAACGGAGAGGTGATTGGCTACGGCAATGGCAT | 5015 |
| (SEQ ID NO: 12) C1-P11_con : | TCCGAGTGGCACTTCAGATCTCCTATTGTTAACAGGAACGGAGAGGTGATTGGCTACGGCAATGGCAT | 4999 |

FIG. 8N

```
                        *         5060         *         5080         *         5100         *
(SEQ ID NO:15) P1_consens  : CCTTGTCGGTGACAACTCCTTCGTGTCCGCCATATCCCAGACTGAGGTGAAGGAAGAAGGAAGAAGGAGGAGCT : 5112
(SEQ ID NO:9)  B-P1_conse  : CCTTGTCGGTGACAACTCCTTCGTGTCCGCCATATCCCAGACTGAGGTGAAGGAAGAAGGAAGAAGGAGGAGCT : 5073
(SEQ ID NO:10) C-P1_genom  : CCTTGTCGGTGACAACTCCTTCGTGTCCGCCATATCCCAGACTGAGGTGAAGGAAGAAGGAAGAAGGAGGAGCT : 5073
(SEQ ID NO:11) B3-P11_con  : CCTTGTCGGTGACAACTCCTTCGTGTCCGCCATATCCCAGACTGAGGTGAAGGAAGAAGGAAGAAGGAGGAGCT : 5087
(SEQ ID NO:12) C1-P11_con  : CCTTGTCGGTGACAACTCCTTCGTGTCCGCCATATCCCAGACTGAGGTGAAGGAAGAAGGAAGAAGGAGGAGCT : 5071

5120         *         5140         *         5160         *         5180
(SEQ ID NO:15) P1_consens  : CCAAGAGATCCCGACAATGCTAAAGAAAGGAATGACAACTGTCCTTGATTTTCATCCTGGAGCTGGGAAGAC : 5184
(SEQ ID NO:9)  B-P1_conse  : CCAAGAGATCCCGACAATGCTAAAGAAAGGAATGACAACTGTCCTTGATTTTCATCCTGGAGCTGGGAAGAC : 5145
(SEQ ID NO:10) C-P1_genom  : CCAAGAGATCCCGACAATGCTAAAGAAAGGAATGACAACTGTCCTTGATTTTCATCCTGGAGCTGGGAAGAC : 5145
(SEQ ID NO:11) B3-P11_con  : CCAAGAGATCCCGACAATGCTAAAGAAAGGAATGACAACTGTCCTTGATTTTCATCCTGGAGCTGGGAAGAC : 5159
(SEQ ID NO:12) C1-P11_con  : CCAAGAGATCCCGACAATGCTAAAGAAAGGAATGACAACTGTCCTTGATTTTCATCCTGGAGCTGGGAAGAC : 5143

*         5200         *         5220         *         5240         *
(SEQ ID NO:15) P1_consens  : AAGACGTTTCCTCCCACAGATCTTGGCCGAGTCGCGCACGGAGAGACGCTTGCGCACTCTTGTGTTGGCCCCAC : 5256
(SEQ ID NO:9)  B-P1_conse  : AAGACGTTTCCTCCCACAGATCTTGGCCGAGTCGCGCACGGAGAGACGCTTGCGCACTCTTGTGTTGGCCCCAC : 5217
(SEQ ID NO:10) C-P1_genom  : AAGACGTTTCCTCCCACAGATCTTGGCCGAGTCGCGCACGGAGAGACGCTTGCGCACTCTTGTGTTGGCCCCAC : 5217
(SEQ ID NO:11) B3-P11_con  : AAGACGTTTCCTCCCACAGATCTTGGCCGAGTCGCGCACGGAGAGACGCTTGCGCACTCTTGTGTTGGCCCCAC : 5231
(SEQ ID NO:12) C1-P11_con  : AAGACGTTTCCTCCCACAGATCTTGGCCGAGTCGCGCACGGAGAGACGCTTGCGCACTCTTGTGTTGGCCCCAC : 5215

5260         *         5280         *         5300         *         5320
(SEQ ID NO:15) P1_consens  : CAGGGTTGTCTTCTTTCTGAAATGAAGGAGGCTTTTCACGGCCTGGACGTGAAATTCCACACACAGGCTTTTC : 5328
(SEQ ID NO:9)  B-P1_conse  : CAGGGTTGTCTTCTTTCTGAAATGAAGGAGGCTTTTCACGGCCTGGACGTGAAATTCCACACACAGGCTTTTC : 5289
(SEQ ID NO:10) C-P1_genom  : CAGGGTTGTCTTCTTTCTGAAATGAAGGAGGCTTTTCACGGCCTGGACGTGAAATTCCACACACAGGCTTTTC : 5289
(SEQ ID NO:11) B3-P11_con  : CAGGGTTGTCTTCTTTCTGAAATGAAGGAGGCTTTTCACGGCCTGGACGTGAAATTCCACACACAGGCTTTTC : 5303
(SEQ ID NO:12) C1-P11_con  : CAGGGTTGTCTTCTTTCTGAAATGAAGGAGGCTTTTCACGGCCTGGACGTGAAATTCCACACACAGGCTTTTC : 5287

*         5340         *         5360         *         5380         *         5400
(SEQ ID NO:15) P1_consens  : CGCTCACGGCAGCGGGAGAGAGAAGTCATTGATGCTATGTGCCACCCTAACTTACAGAGATGTTGGAACC : 5400
(SEQ ID NO:9)  B-P1_conse  : CGCTCACGGCAGCGGGAGAGAGAAGTCATTGATGCTATGTGCCACCCTAACTTACAGAGATGTTGGAACC : 5361
(SEQ ID NO:10) C-P1_genom  : CGCTCACGGCAGCGGGAGAGAGAAGTCATTGATGCTATGTGCCACCCTAACTTACAGAGATGTTGGAACC : 5361
(SEQ ID NO:11) B3-P11_con  : CGCTCACGGCAGCGGGAGAGAGAAGTCATTGATGCTATGTGCCACCCTAACTTACAGAGATGTTGGAACC : 5375
(SEQ ID NO:12) C1-P11_con  : CGCTCACGGCAGCGGGAGAGAGAAGTCATTGATGCTATGTGCCACCCTAACTTACAGAGATGTTGGAACC : 5359
```

FIG. 8O

```
                                                                                                      *              5420            *              5440            *              5460            *
(SEQ ID NO: 15)  P1_consens    : AACTAGGGTTGTTAACTGGGAAGTGATCATTATGGATGAAGCCCATTTTTGGATCCAGTCCAGCTAGCATAGCCGC : 5472
(SEQ ID NO: 9)   B-P1_conse    : AACTAGGGTTGTTAACTGGGAAGTGATCATTATGGATGAAGCCCATTTTTGGATCCAGTCCAGCTAGCATAGCCGC : 5433
(SEQ ID NO: 10)  C-P1_genom    : AACTAGGGTTGTTAACTGGGAAGTGATCATTATGGATGAAGCCCATTTTTGGATCCAGTCCAGCTAGCATAGCCGC : 5433
(SEQ ID NO: 11)  B3-P11_con    : AACTAGGGTTGTTAACTGGGAAGTGATCATTATGGATGAAGCCCATTTTTGGATCCAGTCCAGCTAGCATAGCCGC : 5447
(SEQ ID NO: 12)  C1-P11_con    : AACTAGGGTTGTTAACTGGGAAGTGATCATTATGGATGAAGCCCATTTTTGGATCCAGTCCAGCTAGCATAGCCGC : 5431

5480            *              5500            *              5520            *              5540
(SEQ ID NO: 15)  P1_consens    : TAGAGGTTGGGCAGCGCACAGAGCTAGGGCAAATGAAAGTGCAACAATCTTGATGACAGCCACACCGCCTGG : 5544
(SEQ ID NO: 9)   B-P1_conse    : TAGAGGTTGGGCAGCGCACAGAGCTAGGGCAAATGAAAGTGCAACAATCTTGATGACAGCCACACCGCCTGG : 5505
(SEQ ID NO: 10)  C-P1_genom    : TAGAGGTTGGGCAGCGCACAGAGCTAGGGCAAATGAAAGTGCAACAATCTTGATGACAGCCACACCGCCTGG : 5505
(SEQ ID NO: 11)  B3-P11_con    : TAGAGGTTGGGCAGCGCACAGAGCTAGGGCAAATGAAAGTGCAACAATCTTGATGACAGCCACACCGCCTGG : 5519
(SEQ ID NO: 12)  C1-P11_con    : TAGAGGTTGGGCAGCGCACAGAGCTAGGGCAAATGAAAGTGCAACAATCTTGATGACAGCCACACCGCCTGG : 5503

*              5560            *              5580            *              5600            *
(SEQ ID NO: 15)  P1_consens    : GACTAGTGATGAATTTCCACATTCAAATGGTGAAATAGAAGATGTTCAAACGGACATACCCAGTGAGCCCTG : 5616
(SEQ ID NO: 9)   B-P1_conse    : GACTAGTGATGAATTTCCACATTCAAATGGTGAAATAGAAGATGTTCAAACGGACATACCCAGTGAGCCCTG : 5577
(SEQ ID NO: 10)  C-P1_genom    : GACTAGTGATGAATTTCCACATTCAAATGGTGAAATAGAAGATGTTCAAACGGACATACCCAGTGAGCCCTG : 5577
(SEQ ID NO: 11)  B3-P11_con    : GACTAGTGATGAATTTCCACATTCAAATGGTGAAATAGAAGATGTTCAAACGGACATACCCAGTGAGCCCTG : 5591
(SEQ ID NO: 12)  C1-P11_con    : GACTAGTGATGAATTTCCACATTCAAATGGTGAAATAGAAGATGTTCAAACGGACATACCCAGTGAGCCCTG : 5575

5620            *              5640            *              5660            *              5680            *
(SEQ ID NO: 15)  P1_consens    : GAACACAGGGCATGACTGGATCCTGGCTGACAAAAGGCCCACGGCATGGTTCCTTCCATCCATCAGAGCTGC : 5688
(SEQ ID NO: 9)   B-P1_conse    : GAACACAGGGCATGACTGGATCCTGGCTGACAAAAGGCCCACGGCATGGTTCCTTCCATCCATCAGAGCTGC : 5649
(SEQ ID NO: 10)  C-P1_genom    : GAACACAGGGCATGACTGGATCCTGGCTGACAAAAGGCCCACGGCATGGTTCCTTCCATCCATCAGAGCTGC : 5649
(SEQ ID NO: 11)  B3-P11_con    : GAACACAGGGCATGACTGGATCCTGGCTGACAAAAGGCCCACGGCATGGTTCCTTCCATCCATCAGAGCTGC : 5663
(SEQ ID NO: 12)  C1-P11_con    : GAACACAGGGCATGACTGGATCCTGGCTGACAAAAGGCCCACGGCATGGTTCCTTCCATCCATCAGAGCTGC : 5647

*              5700            *              5720            *              5740            *              5760
(SEQ ID NO: 15)  P1_consens    : AAATGTCATGGCTGCCTCTCTTTGCGTAAGGCTGAAGGCTGAACAGGAGAAAACCTTTGAGAG : 5760
(SEQ ID NO: 9)   B-P1_conse    : AAATGTCATGGCTGCCTCTCTTTGCGTAAGGCTGAAGGCTGAACAGGAGAAAACCTTTGAGAG : 5721
(SEQ ID NO: 10)  C-P1_genom    : AAATGTCATGGCTGCCTCTCTTTGCGTAAGGCTGAAGGCTGAACAGGAGAAAACCTTTGAGAG : 5721
(SEQ ID NO: 11)  B3-P11_con    : AAATGTCATGGCTGCCTCTCTTTGCGTAAGGCTGAAGGCTGAACAGGAGAAAACCTTTGAGAG : 5735
(SEQ ID NO: 12)  C1-P11_con    : AAATGTCATGGCTGCCTCTCTTTGCGTAAGGCTGAAGGCTGAACAGGAGAAAACCTTTGAGAG : 5719
```

FIG. 8P

| | | | |
|---|---|---|---|
| (SEQ ID NO:15) | P1_consens | : AGAATACCCCACGATAAAGCAGAAGAGAAACCTGACTTTATATTGGCCACTGACATAGCTGAAATGGGAGCCAA | : 5832 |
| (SEQ ID NO:9) | B-P1_conse | : AGAATACCCCACGATAAAGCAGAAGAGAAACCTGACTTTATATTGGCCACTGACATAGCTGAAATGGGAGCCAA | : 5793 |
| (SEQ ID NO:10) | C-P1_genom | : AGAATACCCCACGATAAAGCAGAAGAGAAACCTGACTTTATATTGGCCACTGACATAGCTGAAATGGGAGCCAA | : 5793 |
| (SEQ ID NO:11) | B3-P11_con | : AGAATACCCCACGATAAAGCAGAAGAGAAACCTGACTTTATATTGGCCACTGACATAGCTGAAATGGGAGCCAA | : 5807 |
| (SEQ ID NO:12) | C1-P11_con | : AGAATACCCCACGATAAAGCAGAAGAGAAACCTGACTTTATATTGGCCACTGACATAGCTGAAATGGGAGCCAA | : 5791 |

| | | | |
|---|---|---|---|
| (SEQ ID NO:15) | P1_consens | : CCTTTGCGTGGAGCGAGTGCTGGATTGCAGGACGGCTTTAAGCCTGCTTGTGGATGAAGGAGGAGGAAGGT | : 5904 |
| (SEQ ID NO:9) | B-P1_conse | : CCTTTGCGTGGAGCGAGTGCTGGATTGCAGGACGGCTTTAAGCCTGCTTGTGGATGAAGGAGGAGGAAGGT | : 5865 |
| (SEQ ID NO:10) | C-P1_genom | : CCTTTGCGTGGAGCGAGTGCTGGATTGCAGGACGGCTTTAAGCCTGCTTGTGGATGAAGGAGGAGGAAGGT | : 5865 |
| (SEQ ID NO:11) | B3-P11_con | : CCTTTGCGTGGAGCGAGTGCTGGATTGCAGGACGGCTTTAAGCCTGCTTGTGGATGAAGGAGGAGGAAGGT | : 5879 |
| (SEQ ID NO:12) | C1-P11_con | : CCTTTGCGTGGAGCGAGTGCTGGATTGCAGGACGGCTTTAAGCCTGCTTGTGGATGAAGGAGGAGGAAGGT | : 5863 |

| | | | |
|---|---|---|---|
| (SEQ ID NO:15) | P1_consens | : GGCAATAAAAGGGCCACTTCGTATCTCCGCATCCTCGCTCCTCGCTCCTCGCTCCTCAAAGGAGGAGAAATCC | : 5976 |
| (SEQ ID NO:9) | B-P1_conse | : GGCAATAAAAGGGCCACTTCGTATCTCCGCATCCTCGCTCCTCGCTCCTCGCTCCTCAAAGGAGGAGAAATCC | : 5937 |
| (SEQ ID NO:10) | C-P1_genom | : GGCAATAAAAGGGCCACTTCGTATCTCCGCATCCTCGCTCCTCGCTCCTCGCTCCTCAAAGGAGGAGAAATCC | : 5937 |
| (SEQ ID NO:11) | B3-P11_con | : GGCAATAAAAGGGCCACTTCGTATCTCCGCATCCTCGCTCCTCGCTCCTCGCTCCTCAAAGGAGGAGAAATCC | : 5951 |
| (SEQ ID NO:12) | C1-P11_con | : GGCAATAAAAGGGCCACTTCGTATCTCCGCATCCTCGCTCCTCGCTCCTCGCTCCTCAAAGGAGGAGAAATCC | : 5935 |

| | | | |
|---|---|---|---|
| (SEQ ID NO:15) | P1_consens | : CAACAGAGATGGAGACTCATACTACTATTCTGAGCCTACAAGTGAAAATAATGCCCACCACGTCTGCTGGTT | : 6048 |
| (SEQ ID NO:9) | B-P1_conse | : CAACAGAGATGGAGACTCATACTACTATTCTGAGCCTACAAGTGAAAATAATGCCCACCACGTCTGCTGGTT | : 6009 |
| (SEQ ID NO:10) | C-P1_genom | : CAACAGAGATGGAGACTCATACTACTATTCTGAGCCTACAAGTGAAAATAATGCCCACCACGTCTGCTGGTT | : 6009 |
| (SEQ ID NO:11) | B3-P11_con | : CAACAGAGATGGAGACTCATACTACTATTCTGAGCCTACAAGTGAAAATAATGCCCACCACGTCTGCTGGTT | : 6023 |
| (SEQ ID NO:12) | C1-P11_con | : CAACAGAGATGGAGACTCATACTACTATTCTGAGCCTACAAGTGAAAATAATGCCCACCACGTCTGCTGGTT | : 6007 |

| | | | |
|---|---|---|---|
| (SEQ ID NO:15) | P1_consens | : GGAGGCCTCAATGCTCTTGGACAACATGAGGTGAGGGTGGAATGTCGCCCCACTCTATGGCGTTGAAGG | : 6120 |
| (SEQ ID NO:9) | B-P1_conse | : GGAGGCCTCAATGCTCTTGGACAACATGAGGTGAGGGTGGAATGTCGCCCCACTCTATGGCGTTGAAGG | : 6081 |
| (SEQ ID NO:10) | C-P1_genom | : GGAGGCCTCAATGCTCTTGGACAACATGAGGTGAGGGTGGAATGTCGCCCCACTCTATGGCGTTGAAGG | : 6081 |
| (SEQ ID NO:11) | B3-P11_con | : GGAGGCCTCAATGCTCTTGGACAACATGAGGTGAGGGTGGAATGTCGCCCCACTCTATGGCGTTGAAGG | : 6095 |
| (SEQ ID NO:12) | C1-P11_con | : GGAGGCCTCAATGCTCTTGGACAACATGAGGTGAGGGTGGAATGTCGCCCCACTCTATGGCGTTGAAGG | : 6079 |

FIG. 8Q

```
(SEQ ID NO: 15)  P1_consens : AACTAAAACACCAGTTCCCCTGGTGAAATGAGACTGAGGGATGACCAGAGAGGAAAGTCTTCAGAGAACTAGT : 6192
(SEQ ID NO: 9)   B-P1_conse : AACTAAAACACCAGTTCCCCTGGTGAAATGAGACTGAGGGATGACCAGAGAGGAAAGTCTTCAGAGAACTAGT : 6153
(SEQ ID NO: 10)  C-P1_genom : AACTAAAACACCAGTTCCCCTGGTGAAATGAGACTGAGGGATGACCAGAGAGGAAAGTCTTCAGAGAACTAGT : 6153
(SEQ ID NO: 11)  B3-P11_con : AACTAAAACACCAGTTCCCCTGGTGAAATGAGACTGAGGGATGACCAGAGAGGAAAGTCTTCAGAGAACTAGT : 6167
(SEQ ID NO: 12)  C1-P11_con : AACTAAAACACCAGTTCCCCTGGTGAAATGAGACTGAGGGATGACCAGAGAGGAAAGTCTTCAGAGAACTAGT : 6151

(SEQ ID NO: 15)  P1_consens : GAGGAATTGTGACCTGCCGTTGGCTTTCGTGGCAAGTGGCCAAGCTGGTTTGAAGACAGTGAAGTGCAGGCTGAATGATCGTAA : 6264
(SEQ ID NO: 9)   B-P1_conse : GAGGAATTGTGACCTGCCGTTGGCTTTCGTGGCAAGTGGCCAAGCTGGTTTGAAGACAGTGAAGTGCAGGCTGAATGATCGTAA : 6225
(SEQ ID NO: 10)  C-P1_genom : GAGGAATTGTGACCTGCCGTTGGCTTTCGTGGCAAGTGGCCAAGCTGGTTTGAAGACAGTGAAGTGCAGGCTGAATGATCGTAA : 6225
(SEQ ID NO: 11)  B3-P11_con : GAGGAATTGTGACCTGCCGTTGGCTTTCGTGGCAAGTGGCCAAGCTGGTTTGAAGACAGTGAAGTGCAGGCTGAATGATCGTAA : 6239
(SEQ ID NO: 12)  C1-P11_con : GAGGAATTGTGACCTGCCGTTGGCTTTCGTGGCAAGTGGCCAAGCTGGTTTGAAGACAGTGAAGTGCAGGCTGAATGATCGTAA : 6223

(SEQ ID NO: 15)  P1_consens : GTGGTGTTTTGAAGGCCCTGAGGAACATGAGATCTTGAATGACAGCGGTGAAACAGTGAAGTGCAGGCTCC : 6336
(SEQ ID NO: 9)   B-P1_conse : GTGGTGTTTTGAAGGCCCTGAGGAACATGAGATCTTGAATGACAGCGGTGAAACAGTGAAGTGCAGGCTCC : 6297
(SEQ ID NO: 10)  C-P1_genom : GTGGTGTTTTGAAGGCCCTGAGGAACATGAGATCTTGAATGACAGCGGTGAAACAGTGAAGTGCAGGCTCC : 6297
(SEQ ID NO: 11)  B3-P11_con : GTGGTGTTTTGAAGGCCCTGAGGAACATGAGATCTTGAATGACAGCGGTGAAACAGTGAAGTGCAGGCTCC : 6311
(SEQ ID NO: 12)  C1-P11_con : GTGGTGTTTTGAAGGCCCTGAGGAACATGAGATCTTGAATGACAGCGGTGAAACAGTGAAGTGCAGGCTCC : 6295

(SEQ ID NO: 15)  P1_consens : TGGAGGAGCAAAGAAGCCTCTCGCGCCCAAGGTGGTGTCATCTGACCAGAGTGCGCTGTC : 6408
(SEQ ID NO: 9)   B-P1_conse : TGGAGGAGCAAAGAAGCCTCTCGCGCCCAAGGTGGTGTCATCTGACCAGAGTGCGCTGTC : 6369
(SEQ ID NO: 10)  C-P1_genom : TGGAGGAGCAAAGAAGCCTCTCGCGCCCAAGGTGGTGTCATCTGACCAGAGTGCGCTGTC : 6369
(SEQ ID NO: 11)  B3-P11_con : TGGAGGAGCAAAGAAGCCTCTCGCGCCCAAGGTGGTGTCATCTGACCAGAGTGCGCTGTC : 6383
(SEQ ID NO: 12)  C1-P11_con : TGGAGGAGCAAAGAAGCCTCTCGCGCCCAAGGTGGTGTCATCTGACCAGAGTGCGCTGTC : 6367

(SEQ ID NO: 15)  P1_consens : TGAATTTATTAAGTTTGCTGAAGTAGGAGGGAGCTGCTAGTTGTGCTAGTGTGCTGAGTGAACTCCCTGA : 6480
(SEQ ID NO: 9)   B-P1_conse : TGAATTTATTAAGTTTGCTGAAGTAGGAGGGAGCTGCTAGTTGTGCTAGTGTGCTGAGTGAACTCCCTGA : 6441
(SEQ ID NO: 10)  C-P1_genom : TGAATTTATTAAGTTTGCTGAAGTAGGAGGGAGCTGCTAGTTGTGCTAGTGTGCTGAGTGAACTCCCTGA : 6441
(SEQ ID NO: 11)  B3-P11_con : TGAATTTATTAAGTTTGCTGAAGTAGGAGGGAGCTGCTAGTTGTGCTAGTGTGCTGAGTGAACTCCCTGA : 6455
(SEQ ID NO: 12)  C1-P11_con : TGAATTTATTAAGTTTGCTGAAGTAGGAGGGAGCTGCTAGTTGTGCTAGTGTGCTGAGTGAACTCCCTGA : 6439
```

FIG. 8R

|  |  |  |  |
|---|---|---|---|
| (SEQ ID NO: 15) | P1_consens | : TTTCCTGGCTAAAAAAGTGGAGAGGCAATGGATACCATCAGTGTGTTCTCCACTCTGAGGAAGGCTCTAG | : 6552 |
| (SEQ ID NO: 9) | B-P1_conse | : TTTCCTGGCTAAAAAAGTGGAGAGGCAATGGATACCATCAGTGTGTTCTCCACTCTGAGGAAGGCTCTAG | : 6513 |
| (SEQ ID NO: 10) | C-P1_genom | : TTTCCTGGCTAAAAAAGTGGAGAGGCAATGGATACCATCAGTGTGTTCTCCACTCTGAGGAAGGCTCTAG | : 6513 |
| (SEQ ID NO: 11) | B3-P11_con | : TTTCCTGGCTAAAAAAGTGGAGAGGCAATGGATACCATCAGTGTGTTCTCCACTCTGAGGAAGGCTCTAG | : 6527 |
| (SEQ ID NO: 12) | C1-P11_con | : TTTCCTGGCTAAAAAAGTGGAGAGGCAATGGATACCATCAGTGTGTTCTCCACTCTGAGGAAGGCTCTAG | : 6511 |
|  |  |  |  |
| (SEQ ID NO: 15) | P1_consens | : GGCTTACCGCCAATGCACTATCAATGATGCCTGAGGCAATGACAATAGTCATGTGTTTATACTGGCTGGACT | : 6624 |
| (SEQ ID NO: 9) | B-P1_conse | : GGCTTACCGCCAATGCACTATCAATGATGCCTGAGGCAATGACAATAGTCATGTGTTTATACTGGCTGGACT | : 6585 |
| (SEQ ID NO: 10) | C-P1_genom | : GGCTTACCGCCAATGCACTATCAATGATGCCTGAGGCAATGACAATAGTCATGTGTTTATACTGGCTGGACT | : 6585 |
| (SEQ ID NO: 11) | B3-P11_con | : GGCTTACCGCCAATGCACTATCAATGATGCCTGAGGCAATGACAATAGTCATGTGTTTATACTGGCTGGACT | : 6599 |
| (SEQ ID NO: 12) | C1-P11_con | : GGCTTACCGCCAATGCACTATCAATGATGCCTGAGGCAATGACAATAGTCATGTGTTTATACTGGCTGGACT | : 6583 |
|  |  |  |  |
| (SEQ ID NO: 15) | P1_consens | : ACTGACATCGGGAATGGTCATCTTTTTCATGTCTCCCAAAGGCATCAGTAGAATGTCTATGGCGATGGGCAC | : 6696 |
| (SEQ ID NO: 9) | B-P1_conse | : ACTGACATCGGGAATGGTCATCTTTTTCATGTCTCCCAAAGGCATCAGTAGAATGTCTATGGCGATGGGCAC | : 6657 |
| (SEQ ID NO: 10) | C-P1_genom | : ACTGACATCGGGAATGGTCATCTTTTTCATGTCTCCCAAAGGCATCAGTAGAATGTCTATGGCGATGGGCAC | : 6657 |
| (SEQ ID NO: 11) | B3-P11_con | : ACTGACATCGGGAATGGTCATCTTTTTCATGTCTCCCAAAGGCATCAGTAGAATGTCTATGGCGATGGGCAC | : 6671 |
| (SEQ ID NO: 12) | C1-P11_con | : ACTGACATCGGGAATGGTCATCTTTTTCATGTCTCCCAAAGGCATCAGTAGAATGTCTATGGCGATGGGCAC | : 6655 |
|  |  |  |  |
| (SEQ ID NO: 15) | P1_consens | : AATGGCCGGCTGTGGATATCTCCTTGGAGGCGTCAAACCCACTCCACTCCTATATCATGCTCAT | : 6768 |
| (SEQ ID NO: 9) | B-P1_conse | : AATGGCCGGCTGTGGATATCTCCTTGGAGGCGTCAAACCCACTCCACTCCTATATCATGCTCAT | : 6729 |
| (SEQ ID NO: 10) | C-P1_genom | : AATGGCCGGCTGTGGATATCTCCTTGGAGGCGTCAAACCCACTCCACTCCTATATCATGCTCAT | : 6729 |
| (SEQ ID NO: 11) | B3-P11_con | : AATGGCCGGCTGTGGATATCTCCTTGGAGGCGTCAAACCCACTCCACTCCTATATCATGCTCAT | : 6743 |
| (SEQ ID NO: 12) | C1-P11_con | : AATGGCCGGCTGTGGATATCTCCTTGGAGGCGTCAAACCCACTCCACTCCTATATCATGCTCAT | : 6727 |
|  |  |  |  |
| (SEQ ID NO: 15) | P1_consens | : ATTCTTTGTCCTGATGGTGGTTGTGAATCCCGAGCCAGGGCAACAAGTCCATCCAAGACAACCAAGTGGC | : 6840 |
| (SEQ ID NO: 9) | B-P1_conse | : ATTCTTTGTCCTGATGGTGGTTGTGAATCCCGAGCCAGGGCAACAAGTCCATCCAAGACAACCAAGTGGC | : 6801 |
| (SEQ ID NO: 10) | C-P1_genom | : ATTCTTTGTCCTGATGGTGGTTGTGAATCCCGAGCCAGGGCAACAAGTCCATCCAAGACAACCAAGTGGC | : 6801 |
| (SEQ ID NO: 11) | B3-P11_con | : ATTCTTTGTCCTGATGGTGGTTGTGAATCCCGAGCCAGGGCAACAAGTCCATCCAAGACAACCAAGTGGC | : 6815 |
| (SEQ ID NO: 12) | C1-P11_con | : ATTCTTTGTCCTGATGGTGGTTGTGAATCCCGAGCCAGGGCAACAAGTCCATCCAAGACAACCAAGTGGC | : 6799 |

FIG. 8S

```
                                           *         6860          *         6880          *         6900          *
(SEQ ID NO: 15) P1_consens  : ATACCTCATTATTGGCATCCTGACGCTGGTTTCAGCGGTGGCAGCCAACGAGCTAGGCATGCTGGAGAAAAC : 6912
(SEQ ID NO: 9)  B-P1_conse  : ATACCTCATTATTGGCATCCTGACGCTGGTTTCAGCGGTGGCAGCCAACGAGCTAGGCATGCTGGAGAAAAC : 6873
(SEQ ID NO: 10) C-P1_genom  : ATACCTCATTATTGGCATCCTGACGCTGGTTTCAGCGGTGGCAGCCAACGAGCTAGGCATGCTGGAGAAAAC : 6873
(SEQ ID NO: 11) B3-P11_con  : ATACCTCATTATTGGCATCCTGACGCTGGTTTCAGCGGTGGCAGCCAACGAGCTAGGCATGCTGGAGAAAAC : 6887
(SEQ ID NO: 12) C1-P11_con  : ATACCTCATTATTGGCATCCTGACGCTGGTTTCAGCGGTGGCAGCCAACGAGCTAGGCATGCTGGAGAAAAC : 6871

*         6920          *         6940          *         6960          *         6980
(SEQ ID NO: 15) P1_consens  : CAAAGAGGAGACCTCTTTGGGAAGAAGAAGAACTTAATTCCATCTAGTGCTTCACCCTGGAGTTGGCCGATCTTGA : 6984
(SEQ ID NO: 9)  B-P1_conse  : CAAAGAGGAGACCTCTTTGGGAAGAAGAAGAACTTAATTCCATCTAGTGCTTCACCCTGGAGTTGGCCGATCTTGA : 6945
(SEQ ID NO: 10) C-P1_genom  : CAAAGAGGAGACCTCTTTGGGAAGAAGAAGAACTTAATTCCATCTAGTGCTTCACCCTGGAGTTGGCCGATCTTGA : 6945
(SEQ ID NO: 11) B3-P11_con  : CAAAGAGGAGACCTCTTTGGGAAGAAGAAGAACTTAATTCCATCTAGTGCTTCACCCTGGAGTTGGCCGATCTTGA : 6959
(SEQ ID NO: 12) C1-P11_con  : CAAAGAGGAGACCTCTTTGGGAAGAAGAAGAACTTAATTCCATCTAGTGCTTCACCCTGGAGTTGGCCGATCTTGA : 6943

*         7000          *         7020          *         7040          *
(SEQ ID NO: 15) P1_consens  : CCTGAAGCCAGGAGCTGCCTGGACAGTGTACGTTGGCATTGTTACAATGCTCTCTCCAATGTTGCACCACTG : 7056
(SEQ ID NO: 9)  B-P1_conse  : CCTGAAGCCAGGAGCTGCCTGGACAGTGTACGTTGGCATTGTTACAATGCTCTCTCCAATGTTGCACCACTG : 7017
(SEQ ID NO: 10) C-P1_genom  : CCTGAAGCCAGGAGCTGCCTGGACAGTGTACGTTGGCATTGTTACAATGCTCTCTCCAATGTTGCACCACTG : 7017
(SEQ ID NO: 11) B3-P11_con  : CCTGAAGCCAGGAGCTGCCTGGACAGTGTACGTTGGCATTGTTACAATGCTCTCTCCAATGTTGCACCACTG : 7031
(SEQ ID NO: 12) C1-P11_con  : CCTGAAGCCAGGAGCTGCCTGGACAGTGTACGTTGGCATTGTTACAATGCTCTCTCCAATGTTGCACCACTG : 7015

7060          *         7080          *         7100          *         7120          *
(SEQ ID NO: 15) P1_consens  : GATCAAAGTCGAATATGGCAACCTGTCTCTGTCTCTGTCTCTGAATAGCCCAGTCAGCCTCAGTCCTTCTTTCATGGA : 7128
(SEQ ID NO: 9)  B-P1_conse  : GATCAAAGTCGAATATGGCAACCTGTCTCTGTCTCTGTCTCTGAATAGCCCAGTCAGCCTCAGTCCTTCTTTCATGGA : 7089
(SEQ ID NO: 10) C-P1_genom  : GATCAAAGTCGAATATGGCAACCTGTCTCTGTCTCTGTCTCTGAATAGCCCAGTCAGCCTCAGTCCTTCTTTCATGGA : 7089
(SEQ ID NO: 11) B3-P11_con  : GATCAAAGTCGAATATGGCAACCTGTCTCTGTCTCTGTCTCTGAATAGCCCAGTCAGCCTCAGTCCTTCTTTCATGGA : 7103
(SEQ ID NO: 12) C1-P11_con  : GATCAAAGTCGAATATGGCAACCTGTCTCTGTCTCTGTCTCTGAATAGCCCAGTCAGCCTCAGTCCTTCTTTCATGGA : 7087

*         7140          *         7160          *         7180          *         7200
(SEQ ID NO: 15) P1_consens  : CAAGGGGATACCATTCATGAAGATGAATATCTCGGTCATAATGCTGCTGGTCAGTGGCTGGAATTCAATAAC : 7200
(SEQ ID NO: 9)  B-P1_conse  : CAAGGGGATACCATTCATGAAGATGAATATCTCGGTCATAATGCTGCTGGTCAGTGGCTGGAATTCAATAAC : 7161
(SEQ ID NO: 10) C-P1_genom  : CAAGGGGATACCATTCATGAAGATGAATATCTCGGTCATAATGCTGCTGGTCAGTGGCTGGAATTCAATAAC : 7161
(SEQ ID NO: 11) B3-P11_con  : CAAGGGGATACCATTCATGAAGATGAATATCTCGGTCATAATGCTGCTGGTCAGTGGCTGGAATTCAATAAC : 7175
(SEQ ID NO: 12) C1-P11_con  : CAAGGGGATACCATTCATGAAGATGAATATCTCGGTCATAATGCTGCTGGTCAGTGGCTGGAATTCAATAAC : 7159
```

FIG. 8T

| | | | |
|---|---|---|---|
| (SEQ ID NO: 15) | P1_consens  : | AGTGATGCCTCTGCTCTGTGCCATAGGGTGGCGCCATGCTCCACTGGTCTCTCATTTTACCTGGAATCAAAGC | 7272 |
| (SEQ ID NO: 9) | B-P1_conse  : | AGTGATGCCTCTGCTCTGTGCCATAGGGTGGCGCCATGCTCCACTGGTCTCTCATTTTACCTGGAATCAAAGC | 7233 |
| (SEQ ID NO: 10) | C-P1_genom  : | AGTGATGCCTCTGCTCTGTGCCATAGGGTGGCGCCATGCTCCACTGGTCTCTCATTTTACCTGGAATCAAAGC | 7233 |
| (SEQ ID NO: 11) | B3-P11_con  : | AGTGATGCCTCTGCTCTGTGCCATAGGGTGGCGCCATGCTCCACTGGTCTCTCATTTTACCTGGAATCAAAGC | 7247 |
| (SEQ ID NO: 12) | C1-P11_con  : | AGTGATGCCTCTGCTCTGTGCCATAGGGTGGCGCCATGCTCCACTGGTCTCTCATTTTACCTGGAATCAAAGC | 7231 |
| (SEQ ID NO: 15) | P1_consens  : | GCAGCAGTCAAAGCTTGCACAGAGAAGAGGGTGTTCCAAGAACCCTGTGGTTGATGGGAATCC | 7344 |
| (SEQ ID NO: 9) | B-P1_conse  : | GCAGCAGTCAAAGCTTGCACAGAGAAGAGGGTGTTCCAAGAACCCTGTGGTTGATGGGAATCC | 7305 |
| (SEQ ID NO: 10) | C-P1_genom  : | GCAGCAGTCAAAGCTTGCACAGAGAAGAGGGTGTTCCAAGAACCCTGTGGTTGATGGGAATCC | 7305 |
| (SEQ ID NO: 11) | B3-P11_con  : | GCAGCAGTCAAAGCTTGCACAGAGAAGAGGGTGTTCCAAGAACCCTGTGGTTGATGGGAATCC | 7319 |
| (SEQ ID NO: 12) | C1-P11_con  : | GCAGCAGTCAAAGCTTGCACAGAGAAGAGGGTGTTCCAAGAACCCTGTGGTTGATGGGAATCC | 7303 |
| (SEQ ID NO: 15) | P1_consens  : | AACAGTTGACATTGAGGAAGCTCCTGCCCTTTATGAGAAGAAAACTGGCTCTATATCTCCTTCT | 7416 |
| (SEQ ID NO: 9) | B-P1_conse  : | AACAGTTGACATTGAGGAAGCTCCTGCCCTTTATGAGAAGAAAACTGGCTCTATATCTCCTTCT | 7377 |
| (SEQ ID NO: 10) | C-P1_genom  : | AACAGTTGACATTGAGGAAGCTCCTGCCCTTTATGAGAAGAAAACTGGCTCTATATCTCCTTCT | 7377 |
| (SEQ ID NO: 11) | B3-P11_con  : | AACAGTTGACATTGAGGAAGCTCCTGCCCTTTATGAGAAGAAAACTGGCTCTATATCTCCTTCT | 7391 |
| (SEQ ID NO: 12) | C1-P11_con  : | AACAGTTGACATTGAGGAAGCTCCTGCCCTTTATGAGAAGAAAACTGGCTCTATATCTCCTTCT | 7375 |
| (SEQ ID NO: 15) | P1_consens  : | TGCTCTCAGCCTAGCTTCTTCTGTTGCCATGTGCAGAACGCCCTTTCATTGGCTGAAGGCATTGTCCTAGCATC | 7488 |
| (SEQ ID NO: 9) | B-P1_conse  : | TGCTCTCAGCCTAGCTTCTTCTGTTGCCATGTGCAGAACGCCCTTTCATTGGCTGAAGGCATTGTCCTAGCATC | 7449 |
| (SEQ ID NO: 10) | C-P1_genom  : | TGCTCTCAGCCTAGCTTCTTCTGTTGCCATGTGCAGAACGCCCTTTCATTGGCTGAAGGCATTGTCCTAGCATC | 7449 |
| (SEQ ID NO: 11) | B3-P11_con  : | TGCTCTCAGCCTAGCTTCTTCTGTTGCCATGTGCAGAACGCCCTTTCATTGGCTGAAGGCATTGTCCTAGCATC | 7463 |
| (SEQ ID NO: 12) | C1-P11_con  : | TGCTCTCAGCCTAGCTTCTTCTGTTGCCATGTGCAGAACGCCCTTTCATTGGCTGAAGGCATTGTCCTAGCATC | 7447 |
| (SEQ ID NO: 15) | P1_consens  : | AGCTGCCCTAGGGCCGCTCATAGAGGGAAACACCAGCCTTCTTTGGAATGACCCATGGCTGTCTCCATGAC | 7560 |
| (SEQ ID NO: 9) | B-P1_conse  : | AGCTGCCCTAGGGCCGCTCATAGAGGGAAACACCAGCCTTCTTTGGAATGACCCATGGCTGTCTCCATGAC | 7521 |
| (SEQ ID NO: 10) | C-P1_genom  : | AGCTGCCCTAGGGCCGCTCATAGAGGGAAACACCAGCCTTCTTTGGAATGACCCATGGCTGTCTCCATGAC | 7521 |
| (SEQ ID NO: 11) | B3-P11_con  : | AGCTGCCCTAGGGCCGCTCATAGAGGGAAACACCAGCCTTCTTTGGAATGACCCATGGCTGTCTCCATGAC | 7535 |
| (SEQ ID NO: 12) | C1-P11_con  : | AGCTGCCCTAGGGCCGCTCATAGAGGGAAACACCAGCCTTCTTTGGAATGACCCATGGCTGTCTCCATGAC | 7519 |

FIG. 8U

```
                                                       *       7580        *       7600        *       7620        *
(SEQ ID NO: 15)  P1_consens  : AGGAGTCATGAGGGGGAATCACTATGCTTTTGTGGGAGTCATGTACAATCTATGGAAGATGAAAAACTGACG : 7632
(SEQ ID NO: 9)   B-P1_conse  : AGGAGTCATGAGGGGGAATCACTATGCTTTTGTGGGAGTCATGTACAATCTATGGAAGATGAAAAACTGACG : 7593
(SEQ ID NO: 10)  C-P1_genom  : AGGAGTCATGAGGGGGAATCACTATGCTTTTGTGGGAGTCATGTACAATCTATGGAAGATGAAAAACTGACG : 7593
(SEQ ID NO: 11)  B3-P11_con  : AGGAGTCATGAGGGGGAATCACTATGCTTTTGTGGGAGTCATGTACAATCTATGGAAGATGAAAAACTGACG : 7607
(SEQ ID NO: 12)  C1-P11_con  : AGGAGTCATGAGGGGGAATCACTATGCTTTTGTGGGAGTCATGTACAATCTATGGAAGATGAAAAACTGACG : 7591

7640        *       7660        *       7680        *       7700
(SEQ ID NO: 15)  P1_consens  : CCGGGGAGCGCGCGAATGAAAAAACTTTGGGTGAAGTCTGAAGAGGGAACTGAATCTGTTGACAAGCGACA : 7704
(SEQ ID NO: 9)   B-P1_conse  : CCGGGGAGCGCGCGAATGAAAAAACTTTGGGTGAAGTCTGAAGAGGGAACTGAATCTGTTGACAAGCGACA : 7665
(SEQ ID NO: 10)  C-P1_genom  : CCGGGGAGCGCGCGAATGAAAAAACTTTGGGTGAAGTCTGAAGAGGGAACTGAATCTGTTGACAAGCGACA : 7665
(SEQ ID NO: 11)  B3-P11_con  : CCGGGGAGCGCGCGAATGAAAAAACTTTGGGTGAAGTCTGAAGAGGGAACTGAATCTGTTGACAAGCGACA : 7679
(SEQ ID NO: 12)  C1-P11_con  : CCGGGGAGCGCGCGAATGAAAAAACTTTGGGTGAAGTCTGAAGAGGGAACTGAATCTGTTGACAAGCGACA : 7663

*       7720        *       7740        *       7760        *
(SEQ ID NO: 15)  P1_consens  : GTTTGAGTTGTATAAAAGGACCGACATTGTGGAGGTGGATCGTGATACGGCACGCAGGCATTTGGCCGAAGG : 7776
(SEQ ID NO: 9)   B-P1_conse  : GTTTGAGTTGTATAAAAGGACCGACATTGTGGAGGTGGATCGTGATACGGCACGCAGGCATTTGGCCGAAGG : 7737
(SEQ ID NO: 10)  C-P1_genom  : GTTTGAGTTGTATAAAAGGACCGACATTGTGGAGGTGGATCGTGATACGGCACGCAGGCATTTGGCCGAAGG : 7737
(SEQ ID NO: 11)  B3-P11_con  : GTTTGAGTTGTATAAAAGGACCGACATTGTGGAGGTGGATCGTGATACGGCACGCAGGCATTTGGCCGAAGG : 7751
(SEQ ID NO: 12)  C1-P11_con  : GTTTGAGTTGTATAAAAGGACCGACATTGTGGAGGTGGATCGTGATACGGCACGCAGGCATTTGGCCGAAGG : 7735

7780        *       7800        *       7820        *       7840
(SEQ ID NO: 15)  P1_consens  : GAAGGTGGACACCGGGTGGTCGCGCGTGGCGTCTCCAGGGGGACCGGCAAAGTTAAGGTGGTTCCATGAGCGTGGCTATGT : 7848
(SEQ ID NO: 9)   B-P1_conse  : GAAGGTGGACACCGGGTGGTCGCGCGTGGCGTCTCCAGGGGGACCGGCAAAGTTAAGGTGGTTCCATGAGCGTGGCTATGT : 7809
(SEQ ID NO: 10)  C-P1_genom  : GAAGGTGGACACCGGGTGGTCGCGCGTGGCGTCTCCAGGGGGACCGGCAAAGTTAAGGTGGTTCCATGAGCGTGGCTATGT : 7809
(SEQ ID NO: 11)  B3-P11_con  : GAAGGTGGACACCGGGTGGTCGCGCGTGGCGTCTCCAGGGGGACCGGCAAAGTTAAGGTGGTTCCATGAGCGTGGCTATGT : 7823
(SEQ ID NO: 12)  C1-P11_con  : GAAGGTGGACACCGGGTGGTCGCGCGTGGCGTCTCCAGGGGGACCGGCAAAGTTAAGGTGGTTCCATGAGCGTGGCTATGT : 7807

*       7860        *       7880        *       7900        *       7920
(SEQ ID NO: 15)  P1_consens  : CAAGCTGGAAGGTAGGGTGATTGACCTGGCCGCCGCGCGGGTGTGCCGCGAGGCCTGGTTACTACGCTGCGCCAAAA : 7920
(SEQ ID NO: 9)   B-P1_conse  : CAAGCTGGAAGGTAGGGTGATTGACCTGGCCGCCGCGCGGGTGTGCCGCGAGGCCTGGTTACTACGCTGCGCCAAAA : 7881
(SEQ ID NO: 10)  C-P1_genom  : CAAGCTGGAAGGTAGGGTGATTGACCTGGCCGCCGCGCGGGTGTGCCGCGAGGCCTGGTTACTACGCTGCGCCAAAA : 7881
(SEQ ID NO: 11)  B3-P11_con  : CAAGCTGGAAGGTAGGGTGATTGACCTGGCCGCCGCGCGGGTGTGCCGCGAGGCCTGGTTACTACGCTGCGCCAAAA : 7895
(SEQ ID NO: 12)  C1-P11_con  : CAAGCTGGAAGGTAGGGTGATTGACCTGGCCGCCGCGCGGGTGTGCCGCGAGGCCTGGTTACTACGCTGCGCCAAAA : 7879
```

```
                                                               *              8660              *              8680              *              8700              *
(SEQ ID NO: 15)  P1_consens  : GATAGAGGAGGTCACAAGAATGCAATGACTGACACAACCCCTTTTGGACACAGCAAAGAGTGTTTAAAGAAAA : 8712
(SEQ ID NO: 9)   B-P1_conse  : GATAGAGGAGGTCACAAGAATGCAATGACTGACACAACCCCTTTTGGACACAGCAAAGAGTGTTTAAAGAAAA : 8673
(SEQ ID NO: 10)  C-P1_genom  : GATAGAGGAGGTCACAAGAATGCAATGACTGACACAACCCCTTTTGGACACAGCAAAGAGTGTTTAAAGAAAA : 8673
(SEQ ID NO: 11)  B3-P11_con  : GATAGAGGAGGTCACAAGAATGCAATGACTGACACAACCCCTTTTGGACACAGCAAAGAGTGTTTAAAGAAAA : 8687
(SEQ ID NO: 12)  C1-P11_con  : GATAGAGGAGGTCACAAGAATGCAATGACTGACACAACCCCTTTTGGACACAGCAAAGAGTGTTTAAAGAAAA : 8671

*              8720              *              8740              *              8760              *              8780              *
(SEQ ID NO: 15)  P1_consens  : AGTTGACACCAGAGCAAAGGATCCACCAGCGGGAACTAGGAAGATCATGAAAAGTTGTCAACAGGTGGCTGTT : 8784
(SEQ ID NO: 9)   B-P1_conse  : AGTTGACACCAGAGCAAAGGATCCACCAGCGGGAACTAGGAAGATCATGAAAAGTTGTCAACAGGTGGCTGTT : 8745
(SEQ ID NO: 10)  C-P1_genom  : AGTTGACACCAGAGCAAAGGATCCACCAGCGGGAACTAGGAAGATCATGAAAAGTTGTCAACAGGTGGCTGTT : 8745
(SEQ ID NO: 11)  B3-P11_con  : AGTTGACACCAGAGCAAAGGATCCACCAGCGGGAACTAGGAAGATCATGAAAAGTTGTCAACAGGTGGCTGTT : 8759
(SEQ ID NO: 12)  C1-P11_con  : AGTTGACACCAGAGCAAAGGATCCACCAGCGGGAACTAGGAAGATCATGAAAAGTTGTCAACAGGTGGCTGTT : 8743

*              8800              *              8820              *              8840              *
(SEQ ID NO: 15)  P1_consens  : CCGCCACCTGGCCAGAGAAAAGAACCCCAGACTGTGCACAAAGGAAGAATTTATTGCAAAAGTCCGAAGTCA : 8856
(SEQ ID NO: 9)   B-P1_conse  : CCGCCACCTGGCCAGAGAAAAGAACCCCAGACTGTGCACAAAGGAAGAATTTATTGCAAAAGTCCGAAGTCA : 8817
(SEQ ID NO: 10)  C-P1_genom  : CCGCCACCTGGCCAGAGAAAAGAACCCCAGACTGTGCACAAAGGAAGAATTTATTGCAAAAGTCCGAAGTCA : 8817
(SEQ ID NO: 11)  B3-P11_con  : CCGCCACCTGGCCAGAGAAAAGAACCCCAGACTGTGCACAAAGGAAGAATTTATTGCAAAAGTCCGAAGTCA : 8831
(SEQ ID NO: 12)  C1-P11_con  : CCGCCACCTGGCCAGAGAAAAGAACCCCAGACTGTGCACAAAGGAAGAATTTATTGCAAAAGTCCGAAGTCA : 8815

8860              *              8880              *              8900              *              8920              *
(SEQ ID NO: 15)  P1_consens  : TGCAGCCATTGGAGCTTACCTGGAAGAACAAGAACAGTGAAGACTGCCAATGAGGCTGTCCAAGACCCAAAA : 8928
(SEQ ID NO: 9)   B-P1_conse  : TGCAGCCATTGGAGCTTACCTGGAAGAACAAGAACAGTGAAGACTGCCAATGAGGCTGTCCAAGACCCAAAA : 8889
(SEQ ID NO: 10)  C-P1_genom  : TGCAGCCATTGGAGCTTACCTGGAAGAACAAGAACAGTGAAGACTGCCAATGAGGCTGTCCAAGACCCAAAA : 8889
(SEQ ID NO: 11)  B3-P11_con  : TGCAGCCATTGGAGCTTACCTGGAAGAACAAGAACAGTGAAGACTGCCAATGAGGCTGTCCAAGACCCAAAA : 8903
(SEQ ID NO: 12)  C1-P11_con  : TGCAGCCATTGGAGCTTACCTGGAAGAACAAGAACAGTGAAGACTGCCAATGAGGCTGTCCAAGACCCAAAA : 8887

8940              *              8960              *              8980              *              9000
(SEQ ID NO: 15)  P1_consens  : GTTCTGGGAACTGGTGGATGAAGAAAAGGAAGCTGCACCAACAAGGAGCAGGTGTCGGACTTGTGTGTACAACAT : 9000
(SEQ ID NO: 9)   B-P1_conse  : GTTCTGGGAACTGGTGGATGAAGAAAAGGAAGCTGCACCAACAAGGAGCAGGTGTCGGACTTGTGTGTACAACAT : 8961
(SEQ ID NO: 10)  C-P1_genom  : GTTCTGGGAACTGGTGGATGAAGAAAAGGAAGCTGCACCAACAAGGAGCAGGTGTCGGACTTGTGTGTACAACAT : 8961
(SEQ ID NO: 11)  B3-P11_con  : GTTCTGGGAACTGGTGGATGAAGAAAAGGAAGCTGCACCAACAAGGAGCAGGTGTCGGACTTGTGTGTACAACAT : 8975
(SEQ ID NO: 12)  C1-P11_con  : GTTCTGGGAACTGGTGGATGAAGAAAAGGAAGCTGCACCAACAAGGAGCAGGTGTCGGACTTGTGTGTACAACAT : 8959
```

FIG. 8Y

| | | | | |
|---|---|---|---|---|
| (SEQ ID NO: 15) | P1_consens | : | GATGGGGAAAAGAGAAGAGAAGAGAAGAGAAGCTGTCAGAGTTTGGGAAGCAAAGGAAGCCGTGCCATATGGTATATGTG | : 9072 |
| (SEQ ID NO: 9) | B-P1_conse | : | GATGGGGAAAAGAGAAGAGAAGAGAAGAGAAGCTGTCAGAGTTTGGGAAGCAAAGGAAGCCGTGCCATATGGTATATGTG | : 9033 |
| (SEQ ID NO: 10) | C-P1_genom | : | GATGGGGAAAAGAGAAGAGAAGAGAAGAGAAGCTGTCAGAGTTTGGGAAGCAAAGGAAGCCGTGCCATATGGTATATGTG | : 9033 |
| (SEQ ID NO: 11) | B3-P11_con | : | GATGGGGAAAAGAGAAGAGAAGAGAAGAGAAGCTGTCAGAGTTTGGGAAGCAAAGGAAGCCGTGCCATATGGTATATGTG | : 9047 |
| (SEQ ID NO: 12) | C1-P11_con | : | GATGGGGAAAAGAGAAGAGAAGAGAAGAGAAGCTGTCAGAGTTTGGGAAGCAAAGGAAGCCGTGCCATATGGTATATGTG | : 9031 |

| (SEQ ID NO: 15) | P1_consens | : | GCTGGGAGCGCGGTATCTTGAGTTTGAGGCCCTGGATTCCTGAATGAGGACCATTGGGCTTCCAGGGAAAA | : 9144 |
| (SEQ ID NO: 9) | B-P1_conse | : | GCTGGGAGCGCGGTATCTTGAGTTTGAGGCCCTGGATTCCTGAATGAGGACCATTGGGCTTCCAGGGAAAA | : 9105 |
| (SEQ ID NO: 10) | C-P1_genom | : | GCTGGGAGCGCGGTATCTTGAGTTTGAGGCCCTGGATTCCTGAATGAGGACCATTGGGCTTCCAGGGAAAA | : 9105 |
| (SEQ ID NO: 11) | B3-P11_con | : | GCTGGGAGCGCGGTATCTTGAGTTTGAGGCCCTGGATTCCTGAATGAGGACCATTGGGCTTCCAGGGAAAA | : 9119 |
| (SEQ ID NO: 12) | C1-P11_con | : | GCTGGGAGCGCGGTATCTTGAGTTTGAGGCCCTGGATTCCTGAATGAGGACCATTGGGCTTCCAGGGAAAA | : 9103 |

| (SEQ ID NO: 15) | P1_consens | : | CTCAGGAGGAGGAGTGGAAGGCATTGGCTTACAATACCTAGGATATGTGATCAGAGACCTGGCTGCAATGGA | : 9216 |
| (SEQ ID NO: 9) | B-P1_conse | : | CTCAGGAGGAGGAGTGGAAGGCATTGGCTTACAATACCTAGGATATGTGATCAGAGACCTGGCTGCAATGGA | : 9177 |
| (SEQ ID NO: 10) | C-P1_genom | : | CTCAGGAGGAGGAGTGGAAGGCATTGGCTTACAATACCTAGGATATGTGATCAGAGACCTGGCTGCAATGGA | : 9177 |
| (SEQ ID NO: 11) | B3-P11_con | : | CTCAGGAGGAGGAGTGGAAGGCATTGGCTTACAATACCTAGGATATGTGATCAGAGACCTGGCTGCAATGGA | : 9191 |
| (SEQ ID NO: 12) | C1-P11_con | : | CTCAGGAGGAGGAGTGGAAGGCATTGGCTTACAATACCTAGGATATGTGATCAGAGACCTGGCTGCAATGGA | : 9175 |

| (SEQ ID NO: 15) | P1_consens | : | TGGTGGTGGATTCTACGCGGATGACACCGCTGGATGGGACACGCGCATCACAGAGGCAGAGACCTTGATGATGA | : 9288 |
| (SEQ ID NO: 9) | B-P1_conse | : | TGGTGGTGGATTCTACGCGGATGACACCGCTGGATGGGACACGCGCATCACAGAGGCAGAGACCTTGATGATGA | : 9249 |
| (SEQ ID NO: 10) | C-P1_genom | : | TGGTGGTGGATTCTACGCGGATGACACCGCTGGATGGGACACGCGCATCACAGAGGCAGAGACCTTGATGATGA | : 9249 |
| (SEQ ID NO: 11) | B3-P11_con | : | TGGTGGTGGATTCTACGCGGATGACACCGCTGGATGGGACACGCGCATCACAGAGGCAGAGACCTTGATGATGA | : 9263 |
| (SEQ ID NO: 12) | C1-P11_con | : | TGGTGGTGGATTCTACGCGGATGACACCGCTGGATGGGACACGCGCATCACAGAGGCAGAGACCTTGATGATGA | : 9247 |

| (SEQ ID NO: 15) | P1_consens | : | ACAGGAGATCTTGAACTACATGAGCCCACATCACAAAAAACTGGCACAAGCAGTGATGGAAATGACATACAA | : 9360 |
| (SEQ ID NO: 9) | B-P1_conse | : | ACAGGAGATCTTGAACTACATGAGCCCACATCACAAAAAACTGGCACAAGCAGTGATGGAAATGACATACAA | : 9321 |
| (SEQ ID NO: 10) | C-P1_genom | : | ACAGGAGATCTTGAACTACATGAGCCCACATCACAAAAAACTGGCACAAGCAGTGATGGAAATGACATACAA | : 9321 |
| (SEQ ID NO: 11) | B3-P11_con | : | ACAGGAGATCTTGAACTACATGAGCCCACATCACAAAAAACTGGCACAAGCAGTATGGAAATGACATACAA | : 9335 |
| (SEQ ID NO: 12) | C1-P11_con | : | ACAGGAGATCTTGAACTACATGAGCCCACATCACAAAAAACTGGCACAAGCAGTGATGGAAATGACATACAA | : 9319 |

| | | | |
|---|---|---|---|
| (SEQ ID NO: 15) | P1_consens | : ATCTGAATGCAGCCATCAAAAGGGTGGAATGATTGGGAGAATGTGCCCTTCTGTTCCCACCACTTCCATGA : | 9792 |
| (SEQ ID NO: 9) | B-P1_conse | : ATCTGAATGCAGCCATCAAAAGGGTGGAATGATTGGGAGAATGTGCCCTTCTGTTCCCACCACTTCCATGA : | 9753 |
| (SEQ ID NO: 10) | C-P1_genom | : ATCTGAATGCAGCCATCAAAAGGGTGGAATGATTGGGAGAATGTGCCCTTCTGTTCCCACCACTTCCATGA : | 9753 |
| (SEQ ID NO: 11) | B3-P11_con | : ATCTGAATGCAGCCATCAAAAGGGTGGAATGATTGGGAGAATGTGCCCTTCTGTTCCCACCACTTCCATGA : | 9767 |
| (SEQ ID NO: 12) | C1-P11_con | : ATCTGAATGCAGCCATCAAAAGGGTGGAATGATTGGGAGAATGTGCCCTTCTGTTCCCACCACTTCCATGA : | 9751 |

| | | | |
|---|---|---|---|
| (SEQ ID NO: 15) | P1_consens | : ACTACAGCTGAAGGATGGCAGGAGGATTGTGTGCCTTGCCGAGAACAGGACGAGCTCATTGGGAGAGGAAG : | 9864 |
| (SEQ ID NO: 9) | B-P1_conse | : ACTACAGCTGAAGGATGGCAGGAGGATTGTGTGCCTTGCCGAGAACAGGACGAGCTCATTGGGAGAGGAAG : | 9825 |
| (SEQ ID NO: 10) | C-P1_genom | : ACTACAGCTGAAGGATGGCAGGAGGATTGTGTGCCTTGCCGAGAACAGGACGAGCTCATTGGGAGAGGAAG : | 9825 |
| (SEQ ID NO: 11) | B3-P11_con | : ACTACAGCTGAAGGATGGCAGGAGGATTGTGTGCCTTGCCGAGAACAGGACGAGCTCATTGGGAGAGGAAG : | 9839 |
| (SEQ ID NO: 12) | C1-P11_con | : ACTACAGCTGAAGGATGGCAGGAGGATTGTGTGCCTTGCCGAGAACAGGACGAGCTCATTGGGAGAGGAAG : | 9823 |

| | | | |
|---|---|---|---|
| (SEQ ID NO: 15) | P1_consens | : GGTGTCTCCAGGAAACGGCTGATGATCAAGGAAACAGCTTGCCTCAGCAAAGCCTATGCCAACATGTGGTC : | 9936 |
| (SEQ ID NO: 9) | B-P1_conse | : GGTGTCTCCAGGAAACGGCTGATGATCAAGGAAACAGCTTGCCTCAGCAAAGCCTATGCCAACATGTGGTC : | 9897 |
| (SEQ ID NO: 10) | C-P1_genom | : GGTGTCTCCAGGAAACGGCTGATGATCAAGGAAACAGCTTGCCTCAGCAAAGCCTATGCCAACATGTGGTC : | 9897 |
| (SEQ ID NO: 11) | B3-P11_con | : GGTGTCTCCAGGAAACGGCTGATGATCAAGGAAACAGCTTGCCTCAGCAAAGCCTATGCCAACATGTGGTC : | 9911 |
| (SEQ ID NO: 12) | C1-P11_con | : GGTGTCTCCAGGAAACGGCTGATGATCAAGGAAACAGCTTGCCTCAGCAAAGCCTATGCCAACATGTGGTC : | 9895 |

| | | | |
|---|---|---|---|
| (SEQ ID NO: 15) | P1_consens | : ACTGATGTATTTCACAAAAGGGACATGAGGCTACTGTCATTGGCTGTTCCTCAGCTGTTCCTCCACCTCATG : | 10008 |
| (SEQ ID NO: 9) | B-P1_conse | : ACTGATGTATTTCACAAAAGGGACATGAGGCTACTGTCATTGGCTGTTCCTCAGCTGTTCCTCCACCTCATG : | 9969 |
| (SEQ ID NO: 10) | C-P1_genom | : ACTGATGTATTTCACAAAAGGGACATGAGGCTACTGTCATTGGCTGTTCCTCAGCTGTTCCTCCACCTCATG : | 9969 |
| (SEQ ID NO: 11) | B3-P11_con | : ACTGATGTATTTCACAAAAGGGACATGAGGCTACTGTCATTGGCTGTTCCTCAGCTGTTCCTCCACCTCATG : | 9983 |
| (SEQ ID NO: 12) | C1-P11_con | : ACTGATGTATTTCACAAAAGGGACATGAGGCTACTGTCATTGGCTGTTCCTCAGCTGTTCCTCCACCTCATG : | 9967 |

| | | | |
|---|---|---|---|
| (SEQ ID NO: 15) | P1_consens | : GGTTCCACAAGGACGCACAACATGGTCGATTCATGGGAAAGGGAGTGGATGACCACGAAGACATGCTTGA : | 10080 |
| (SEQ ID NO: 9) | B-P1_conse | : GGTTCCACAAGGACGCACAACATGGTCGATTCATGGGAAAGGGAGTGGATGACCACGAAGACATGCTTGA : | 10041 |
| (SEQ ID NO: 10) | C-P1_genom | : GGTTCCACAAGGACGCACAACATGGTCGATTCATGGGAAAGGGAGTGGATGACCACGAAGACATGCTTGA : | 10041 |
| (SEQ ID NO: 11) | B3-P11_con | : GGTTCCACAAGGACGCACAACATGGTCGATTCATGGGAAAGGGAGTGGATGACCACGAAGACATGCTTGA : | 10055 |
| (SEQ ID NO: 12) | C1-P11_con | : GGTTCCACAAGGACGCACAACATGGTCGATTCATGGGAAAGGGAGTGGATGACCACGAAGACATGCTTGA : | 10039 |

| | | | |
|---|---|---|---|
| (SEQ ID NO: 15) | P1_consens : | GCTGGAGAACCGGACTCCGCACTTAAAATGAAACAGAACGGATAAAAACTACGATGAGAACCGGACT | : 10512 |
| (SEQ ID NO: 9) | B-P1_conse : | GCTGGAGAACCGGACTCCGCACTTAAAATGAAACAGAACGGATAAAAACTACGATGAGAACCGGACT | : 10473 |
| (SEQ ID NO: 10) | C-P1_genom : | GCTGGAGAACCGGACTCCGCACTTAAAATGAAACAGAACGGATAAAAACTACGATGAGAACCGGACT | : 10473 |
| (SEQ ID NO: 11) | B3-P11_con : | GCTGGAGAACCGGACTCCGCACTTAAAATGAAACAGAACGGATAAAAACTACGATGAGAACCGGACT | : 10487 |
| (SEQ ID NO: 12) | C1-P11_con : | GCTGGAGAACCGGACTCCGCACTTAAAATGAAACAGAACGGATAAAAACTACGATGAGAACCGGACT | : 10471 |
| (SEQ ID NO: 15) | P1_consens : | CCACACATTGAGACAGAAGAAGTTGTCAGCCCAGAACCCCACACGAGTTTTGCCACTGCTAAGCTGTGAGGC | : 10584 |
| (SEQ ID NO: 9) | B-P1_conse : | CCACACATTGAGACAGAAGAAGTTGTCAGCCCAGAACCCCACACGAGTTTTGCCACTGCTAAGCTGTGAGGC | : 10545 |
| (SEQ ID NO: 10) | C-P1_genom : | CCACACATTGAGACAGAAGAAGTTGTCAGCCCAGAACCCCACACGAGTTTTGCCACTGCTAAGCTGTGAGGC | : 10545 |
| (SEQ ID NO: 11) | B3-P11_con : | CCACACATTGAGACAGAAGAAGTTGTCAGCCCAGAACCCCACACGAGTTTTGCCACTGCTAAGCTGTGAGGC | : 10559 |
| (SEQ ID NO: 12) | C1-P11_con : | CCACACATTGAGACAGAAGAAGTTGTCAGCCCAGAACCCCACACGAGTTTTGCCACTGCTAAGCTGTGAGGC | : 10543 |
| (SEQ ID NO: 15) | P1_consens : | AGTGCAGGCTGGGACAGCCGACCTCCAGGTTGCGAAAAAACCTGGTTTCTCGGGACCTCCCACCCCAGAGTAAA | : 10656 |
| (SEQ ID NO: 9) | B-P1_conse : | AGTGCAGGCTGGGACAGCCGACCTCCAGGTTGCGAAAAAACCTGGTTTCTCGGGACCTCCCACCCCAGAGTAAA | : 10617 |
| (SEQ ID NO: 10) | C-P1_genom : | AGTGCAGGCTGGGACAGCCGACCTCCAGGTTGCGAAAAAACCTGGTTTCTCGGGACCTCCCACCCCAGAGTAAA | : 10617 |
| (SEQ ID NO: 11) | B3-P11_con : | AGTGCAGGCTGGGACAGCCGACCTCCAGGTTGCGAAAAAACCTGGTTTCTCGGGACCTCCCACCCCAGAGTAAA | : 10631 |
| (SEQ ID NO: 12) | C1-P11_con : | AGTGCAGGCTGGGACAGCCGACCTCCAGGTTGCGAAAAAACCTGGTTTCTCGGGACCTCCCACCCCAGAGTAAA | : 10615 |
| (SEQ ID NO: 15) | P1_consens : | AAGAACGGAGCCCTTCCGCTACCACCCTCCCACACGTGGTGGTAGAAAGACGGGGTCTAGAGGTTAGAGGAGACCC | : 10728 |
| (SEQ ID NO: 9) | B-P1_conse : | AAGAACGGAGCCCTTCCGCTACCACCCTCCCACACGTGGTGGTAGAAAGACGGGGTCTAGAGGTTAGAGGAGACCC | : 10689 |
| (SEQ ID NO: 10) | C-P1_genom : | AAGAACGGAGCCCTTCCGCTACCACCCTCCCACACGTGGTGGTAGAAAGACGGGGTCTAGAGGTTAGAGGAGACCC | : 10689 |
| (SEQ ID NO: 11) | B3-P11_con : | AAGAACGGAGCCCTTCCGCTACCACCCTCCCACACGTGGTGGTAGAAAGACGGGGTCTAGAGGTTAGAGGAGACCC | : 10703 |
| (SEQ ID NO: 12) | C1-P11_con : | AAGAACGGAGCCCTTCCGCTACCACCCTCCCACACGTGGTGGTAGAAAGACGGGGTCTAGAGGTTAGAGGAGACCC | : 10687 |
| (SEQ ID NO: 15) | P1_consens : | TCCAGGGAACAAATAGTGGGACCATATTGACGCCAGGGAAAGACCGGAGTGGTTCTCTGCTTTTCCTCCAGA | : 10800 |
| (SEQ ID NO: 9) | B-P1_conse : | TCCAGGGAACAAATAGTGGGACCATATTGACGCCAGGGAAAGACCGGAGTGGTTCTCTGCTTTTCCTCCAGA | : 10761 |
| (SEQ ID NO: 10) | C-P1_genom : | TCCAGGGAACAAATAGTGGGACCATATTGACGCCAGGGAAAGACCGGAGTGGTTCTCTGCTTTTCCTCCAGA | : 10761 |
| (SEQ ID NO: 11) | B3-P11_con : | TCCAGGGAACAAATAGTGGGACCATATTGACGCCAGGGAAAGACCGGAGTGGTTCTCTGCTTTTCCTCCAGA | : 10775 |
| (SEQ ID NO: 12) | C1-P11_con : | TCCAGGGAACAAATAGTGGGACCATATTGACGCCAGGGAAAGACCGGAGTGGTTCTCTGCTTTTCCTCCAGA | : 10759 |

FIG. 8DD

```
                     *        10820         *        10840         *        10860
(SEQ ID NO: 15) P1_consens  : GGTCTGTGAGCACAGTTTGCTCAAGAATAAGCAGACCTTTGGATGACAAACACAAAACCACT : 10862
(SEQ ID NO: 9)  B-P1_conse  : GGTCTGTGAGCACACAG-------------------------------------------- : 10776
(SEQ ID NO: 10) C-P1_genom  : GGTCTGTGAGCACAGTTTGCTCAAGAA---------------------------------- : 10788
(SEQ ID NO: 11) B3-P11_con  : GGTCTGTGAGCACAGTTTGCTCAAGAATAAGCAGAC------------------------- : 10811
(SEQ ID NO: 12) C1-P11_con  : GGTCTGTGAGCACAGTTTGCTCAAGA----------------------------------- : 10785
```

FIG. 8EE

|  |  |  |  |
|---|---|---|---|
| (SEQ ID NO: 13) | B-P1_polyp | : MSGRKAQGKTLGVNMVRRGVRSLSNKIKQKTKQIGNRPGPSRGVQGFIFFFLFNILTGKKITAHLKRLWKMLD | 73 |
| (SEQ ID NO: 7) | B3-P11_pol | : MSGRKAQGKTLGVNMVRRGVRSLSNKIKQKTKQIGNRPGPSRGVQGFIFFFLFNILTGKKITAHLKRLWKMLD | 73 |
| (SEQ ID NO: 13) | B-P1_polyp | : PRQGLAVLRKVKRVVASLMRGLSSRKRRSHDVLTVQFLILGMLLMTGGVTLVRKNRWLLLNVTSEDLGKIFSV | 146 |
| (SEQ ID NO: 7) | B3-P11_pol | : PRQGLAVLRKVKRVVASLMRGLSSRKRRSHDVLTVQFLILGMLLMTGGVTLVRKNRWLLLNVTSEDLGKIFSV | 146 |
| (SEQ ID NO: 13) | B-P1_polyp | : GTGNCTTNILEAKYWCPDSMEYNCPNLSPREEPDDIDCWCYGVENVRVAYGKCDSAGRSRRSRRAIDLPTHEN | 219 |
| (SEQ ID NO: 7) | B3-P11_pol | : GTGNCTTNILEAKYWCPDSMEYNCPNLSPREEPDDIDCWCYGVENVRVAYGKCDSAGRSRRSRRAIDLPTHEN | 219 |
| (SEQ ID NO: 13) | B-P1_polyp | : HGLKTRQEKWMTGRMGERQLQKIERWFVRNPFFAVTALTIAYLVGSNMTQRVVIALLVLAVGPAYSAHCIGIT | 292 |
| (SEQ ID NO: 7) | B3-P11_pol | : HGLKTRQEKWMTGRMGERQLQKIERWFVRNPFFAVTALTIAYLVGSNMTQRVVIALLVLAVGPAYSAHCIGIT | 292 |
| (SEQ ID NO: 13) | B-P1_polyp | : DRDFIEGVHGGTWVSATLEQDKCVTVMAPDKPSLDISLETVAIDRPAEVRKVCYNAVLTHVKINDKCPSTGEA | 365 |
| (SEQ ID NO: 7) | B3-P11_pol | : DRDFIEGVHGGTWVSATLEQDKCVTVMAPDKPSLDISLETVAIDRPAEVRKVCYNAVLTHVKINDKCPSTGEA | 365 |
| (SEQ ID NO: 13) | B-P1_polyp | : HLAEENEGDNACKRTYSDRGWGNGCGLFGKGSIVACAKFTCAKSMSLFEVDQTKIQYVIRAQLHVGAKQENWT | 438 |
| (SEQ ID NO: 7) | B3-P11_pol | : HLAEENEGDNACKRTYSDRGWGNGCGLFGKGSIVACAKFTCAKSMSLFEVDQTKIQYVIRAQLHVGAKQENWT | 438 |
| (SEQ ID NO: 13) | B-P1_polyp | : TDIKTLKFDALSGSQEVEFIGYGKATLECQVQTAVDFGNSYIAEMETESWIVDRQWAQDLTLPWQSGSGGVWR | 511 |
| (SEQ ID NO: 7) | B3-P11_pol | : TDIKTLKFDALSGSQEVEFIGYGKATLECQVQTAVDFGNSYIAEMETESWIVDRQWAQDLTLPWQSGSGGVWR | 511 |
| (SEQ ID NO: 13) | B-P1_polyp | : EMHHLVEFEPPHAATIRVLALGNQEGSLKTALTGAMRVTKDTNDNNLYKLHGGHVSCRVKLSALTILKGISYKI | 584 |
| (SEQ ID NO: 7) | B3-P11_pol | : EMHHLVEFEPPHAATIRVLALGNQEGSLKTALTGAMRVTKDTNDNNLYKLHGGHVSCRVKLSALTILKGISYKI | 584 |

FIG. 9A

```
                              *         600         *         620         *         640         *
(SEQ ID NO:13) B-P1_polyp  : CTDKMFFVKNPTDTGHGTVVMQVKVSKGAPCRIPVIVADDLTAAINKGILVTVNPIASTNDDEVLIEVNPPFG :  657
(SEQ ID NO:7)  B3-P11_pol  : CTDKMFFVKNPTDTGHGTVVMQVKVSKGAPCRIPVIVADDLTAAINKGILVTVNPIASTNDDEVLIEVNPPFG :  657

660         *         680         *         700         *         720         *
(SEQ ID NO:13) B-P1_polyp  : DSYIIVGRGDSRLTYQWHKEGSSIGKLFTQTMKGVERLAVMGDTAWDFSSAGGFFTSVGKGIHTVFGSAFQGL :  730
(SEQ ID NO:7)  B3-P11_pol  : DSYIIVGRGDSRLTYQWHKEGSSIGKLFTQTMKGVERLAVMGDTAWDFSSAGGFFTSVGKGIHTVFGSAFQGL :  730

740         *         760         *         780         *         800
(SEQ ID NO:13) B-P1_polyp  : FGGLNWITKVIMGAVLIWVGINTRNMTMSMSMILVGVIMMFLSLGVGADQGCAINFGKRELKCGDGIFIFRDS :  803
(SEQ ID NO:7)  B3-P11_pol  : FGGLNWITKVIMGAVLIWVGINTRNMTMSMSMILVGVIMMFLSLGVGADQGCAINFGKRELKCGDGIFIFRDS :  803

*         820         *         840         *         860         *
(SEQ ID NO:13) B-P1_polyp  : DDWLNKYSYYPEDPVKLASIVKASFEEGKCGLNSVDSLEHEMWRSRADEINAIFEENEVDISVVVQDPKNVYQ :  876
(SEQ ID NO:7)  B3-P11_pol  : DDWLNKYSYYPEDPVKLASIVKASFEEGKCGLNSVDSLEHEMWRSRADEINAIFEENEVDISVVVQDPKNVYQ :  876

880         *         900         *         920         *         940
(SEQ ID NO:13) B-P1_polyp  : RGTHPFSRIRDGLQYGWKTWGKNLVFSPGRKNGSFIIDGKSRKECPFSNRVWNSFQIEEFGTGVFTTRVYMDA :  949
(SEQ ID NO:7)  B3-P11_pol  : RGTHPFSRIRDGLQYGWKTWGKNLVFSPGRKNGSFIIDGKSRKECPFSNRVWNSFQIEEFGTGVFTTRVYMDA :  949

*         960         *         980         *         1000        *         1020
(SEQ ID NO:13) B-P1_polyp  : VFEYTIDCDGSILGAAVNGKKSAHGSPTFWMGSHEVNGTWMIHTLEALDYKECEWPLIHTIGTSVEESEMFMP : 1022
(SEQ ID NO:7)  B3-P11_pol  : VFEYTIDCDGSILGAAVNGKKSAHGSPTFWMGSHEVNGTWMIHTLEALDYKECEWPLIHTIGTSVEESEMFMP : 1022

1040        *         1060        *         1080        *
(SEQ ID NO:13) B-P1_polyp  : RSIGGPVSSHNHIPGYKVQTNGPWMQVPLEVKREACPGTSVIIDGNCDGRGKSTRSTTDSGKVIPEWCCRSCT : 1095
(SEQ ID NO:7)  B3-P11_pol  : RSIGGPVSSHNHIPGYKVQTNGPWMQVPLEVKREACPGTSVIIDGNCDGRGKSTRSTTDSGKVIPEWCCRSC▨ : 1095

1100        *         1120        *         1140        *         1160
(SEQ ID NO:13) B-P1_polyp  : MPPVSFHGSDGCWYPMEIRPRKTHESHLVRSWVTAGEIHAVPFGLVSMMIAMEVVLRKRQGPKQMLVGGVVLL : 1168
(SEQ ID NO:7)  B3-P11_pol  : MPPVSFHGSDGCWYPMEIRPRKTHESHLVRSWVTAGEIHAVPFGLVSMMIAMEVVLRKRQGPKQMLVGGVVLL : 1168
```

FIG. 9B

```
(SEQ ID NO:13)  B-P1_polyp :  GAMLVGQVTLLDLLKLTVAVGLHFHEMNNGGDAMYMALIAAFSIRPGLLIGFGLRTLWSPRERLVLTLGAAMV : 1241
(SEQ ID NO:7)   B3-P11_pol :  GAMLVGQVTLLDLLKLTVAVGLHFHEMNNGGDAMYMALIAAFSIRPGLLIGFGLRTLWSPRERLVLTLGAAMV : 1241

(SEQ ID NO:13)  B-P1_polyp :  EIALGGVMGGLWKYLNAVSLCILTINAVASRKASNTILPLMALLTPVTMAEVRLAAMFFCAVVIIGVLHQNFK : 1314
(SEQ ID NO:7)   B3-P11_pol :  EIALGGVMGGLWKYLNAVSLCILTINAVASRKASNTILPLMALLTPVTMAEVRLAAMF CAVVIIGVLHQNFK : 1314

(SEQ ID NO:13)  B-P1_polyp :  DTSMQKTIPLVALTLTSYLGLTQPFLGLCAFLATRIFGRRSIPVNEALAAAGLVGVLAGLAFQEMENFLGPIA : 1387
(SEQ ID NO:7)   B3-P11_pol :  DTSMQKTIPLVALTLTSYLGLTQPFLGLCAFLATRIFGRRSIPVNEALAAAGLVGVLAGLAFQEMENFLGPIA : 1387

(SEQ ID NO:13)  B-P1_polyp :  VGGLLMMLVSVAGRVDGLELKKLGEVSWEEEAEISGSSARYDVALSEQGEFKLLSEEKVPWDQVVMTSLALVG : 1460
(SEQ ID NO:7)   B3-P11_pol :  VGGLLMMLVSVAGRVDGLELKKLGEVSWEEEAEISGSSARYDVALSEQGEFKLLSEEKVPWDQVVMTSLALVG : 1460

(SEQ ID NO:13)  B-P1_polyp :  AALHPFALLLVLAGWLFHVRGARRSGDVLWDIPTPKIIEECEHLEDGIYGIFQSTFLGASQRGVGVAQGGVFH : 1533
(SEQ ID NO:7)   B3-P11_pol :  AALHPFALLLVLAGWLFHVRGARRSGDVLWDIPTPKIIEECEHLEDGIYGIFQSTFLGASQRGVGVAQGGVFH : 1533

(SEQ ID NO:13)  B-P1_polyp :  TMWHVTRGAFLVRNGKKLIPSWASVKEDLVAYGGSWKLEGRWDGEEEVQLIAAVPGKNVNVQTKPSLFKVRN : 1606
(SEQ ID NO:7)   B3-P11_pol :  TMWHVTRGAFLVRNGKKLIPSWASVKEDLVAYGGSWKLEGRWDGEEEVQLIAAVPGKNVNVQTKPSLFKVRN : 1606

(SEQ ID NO:13)  B-P1_polyp :  GGEIGAVALDYPSGTSGSPIVNRNGEVIGLYGNGILVGDNSFVSAISQTEVKEEGKEELQEIPTMLKKGMTTV : 1679
(SEQ ID NO:7)   B3-P11_pol :  GGEIGAVALDYPSGTSGSPIVNRNGEVIGLYGNGILVGDNSFVSAISQTEVKEEGKEELQEIPTMLKKGMTTV : 1679

(SEQ ID NO:13)  B-P1_polyp :  LDFHPGAGKTRRFLPQILAECARRRLRTLVLAPTRVVLSEMKEAFHGLDVKFHTQAFSAHGSGREVIDAMCHA : 1752
(SEQ ID NO:7)   B3-P11_pol :  LDFHPGAGKTRRFLPQILAECARRRLRTLVLAPTRVVLSEMKEAFHGLDVKFHTQAFSAHGSGREVIDAMCHA : 1752
```

FIG. 9C

| | | | |
|---|---|---|---|
| | | 1760 * 1780 * 1800 * 1820 | |
| (SEQ ID NO: 13) | B-P1_polyp : | TLTYRMLEPTRVVNWEVIIMDEAHFLDPASIAARGWAAHRARANESATILMTATPPGTSDEFPHSNGEIEDVQ | : 1825 |
| (SEQ ID NO: 7) | B3-P11_pol : | TLTYRMLEPTRVVNWEVIIMDEAHFLDPASIAARGWAAHRARANESATILMTATPPGTSDEFPHSNGEIEDVQ | : 1825 |
| | | * 1840 * 1860 * 1880 * 19 | |
| (SEQ ID NO: 13) | B-P1_polyp : | TDIPSEPWNTGHDWILADKRPTAWFLPSIRAANVMAASLRKAGKSVVVLNRKTFEREYPTIKQKKPDFILATD | : 1898 |
| (SEQ ID NO: 7) | B3-P11_pol : | TDIPSEPWNTGHDWILADKRPTAWFLPSIRAANVMAASLRKAGKSVVVLNRKTFEREYPTIKQKKPDFILATD | : 1898 |
| | | 00 * 1920 * 1940 * 1960 * | |
| (SEQ ID NO: 13) | B-P1_polyp : | IAEMGANLCVERVLDCRTAFKPVLVDEGRKVAIKGPLRISASSAAQRRGRIGRNPNRDGDSYYYSEPTSENNA | : 1971 |
| (SEQ ID NO: 7) | B3-P11_pol : | IAEMGANLCVERVLDCRTAFKPVLVDEGRKVAIKGPLRISASSAAQRRGRIGRNPNRDGDSYYYSEPTSENNA | : 1971 |
| | | 1980 * 2000 * 2020 * 2040 | |
| (SEQ ID NO: 13) | B-P1_polyp : | HHVCWLEASMLLDNMEVRGGMVAPLYGVEGTKTPVSPGEMRLRDDQRKVFRELVRNCDLPVWLSWQVAKAGLK | : 2044 |
| (SEQ ID NO: 7) | B3-P11_pol : | HHVCWLEASMLLDNMEVRGGMVAPLYGVEGTKTPVSPGEMRLRDDQRKVFRELVRNCDLPVWLSWQVAKAGLK | : 2044 |
| | | * 2060 * 2080 * 2100 * 2 | |
| (SEQ ID NO: 13) | B-P1_polyp : | TNDRKWCFEGPEEHEILNDSGETVKCRAPGGAKKPLRPWCDERVSSDQSALSEFIKFAEGRRGAAEVLVVLS | : 2117 |
| (SEQ ID NO: 7) | B3-P11_pol : | TNDRKWCFEGPEEHEILNDSGETVKCRAPGGAKKPLRPWCDERVSSDQSALSEFIKFAEGRRGAAEVLVVLS | : 2117 |
| | | 120 * 2140 * 2160 * 2180 * | |
| (SEQ ID NO: 13) | B-P1_polyp : | ELPDFLAKKGGEAMDTISVFLHSEEGSRAYRNALSMMPEAMTIVMLFILAGLLTSGMVIFFMSPKGISRMSMA | : 2190 |
| (SEQ ID NO: 7) | B3-P11_pol : | ELPDFLAKKGGEAMDTISVFLHSEEGSRAYRNALSMMPEAMTIVMLFILAGLLTSGMVIFFMSPKGISRMSMA | : 2190 |
| | | * 2200 * 2220 * 2240 * 2260 | |
| (SEQ ID NO: 13) | B-P1_polyp : | MGTMAGCGYLMFLGGVKPTHISYIMLIFFVLMVVVIPEPGQQRSIQDNQVAYLIIGILTLVSAVAANELGMLE | : 2263 |
| (SEQ ID NO: 7) | B3-P11_pol : | MGTMAGCGYLMFLGGVKPTHISYIMLIFFVLMVVVIPEPGQQRSIQDNQVAYLIIGILTLVSAVAANELGMLE | : 2263 |
| | | * 2280 * 2300 * 2320 * | |
| (SEQ ID NO: 13) | B-P1_polyp : | KTIKEDLFGKKNLIPSSASPWSWPDLDLKPGAAWTVYVGIVTMLSPMLHHWIKVEYGNLSLSGIAQSASVLSFM | : 2336 |
| (SEQ ID NO: 7) | B3-P11_pol : | KTIKEDLFGKKNLIPSSASPWSWPDLDLKPGAAWTVYVGIVTMLSPMLHHWIKVEYGNLSLSGIAQSASVLSFM | : 2336 |

FIG. 9D

```
                          2340              *              2360              *              2380              *              2400              *
(SEQ ID NO: 13) B-P1_polyp : DKGIPFMKMNISVIMLLVSGWNSITVMPLLCGIGCAMLHWSLILPGIKAQQSKLAQRRVFHGVAKNPVVDGNP : 2409
(SEQ ID NO: 7)  B3-P11_pol : DKGIPFMKMNISVIMLLVSGWNSITVMPLLCGIGCAMLHWSLILPGIKAQQSKLAQRRVFHGVAKNPVVDGNP : 2409

*              2420              *              2440              *              2460              *              2480
(SEQ ID NO: 13) B-P1_polyp : TVDIEEAPEMPALYEKKLALYLLLALSLASVAMCRTPFSLAEGIVLASAALGPLIEGNTSLLWNGPMAVSMTG : 2482
(SEQ ID NO: 7)  B3-P11_pol : TVDIEEAPEMPALYEKKLALYLLLALSLASVAMCRTPFSLAEGIVLASAALGPLIEGNTSLLWNGPMAVSMTG : 2482

*              2500              *              2520              *              2540              *
(SEQ ID NO: 13) B-P1_polyp : VMRGNHYAFVGVMYNLWKMKTGRRGSANGKTLGEVWKRELNLLDKRQFELYKRIDIVEVDRDTARRHLAEGKV : 2555
(SEQ ID NO: 7)  B3-P11_pol : VMRGNHYAFVGVMYNLWKMKTGRRGSANGKTLGEVWKRELNLLDKRQFELYKRIDIVEVDRDTARRHLAEGKV : 2555

2560              *              2580              *              2600              *              2620              *
(SEQ ID NO: 13) B-P1_polyp : DIGVAVSRGTAKLRWFHERGYVKLEGRVIDLGCGRGGWCYYAAAQKEVSGVKGFTLGRDGHEKPMNVQSLGWN : 2628
(SEQ ID NO: 7)  B3-P11_pol : DIGVAVSRGTAKLRWFHERGYVKLEGRVIDLGCGRGGWCYYAAAQKEVSGVKGFTLGRDGHEKPMNVQSLGWN : 2628

*              2640              *              2660              *              2680              *              2700
(SEQ ID NO: 13) B-P1_polyp : IITFKDKTDIHRLEPVKCDILLCDIGESSSSVIEGERIVRVLDTVEKWLACGVDNFCVKVLAPYMPDVLEKL : 2701
(SEQ ID NO: 7)  B3-P11_pol : IITFKDKTDIHRLEPVKCDILLCDIGESSSSVIEGERIVRVLDTVEKWLACGVDNFCVKVLAPYMPDVLEKL : 2701

*              2720              *              2740              *              2760              *
(SEQ ID NO: 13) B-P1_polyp : ELLQRRFGGTVIRMPLSRNSTHEMYYVSGARSNVTFTVNQTSRLLMRRMRRPTGKVTLEADVILPIGTRSVET : 2774
(SEQ ID NO: 7)  B3-P11_pol : ELLQRRFGGTVIRMPLSRNSTHEMYYVSGARSNVTFTVNQTSRLLMRRMRRPTGKVTLEADVILPIGTRSVET : 2774

2780              *              2800              *              2820              *              2840              *
(SEQ ID NO: 13) B-P1_polyp : DKGPLDKEALEEERVERIKSEYMTSWFYDNDNPYRTHHYCGSYVTKTSGSAASMVNGVIKILTYPWDRIEEVTR : 2847
(SEQ ID NO: 7)  B3-P11_pol : DKGPLDKEALEEERVERIKSEYMTSWFYDNDNPYRTHHYCGSYVTKTSGSAASMVNGVIKILTYPWDRIEEVTR : 2847

*              2860              *              2880              *              2900              *              2920
(SEQ ID NO: 13) B-P1_polyp : NAMIDTTPFSQQRVFKEKVDTRAKDPPAGTRKIMKVVNRWLFRHLAEKNPRLCTNEEFIAKVRSHAAIGAYL : 2920
(SEQ ID NO: 7)  B3-P11_pol : NAMIDTTPFSQQRVFKEKVDTRAKDPPAGTRKIMKVVNRWLFRHLAEKNPRLCTKEEFIAKVRSRAAIGAYL : 2920
```

FIG. 9E

```
                              *      2940         *      2960         *      2980         *
(SEQ ID NO:13)  B-P1_polyp : EEQEQWKTANEAVQDPKFWELVDEERKLHQQGRCRTCVYNMGKREKKLSEFGKAKGSRAIWYMWLGARYLEF : 2993
(SEQ ID NO:7)   B3-P11_pol : EEQEQWKTANEAVQDPKFWELVDEERKLHQQGRCRTCVYNMGKREKKLSEFGKAKGSRAIWYMWLGARYLEF : 2993

3000         *      3020         *      3040         *      3060
(SEQ ID NO:13)  B-P1_polyp : EALGFLNEDHWASRENSGGGVEGIGLQYLGYVIRDLAAMDGGGFYADDTAGWDTRITEADLDDEQEILNYMSP : 3066
(SEQ ID NO:7)   B3-P11_pol : EALGFLNEDHWASRENSGGGVEGIGLQYLGYVIRDLAAMDGGGFYADDTAGWDTRITEADLDDEQEILNYMSP : 3066

*      3080         *      3100         *      3120         *      314
(SEQ ID NO:13)  B-P1_polyp : HHKKLAQAVMEMTYKNKVVKVLRPAPGGKAYMDVISRRDQRGSGQVVTYALNTITNLKVQLIRMAEAEMVIHH : 3139
(SEQ ID NO:7)   B3-P11_pol : HHKKLAQAVMEMTYKNKVVKVLRPAPGGKAYMDVISRRDQRGSGQVVTYALNTITNLKVQLIRMAEAEMVIHH : 3139

0         *      3160         *      3180         *      3200         *
(SEQ ID NO:13)  B-P1_polyp : QHVQDCDESVLTRLEAWLTEHGCNRLKRMAVSGDDCVVRPIDDRFGLALSHLNAMSKVRKDISEWQPSKGWND : 3212
(SEQ ID NO:7)   B3-P11_pol : QHVQDCDESVLTRLEAWLTEHGCNRLKRMAVSGDDCVVRPIDDRFGLALSHLNAMSKVRKDISEWQPSKGWND : 3212

3220         *      3240         *      3260         *      3280
(SEQ ID NO:13)  B-P1_polyp : WENVPFCSHHFHELQLKDGRRIVVPCREQDELIGRGRVSPGNGWMIKETACLSKAYANMWSLMYFHKRDMRLL : 3285
(SEQ ID NO:7)   B3-P11_pol : WENVPFCSHHFHELQLKDGRRIVVPCREQDELIGRGRVSPGNGWMIKETACLSKAYANMWSLMYFHKRDMRLL : 3285

*      3300         *      3320         *      3340         *      33
(SEQ ID NO:13)  B-P1_polyp : SLAVSSAVPTSWVPQGRTTWSIHGKGEWMTTEDMLEVWNRVWITNNPHMQDKTMVKKWRDVPYLTKRQDKLCG : 3358
(SEQ ID NO:7)   B3-P11_pol : SLAVSSAVPTSWVPQGRTTWSIHGKGEWMTTEDMLEVWNRVWITNNPHMQDKTMVKKWRDVPYLTKRQDKLCG : 3358

60         *      3380         *      3400         *
(SEQ ID NO:13)  B-P1_polyp : SLIGMTNRATWASHIHLVIHRIRTLIGQEKYTDYLTVMDRYSVDADLQLGELI : 3411
(SEQ ID NO:7)   B3-P11_pol : SLIGMTNRATWASHIHLVIHRIRTLIGQEKYTDYLTVMDRYSVDADLQLGELI : 3411
```

FIG. 9F

| | | | |
|---|---|---|---|
| | | * 20 * 40 * 60 * | |
| (SEQ ID NO: 14) | C-P1_polyp : | MSGRKAQGKTLGVNMVRRGVRSLSNKIKQKTKQIGNRPGPSRGVQGFIFFFLFNILTGKKITAHLKRLWKMLD : | 73 |
| (SEQ ID NO: 8) | C1-P11_pol : | MSGRKAQGKTLGVNMVRRGVRSLSNKIKQKTKQIGNRPGPSRGVQGFIFFFLFNILTGKKITAHLKRLWKMLD : | 73 |
| | | * 80 * 100 * 120 * 140 | |
| (SEQ ID NO: 14) | C-P1_polyp : | PRQGLAVLRKVKRVVASLMRGLSSRKKRRSHDVLITVQFLILGMLLMTGGVTLVRKNRWLLNVTSEDLGKTFSV : | 146 |
| (SEQ ID NO: 8) | C1-P11_pol : | PRQGLAVLRKVKRVVASLMRGLSSRKKRRSHDVLITVQFLILGMLLMTGGVTLVRKNRWLLNVTSEDLGKTFSV : | 146 |
| | | * 160 * 180 * 200 * 220 | |
| (SEQ ID NO: 14) | C-P1_polyp : | GTGNCTTNILEAKYWCPDSMEYNCPNLSPREEPDDIDCWCYGVENVRVAYGKCDSAGRSRRSRRAIDLPTHEN : | 219 |
| (SEQ ID NO: 8) | C1-P11_pol : | GTGNCTTNILEAKYWCPDSMEYNCPNLSPREEPDDIDCWCYGVENVRVAYGKCDSAGRSRRSRRAIDLPTHEN : | 219 |
| | | * 240 * 260 * 280 * | |
| (SEQ ID NO: 14) | C-P1_polyp : | HGLKTRQEKWMTGRMGERQLQKIERWFVRNPFFAVTALTIAYLVGSNMTQRVVIALLVLAVGPAYSAHCIGIT : | 292 |
| (SEQ ID NO: 8) | C1-P11_pol : | HGLKTRQEKWMTGRMGERQLQKIERWFVRNPFFAVTALTIAYLVGSNMTQRVVIALLVLAVGPAYSAHCIGIT : | 292 |
| | | * 300 * 320 * 340 * 360 | |
| (SEQ ID NO: 14) | C-P1_polyp : | DRDFIEGVHGGTWVSATLEQDKCVTVMAPDKPSLDISLETVAIDRPAEVRKVCYNAVLTHVKINDKCPSTGEA : | 365 |
| (SEQ ID NO: 8) | C1-P11_pol : | DRDFIEGVHGGTWVSATLEQDKCVTVMAPDKPSLDISLETVAIDRPAEVRKVCYNAVLTHVKINDKCPSTGEA : | 365 |
| | | * 380 * 400 * 420 * | |
| (SEQ ID NO: 14) | C-P1_polyp : | HLAEENEGDNACKRTYSDRGWGNGCGLFGKGSIVACAKFTCAKSMSLFEVDQTKIQYVIRAQLHVGAKQENWT : | 438 |
| (SEQ ID NO: 8) | C1-P11_pol : | HLAEENEGDNACKRTYSDRGWGNGCGLFGKGSIVACAKFTCAKSMSLFEVDQTKIQYVIRAQLHVGAKQENWT : | 438 |
| | | 440 * 460 * 480 * 500 * | |
| (SEQ ID NO: 14) | C-P1_polyp : | TDIKTLKFDALSGSQEVEFIGYGKATLECQVQTAVDFGNSYIAEMETESWIVDRQWAQDLITLPWQSGSGGVWR : | 511 |
| (SEQ ID NO: 8) | C1-P11_pol : | TDIKTLKFDALSGSQEVEFIGYGKATLECQVQTAVDFGNSYIAEMETESWIVDRQWAQDLITLPWQSGSGGVWR : | 511 |
| | | 520 * 540 * 560 * 580 | |
| (SEQ ID NO: 14) | C-P1_polyp : | EMHHLVEFEPPHAATIRVLALGNQEGSLKTALTGAMRVTKDTNDNNLYKLHGGHVSCRVKLSALTLKGTSYKI : | 584 |
| (SEQ ID NO: 8) | C1-P11_pol : | EMHHLVEFEPPHAATIRVLALGNQEGSLKTALTGAMRVTKDTNDNNLYKLHGGHVSCRVKLSALTLKGTSYKI : | 584 |

FIG. 10A

| | | | |
|---|---|---|---|
| (SEQ ID NO: 14) | C-P1_polyp | : CTDKMFFVKNPTDIGHGTVVMQVKVSKGAPCRIPVIVADDLTAAINKGILVTVNPIASTNDDEVLIEVNPPFG | : 657 |
| (SEQ ID NO: 8) | C1-P11_pol | : CTDKMFFVKNPTDIGHGTVVMQVKVSKGAPCRIPVIVADDLTAAINKGILVTVNPIASTNDDEVLIEVNPPFG | : 657 |
| (SEQ ID NO: 14) | C-P1_polyp | : DSYIIVGRGDSRLTYQWHKEGSSIGKLFTQTMKGVERLAVMGDTAWDFSSAGGFFTSVGKGIHTVFGSAFQGL | : 730 |
| (SEQ ID NO: 8) | C1-P11_pol | : DSYIIVGRGDSRLTYQWHKEGSSIGKLFTQTMKGVERLAVMGDTAWDFSSAGGFFTSVGKGIHTVFGSAFQGL | : 730 |
| (SEQ ID NO: 14) | C-P1_polyp | : FGGLNWITKVIMGAVLIWVGINTRNMTMSMSMILVGVIMFLSLGVGADQGCAINFGKRELKCGDGIFIFRDS | : 803 |
| (SEQ ID NO: 8) | C1-P11_pol | : FGGLNWITKVIMGAVLIWVGINTRNMTMSMSMILVGVIMFLSLGVGADQGCAINFGKRELKCGDGIFIFRDS | : 803 |
| (SEQ ID NO: 14) | C-P1_polyp | : DDWLNKYSYPEDPVKLASIVKASFEEGKCGLNSVDSLEHEMWRSRADEINAIFEENEVDISVVVQDPKNVYQ | : 876 |
| (SEQ ID NO: 8) | C1-P11_pol | : DDWLNKYSYPEDPVKLASIVKASFEEGKCGLNSVDSLEHEMWRSRADEINAIFEENEVDISVVVQDPKNVYQ | : 876 |
| (SEQ ID NO: 14) | C-P1_polyp | : RGTHPFSRIRDGLQYGWKTWGKNLVFSPGRKNGSFIIDGKSRKECPFSNRVWNSFQIEEFGTGVFTTRVYMDA | : 949 |
| (SEQ ID NO: 8) | C1-P11_pol | : RGTHPFSRIRDGLQYGWKTWGKNLVFSPGRKNGSFIIDGKSRKECPFSNRVWNSFQIEEFGTGVFTTRVYMDA | : 949 |
| (SEQ ID NO: 14) | C-P1_polyp | : VFEYTIDCDGSILGAAVNGKKSAHGSPTFWMGSHEVNGTWMIHTLEALDYKECEWPLTHTIGTSVEESEMFMP | : 1022 |
| (SEQ ID NO: 8) | C1-P11_pol | : VFEYTIDCDGSILGAAVNGKKSAHGSPTFWMGSHEVNGTWMIHTLEALDYKECEWPLTHTIGTSVEESEMFMP | : 1022 |
| (SEQ ID NO: 14) | C-P1_polyp | : RSIGGPVSSHNHIPGYKVQTNGPWMQVPLEVKREACPGTSVIIDGNCDGRGKSTRSTTDSGKVIPEWCCRSCI | : 1095 |
| (SEQ ID NO: 8) | C1-P11_pol | : RSIGGPVSSHNHIPGYKVQTNGPWMQVPLEVKREACPGTSVIIDGNCDGRGKSTRSTTDSGKVIPEWCCRSCI | : 1095 |
| (SEQ ID NO: 14) | C-P1_polyp | : MPPVSFHGSDGCWYPMEIRPRKTHESHLVRSWVTAGEIHAVPFGLVSMMIAMEVVLRKRQGPKQMLVGGVVLL | : 1168 |
| (SEQ ID NO: 8) | C1-P11_pol | : MPPVSFHGSDGCWYPMEIRPRKTHESHLVRSWVTAGEIHAVPFGLVSMMIAMEVVLRKRQGPKQMLVGGVVLL | : 1168 |

FIG. 10B

```
YF114-US
                           *      1180         *      1200         *      1220         *      1240
(SEQ ID NO: 14)  C-P1_polyp  : GAMLVGQVTLLDLLKLTVAVGLHFHEMNNGGDAMYMALIAAFSIRPGLLIGFGLRTLWSPRERLVLTLGAAMV : 1241
(SEQ ID NO: 8)   C1-P11_pol  : GAMLVGQVTLLDLLKLTVAVGLHFHEMNNGGDAMYMALIAAFSIRPGLLIGFGLRTLWSPRERLVLTLGAAMV : 1241

*      1260         *      1280         *      1300         *
(SEQ ID NO: 14)  C-P1_polyp  : EIALGGVMGGLWKYLNAVSLCILTINAVASRKASNTILPLMALLTPVTMAEVRLAAMFFCAVVIIGVLHQNFK : 1314
(SEQ ID NO: 8)   C1-P11_pol  : EIALGGVMGGLWKYLNAVSLCILTINAVASRKASNTILPLMALLTPVTMAEVRLAAMFFCAVVIIGVLHQNFK : 1314

1320         *      1340         *      1360         *      1380
(SEQ ID NO: 14)  C-P1_polyp  : DTSMQKTIPLVALTLTSYLGLTQPFLGLCAFLATRIFGRRSIPVNEALAAAGLVGVLAGLAFQEMENFLGPIA : 1387
(SEQ ID NO: 8)   C1-P11_pol  : DTSMQKTIPLVALTLTSYLGLTQPFLGLCAFLATRIFGRRSIPVNEALAAAGLVGVLAGLAFQEMENFLGPIA : 1387

*      1400         *      1420         *      1440         *      1460
(SEQ ID NO: 14)  C-P1_polyp  : VGGLLMMLVSVAGRVDGLELKKLGEVSWEEEAEISGSSARYDVALSEQGEFKLLSEEKVPWDQVVMTSLALVG : 1460
(SEQ ID NO: 8)   C1-P11_pol  : VGGLLMMLVSVAGRVDGLELKKLGEVSWEEEAEISGSSARYDVALSEQGEFKLLSEEKVPWDQVVMTSLALVG : 1460

*      1480         *      1500         *      1520         *
(SEQ ID NO: 14)  C-P1_polyp  : AALHPFALLLVLAGWLFHVRGARRSGDVLWDIPTPKIIEECEHLEDGIYGIFQSTFLGASQRGVGVAQGGVFH : 1533
(SEQ ID NO: 8)   C1-P11_pol  : AALHPFALLLVLAGWLFHVRGARRSGDVLWDIPTPKIIEECEHLEDGIYGIFQSTFLGASQRGVGVAQGGVFH : 1533

1540         *      1560         *      1580         *      1600
(SEQ ID NO: 14)  C-P1_polyp  : TMWHVTRGAFLVRNGKKLIPSWASVKEDLVAYGGSWKLEGRWDGEEEVQLIAAVPGKNVVNVQTKPSLFKVRN : 1606
(SEQ ID NO: 8)   C1-P11_pol  : TMWHVTRGAFLVRNGKKLIPSWASVKEDLVAYGGSWKLEGRWDGEEEVQLIAAVPGKNVVNVQTKPSLFKVRN : 1606

*      1620         *      1640         *      1660         *      168
(SEQ ID NO: 14)  C-P1_polyp  : GGEIGAVALDYPSGTSGSPIVNRNGEVIGLYGNGILVGDNSFVSAISQTEVKEEGKEELQEIPTMLKKGMTTV : 1679
(SEQ ID NO: 8)   C1-P11_pol  : GGEIGAVALDYPSGTSGSPIVNRNGEVIGLYGNGILVGDNSFVSAISQTEVKEEGKEELQEIPTMLKKGMTTV : 1679

0         *      1700         *      1720         *      1740         *
(SEQ ID NO: 14)  C-P1_polyp  : LDFHPGAGKTRRFLPQILAECARRLRTLVLAPTRVVLSEMKEAFHGLDVKFHTQAFSAHGSGREVIDAMCHA : 1752
(SEQ ID NO: 8)   C1-P11_pol  : LDFHPGAGKTRRFLPQILAECARRLRTLVLAPTRVVLSEMKEAFHGLDVKFHTQAFSAHGSGREVIDAMCHA : 1752
```

FIG. 10C

```
(SEQ ID NO: 14) C-P1_polyp :                    1760         *         1780         *         1800         *         1820
(SEQ ID NO: 8)  C1-P11_pol : TLTYRMLEPTRVVNWEVIIMDEAHFLDPASIAARGWAAHRARANESATILMTATPPGTSDEFPHSNGEIEDVQ : 1825
                             TLTYRMLEPTRVVNWEVIIMDEAHFLDPASIAARGWAAHRARANESATILMTATPPGTSDEFPHSNGEIEDVQ : 1825

*         1840         *         1860         *         1880         *         19
(SEQ ID NO: 14) C-P1_polyp : TDIPSEPWNTGHDWILADKRPTAWFLPSIRAANVMAASLRKAGKSVVVLNRKTFEREYPTIKQKKPDFILATD : 1898
(SEQ ID NO: 8)  C1-P11_pol : TDIPSEPWNTGHDWILADKRPTAWFLPSIRAANVMAASLRKAGKSVVVLNRKTFEREYPTIKQKKPDFILATD : 1898

00         *         1920         *         1940         *         1960         *
(SEQ ID NO: 14) C-P1_polyp : IAEMGANLCVERVLDCRTAFKPVLVDEGRKVAIKGPLRISASSAAQRRGRIGRNPNRDGDSYYYSEPTSENNA : 1971
(SEQ ID NO: 8)  C1-P11_pol : IAEMGANLCVERVLDCRTAFKPVLVDEGRKVAIKGPLRISASSAAQRRGRIGRNPNRDGDSYYYSEPTSENNA : 1971

1980         *         2000         *         2020         *         2040
(SEQ ID NO: 14) C-P1_polyp : HHVCWLEASMLLDNMEVRGGMVAPLYGVEGTKTPVSPGEMRLRDDQRKVFRELVRNCDLPVWLSWQVAKAGLK : 2044
(SEQ ID NO: 8)  C1-P11_pol : HHVCWLEASMLLDNMEVRGGMVAPLYGVEGTKTPVSPGEMRLRDDQRKVFRELVRNCDLPVWLSWQVAKAGLK : 2044

*         2060         *         2080         *         2100         *         2
(SEQ ID NO: 14) C-P1_polyp : TNDRKWCFEGPEEHEILNDSGETVKCRAPGGAKKPLRPWCDERVSSDQSALSEFIKFAEGRRGAAEVLVVLS : 2117
(SEQ ID NO: 8)  C1-P11_pol : TNDRKWCFEGPEEHEILNDSGETVKCRAPGGAKKPLRPWCDERVSSDQSALSEFIKFAEGRRGAAEVLVVLS : 2117

120         *         2140         *         2160         *         2180         *
(SEQ ID NO: 14) C-P1_polyp : ELPDFLAKKGGEAMDTISVFLHSEEGSRAYRNALSMMPEAMTIVMLFILAGLLTSGMVIFFMSPKGISRMSMA : 2190
(SEQ ID NO: 8)  C1-P11_pol : ELPDFLAKKGGEAMDTISVFLHSEEGSRAYRNALSMMPEAMTIVMLFILAGLLTSGMVIFFMSPKGISRMSMA : 2190

2200         *         2220         *         2240         *         2260
(SEQ ID NO: 14) C-P1_polyp : MGTMAGCGYLMFLGGVKPTHISYIMLIFFVLMVVVIPEPGQQRSIQDNQVAYLIIGILTLVSAVAANELGMLE : 2263
(SEQ ID NO: 8)  C1-P11_pol : MGTMAGCGYLMFLGGVKPTHISYIMLIFFVLMVVVIPEPGQQRSIQDNQVAYLIIGILTLVSAVAANELGMLE : 2263

*         2280         *         2300         *         2320         *
(SEQ ID NO: 14) C-P1_polyp : KTKEDLFGKKNLIPSSASPWSWPDLDLKPGAAWTVYVGIVTMLSPMLHHWIKVEYGNLSLSGIAQSASVLSFM : 2336
(SEQ ID NO: 8)  C1-P11_pol : KTKEDLFGKKNLIPSSASPWSWPDLDLKPGAAWTVYVGIVTMLSPMLHHWIKVEYGNLSLSGIAQSASVLSFM : 2336
```

FIG. 10D

```
(SEQ ID NO:14)  C-P1_polyp :      2340        *         2360        *         2380        *         2400
(SEQ ID NO:8)   C1-P11_pol : DKGIPFMKMNISVIMLLVSGWNSITVMPLLCGIGCAMLHWSLILPGIKAQQSKLAQRRVFHGVAKNPVVDGNP : 2409
                             DKGIPFMKMNISVIMLLVSGWNSITVMPLLCGGCAMLHWSLILPGIKAQQSKLAQRRVFHGVAKNPVVDGNP : 2409

(SEQ ID NO:14)  C-P1_polyp :       *         2420        *         2440        *         2460        *         2480
(SEQ ID NO:8)   C1-P11_pol : TVDIEEAPEMPALYEKKLALYLLLALSLASVAMCRTPFSLAEGIVLASAALGPLIEGNTSLLWNGPMAVSMTG : 2482
                             TVDIEEAPEMPALYEKKLALYLLLALSLASVAMCRTPFSLAEGIVLASAALGPLIEGNTSLLWNGPMAVSMTG : 2482

(SEQ ID NO:14)  C-P1_polyp :       *         2500        *         2520        *         2540        *
(SEQ ID NO:8)   C1-P11_pol : VMRGNHYAFVGVMYNLWKMKTGRRGSANGKTLGEVWKRELNLLDKRQFELYKRTDIVEVDRDTARRHLAEGKV : 2555
                             VMRGNHYAFVGVMYNLWKMKTGRRGSANGKTLGEVWKRELNLLDKRQFELYKRTDIVEVDRDTARRHLAEGKV : 2555

(SEQ ID NO:14)  C-P1_polyp :      2560        *         2580        *         2600        *         2620
(SEQ ID NO:8)   C1-P11_pol : DTGVAVSRGTAKLRWFHERGYVKLEGRVIDLGCGRGWCYYAAAQKEVSGVKGFTLGRDGHEKPMNVQSLGWN : 2628
                             DTGVAVSRGTAKLRWFHERGYVKLEGRVIDLGCGRGWCYYAAAQKEVSGVKGFTLGRDGHEKPMNVQSLGWN : 2628

(SEQ ID NO:14)  C-P1_polyp :       *         2640        *         2660        *         2680        *         2700
(SEQ ID NO:8)   C1-P11_pol : IITFKDKTDIHRLEPVKCDTLLCDIGESSSSSVTEGERTVRVLDTVEKWLACGVDNFCVKVLAPYMPDVLEKL : 2701
                             IITFKDKTDIHRLEPVKCDTLLCDIGESSSSSVTEGERTVRVLDTVEKWLACGVDNFCVKVLAPYMPDVLEKL : 2701

(SEQ ID NO:14)  C-P1_polyp :       *         2720        *         2740        *         2760        *
(SEQ ID NO:8)   C1-P11_pol : ELLQRRFGGTVIRNPLSRNSTHEMYYVSGARSNVTFTVNQTSRLLMRRMRRPTGKVTLEADVILPIGTRSVET : 2774
                             ELLQRRFGGTVIRNPLSRNSTHEMYYVSGARSNVTFTVNQTSRLLMRRMRRPTGKVTLEADVILPIGTRSVET : 2774

(SEQ ID NO:14)  C-P1_polyp :      2780        *         2800        *         2820        *         2840
(SEQ ID NO:8)   C1-P11_pol : DKGPLDKEAIEERVERIKSEYMTSWFYDNDNPYRTWHYCGSYVTKTSGSAASMVNGVIKILTYPWDRIEEVTR : 2847
                             DKGPLDKEAIEERVERIKSEYMTSWFYDNDNPYRTWHYCGSYVTKTSGSAASMVNGVIKILTYPWDRIEEVTR : 2847

(SEQ ID NO:14)  C-P1_polyp :       *         2860        *         2880        *         2900        *         2920
(SEQ ID NO:8)   C1-P11_pol : MAMTDTTPFGQQRVFKEKVDTRAKDPPAGTRKIMKVVNRWLFRHLAREKNPRLCTKEEFIAKVRSHAAIGAYL : 2920
                             MAMTDTTPFGQQRVFKEKVDTRAKDPPAGTRKIMKVVNRWLFRHLAREKNPRLCTKEEFIAKVRSHAAIGAYL : 2920
```

FIG. 10E

| (SEQ ID NO: 14) | C-P1_polyp | : EEQEQWKTANEAVQDPKFWELVDEERRKLHQQGRCRTCVYNMGKREKKLSEFGKAKGSRAIWYMWLGARYLEF : 2993 |
| (SEQ ID NO: 8)  | C1-P11_pol | : EEQEQWKTANEAVQDPKFWELVDEERRKLHQQGRCRTCVYNMGKREKKLSEFGKAKGSRAIWYMWLGARYLEF : 2993 |

| (SEQ ID NO: 14) | C-P1_polyp | : EALGFLNEDHWASRENSGGGVEGIGLQYLGYVIRDLAAMDGGGFYADDTAGWDTRITEADLDDEQEILNYMSP : 3066 |
| (SEQ ID NO: 8)  | C1-P11_pol | : EALGFLNEDHWASRENSGGGVEGIGLQYLGYVIRDLAAMDGGGFYADDTAGWDTRITEADLDDEQEILNYMSP : 3066 |

| (SEQ ID NO: 14) | C-P1_polyp | : HHKKLAQAVMEMTYKNKVKVKVLRPAPGGKAYMDVISRRDQRGSGQVVTYALNTITNLKVQLIRMAEAEMVIHH : 3139 |
| (SEQ ID NO: 8)  | C1-P11_pol | : HHKKLAQAVMEMTYKNKVKVKVLRPAPGGKAYMDVISRRDQRGSGQVVTYALNTITNLKVQLIRMAEAEMVIHH : 3139 |

| (SEQ ID NO: 14) | C-P1_polyp | : QHVQDCDESVLTRLEAWLTEHGCNRLKRMAVSGDDCVVRPIDDRFGLALSHLNAMSKVRKDISEWQPSKGWND : 3212 |
| (SEQ ID NO: 8)  | C1-P11_pol | : QHVQDCDESVLTRLEAWLTEHGCNRLKRMAVSGDDCVVRPIDDRFGLALSHLNAMSKVRKDISEWQPSKGWND : 3212 |

| (SEQ ID NO: 14) | C-P1_polyp | : WENVPFCSHHFHELQLKDGRRIVVPCREQDELIGRGRVSPGNGWMIKETACLSKAYANMWSLMYFHKRDMRLL : 3285 |
| (SEQ ID NO: 8)  | C1-P11_pol | : WENVPFCSHHFHELQLKDGRRIVVPCREQDELIGRGRVSPGNGWMIKETACLSKAYANMWSLMYFHKRDMRLL : 3285 |

| (SEQ ID NO: 14) | C-P1_polyp | : SLAVSSAVPTSWVPQGRTTWSIHGKGEWMTTEDMLEVWNRVWITNNPHMQDKTMVKKWRDVPYLTKRQDKLCG : 3358 |
| (SEQ ID NO: 8)  | C1-P11_pol | : SLAVSSAVPTSWVPQGRTTWSIHGKGEWMTTEDMLEVWNRVWITNNPHMQDKTMVKKWRDVPYLTKRQDKLCG : 3358 |

| (SEQ ID NO: 14) | C-P1_polyp | : SLIGMTNRATWASHIHLVIHRIRTLIGQEKYTDYLTVMDRYSVDADLQLGELI : 3411 |
| (SEQ ID NO: 8)  | C1-P11_pol | : SLIGMTNRATWASHIHLVIHRIRTLIGQEKYTDYLTVMDRYSVDADLQLGELI : 3411 |

FIG. 10F

SEQUENCE LISTING

<160> NUMBER OF SEQ ID NOS: 15

<210> SEQ ID NO 1
<211> LENGTH: 6300
<212> TYPE: DNA
<213> ORGANISM: Artificial Sequence
<220> FEATURE:
<223> OTHER INFORMATION: Flaviviridae Flavivirus Yellow Fever Virus

<400> SEQUENCE: 1

```
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaccct gggcgtcaat atggtacgac gaggagttcg     180
ctccttgtca aacaaataa aacaaaaaac aaaacaaatt ggaaacagac ctggaccttc     240
aagaggtgtt caaggattta tcttttctt tttgttcaac attttgactg gaaaaaagat     300
cacagcccac ctaaagaggt tgtggaaaat gctgacccca agacaaggct tggctgttct     360
aaggaaagtc aagagagtgg tggccagttt gatgagagga ttgtcctcaa ggaaacgccg     420
ttcccatgat gttctgactg tgcaattcct aattttggga atgctgttga tgacgggtgg     480
agtgaccttg gtgcggaaaa acagatggtt gctcctaaat gtgacatctg aggacctcgg     540 gaaacattc tctgtgggca caggcaactg cacaacaaac attttggaag ccaagtactg     600
gtgcccagac tcaatggaat acaactgtcc caatctcagt ccaagagagg agccagatga     660
```

```
cattgattgc tggtgctatg gggtggaaaa cgttagagtc gcatatggta agtgtgactc    720
agcaggcagg tctaggaggt caagaagggc cattgacttg cctacgcatg aaaaccatgg    780
tttgaagacc cggcaagaaa aatggatgac tggaagaatg ggtgaaaggc aactccaaaa    840
gattgagaga tggttcgtga ggaaccccctt ttttgcagtg acggctctga ccattgccta    900
ccttgtggga agcaacatga cgcaacgagt cgtgattgcc ctactggtct ggctgttgg     960
tccggcctac tcagctcact gcattggaat tactgacagg gatttcattg agggggtgca   1020
tggaggaact tgggtttcag ctaccctgga gcaagacaag tgtgtcactg ttatggcccc   1080
tgacaagcct tcattggaca tctcactaga gacagtagcc attgatagac ctgctgaggt   1140
gaggaaagtg tgttacaatg cagttctcac tcatgtgaag attaatgaca agtgccccag   1200
cactggagag gcccacctag ctgaagagaa cgaaggggac aatgcgtgca agcgcactta   1260
ttctgataga ggctggggca atggctgtgg cctatttggg aaagggagca ttgtggcatg   1320
cgccaaattc acttgtgcca aatccatgag tttgtttgag gttgatcaga ccaaaattca   1380
gtatgtcatc agagcacaat tgcatgtagg ggccaagcag gaaaattgga ctaccgacat   1440
taagactctc aagtttgatg ccctgtcagg ctcccaggaa gtcgagttca ttgggtatgg   1500
aaaagctaca ctggaatgcc aggtgcaaac tgcggtggac tttggtaaca gttacatcgc   1560
tgagatggaa acagagagct ggatagtgga cagacagtgg gcccaggact tgaccctgcc   1620
atggcagagt ggaagtggcg gggtgtggag agagatgcat catcttgtcg aatttgaacc   1680
tccgcatgcc gccactatca gagtactggc cctgggaaac caggaaggct ccttgaaaac   1740
agctcttact ggcgcaatga gggttacaaa ggacacaaat gacaacaacc tttacaaact   1800
acatggtgga catgtttctt gcagagtgaa attgtcagct ttgacactca aggggacatc   1860
ctacaaaata tgcactgaca aaatgttttt tgtcaagaac ccaactgaca ctggccatgg   1920
cactgttgtg atgcaggtga aagtgtcaaa aggagccccc tgcaggattc cagtgatagt   1980
agctgatgat cttacagcgg caatcaataa aggcattttg gttacagtta ccccatcgc    2040
ctcaaccaat gatgatgaag tgctgattga ggtgaaccca ccttttggag acagctacat   2100
tatcgttggg agaggagatt cacgtctcac ttaccagtgg cacaaagagg gaagctcaat   2160
aggaaagttg ttcactcaga ccatgaaagg cgtggaacgc ctggccgtca tgggagacac   2220
cgcctgggat ttcagctccg ctggagggtt cttcacttcg gttgggaaag gaattcatac   2280
ggtgtttggc tctgcctttc aggggctatt tggcggcttg aactggataa caaaggtcat   2340
catgggggcg gtacttatat gggttggcat caacacaaga aacatgacaa tgtccatgag   2400
catgatcttg gtaggagtga tcatgatgtt tttgtctcta ggagttgggg cggatcaagg   2460
atgcgccatc aactttggca agagagagct caagtgcgga gatggtatct tcatatttag   2520
agactctgat gactggctga acaagtactc atactatcca gaagatcctg tgaagcttgc   2580
atcaatagtg aaagcctctt ttgaagaagg aagtgtggc ctaaattcag ttgactccct   2640
tgagcatgag atgtggagaa gcagggcaga tgagatcaat gccatttttg aggaaaacga   2700
ggtggacatt tctgttgtcg tgcaggatcc aaagaatgtt taccagagag gaactcatcc   2760
attttccaga attcgggatg gtctgcagta tggttggaag acttggggta agaaccttgt   2820
gttctccca gggaggaaga atggaagctt catcatagat ggaaagtcca ggaaagaatg   2880
cccgttttca aaccgggtct ggaattcttt ccagatagag gagtttggga cgggagtgtt   2940
caccacacgc gtgtacatgg acgcagtctt tgaatacacc atagactgcg atggatctat   3000
cttgggtgca gcggtgaacg gaaaaaagag tgcccatggc tctccaacat ttggatggg    3060
```

```
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct tgggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggcttttgg   3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgccccct  3960
catggctctg ttgacacctg tcactatggc tgaggtgaga cttgccgcaa tgttcttttg    4020
tgccgtggtt atcataggg tccttcacca gaatttcaag gacacctcca tgcagaagac    4080
tatacctctg gtggccctca cactcacatc ttacctgggc ttgacacaac ctttttttggg   4140
cctgtgtgca tttctggcaa cccgcatatt tgggcgaagg agtatcccag tgaatgaggc    4200
actcgcagca gctggtctag tgggagtgct ggcaggactg gcttttcagg agatgggagaa  4260
cttccttggt ccgattgcag ttggaggact cctgatgatg ctggttagcg tggctgggag    4320
ggtggatggg ctagagctca agaagcttgg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtgggggatg tcttgtggga tattcccact cctaagatca tcgaggaatg   4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg gcaagaagtt gattccatct tgggcttcag taaaggaaga    4800
ccttgtcgcc tatggtggct catggaagtt ggaaggcaga tgggatggag aggaagaggt    4860
ccagttgatc gcgctgttc caggaaagaa cgtggtcaac gtccagacaa accgagctt     4920
gttcaaagtg aggaatgggg gagaaatcgg ggctgtcgct cttgactatc cgagtggcac   4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gctttttccg ctcacggcag    5340
cgggagagaa gtcattgatg ctatgtgcca tgccacccta acttacagga tgttggaacc    5400
```

```
aactagggtt gttaactggg aagtgatcat tatggatgaa gcccattttt tggatccagc   5460
tagcatagcc gctagaggtt gggcagcgca cagagctagg gcaaatgaaa gtgcaacaat   5520
cttgatgaca gccacaccgc ctgggactag tgatgaattt ccacattcaa atggtgaaat   5580
agaagatgtt caaacggaca tacccagtga gccctggaac acagggcatg actggatcct   5640
ggctgacaaa aggcccacgg catggttcct tccatccatc agagctgcaa atgtcatggc   5700
tgcctctttg cgtaaggctg aaagagtgt ggtggtcctg aacaggaaaa cctttgagag   5760
agaatacccc acgataaagc agaagaaacc tgactttata ttggccactg acatagctga   5820
aatgggagcc aacctttgcg tggagcgagt gctggattgc aggacggctt ttaagcctgt   5880
gcttgtggat gaagggagga aggtggcaat aaaagggcca cttcgtatct ccgcatcctc   5940
tgctgctcaa aggaggggc gcattgggag aaatcccaac agagatggag actcatacta   6000
ctattctgag cctacaagtg aaaataatgc ccaccacgtc tgctggttgg aggcctcaat   6060
gctcttggac aacatggagg tgaggggtgg aatggtcgcc ccactctatg gcgttgaagg   6120
aactaaaaca ccagtttccc ctggtgaaat gagactgagg gatgaccaga ggaaagtctt   6180
cagagaacta gtgaggaatt gtgacctgcc cgtttggctt tcgtggcaag tggccaaggc   6240
tggtttgaag acgaatgatc gtaagtggtg ttttgaaggc cctgaggaac atgagatctt   6300

<210> SEQ ID NO 2
<211> LENGTH: 6300
<212> TYPE: DNA
<213> ORGANISM: Artificial Sequence
<220> FEATURE:
<223> OTHER INFORMATION: Flaviviridae Flavivirus Yellow Fever Virus

<400> SEQUENCE: 2
agtaaatcct gtgtgctaat tgaggtgcat tggtctgcaa atcgagttgc taggcaataa     60
acacatttgg attaatttta atcgttcgtt gagcgattag cagagaactg accagaacat    120
gtctggtcgt aaagctcagg gaaaaaccct gggcgtcaat atggtacgac gaggagttcg    180
ctccttgtca acaaaataa aacaaaaaac gaaacaaatt ggaaacagac ctggaccttc    240
aagaggtgtt caaggattta tcttttttctt tttgttcaac attttgactg gaaaaaagat    300
cacagcccac ctaaagaggt tgtggaaaat gctggaccca agacaaggct tggctgttct    360
aaggaaagtc aagagagtgg tggccagttt gatgagagga ttgtcctcaa ggaaacgccg    420
ttcccatgat gttctgactg tgcaattcct aattttggga atgctgttga tgacgggtgg    480
agtgaccttg gtgcggaaaa acagatggtt gctcctaaat gtgacatctg aggacctcgg    540
gaaaacattc tctgtgggca caggcaactg cacaacaaac attttggaag ccaagtactg    600
gtgcccagac tcaatggaat acaactgtcc caatctcagt ccaagagagg agccagatga    660
cattgattgc tggtgctatg gggtggaaaa cgttagagtc gcatatggta agtgtgactc    720
agcaggcagg tctaggaggt caagaagggc cattgacttg cctacgcatg aaaaccatgg    780
tttgaagacc cggcaagaaa aatggatgac tggaagaatg ggtgaaaggc aactccaaaa    840
gattgagaga tggttcgtga ggaacccctt ttttgcagtg acggctctga ccattgccta    900
ccttgtggga agcaacatga cgcaacgagt cgtgattgcc ctactggtct tggctgttgg    960
tccggcctac tcagctcact gcattggaat tactgacagg gatttcattg aggggtgca   1020 tggaggaact tgggttcag ctacccttgga gcaagacaag tgtgtcactg ttatggccc   1080 tgacaagcct tcattggaca tctcactaga gacagtagcc attgatagac tgctgaggt   1140 gaggaaagtg tgttacaatg cagttctcac tcatgtgaag attaatgaca agtgccccag   1200
```

```
cactggagag gcccacctag ctgaagagaa cgaaggggac aatgcgtgca agcgcactta    1260
ttctgataga ggctggggca atggctgtgg cctatttggg aaagggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ctaccgacat    1440
taagactctc aggtttgatg ccctgtcagg ctcccaggaa gtcgagttca ttgggtatgg    1500
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
agctgatgat cttacagcgg caatcaataa aggcattttg gttacagtta accccatcgc    2040
ctcaaccaat gatgatgaag tgctgattga ggtgaaccca ccttttggag acagctacat    2100
tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
ggtgtttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga acaagtactc atactatcca gaagatcctg tgaagcttgc    2580
atcaatagtg aaagcctctt ttgaagaagg gaagtgtggc ctaaattcag ttgactccct    2640
tgagcatgag atgtggagaa gcagggcaga tgagatcaat gccatttttg aggaaaacga    2700
ggtggacatt tctgttgtcg tgcaggatcc aaagaatgtt taccagagag gaactcatcc    2760
attttccaga attcgggatg gtctgcagta tggttggaag acttggggta agaaccttgt    2820
gttctcccca gggaggaaga atggaagctt catcatagat ggaaagtcca ggaaagaatg    2880
cccgttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
```

-continued

```
gagcatgatg atagcaatgg aagtggtcct aaggaaaaga cagggaccaa agcaaatgtt    3600
ggttggagga gtagtgctct tgggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgcccct    3960
catggctctg ttgacacctg tcactatggc tgaggtgaga cttgccgcaa tgttcttttg    4020
tgccgtggtt atcatagggg tccttcacca gaatttcaag gacacctcca tgcagaagac    4080
tatacctctg gtggccctca cactcacatc ttacctgggc ttgacacaac cttttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca agaagcttgg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740
agctttcctt gtcaggaatg gcaagaagtt gattccatct tgggcttcag taaggaagaa    4800
ccttgtcgcc tatggtggct catggaagtt ggaaggcaga tgggatggag aggaagaggt    4860
ccagttgatc gcggctgttc caggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg caatggcat     5040 ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gctttttccg ctcacggcag    5340
cgggagagaa gtcattgatg ctatgtgcca tgccacccta acttacagga tgttggaacc    5400
aactagggtt gttaactggg aagtgatcat tatggatgaa gcccattttt tggatccagc    5460
tagcatagcc gctagaggtt gggcagcgca cagagctagg gcaaatgaaa gtgcaacaat    5520
cttgatgaca gccacaccgc tgggactagt gatgaatttt ccacattcaa atggtgaaat    5580
agaagatgtt caaacggaca tacccagtga gccctggaac acagggcatg actggatcct    5640
ggctgacaaa aggcccacgg catgttcct tccatccatc agagctgcaa atgtcatggc    5700
tgcctctttg cgtaaggctg aaagagtgt ggtggtcctg aacaggaaaa cctttgagag    5760
agaatacccc acgataaagc agaagaaacc tgactttata ttggccactg acatagctga    5820
aatgggagcc aaccctttgcg tggagcgagt gctggattgc aggacggctt ttaagcctgt    5880
gcttgtggat gaagggagga aggtggcaat aaaagggcca cttcgtatct ccgcatcctc    5940
```

```
tgctgctcaa aggaggggc gcattgggag aaatcccaac agagatgagg actcatacta   6000
ctattctgag cctacaagtg aaaataatgc ccaccacgtc tgctggttgg aggcctcaat   6060
gctcttggac aacatggagg tgaggggtgg aatggtcgcc ccactctatg cgttgaagg    6120 aactaaaaca ccagttttcc ctggtgaaat gagactgagg gatgaccaga ggaaagtctt   6180
cagagaacta gtgaggaatt gtgacctgcc cgtttggctt tcgtggcaag tggccaaggc   6240
tggtttgaag acgaatgatc gtaagtggtg ttttgaaggc cctgaggaac atgagatctt   6300
```

<210> SEQ ID NO 3
<211> LENGTH: 3411
<212> TYPE: PRT
<213> ORGANISM: Artificial Sequence
<220> FEATURE:
<223> OTHER INFORMATION: Flaviviridae Flavivirus Yellow Fever Virus

<400> SEQUENCE: 3

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
                20                  25                  30

Gln Ile Gly Asn Arg Pro Gly Pro Ser Arg Gly Val Gln Gly Phe Ile
            35                  40                  45

Phe Phe Phe Leu Phe Asn Ile Leu Thr Gly Lys Lys Ile Thr Ala His
        50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
                100                 105                 110

Leu Gly Met Leu Leu Met Thr Gly Gly Val Thr Leu Val Arg Lys Asn
            115                 120                 125

Arg Trp Leu Leu Leu Asn Val Thr Ser Glu Asp Leu Gly Lys Thr Phe
        130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
                180                 185                 190

Arg Val Ala Tyr Gly Lys Cys Asp Ser Ala Gly Arg Ser Arg Arg Ser
            195                 200                 205

Arg Arg Ala Ile Asp Leu Pro Thr His Glu Asn His Gly Leu Lys Thr
        210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
                260                 265                 270

Ile Ala Leu Leu Val Leu Ala Val Gly Pro Ala Tyr Ser Ala His Cys
            275                 280                 285

Ile Gly Ile Thr Asp Arg Asp Phe Ile Glu Gly Val His Gly Gly Thr
        290                 295                 300
```

```
Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
            325                 330                 335

Arg Pro Ala Glu Val Arg Lys Val Cys Tyr Asn Ala Val Leu Thr His
                340                 345                 350

Val Lys Ile Asn Asp Lys Cys Pro Ser Thr Gly Glu Ala His Leu Ala
        355                 360                 365

Glu Glu Asn Glu Gly Asp Asn Ala Cys Lys Arg Thr Tyr Ser Asp Arg
    370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
            405                 410                 415

Gln Thr Lys Ile Gln Tyr Val Ile Arg Ala Gln Leu His Val Gly Ala
                420                 425                 430

Lys Gln Glu Asn Trp Thr Thr Asp Ile Lys Thr Leu Lys Phe Asp Ala
        435                 440                 445

Leu Ser Gly Ser Gln Glu Val Glu Phe Ile Gly Tyr Gly Lys Ala Thr
450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
            485                 490                 495

Asp Leu Thr Leu Pro Trp Gln Ser Gly Ser Gly Val Trp Arg Glu
                500                 505                 510

Met His His Leu Val Glu Phe Glu Pro Pro His Ala Ala Thr Ile Arg
        515                 520                 525

Val Leu Ala Leu Gly Asn Gln Glu Gly Ser Leu Lys Thr Ala Leu Thr
530                 535                 540

Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
            565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
        595                 600                 605

Val Ser Lys Gly Ala Pro Cys Arg Ile Pro Val Ile Val Ala Asp Asp
610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
            645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
        675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720
```

-continued

```
Thr Val Phe Gly Ser Ala Phe Gln Gly Leu Phe Gly Gly Leu Asn Trp
            725                 730                 735
Ile Thr Lys Val Ile Met Gly Ala Val Leu Ile Trp Val Gly Ile Asn
            740                 745                 750
Thr Arg Asn Met Thr Met Ser Met Ser Met Ile Leu Val Gly Val Ile
            755                 760                 765
Met Met Phe Leu Ser Leu Gly Val Gly Ala Asp Gln Gly Cys Ala Ile
770                 775                 780
Asn Phe Gly Lys Arg Glu Leu Lys Cys Gly Asp Gly Ile Phe Ile Phe
785                 790                 795                 800
Arg Asp Ser Asp Asp Trp Leu Asn Lys Tyr Ser Tyr Tyr Pro Glu Asp
            805                 810                 815
Pro Val Lys Leu Ala Ser Ile Val Lys Ala Ser Phe Glu Glu Gly Lys
            820                 825                 830
Cys Gly Leu Asn Ser Val Asp Ser Leu Glu His Glu Met Trp Arg Ser
            835                 840                 845
Arg Ala Asp Glu Ile Asn Ala Ile Phe Glu Glu Asn Glu Val Asp Ile
            850                 855                 860
Ser Val Val Val Gln Asp Pro Lys Asn Val Tyr Gln Arg Gly Thr His
865                 870                 875                 880
Pro Phe Ser Arg Ile Arg Asp Gly Leu Gln Tyr Gly Trp Lys Thr Trp
            885                 890                 895
Gly Lys Asn Leu Val Phe Ser Pro Gly Arg Lys Asn Gly Ser Phe Ile
            900                 905                 910
Ile Asp Gly Lys Ser Arg Lys Glu Cys Pro Phe Ser Asn Arg Val Trp
            915                 920                 925
Asn Ser Phe Gln Ile Glu Glu Phe Gly Thr Gly Val Phe Thr Thr Arg
930                 935                 940
Val Tyr Met Asp Ala Val Phe Glu Tyr Thr Ile Asp Cys Asp Gly Ser
945                 950                 955                 960
Ile Leu Gly Ala Ala Val Asn Gly Lys Lys Ser Ala His Gly Ser Pro
            965                 970                 975
Thr Phe Trp Met Gly Ser His Glu Val Asn Gly Thr Trp Met Ile His
            980                 985                 990
Thr Leu Glu Ala Leu Asp Tyr Lys Glu Cys Glu Trp Pro Leu Thr His
            995                 1000                1005
Thr Ile Gly Thr Ser Val Glu Glu Ser Glu Met Phe Met Pro Arg
            1010                1015                1020
Ser Ile Gly Gly Pro Val Ser Ser His Asn His Ile Pro Gly Tyr
            1025                1030                1035
Lys Val Gln Thr Asn Gly Pro Trp Met Gln Val Pro Leu Glu Val
            1040                1045                1050
Lys Arg Glu Ala Cys Pro Gly Thr Ser Val Ile Ile Asp Gly Asn
            1055                1060                1065
Cys Asp Gly Arg Gly Lys Ser Thr Arg Ser Thr Thr Asp Ser Gly
            1070                1075                1080
Lys Val Ile Pro Glu Trp Cys Cys Arg Ser Cys Thr Met Pro Pro
            1085                1090                1095
Val Ser Phe His Gly Ser Asp Gly Cys Trp Tyr Pro Met Glu Ile
            1100                1105                1110
Arg Pro Arg Lys Thr His Glu Ser His Leu Val Arg Ser Trp Val
            1115                1120                1125
Thr Ala Gly Glu Ile His Ala Val Pro Phe Gly Leu Val Ser Met
```

-continued

```
                1130                1135                1140
Met Ile Ala Met Glu Val Val Leu Arg Lys Arg Gln Gly Pro Lys
    1145                1150                1155
Gln Met Leu Val Gly Gly Val Val Leu Leu Gly Ala Met Leu Val
    1160                1165                1170
Gly Gln Val Thr Leu Leu Asp Leu Leu Lys Leu Thr Val Ala Val
    1175                1180                1185
Gly Leu His Phe His Glu Met Asn Asn Gly Gly Asp Ala Met Tyr
    1190                1195                1200
Met Ala Leu Ile Ala Ala Phe Ser Ile Arg Pro Gly Leu Leu Ile
    1205                1210                1215
Gly Phe Gly Leu Arg Thr Leu Trp Ser Pro Arg Glu Arg Leu Val
    1220                1225                1230
Leu Thr Leu Gly Ala Ala Met Val Glu Ile Ala Leu Gly Gly Val
    1235                1240                1245
Met Gly Gly Leu Trp Lys Tyr Leu Asn Ala Val Ser Leu Cys Ile
    1250                1255                1260
Leu Thr Ile Asn Ala Val Ala Ser Arg Lys Ala Ser Asn Thr Ile
    1265                1270                1275
Leu Pro Leu Met Ala Leu Leu Thr Pro Val Thr Met Ala Glu Val
    1280                1285                1290
Arg Leu Ala Ala Met Phe Phe Cys Ala Val Val Ile Ile Gly Val
    1295                1300                1305
Leu His Gln Asn Phe Lys Asp Thr Ser Met Gln Lys Thr Ile Pro
    1310                1315                1320
Leu Val Ala Leu Thr Leu Thr Ser Tyr Leu Gly Leu Thr Gln Pro
    1325                1330                1335
Phe Leu Gly Leu Cys Ala Phe Leu Ala Thr Arg Ile Phe Gly Arg
    1340                1345                1350
Arg Ser Ile Pro Val Asn Glu Ala Leu Ala Ala Gly Leu Val
    1355                1360                1365
Gly Val Leu Ala Gly Leu Ala Phe Gln Glu Met Glu Asn Phe Leu
    1370                1375                1380
Gly Pro Ile Ala Val Gly Gly Leu Leu Met Met Leu Val Ser Val
    1385                1390                1395
Ala Gly Arg Val Asp Gly Leu Glu Leu Lys Lys Leu Gly Glu Val
    1400                1405                1410
Ser Trp Glu Glu Glu Ala Glu Ile Ser Gly Ser Ser Ala Arg Tyr
    1415                1420                1425
Asp Val Ala Leu Ser Glu Gln Gly Glu Phe Lys Leu Leu Ser Glu
    1430                1435                1440
Glu Lys Val Pro Trp Asp Gln Val Val Met Thr Ser Leu Ala Leu
    1445                1450                1455
Val Gly Ala Ala Leu His Pro Phe Ala Leu Leu Leu Val Leu Ala
    1460                1465                1470
Gly Trp Leu Phe His Val Arg Gly Ala Arg Arg Ser Gly Asp Val
    1475                1480                1485
Leu Trp Asp Ile Pro Thr Pro Lys Ile Ile Glu Glu Cys Glu His
    1490                1495                1500
Leu Glu Asp Gly Ile Tyr Gly Ile Phe Gln Ser Thr Phe Leu Gly
    1505                1510                1515
Ala Ser Gln Arg Gly Val Gly Val Ala Gln Gly Gly Val Phe His
    1520                1525                1530
```

```
Thr Met Trp His Val Thr Arg Gly Ala Phe Leu Val Arg Asn Gly
1535                1540                1545

Lys Lys Leu Ile Pro Ser Trp Ala Ser Val Lys Glu Asp Leu Val
1550                1555                1560

Ala Tyr Gly Gly Ser Trp Lys Leu Glu Gly Arg Trp Asp Gly Glu
1565                1570                1575

Glu Glu Val Gln Leu Ile Ala Ala Val Pro Gly Lys Asn Val Val
1580                1585                1590

Asn Val Gln Thr Lys Pro Ser Leu Phe Lys Val Arg Asn Gly Gly
1595                1600                1605

Glu Ile Gly Ala Val Ala Leu Asp Tyr Pro Ser Gly Thr Ser Gly
1610                1615                1620

Ser Pro Ile Val Asn Arg Asn Gly Glu Val Ile Gly Leu Tyr Gly
1625                1630                1635

Asn Gly Ile Leu Val Gly Asp Asn Ser Phe Val Ser Ala Ile Ser
1640                1645                1650

Gln Thr Glu Val Lys Glu Glu Gly Lys Glu Glu Leu Gln Glu Ile
1655                1660                1665

Pro Thr Met Leu Lys Lys Gly Met Thr Thr Val Leu Asp Phe His
1670                1675                1680

Pro Gly Ala Gly Lys Thr Arg Arg Phe Leu Pro Gln Ile Leu Ala
1685                1690                1695

Glu Cys Ala Arg Arg Arg Leu Arg Thr Leu Val Leu Ala Pro Thr
1700                1705                1710

Arg Val Val Leu Ser Glu Met Lys Glu Ala Phe His Gly Leu Asp
1715                1720                1725

Val Lys Phe His Thr Gln Ala Phe Ser Ala His Gly Ser Gly Arg
1730                1735                1740

Glu Val Ile Asp Ala Met Cys His Ala Thr Leu Thr Tyr Arg Met
1745                1750                1755

Leu Glu Pro Thr Arg Val Val Asn Trp Glu Val Ile Ile Met Asp
1760                1765                1770

Glu Ala His Phe Leu Asp Pro Ala Ser Ile Ala Ala Arg Gly Trp
1775                1780                1785

Ala Ala His Arg Ala Arg Ala Asn Glu Ser Ala Thr Ile Leu Met
1790                1795                1800

Thr Ala Thr Pro Pro Gly Thr Ser Asp Glu Phe Pro His Ser Asn
1805                1810                1815

Gly Glu Ile Glu Asp Val Gln Thr Asp Ile Pro Ser Glu Pro Trp
1820                1825                1830

Asn Thr Gly His Asp Trp Ile Leu Ala Asp Lys Arg Pro Thr Ala
1835                1840                1845

Trp Phe Leu Pro Ser Ile Arg Ala Ala Asn Val Met Ala Ala Ser
1850                1855                1860

Leu Arg Lys Ala Gly Lys Ser Val Val Val Leu Asn Arg Lys Thr
1865                1870                1875

Phe Glu Arg Glu Tyr Pro Thr Ile Lys Gln Lys Lys Pro Asp Phe
1880                1885                1890

Ile Leu Ala Thr Asp Ile Ala Glu Met Gly Ala Asn Leu Cys Val
1895                1900                1905

Glu Arg Val Leu Asp Cys Arg Thr Ala Phe Lys Pro Val Leu Val
1910                1915                1920
```

Asp Glu Gly Arg Lys Val Ala Ile Lys Gly Pro Leu Arg Ile Ser
1925                1930                1935

Ala Ser Ser Ala Ala Gln Arg Arg Gly Arg Ile Gly Arg Asn Pro
1940                1945                1950

Asn Arg Asp Gly Asp Ser Tyr Tyr Tyr Ser Glu Pro Thr Ser Glu
1955                1960                1965

Asn Asn Ala His His Val Cys Trp Leu Glu Ala Ser Met Leu Leu
1970                1975                1980

Asp Asn Met Glu Val Arg Gly Gly Met Val Ala Pro Leu Tyr Gly
1985                1990                1995

Val Glu Gly Thr Lys Thr Pro Val Ser Pro Gly Glu Met Arg Leu
2000                2005                2010

Arg Asp Asp Gln Arg Lys Val Phe Arg Glu Leu Val Arg Asn Cys
2015                2020                2025

Asp Leu Pro Val Trp Leu Ser Trp Gln Val Ala Lys Ala Gly Leu
2030                2035                2040

Lys Thr Asn Asp Arg Lys Trp Cys Phe Glu Gly Pro Glu Glu His
2045                2050                2055

Glu Ile Leu Asn Asp Ser Gly Glu Thr Val Lys Cys Arg Ala Pro
2060                2065                2070

Gly Gly Ala Lys Lys Pro Leu Arg Pro Arg Trp Cys Asp Glu Arg
2075                2080                2085

Val Ser Ser Asp Gln Ser Ala Leu Ser Glu Phe Ile Lys Phe Ala
2090                2095                2100

Glu Gly Arg Arg Gly Ala Ala Glu Val Leu Val Val Leu Ser Glu
2105                2110                2115

Leu Pro Asp Phe Leu Ala Lys Lys Gly Gly Glu Ala Met Asp Thr
2120                2125                2130

Ile Ser Val Phe Leu His Ser Glu Glu Gly Ser Arg Ala Tyr Arg
2135                2140                2145

Asn Ala Leu Ser Met Met Pro Glu Ala Met Thr Ile Val Met Leu
2150                2155                2160

Phe Ile Leu Ala Gly Leu Leu Thr Ser Gly Met Val Ile Phe Phe
2165                2170                2175

Met Ser Pro Lys Gly Ile Ser Arg Met Ser Met Ala Met Gly Thr
2180                2185                2190

Met Ala Gly Cys Gly Tyr Leu Met Phe Leu Gly Gly Val Lys Pro
2195                2200                2205

Thr His Ile Ser Tyr Ile Met Leu Ile Phe Phe Val Leu Met Val
2210                2215                2220

Val Val Ile Pro Glu Pro Gly Gln Gln Arg Ser Ile Gln Asp Asn
2225                2230                2235

Gln Val Ala Tyr Leu Ile Ile Gly Ile Leu Thr Leu Val Ser Ala
2240                2245                2250

Val Ala Ala Asn Glu Leu Gly Met Leu Glu Lys Thr Lys Glu Asp
2255                2260                2265

Leu Phe Gly Lys Lys Asn Leu Ile Pro Ser Ser Ala Ser Pro Trp
2270                2275                2280

Ser Trp Pro Asp Leu Asp Leu Lys Pro Gly Ala Ala Trp Thr Val
2285                2290                2295

Tyr Val Gly Ile Val Thr Met Leu Ser Pro Met Leu His His Trp
2300                2305                2310

Ile Lys Val Glu Tyr Gly Asn Leu Ser Leu Ser Gly Ile Ala Gln

-continued

```
            2315                2320                2325
Ser Ala Ser Val Leu Ser Phe Met Asp Lys Gly Ile Pro Phe Met
    2330                2335                2340
Lys Met Asn Ile Ser Val Ile Met Leu Leu Val Ser Gly Trp Asn
    2345                2350                2355
Ser Ile Thr Val Met Pro Leu Leu Cys Gly Ile Gly Cys Ala Met
    2360                2365                2370
Leu His Trp Ser Leu Ile Leu Pro Gly Ile Lys Ala Gln Gln Ser
    2375                2380                2385
Lys Leu Ala Gln Arg Arg Val Phe His Gly Val Ala Lys Asn Pro
    2390                2395                2400
Val Val Asp Gly Asn Pro Thr Val Asp Ile Glu Glu Ala Pro Glu
    2405                2410                2415
Met Pro Ala Leu Tyr Glu Lys Lys Leu Ala Leu Tyr Leu Leu Leu
    2420                2425                2430
Ala Leu Ser Leu Ala Ser Val Ala Met Cys Arg Thr Pro Phe Ser
    2435                2440                2445
Leu Ala Glu Gly Ile Val Leu Ala Ser Ala Ala Leu Gly Pro Leu
    2450                2455                2460
Ile Glu Gly Asn Thr Ser Leu Leu Trp Asn Gly Pro Met Ala Val
    2465                2470                2475
Ser Met Thr Gly Val Met Arg Gly Asn His Tyr Ala Phe Val Gly
    2480                2485                2490
Val Met Tyr Asn Leu Trp Lys Met Lys Thr Gly Arg Arg Gly Ser
    2495                2500                2505
Ala Asn Gly Lys Thr Leu Gly Glu Val Trp Lys Arg Glu Leu Asn
    2510                2515                2520
Leu Leu Asp Lys Arg Gln Phe Glu Leu Tyr Lys Arg Thr Asp Ile
    2525                2530                2535
Val Glu Val Asp Arg Asp Thr Ala Arg Arg His Leu Ala Glu Gly
    2540                2545                2550
Lys Val Asp Thr Gly Val Ala Val Ser Arg Gly Thr Ala Lys Leu
    2555                2560                2565
Arg Trp Phe His Glu Arg Gly Tyr Val Lys Leu Glu Gly Arg Val
    2570                2575                2580
Ile Asp Leu Gly Cys Gly Arg Gly Gly Trp Cys Tyr Tyr Ala Ala
    2585                2590                2595
Ala Gln Lys Glu Val Ser Gly Val Lys Gly Phe Thr Leu Gly Arg
    2600                2605                2610
Asp Gly His Glu Lys Pro Met Asn Val Gln Ser Leu Gly Trp Asn
    2615                2620                2625
Ile Ile Thr Phe Lys Asp Lys Thr Asp Ile His Arg Leu Glu Pro
    2630                2635                2640
Val Lys Cys Asp Thr Leu Leu Cys Asp Ile Gly Glu Ser Ser Ser
    2645                2650                2655
Ser Ser Val Thr Glu Gly Glu Arg Thr Val Arg Val Leu Asp Thr
    2660                2665                2670
Val Glu Lys Trp Leu Ala Cys Gly Val Asp Asn Phe Cys Val Lys
    2675                2680                2685
Val Leu Ala Pro Tyr Met Pro Asp Val Leu Glu Lys Leu Glu Leu
    2690                2695                2700
Leu Gln Arg Arg Phe Gly Gly Thr Val Ile Arg Asn Pro Leu Ser
    2705                2710                2715
```

```
Arg Asn Ser Thr His Glu Met Tyr Tyr Val Ser Gly Ala Arg Ser
2720                2725                2730

Asn Val Thr Phe Thr Val Asn Gln Thr Ser Arg Leu Leu Met Arg
2735                2740                2745

Arg Met Arg Arg Pro Thr Gly Lys Val Thr Leu Glu Ala Asp Val
2750                2755                2760

Ile Leu Pro Ile Gly Thr Arg Ser Val Glu Thr Asp Lys Gly Pro
2765                2770                2775

Leu Asp Lys Glu Ala Ile Glu Glu Arg Val Glu Arg Ile Lys Ser
2780                2785                2790

Glu Tyr Met Thr Ser Trp Phe Tyr Asp Asn Asp Asn Pro Tyr Arg
2795                2800                2805

Thr Trp His Tyr Cys Gly Ser Tyr Val Thr Lys Thr Ser Gly Ser
2810                2815                2820

Ala Ala Ser Met Val Asn Gly Val Ile Lys Ile Leu Thr Tyr Pro
2825                2830                2835

Trp Asp Arg Ile Glu Glu Val Thr Arg Met Ala Met Thr Asp Thr
2840                2845                2850

Thr Pro Phe Gly Gln Gln Arg Val Phe Lys Glu Lys Val Asp Thr
2855                2860                2865

Arg Ala Lys Asp Pro Pro Ala Gly Thr Arg Lys Ile Met Lys Val
2870                2875                2880

Val Asn Arg Trp Leu Phe Arg His Leu Ala Arg Glu Lys Asn Pro
2885                2890                2895

Arg Leu Cys Thr Lys Glu Glu Phe Ile Ala Lys Val Arg Ser His
2900                2905                2910

Ala Ala Ile Gly Ala Tyr Leu Glu Glu Gln Glu Gln Trp Lys Thr
2915                2920                2925

Ala Asn Glu Ala Val Gln Asp Pro Lys Phe Trp Glu Leu Val Asp
2930                2935                2940

Glu Glu Arg Lys Leu His Gln Gln Gly Arg Cys Arg Thr Cys Val
2945                2950                2955

Tyr Asn Met Met Gly Lys Arg Glu Lys Lys Leu Ser Glu Phe Gly
2960                2965                2970

Lys Ala Lys Gly Ser Arg Ala Ile Trp Tyr Met Trp Leu Gly Ala
2975                2980                2985

Arg Tyr Leu Glu Phe Glu Ala Leu Gly Phe Leu Asn Glu Asp His
2990                2995                3000

Trp Ala Ser Arg Glu Asn Ser Gly Gly Gly Val Glu Gly Ile Gly
3005                3010                3015

Leu Gln Tyr Leu Gly Tyr Val Ile Arg Asp Leu Ala Ala Met Asp
3020                3025                3030

Gly Gly Gly Phe Tyr Ala Asp Asp Thr Ala Gly Trp Asp Thr Arg
3035                3040                3045

Ile Thr Glu Ala Asp Leu Asp Asp Glu Gln Glu Ile Leu Asn Tyr
3050                3055                3060

Met Ser Pro His His Lys Lys Leu Ala Gln Ala Val Met Glu Met
3065                3070                3075

Thr Tyr Lys Asn Lys Val Val Lys Val Leu Arg Pro Ala Pro Gly
3080                3085                3090

Gly Lys Ala Tyr Met Asp Val Ile Ser Arg Arg Asp Gln Arg Gly
3095                3100                3105
```

```
Ser Gly Gln Val Val Thr Tyr Ala Leu Asn Thr Ile Thr Asn Leu
    3110                3115                3120

Lys Val Gln Leu Ile Arg Met Ala Glu Ala Glu Met Val Ile His
3125                3130                3135

His Gln His Val Gln Asp Cys Asp Glu Ser Val Leu Thr Arg Leu
    3140                3145                3150

Glu Ala Trp Leu Thr Glu His Gly Cys Asn Arg Leu Lys Arg Met
3155                3160                3165

Ala Val Ser Gly Asp Asp Cys Val Val Arg Pro Ile Asp Asp Arg
    3170                3175                3180

Phe Gly Leu Ala Leu Ser His Leu Asn Ala Met Ser Lys Val Arg
3185                3190                3195

Lys Asp Ile Ser Glu Trp Gln Pro Ser Lys Gly Trp Asn Asp Trp
    3200                3205                3210

Glu Asn Val Pro Phe Cys Ser His His Phe His Glu Leu Gln Leu
3215                3220                3225

Lys Asp Gly Arg Arg Ile Val Val Pro Cys Arg Glu Gln Asp Glu
    3230                3235                3240

Leu Ile Gly Arg Gly Arg Val Ser Pro Gly Asn Gly Trp Met Ile
3245                3250                3255

Lys Glu Thr Ala Cys Leu Ser Lys Ala Tyr Ala Asn Met Trp Ser
    3260                3265                3270

Leu Met Tyr Phe His Lys Arg Asp Met Arg Leu Leu Ser Leu Ala
3275                3280                3285

Val Ser Ser Ala Val Pro Thr Ser Trp Val Pro Gln Gly Arg Thr
    3290                3295                3300

Thr Trp Ser Ile His Gly Lys Gly Glu Trp Met Thr Thr Glu Asp
3305                3310                3315

Met Leu Glu Val Trp Asn Arg Val Trp Ile Thr Asn Asn Pro His
    3320                3325                3330

Met Gln Asp Lys Thr Met Val Lys Lys Trp Arg Asp Val Pro Tyr
3335                3340                3345

Leu Thr Lys Arg Gln Asp Lys Leu Cys Gly Ser Leu Ile Gly Met
    3350                3355                3360

Thr Asn Arg Ala Thr Trp Ala Ser His Ile His Leu Val Ile His
3365                3370                3375

Arg Ile Arg Thr Leu Ile Gly Gln Glu Lys Tyr Thr Asp Tyr Leu
    3380                3385                3390

Thr Val Met Asp Arg Tyr Ser Val Asp Ala Asp Leu Gln Leu Gly
3395                3400                3405

Glu Leu Ile
    3410

<210> SEQ ID NO 4
<211> LENGTH: 3411
<212> TYPE: PRT
<213> ORGANISM: Artificial Sequence
<220> FEATURE:
<223> OTHER INFORMATION: Flaviviridae Flavivirus Yellow Fever Virus

<400> SEQUENCE: 4

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30
```

```
Gln Ile Gly Asn Arg Pro Gly Pro Ser Arg Gly Val Gln Gly Phe Ile
         35                  40                  45

Phe Phe Phe Leu Phe Asn Ile Leu Thr Gly Lys Lys Ile Thr Ala His
 50                  55                  60

Leu Lys Arg Leu Trp Lys Met Leu Asp Pro Arg Gln Gly Leu Ala Val
 65                  70                  75                  80

Leu Arg Lys Val Lys Arg Val Ala Ser Leu Met Arg Gly Leu Ser
                 85                  90                  95

Ser Arg Lys Arg Arg Ser His Asp Val Leu Thr Val Gln Phe Leu Ile
                100                 105                 110

Leu Gly Met Leu Leu Met Thr Gly Gly Val Thr Leu Val Arg Lys Asn
         115                 120                 125

Arg Trp Leu Leu Leu Asn Val Thr Ser Glu Asp Leu Gly Lys Thr Phe
 130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
                180                 185                 190

Arg Val Ala Tyr Gly Lys Cys Asp Ser Ala Gly Arg Ser Arg Arg Ser
         195                 200                 205

Arg Arg Ala Ile Asp Leu Pro Thr His Glu Asn His Gly Leu Lys Thr
225         210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
         260                 265                 270

Ile Ala Leu Leu Val Leu Ala Val Gly Pro Ala Tyr Ser Ala His Cys
         275                 280                 285

Ile Gly Ile Thr Asp Arg Asp Phe Ile Glu Gly Val His Gly Gly Thr
         290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Arg Pro Ala Glu Val Arg Lys Val Cys Tyr Asn Ala Val Leu Thr His
         340                 345                 350

Val Lys Ile Asn Asp Lys Cys Pro Ser Thr Gly Glu Ala His Leu Ala
         355                 360                 365

Glu Glu Asn Glu Gly Asp Asn Ala Cys Lys Arg Thr Tyr Ser Asp Arg
         370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
                405                 410                 415

Gln Thr Lys Ile Gln Tyr Val Ile Arg Ala Gln Leu His Val Gly Ala
         420                 425                 430

Lys Gln Glu Asn Trp Thr Thr Asp Ile Lys Thr Leu Arg Phe Asp Ala
         435                 440                 445

Leu Ser Gly Ser Gln Glu Val Glu Phe Ile Gly Tyr Gly Lys Ala Thr
```

```
            450                 455                 460
Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
                485                 490                 495

Asp Leu Thr Leu Pro Trp Gln Ser Gly Ser Gly Val Trp Arg Glu
                500                 505                 510

Met His His Leu Val Glu Phe Glu Pro Pro His Ala Ala Thr Ile Arg
                515                 520                 525

Val Leu Ala Leu Gly Asn Gln Glu Gly Ser Leu Lys Thr Ala Leu Thr
                530                 535                 540

Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
                595                 600                 605

Val Ser Lys Gly Ala Pro Cys Arg Ile Pro Val Ile Val Ala Asp Asp
                610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
                675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
                755                 760                 765

Met Met Phe Leu Ser Leu Gly Val Gly Ala Asp Gln Gly Cys Ala Ile
770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Tyr Pro Glu Asp
                805                 810                 815

Pro Val Lys Leu Ala Ser Ile Val Lys Ala Ser Phe Glu Glu Gly Lys
                820                 825                 830

Cys Gly Leu Asn Ser Val Asp Ser Leu Glu His Glu Met Trp Arg Ser
                835                 840                 845

Arg Ala Asp Glu Ile Asn Ala Ile Phe Glu Glu Asn Glu Val Asp Ile
                850                 855                 860

Ser Val Val Val Gln Asp Pro Lys Asn Val Tyr Gln Arg Gly Thr His
865                 870                 875                 880
```

```
Pro Phe Ser Arg Ile Arg Asp Gly Leu Gln Tyr Gly Trp Lys Thr Trp
            885                 890                 895

Gly Lys Asn Leu Val Phe Ser Pro Gly Arg Lys Asn Gly Ser Phe Ile
        900                 905                 910

Ile Asp Gly Lys Ser Arg Lys Glu Cys Pro Phe Ser Asn Arg Val Trp
            915                 920                 925

Asn Ser Phe Gln Ile Glu Glu Phe Gly Thr Gly Val Phe Thr Thr Arg
        930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
            965                 970                 975

Thr Phe Trp Met Gly Ser His Glu Val Asn Gly Thr Trp Met Ile His
            980                 985                 990

Thr Leu Glu Ala Leu Asp Tyr Lys Glu Cys Glu Trp Pro Leu Thr His
            995                 1000                1005

Thr Ile Gly Thr Ser Val Glu Glu Ser Glu Met Phe Met Pro Arg
        1010                1015                1020

Ser Ile Gly Gly Pro Val Ser Ser His Asn His Ile Pro Gly Tyr
        1025                1030                1035

Lys Val Gln Thr Asn Gly Pro Trp Met Gln Val Pro Leu Glu Val
        1040                1045                1050

Lys Arg Glu Ala Cys Pro Gly Thr Ser Val Ile Ile Asp Gly Asn
        1055                1060                1065

Cys Asp Gly Arg Gly Lys Ser Thr Arg Ser Thr Thr Asp Ser Gly
        1070                1075                1080

Lys Val Ile Pro Glu Trp Cys Cys Arg Ser Cys Thr Met Pro Pro
        1085                1090                1095

Val Ser Phe His Gly Ser Asp Gly Cys Trp Tyr Pro Met Glu Ile
        1100                1105                1110

Arg Pro Arg Lys Thr His Glu Ser His Leu Val Arg Ser Trp Val
        1115                1120                1125

Thr Ala Gly Glu Ile His Ala Val Pro Phe Gly Leu Val Ser Met
        1130                1135                1140

Met Ile Ala Met Glu Val Val Leu Arg Lys Arg Gln Gly Pro Lys
        1145                1150                1155

Gln Met Leu Val Gly Gly Val Leu Leu Gly Ala Met Leu Val
        1160                1165                1170

Gly Gln Val Thr Leu Leu Asp Leu Leu Lys Leu Thr Val Ala Val
        1175                1180                1185

Gly Leu His Phe His Glu Met Asn Asn Gly Gly Asp Ala Met Tyr
        1190                1195                1200

Met Ala Leu Ile Ala Ala Phe Ser Ile Arg Pro Gly Leu Leu Ile
        1205                1210                1215

Gly Phe Gly Leu Arg Thr Leu Trp Ser Pro Arg Glu Arg Leu Val
        1220                1225                1230

Leu Thr Leu Gly Ala Ala Met Val Glu Ile Ala Leu Gly Gly Val
        1235                1240                1245

Met Gly Gly Leu Trp Lys Tyr Leu Asn Ala Val Ser Leu Cys Ile
        1250                1255                1260

Leu Thr Ile Asn Ala Val Ala Ser Arg Lys Ala Ser Asn Thr Ile
        1265                1270                1275
```

```
Leu Pro Leu Met Ala Leu Leu Thr Pro Val Thr Met Ala Glu Val
    1280                1285                1290

Arg Leu Ala Ala Met Phe Phe Cys Ala Val Val Ile Ile Gly Val
    1295                1300                1305

Leu His Gln Asn Phe Lys Asp Thr Ser Met Gln Lys Thr Ile Pro
    1310                1315                1320

Leu Val Ala Leu Thr Leu Thr Ser Tyr Leu Gly Leu Thr Gln Pro
    1325                1330                1335

Phe Leu Gly Leu Cys Ala Phe Leu Ala Thr Arg Ile Phe Gly Arg
    1340                1345                1350

Arg Ser Ile Pro Val Asn Glu Ala Leu Ala Ala Gly Leu Val
    1355                1360                1365

Gly Val Leu Ala Gly Leu Ala Phe Gln Glu Met Glu Asn Phe Leu
    1370                1375                1380

Gly Pro Ile Ala Val Gly Gly Leu Leu Met Met Leu Val Ser Val
    1385                1390                1395

Ala Gly Arg Val Asp Gly Leu Glu Leu Lys Lys Leu Gly Glu Val
    1400                1405                1410

Ser Trp Glu Glu Glu Ala Glu Ile Ser Gly Ser Ser Ala Arg Tyr
    1415                1420                1425

Asp Val Ala Leu Ser Glu Gln Gly Glu Phe Lys Leu Leu Ser Glu
    1430                1435                1440

Glu Lys Val Pro Trp Asp Gln Val Val Met Thr Ser Leu Ala Leu
    1445                1450                1455

Val Gly Ala Ala Leu His Pro Phe Ala Leu Leu Leu Val Leu Ala
    1460                1465                1470

Gly Trp Leu Phe His Val Arg Gly Ala Arg Arg Ser Gly Asp Val
    1475                1480                1485

Leu Trp Asp Ile Pro Thr Pro Lys Ile Ile Glu Glu Cys Glu His
    1490                1495                1500

Leu Glu Asp Gly Ile Tyr Gly Ile Phe Gln Ser Thr Phe Leu Gly
    1505                1510                1515

Ala Ser Gln Arg Gly Val Gly Val Ala Gln Gly Gly Val Phe His
    1520                1525                1530

Thr Met Trp His Val Thr Arg Gly Ala Phe Leu Val Arg Asn Gly
    1535                1540                1545

Lys Lys Leu Ile Pro Ser Trp Ala Ser Val Lys Glu Asp Leu Val
    1550                1555                1560

Ala Tyr Gly Gly Ser Trp Lys Leu Glu Gly Arg Trp Asp Gly Glu
    1565                1570                1575

Glu Glu Val Gln Leu Ile Ala Ala Val Pro Gly Lys Asn Val Val
    1580                1585                1590

Asn Val Gln Thr Lys Pro Ser Leu Phe Lys Val Arg Asn Gly Gly
    1595                1600                1605

Glu Ile Gly Ala Val Ala Leu Asp Tyr Pro Ser Gly Thr Ser Gly
    1610                1615                1620

Ser Pro Ile Val Asn Arg Asn Gly Glu Val Ile Gly Leu Tyr Gly
    1625                1630                1635

Asn Gly Ile Leu Val Gly Asp Asn Ser Phe Val Ser Ala Ile Ser
    1640                1645                1650

Gln Thr Glu Val Lys Glu Glu Gly Lys Glu Glu Leu Gln Glu Ile
    1655                1660                1665

Pro Thr Met Leu Lys Lys Gly Met Thr Thr Val Leu Asp Phe His
```

-continued

```
              1670                1675                1680
Pro Gly Ala Gly Lys Thr Arg Arg Phe Leu Pro Gln Ile Leu Ala
              1685                1690                1695
Glu Cys Ala Arg Arg Arg Leu Arg Thr Leu Val Leu Ala Pro Thr
              1700                1705                1710
Arg Val Val Leu Ser Glu Met Lys Glu Ala Phe His Gly Leu Asp
              1715                1720                1725
Val Lys Phe His Thr Gln Ala Phe Ser Ala His Gly Ser Gly Arg
              1730                1735                1740
Glu Val Ile Asp Ala Met Cys His Ala Thr Leu Thr Tyr Arg Met
              1745                1750                1755
Leu Glu Pro Thr Arg Val Val Asn Trp Glu Val Ile Ile Met Asp
              1760                1765                1770
Glu Ala His Phe Leu Asp Pro Ala Ser Ile Ala Ala Arg Gly Trp
              1775                1780                1785
Ala Ala His Arg Ala Arg Ala Asn Glu Ser Ala Thr Ile Leu Met
              1790                1795                1800
Thr Ala Thr Pro Pro Gly Thr Ser Asp Glu Phe Pro His Ser Asn
              1805                1810                1815
Gly Glu Ile Glu Asp Val Gln Thr Asp Ile Pro Ser Glu Pro Trp
              1820                1825                1830
Asn Thr Gly His Asp Trp Ile Leu Ala Asp Lys Arg Pro Thr Ala
              1835                1840                1845
Trp Phe Leu Pro Ser Ile Arg Ala Ala Asn Val Met Ala Ala Ser
              1850                1855                1860
Leu Arg Lys Ala Gly Lys Ser Val Val Leu Asn Arg Lys Thr
              1865                1870                1875
Phe Glu Arg Glu Tyr Pro Thr Ile Lys Gln Lys Lys Pro Asp Phe
              1880                1885                1890
Ile Leu Ala Thr Asp Ile Ala Glu Met Gly Ala Asn Leu Cys Val
              1895                1900                1905
Glu Arg Val Leu Asp Cys Arg Thr Ala Phe Lys Pro Val Leu Val
              1910                1915                1920
Asp Glu Gly Arg Lys Val Ala Ile Lys Gly Pro Leu Arg Ile Ser
              1925                1930                1935
Ala Ser Ser Ala Ala Gln Arg Arg Gly Arg Ile Gly Arg Asn Pro
              1940                1945                1950
Asn Arg Asp Gly Asp Ser Tyr Tyr Tyr Ser Glu Pro Thr Ser Glu
              1955                1960                1965
Asn Asn Ala His His Val Cys Trp Leu Glu Ala Ser Met Leu Leu
              1970                1975                1980
Asp Asn Met Glu Val Arg Gly Gly Met Val Ala Pro Leu Tyr Gly
              1985                1990                1995
Val Glu Gly Thr Lys Thr Pro Val Ser Pro Gly Glu Met Arg Leu
              2000                2005                2010
Arg Asp Asp Gln Arg Lys Val Phe Arg Glu Leu Val Arg Asn Cys
              2015                2020                2025
Asp Leu Pro Val Trp Leu Ser Trp Gln Val Ala Lys Ala Gly Leu
              2030                2035                2040
Lys Thr Asn Asp Arg Lys Trp Cys Phe Glu Gly Pro Glu Glu His
              2045                2050                2055
Glu Ile Leu Asn Asp Ser Gly Glu Thr Val Lys Cys Arg Ala Pro
              2060                2065                2070
```

```
Gly Gly Ala Lys Lys Pro Leu Arg Pro Arg Trp Cys Asp Glu Arg
        2075            2080            2085

Val Ser Ser Asp Gln Ser Ala Leu Ser Glu Phe Ile Lys Phe Ala
2090            2095            2100

Glu Gly Arg Arg Gly Ala Ala Glu Val Leu Val Val Leu Ser Glu
2105            2110            2115

Leu Pro Asp Phe Leu Ala Lys Lys Gly Gly Ala Met Asp Thr
    2120            2125            2130

Ile Ser Val Phe Leu His Ser Glu Glu Gly Ser Arg Ala Tyr Arg
2135            2140            2145

Asn Ala Leu Ser Met Met Pro Glu Ala Met Thr Ile Val Met Leu
    2150            2155            2160

Phe Ile Leu Ala Gly Leu Leu Thr Ser Gly Met Val Ile Phe Phe
2165            2170            2175

Met Ser Pro Lys Gly Ile Ser Arg Met Ser Met Ala Met Gly Thr
    2180            2185            2190

Met Ala Gly Cys Gly Tyr Leu Met Phe Leu Gly Gly Val Lys Pro
    2195            2200            2205

Thr His Ile Ser Tyr Ile Met Leu Ile Phe Phe Val Leu Met Val
    2210            2215            2220

Val Val Ile Pro Glu Pro Gly Gln Gln Arg Ser Ile Gln Asp Asn
2225            2230            2235

Gln Val Ala Tyr Leu Ile Ile Gly Ile Leu Thr Leu Val Ser Ala
    2240            2245            2250

Val Ala Ala Asn Glu Leu Gly Met Leu Glu Lys Thr Lys Glu Asp
2255            2260            2265

Leu Phe Gly Lys Lys Asn Leu Ile Pro Ser Ser Ala Ser Pro Trp
    2270            2275            2280

Ser Trp Pro Asp Leu Asp Leu Lys Pro Gly Ala Ala Trp Thr Val
    2285            2290            2295

Tyr Val Gly Ile Val Thr Met Leu Ser Pro Met Leu His His Trp
    2300            2305            2310

Ile Lys Val Glu Tyr Gly Asn Leu Ser Leu Ser Gly Ile Ala Gln
    2315            2320            2325

Ser Ala Ser Val Leu Ser Phe Met Asp Lys Gly Ile Pro Phe Met
    2330            2335            2340

Lys Met Asn Ile Ser Val Ile Met Leu Leu Val Ser Gly Trp Asn
    2345            2350            2355

Ser Ile Thr Val Met Pro Leu Leu Cys Gly Ile Gly Cys Ala Met
    2360            2365            2370

Leu His Trp Ser Leu Ile Leu Pro Gly Ile Lys Ala Gln Gln Ser
    2375            2380            2385

Lys Leu Ala Gln Arg Arg Val Phe His Gly Val Ala Lys Asn Pro
    2390            2395            2400

Val Val Asp Gly Asn Pro Thr Val Asp Ile Glu Glu Ala Pro Glu
2405            2410            2415

Met Pro Ala Leu Tyr Glu Lys Lys Leu Ala Leu Tyr Leu Leu Leu
    2420            2425            2430

Ala Leu Ser Leu Ala Ser Val Ala Met Cys Arg Thr Pro Phe Ser
    2435            2440            2445

Leu Ala Glu Gly Ile Val Leu Ala Ser Ala Ala Leu Gly Pro Leu
    2450            2455            2460
```

```
Ile Glu Gly Asn Thr Ser Leu Leu Trp Asn Gly Pro Met Ala Val
2465                2470                2475

Ser Met Thr Gly Val Met Arg Gly Asn His Tyr Ala Phe Val Gly
    2480                2485                2490

Val Met Tyr Asn Leu Trp Lys Met Lys Thr Gly Arg Arg Gly Ser
    2495                2500                2505

Ala Asn Gly Lys Thr Leu Gly Glu Val Trp Lys Arg Glu Leu Asn
    2510                2515                2520

Leu Leu Asp Lys Arg Gln Phe Glu Leu Tyr Lys Arg Thr Asp Ile
    2525                2530                2535

Val Glu Val Asp Arg Asp Thr Ala Arg Arg His Leu Ala Glu Gly
    2540                2545                2550

Lys Val Asp Thr Gly Val Ala Val Ser Arg Gly Thr Ala Lys Leu
    2555                2560                2565

Arg Trp Phe His Glu Arg Gly Tyr Val Lys Leu Glu Gly Arg Val
    2570                2575                2580

Ile Asp Leu Gly Cys Gly Arg Gly Gly Trp Cys Tyr Tyr Ala Ala
    2585                2590                2595

Ala Gln Lys Glu Val Ser Gly Val Lys Gly Phe Thr Leu Gly Arg
    2600                2605                2610

Asp Gly His Glu Lys Pro Met Asn Val Gln Ser Leu Gly Trp Asn
    2615                2620                2625

Ile Ile Thr Phe Lys Asp Lys Thr Asp Ile His Arg Leu Glu Pro
    2630                2635                2640

Val Lys Cys Asp Thr Leu Leu Cys Asp Ile Gly Glu Ser Ser Ser
    2645                2650                2655

Ser Ser Val Thr Glu Gly Glu Arg Thr Val Arg Val Leu Asp Thr
    2660                2665                2670

Val Glu Lys Trp Leu Ala Cys Gly Val Asp Asn Phe Cys Val Lys
    2675                2680                2685

Val Leu Ala Pro Tyr Met Pro Asp Val Leu Glu Lys Leu Glu Leu
    2690                2695                2700

Leu Gln Arg Arg Phe Gly Gly Thr Val Ile Arg Asn Pro Leu Ser
    2705                2710                2715

Arg Asn Ser Thr His Glu Met Tyr Tyr Val Ser Gly Ala Arg Ser
    2720                2725                2730

Asn Val Thr Phe Thr Val Asn Gln Thr Ser Arg Leu Leu Met Arg
    2735                2740                2745

Arg Met Arg Arg Pro Thr Gly Lys Val Thr Leu Glu Ala Asp Val
    2750                2755                2760

Ile Leu Pro Ile Gly Thr Arg Ser Val Glu Thr Asp Lys Gly Pro
    2765                2770                2775

Leu Asp Lys Glu Ala Ile Glu Glu Arg Val Glu Arg Ile Lys Ser
    2780                2785                2790

Glu Tyr Met Thr Ser Trp Phe Tyr Asp Asn Asp Asn Pro Tyr Arg
    2795                2800                2805

Thr Trp His Tyr Cys Gly Ser Tyr Val Thr Lys Thr Ser Gly Ser
    2810                2815                2820

Ala Ala Ser Met Val Asn Gly Val Ile Lys Ile Leu Thr Tyr Pro
    2825                2830                2835

Trp Asp Arg Ile Glu Glu Val Thr Arg Met Ala Met Thr Asp Thr
    2840                2845                2850

Thr Pro Phe Gly Gln Gln Arg Val Phe Lys Glu Lys Val Asp Thr
```

-continued

```
            2855              2860              2865
Arg Ala Lys Asp Pro Pro Ala Gly Thr Arg Lys Ile Met Lys Val
            2870              2875              2880
Val Asn Arg Trp Leu Phe Arg His Leu Ala Arg Glu Lys Asn Pro
            2885              2890              2895
Arg Leu Cys Thr Lys Glu Glu Phe Ile Ala Lys Val Arg Ser His
            2900              2905              2910
Ala Ala Ile Gly Ala Tyr Leu Glu Glu Gln Glu Gln Trp Lys Thr
            2915              2920              2925
Ala Asn Glu Ala Val Gln Asp Pro Lys Phe Trp Glu Leu Val Asp
            2930              2935              2940
Glu Glu Arg Lys Leu His Gln Gln Gly Arg Cys Arg Thr Cys Val
            2945              2950              2955
Tyr Asn Met Met Gly Lys Arg Glu Lys Lys Leu Ser Glu Phe Gly
            2960              2965              2970
Lys Ala Lys Gly Ser Arg Ala Ile Trp Tyr Met Trp Leu Gly Ala
            2975              2980              2985
Arg Tyr Leu Glu Phe Glu Ala Leu Gly Phe Leu Asn Glu Asp His
            2990              2995              3000
Trp Ala Ser Arg Glu Asn Ser Gly Gly Gly Val Glu Gly Ile Gly
            3005              3010              3015
Leu Gln Tyr Leu Gly Tyr Val Ile Arg Asp Leu Ala Ala Met Asp
            3020              3025              3030
Gly Gly Gly Phe Tyr Ala Asp Asp Thr Ala Gly Trp Asp Thr Arg
            3035              3040              3045
Ile Thr Glu Ala Asp Leu Asp Asp Glu Gln Glu Ile Leu Asn Tyr
            3050              3055              3060
Met Ser Pro His His Lys Lys Leu Ala Gln Ala Val Met Glu Met
            3065              3070              3075
Thr Tyr Lys Asn Lys Val Val Lys Val Leu Arg Pro Ala Pro Gly
            3080              3085              3090
Gly Lys Ala Tyr Met Asp Val Ile Ser Arg Arg Asp Gln Arg Gly
            3095              3100              3105
Ser Gly Gln Val Val Thr Tyr Ala Leu Asn Thr Ile Thr Asn Leu
            3110              3115              3120
Lys Val Gln Leu Ile Arg Met Ala Glu Ala Glu Met Val Ile His
            3125              3130              3135
His Gln His Val Gln Asp Cys Asp Glu Ser Val Leu Thr Arg Leu
            3140              3145              3150
Glu Ala Trp Leu Thr Glu His Gly Cys Asn Arg Leu Lys Arg Met
            3155              3160              3165
Ala Val Ser Gly Asp Asp Cys Val Val Arg Pro Ile Asp Asp Arg
            3170              3175              3180
Phe Gly Leu Ala Leu Ser His Leu Asn Ala Met Ser Lys Val Arg
            3185              3190              3195
Lys Asp Ile Ser Glu Trp Gln Pro Ser Lys Gly Trp Asn Asp Trp
            3200              3205              3210
Glu Asn Val Pro Phe Cys Ser His His Phe His Glu Leu Gln Leu
            3215              3220              3225
Lys Asp Gly Arg Arg Ile Val Val Pro Cys Arg Glu Gln Asp Glu
            3230              3235              3240
Leu Ile Gly Arg Gly Arg Val Ser Pro Gly Asn Gly Trp Met Ile
            3245              3250              3255
```

-continued

```
Lys Glu Thr Ala Cys Leu Ser Lys Ala Tyr Ala Asn Met Trp Ser
    3260                3265                3270

Leu Met Tyr Phe His Lys Arg Asp Met Arg Leu Leu Ser Leu Ala
    3275                3280                3285

Val Ser Ser Ala Val Pro Thr Ser Trp Val Pro Gln Gly Arg Thr
    3290                3295                3300

Thr Trp Ser Ile His Gly Lys Gly Glu Trp Met Thr Thr Glu Asp
    3305                3310                3315

Met Leu Glu Val Trp Asn Arg Val Trp Ile Thr Asn Asn Pro His
    3320                3325                3330

Met Gln Asp Lys Thr Met Val Lys Lys Trp Arg Asp Val Pro Tyr
    3335                3340                3345

Leu Thr Lys Arg Gln Asp Lys Leu Cys Gly Ser Leu Ile Gly Met
    3350                3355                3360

Thr Asn Arg Ala Thr Trp Ala Ser His Ile His Leu Val Ile His
    3365                3370                3375

Arg Ile Arg Thr Leu Ile Gly Gln Glu Lys Tyr Thr Asp Tyr Leu
    3380                3385                3390

Thr Val Met Asp Arg Tyr Ser Val Asp Ala Asp Leu Gln Leu Gly
    3395                3400                3405

Glu Leu Ile
    3410

<210> SEQ ID NO 5
<211> LENGTH: 684
<212> TYPE: PRT
<213> ORGANISM: Artificial Sequence
<220> FEATURE:
<223> OTHER INFORMATION: Flaviviridae Flavivirus Yellow Fever Virus

<400> SEQUENCE: 5

Ile Leu Gly Met Leu Leu Met Thr Gly Gly Val Thr Leu Val Arg Lys
1               5                   10                  15

Asn Arg Trp Leu Leu Leu Asn Val Thr Ser Glu Asp Leu Gly Lys Thr
                20                  25                  30

Phe Ser Val Gly Thr Gly Asn Cys Thr Thr Asn Ile Leu Glu Ala Lys
            35                  40                  45

Tyr Trp Cys Pro Asp Ser Met Glu Tyr Asn Cys Pro Asn Leu Ser Pro
        50                  55                  60

Arg Glu Glu Pro Asp Asp Ile Asp Cys Trp Cys Tyr Gly Val Glu Asn
65                  70                  75                  80

Val Arg Val Ala Tyr Gly Lys Cys Asp Ser Ala Gly Arg Ser Arg Arg
                85                  90                  95

Ser Arg Arg Ala Ile Asp Leu Pro Thr His Glu Asn His Gly Leu Lys
            100                 105                 110

Thr Arg Gln Glu Lys Trp Met Thr Gly Arg Met Gly Glu Arg Gln Leu
        115                 120                 125

Gln Lys Ile Glu Arg Trp Phe Val Arg Asn Pro Phe Phe Ala Val Thr
    130                 135                 140

Ala Leu Thr Ile Ala Tyr Leu Val Gly Ser Asn Met Thr Gln Arg Val
145                 150                 155                 160

Val Ile Ala Leu Leu Val Leu Ala Val Gly Pro Ala Tyr Ser Ala His
                165                 170                 175

Cys Ile Gly Ile Thr Asp Arg Asp Phe Ile Glu Gly Val His Gly Gly
            180                 185                 190
```

```
Thr Trp Val Ser Ala Thr Leu Glu Gln Asp Lys Cys Val Thr Val Met
        195                 200                 205

Ala Pro Asp Lys Pro Ser Leu Asp Ile Ser Leu Glu Thr Val Ala Ile
210                 215                 220

Asp Arg Pro Ala Glu Val Arg Lys Val Cys Tyr Asn Ala Val Leu Thr
225                 230                 235                 240

His Val Lys Ile Asn Asp Lys Cys Pro Ser Thr Gly Glu Ala His Leu
                245                 250                 255

Ala Glu Glu Asn Glu Gly Asp Asn Ala Cys Lys Arg Thr Tyr Ser Asp
                260                 265                 270

Arg Gly Trp Gly Asn Gly Cys Gly Leu Phe Gly Lys Gly Ser Ile Val
                275                 280                 285

Ala Cys Ala Lys Phe Thr Cys Ala Lys Ser Met Ser Leu Phe Glu Val
290                 295                 300

Asp Gln Thr Lys Ile Gln Tyr Val Ile Arg Ala Gln Leu His Val Gly
305                 310                 315                 320

Ala Lys Gln Glu Asn Trp Thr Thr Asp Ile Lys Thr Leu Lys Phe Asp
                325                 330                 335

Ala Leu Ser Gly Ser Gln Glu Val Glu Phe Ile Gly Tyr Gly Lys Ala
                340                 345                 350

Thr Leu Glu Cys Gln Val Gln Thr Ala Val Asp Phe Gly Asn Ser Tyr
                355                 360                 365

Ile Ala Glu Met Glu Thr Glu Ser Trp Ile Val Asp Arg Gln Trp Ala
370                 375                 380

Gln Asp Leu Thr Leu Pro Trp Gln Ser Gly Ser Gly Val Trp Arg
385                 390                 395                 400

Glu Met His His Leu Val Glu Phe Glu Pro Pro His Ala Ala Thr Ile
                405                 410                 415

Arg Val Leu Ala Leu Gly Asn Gln Glu Gly Ser Leu Lys Thr Ala Leu
                420                 425                 430

Thr Gly Ala Met Arg Val Thr Lys Asp Thr Asn Asp Asn Asn Leu Tyr
                435                 440                 445

Lys Leu His Gly Gly His Val Ser Cys Arg Val Lys Leu Ser Ala Leu
450                 455                 460

Thr Leu Lys Gly Thr Ser Tyr Lys Ile Cys Thr Asp Lys Met Phe Phe
465                 470                 475                 480

Val Lys Asn Pro Thr Asp Thr Gly His Gly Thr Val Val Met Gln Val
                485                 490                 495

Lys Val Ser Lys Gly Ala Pro Cys Arg Ile Pro Val Ile Val Ala Asp
                500                 505                 510

Asp Leu Thr Ala Ala Ile Asn Lys Gly Ile Leu Val Thr Val Asn Pro
                515                 520                 525

Ile Ala Ser Thr Asn Asp Asp Glu Val Leu Ile Glu Val Asn Pro Pro
530                 535                 540

Phe Gly Asp Ser Tyr Ile Ile Val Gly Arg Gly Asp Ser Arg Leu Thr
545                 550                 555                 560

Tyr Gln Trp His Lys Glu Gly Ser Ser Ile Gly Lys Leu Phe Thr Gln
                565                 570                 575

Thr Met Lys Gly Val Glu Arg Leu Ala Val Met Gly Asp Thr Ala Trp
                580                 585                 590

Asp Phe Ser Ser Ala Gly Gly Phe Phe Thr Ser Val Gly Lys Gly Ile
                595                 600                 605
```

-continued

His Thr Val Phe Gly Ser Ala Phe Gln Gly Leu Phe Gly Gly Leu Asn
            610                 615                 620

Trp Ile Thr Lys Val Ile Met Gly Ala Val Leu Ile Trp Val Gly Ile
625                 630                 635                 640

Asn Thr Arg Asn Met Thr Met Ser Met Ser Met Ile Leu Val Gly Val
                645                 650                 655

Ile Met Met Phe Leu Ser Leu Gly Val Gly Ala Asp Gln Gly Cys Ala
            660                 665                 670

Ile Asn Phe Gly Lys Arg Glu Leu Lys Cys Gly Asp
            675                 680

<210> SEQ ID NO 6
<211> LENGTH: 678
<212> TYPE: PRT
<213> ORGANISM: Artificial Sequence
<220> FEATURE:
<223> OTHER INFORMATION: Flaviviridae Flavivirus Yellow Fever Virus

<400> SEQUENCE: 6

Gly Met Leu Leu Met Thr Gly Gly Val Thr Leu Val Arg Lys Asn Arg
1               5                   10                  15

Trp Leu Leu Leu Asn Val Thr Ser Glu Asp Leu Gly Lys Thr Phe Ser
            20                  25                  30

Val Gly Thr Gly Asn Cys Thr Thr Asn Ile Leu Glu Ala Lys Tyr Trp
            35                  40                  45

Cys Pro Asp Ser Met Glu Tyr Asn Cys Pro Asn Leu Ser Pro Arg Glu
        50                  55                  60

Glu Pro Asp Asp Ile Asp Cys Trp Cys Tyr Gly Val Glu Asn Val Arg
65                  70                  75                  80

Val Ala Tyr Gly Lys Cys Asp Ser Ala Gly Arg Ser Arg Arg Ser Arg
            85                  90                  95

Arg Ala Ile Asp Leu Pro Thr His Glu Asn His Gly Leu Lys Thr Arg
            100                 105                 110

Gln Glu Lys Trp Met Thr Gly Arg Met Gly Glu Arg Gln Leu Gln Lys
        115                 120                 125

Ile Glu Arg Trp Phe Val Arg Asn Pro Phe Phe Ala Val Thr Ala Leu
    130                 135                 140

Thr Ile Ala Tyr Leu Val Gly Ser Asn Met Thr Gln Arg Val Val Ile
145                 150                 155                 160

Ala Leu Leu Val Leu Ala Val Gly Pro Ala Tyr Ser Ala His Cys Ile
            165                 170                 175

Gly Ile Thr Asp Arg Asp Phe Ile Glu Gly Val His Gly Gly Thr Trp
            180                 185                 190

Val Ser Ala Thr Leu Glu Gln Asp Lys Cys Val Thr Val Met Ala Pro
        195                 200                 205

Asp Lys Pro Ser Leu Asp Ile Ser Leu Glu Thr Val Ala Ile Asp Arg
    210                 215                 220

Pro Ala Glu Val Arg Lys Val Cys Tyr Asn Ala Val Leu Thr His Val
225                 230                 235                 240

Lys Ile Asn Asp Lys Cys Pro Ser Thr Gly Glu Ala His Leu Ala Glu
            245                 250                 255

Glu Asn Glu Gly Asp Asn Ala Cys Lys Arg Thr Tyr Ser Asp Arg Gly
            260                 265                 270

Trp Gly Asn Gly Cys Gly Leu Phe Gly Lys Gly Ser Ile Val Ala Cys
        275                 280                 285

```
Ala Lys Phe Thr Cys Ala Lys Ser Met Ser Leu Phe Glu Val Asp Gln
    290                 295                 300

Thr Lys Ile Gln Tyr Val Ile Arg Ala Gln Leu His Val Gly Ala Lys
305                 310                 315                 320

Gln Glu Asn Trp Thr Thr Asp Ile Lys Thr Leu Arg Phe Asp Ala Leu
                325                 330                 335

Ser Gly Ser Gln Glu Val Glu Phe Ile Gly Tyr Gly Lys Ala Thr Leu
            340                 345                 350

Glu Cys Gln Val Gln Thr Ala Val Asp Phe Gly Asn Ser Tyr Ile Ala
        355                 360                 365

Glu Met Glu Thr Glu Ser Trp Ile Val Asp Arg Gln Trp Ala Gln Asp
    370                 375                 380

Leu Thr Leu Pro Trp Gln Ser Gly Ser Gly Val Trp Arg Glu Met
385                 390                 395                 400

His His Leu Val Glu Phe Glu Pro Pro His Ala Ala Thr Ile Arg Val
                405                 410                 415

Leu Ala Leu Gly Asn Gln Glu Gly Ser Leu Lys Thr Ala Leu Thr Gly
            420                 425                 430

Ala Met Arg Val Thr Lys Asp Thr Asn Asp Asn Asn Leu Tyr Lys Leu
        435                 440                 445

His Gly Gly His Val Ser Cys Arg Val Lys Leu Ser Ala Leu Thr Leu
    450                 455                 460

Lys Gly Thr Ser Tyr Lys Ile Cys Thr Asp Lys Met Phe Phe Val Lys
465                 470                 475                 480

Asn Pro Thr Asp Thr Gly His Gly Thr Val Val Met Gln Val Lys Val
                485                 490                 495

Ser Lys Gly Ala Pro Cys Arg Ile Pro Val Ile Val Ala Asp Asp Leu
            500                 505                 510

Thr Ala Ala Ile Asn Lys Gly Ile Leu Val Thr Val Asn Pro Ile Ala
        515                 520                 525

Ser Thr Asn Asp Asp Glu Val Leu Ile Glu Val Asn Pro Pro Phe Gly
    530                 535                 540

Asp Ser Tyr Ile Ile Val Gly Arg Gly Asp Ser Arg Leu Thr Tyr Gln
545                 550                 555                 560

Trp His Lys Glu Gly Ser Ser Ile Gly Lys Leu Phe Thr Gln Thr Met
                565                 570                 575

Lys Gly Val Glu Arg Leu Ala Val Met Gly Asp Thr Ala Trp Asp Phe
            580                 585                 590

Ser Ser Ala Gly Gly Phe Phe Thr Ser Val Gly Lys Gly Ile His Thr
        595                 600                 605

Val Phe Gly Ser Ala Phe Gln Gly Leu Phe Gly Gly Leu Asn Trp Ile
    610                 615                 620

Thr Lys Val Ile Met Gly Ala Val Leu Ile Trp Val Gly Ile Asn Thr
625                 630                 635                 640

Arg Asn Met Thr Met Ser Met Ser Met Ile Leu Val Gly Val Ile Met
                645                 650                 655

Met Phe Leu Ser Leu Gly Val Gly Ala Asp Gln Gly Cys Ala Ile Asn
            660                 665                 670

Phe Gly Lys Arg Glu Leu
            675

<210> SEQ ID NO 7
<211> LENGTH: 3411
<212> TYPE: PRT
```

<213> ORGANISM: Artificial Sequence
<220> FEATURE:
<223> OTHER INFORMATION: Flaviviridae Flavivirus Yellow Fever Virus

<400> SEQUENCE: 7

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
        275                 280                 285

Ile Gly Ile Thr Asp Arg Asp Phe Ile Glu Gly Val His Gly Gly Thr
    290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Arg Pro Ala Glu Val Arg Lys Val Cys Tyr Asn Ala Val Leu Thr His
            340                 345                 350

Val Lys Ile Asn Asp Lys Cys Pro Ser Thr Gly Glu Ala His Leu Ala
        355                 360                 365

Glu Glu Asn Glu Gly Asp Asn Ala Cys Lys Arg Thr Tyr Ser Asp Arg
    370                 375                 380

Gly Trp Gly Asn Gly Cys Gly Leu Phe Gly Lys Gly Ser Ile Val Ala
```

```
              385                 390                 395                 400
Cys Ala Lys Phe Thr Cys Ala Lys Ser Met Ser Leu Phe Glu Val Asp
                    405                 410                 415

Gln Thr Lys Ile Gln Tyr Val Ile Arg Ala Gln Leu His Val Gly Ala
                420                 425                 430

Lys Gln Glu Asn Trp Thr Thr Asp Ile Lys Thr Leu Arg Phe Asp Ala
                435                 440                 445

Leu Ser Gly Ser Gln Glu Val Glu Phe Ile Gly Tyr Gly Lys Ala Thr
    450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
                    485                 490                 495

Asp Leu Thr Leu Pro Trp Gln Ser Gly Ser Gly Val Trp Arg Glu
                500                 505                 510

Met His His Leu Val Glu Phe Glu Pro Pro His Ala Ala Thr Ile Arg
            515                 520                 525

Val Leu Ala Leu Gly Asn Gln Glu Gly Ser Leu Lys Thr Ala Leu Thr
        530                 535                 540

Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                    565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
                595                 600                 605

Val Ser Lys Gly Ala Pro Cys Arg Ile Pro Val Ile Val Ala Asp Asp
            610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                    645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
                675                 680                 685

Met Lys Gly Val Glu Arg Leu Ala Val Met Gly Asp Thr Ala Trp Asp
        690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                    725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
                755                 760                 765

Met Met Phe Leu Ser Leu Gly Val Gly Ala Asp Gln Gly Cys Ala Ile
        770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Tyr Pro Glu Asp
                    805                 810                 815
```

-continued

```
Pro Val Lys Leu Ala Ser Ile Val Lys Ala Ser Phe Glu Glu Gly Lys
            820                 825                 830

Cys Gly Leu Asn Ser Val Asp Ser Leu Glu His Glu Met Trp Arg Ser
            835                 840                 845

Arg Ala Asp Glu Ile Asn Ala Ile Phe Glu Glu Asn Glu Val Asp Ile
            850                 855                 860

Ser Val Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                885                 890                 895

Gly Lys Asn Leu Val Phe Ser Pro Gly Arg Lys Asn Gly Ser Phe Ile
            900                 905                 910

Ile Asp Gly Lys Ser Arg Lys Glu Cys Pro Phe Ser Asn Arg Val Trp
            915                 920                 925

Asn Ser Phe Gln Ile Glu Glu Phe Gly Thr Gly Val Phe Thr Thr Arg
            930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
                965                 970                 975

Thr Phe Trp Met Gly Ser His Glu Val Asn Gly Thr Trp Met Ile His
                980                 985                 990

Thr Leu Glu Ala Leu Asp Tyr Lys  Glu Cys Glu Trp Pro  Leu Thr His
            995                1000                 1005

Thr Ile  Gly Thr Ser Val Glu  Glu Ser Glu Met Phe  Met Pro Arg
    1010                 1015                 1020

Ser Ile  Gly Gly Pro Val Ser  Ser His Asn His Ile  Pro Gly Tyr
    1025                 1030                 1035

Lys Val  Gln Thr Asn Gly Pro  Trp Met Gln Val Pro  Leu Glu Val
    1040                 1045                 1050

Lys Arg  Glu Ala Cys Pro Gly  Thr Ser Val Ile Ile  Asp Gly Asn
    1055                 1060                 1065

Cys Asp  Gly Arg Gly Lys Ser  Thr Arg Ser Thr Thr  Asp Ser Gly
    1070                 1075                 1080

Lys Val  Ile Pro Glu Trp Cys  Cys Arg Ser Cys Ile  Met Pro Pro
    1085                 1090                 1095

Val Ser  Phe His Gly Ser Asp  Gly Cys Trp Tyr Pro  Met Glu Ile
    1100                 1105                 1110

Arg Pro  Arg Lys Thr His Glu  Ser His Leu Val Arg  Ser Trp Val
    1115                 1120                 1125

Thr Ala  Gly Glu Ile His Ala  Val Pro Phe Gly Leu  Val Ser Met
    1130                 1135                 1140

Met Ile  Ala Met Glu Val Val  Leu Arg Lys Arg Gln  Gly Pro Lys
    1145                 1150                 1155

Gln Met  Leu Val Gly Gly Val  Val Leu Leu Gly Ala  Met Leu Val
    1160                 1165                 1170

Gly Gln  Val Thr Leu Leu Asp  Leu Leu Lys Leu Thr  Val Ala Val
    1175                 1180                 1185

Gly Leu  His Phe His Glu Met  Asn Asn Gly Gly Asp  Ala Met Tyr
    1190                 1195                 1200

Met Ala  Leu Ile Ala Ala Phe  Ser Ile Arg Pro Gly  Leu Leu Ile
    1205                 1210                 1215
```

```
Gly Phe Gly Leu Arg Thr Leu Trp Ser Pro Arg Glu Arg Leu Val
1220                1225                1230

Leu Thr Leu Gly Ala Ala Met Val Glu Ile Ala Leu Gly Gly Val
    1235                1240                1245

Met Gly Gly Leu Trp Lys Tyr Leu Asn Ala Val Ser Leu Cys Ile
1250                1255                1260

Leu Thr Ile Asn Ala Val Ala Ser Arg Lys Ala Ser Asn Thr Ile
    1265                1270                1275

Leu Pro Leu Met Ala Leu Leu Thr Pro Val Thr Met Ala Glu Val
1280                1285                1290

Arg Leu Ala Ala Met Phe Leu Cys Ala Val Val Ile Ile Gly Val
    1295                1300                1305

Leu His Gln Asn Phe Lys Asp Thr Ser Met Gln Lys Thr Ile Pro
1310                1315                1320

Leu Val Ala Leu Thr Leu Thr Ser Tyr Leu Gly Leu Thr Gln Pro
    1325                1330                1335

Phe Leu Gly Leu Cys Ala Phe Leu Ala Thr Arg Ile Phe Gly Arg
1340                1345                1350

Arg Ser Ile Pro Val Asn Glu Ala Leu Ala Ala Gly Leu Val
    1355                1360                1365

Gly Val Leu Ala Gly Leu Ala Phe Gln Glu Met Glu Asn Phe Leu
1370                1375                1380

Gly Pro Ile Ala Val Gly Gly Leu Leu Met Met Leu Val Ser Val
    1385                1390                1395

Ala Gly Arg Val Asp Gly Leu Glu Leu Lys Lys Leu Gly Glu Val
1400                1405                1410

Ser Trp Glu Glu Glu Ala Glu Ile Ser Gly Ser Ser Ala Arg Tyr
    1415                1420                1425

Asp Val Ala Leu Ser Glu Gln Gly Glu Phe Lys Leu Leu Ser Glu
1430                1435                1440

Glu Lys Val Pro Trp Asp Gln Val Val Met Thr Ser Leu Ala Leu
    1445                1450                1455

Val Gly Ala Ala Leu His Pro Phe Ala Leu Leu Leu Val Leu Ala
1460                1465                1470

Gly Trp Leu Phe His Val Arg Gly Ala Arg Arg Ser Gly Asp Val
    1475                1480                1485

Leu Trp Asp Ile Pro Thr Pro Lys Ile Ile Glu Glu Cys Glu His
1490                1495                1500

Leu Glu Asp Gly Ile Tyr Gly Ile Phe Gln Ser Thr Phe Leu Gly
    1505                1510                1515

Ala Ser Gln Arg Gly Val Gly Val Ala Gln Gly Gly Val Phe His
1520                1525                1530

Thr Met Trp His Val Thr Arg Gly Ala Phe Leu Val Arg Asn Gly
    1535                1540                1545

Lys Lys Leu Ile Pro Ser Trp Ala Ser Val Lys Glu Asp Leu Val
1550                1555                1560

Ala Tyr Gly Gly Ser Trp Lys Leu Glu Gly Arg Trp Asp Gly Glu
    1565                1570                1575

Glu Glu Val Gln Leu Ile Ala Ala Val Pro Gly Lys Asn Val Val
1580                1585                1590

Asn Val Gln Thr Lys Pro Ser Leu Phe Lys Val Arg Asn Gly Gly
    1595                1600                1605

Glu Ile Gly Ala Val Ala Leu Asp Tyr Pro Ser Gly Thr Ser Gly
```

```
                   1610                1615               1620
Ser Pro Ile Val Asn Arg Asn Gly Glu Val Ile Gly Leu Tyr Gly
    1625                1630               1635

Asn Gly Ile Leu Val Gly Asp Asn Ser Phe Val Ser Ala Ile Ser
    1640                1645               1650

Gln Thr Glu Val Lys Glu Glu Gly Lys Glu Glu Leu Gln Glu Ile
    1655                1660               1665

Pro Thr Met Leu Lys Lys Gly Met Thr Thr Val Leu Asp Phe His
    1670                1675               1680

Pro Gly Ala Gly Lys Thr Arg Arg Phe Leu Pro Gln Ile Leu Ala
    1685                1690               1695

Glu Cys Ala Arg Arg Arg Leu Arg Thr Leu Val Leu Ala Pro Thr
    1700                1705               1710

Arg Val Val Leu Ser Glu Met Lys Glu Ala Phe His Gly Leu Asp
    1715                1720               1725

Val Lys Phe His Thr Gln Ala Phe Ser Ala His Gly Ser Gly Arg
    1730                1735               1740

Glu Val Ile Asp Ala Met Cys His Ala Thr Leu Thr Tyr Arg Met
    1745                1750               1755

Leu Glu Pro Thr Arg Val Val Asn Trp Glu Val Ile Ile Met Asp
    1760                1765               1770

Glu Ala His Phe Leu Asp Pro Ala Ser Ile Ala Ala Arg Gly Trp
    1775                1780               1785

Ala Ala His Arg Ala Arg Ala Asn Glu Ser Ala Thr Ile Leu Met
    1790                1795               1800

Thr Ala Thr Pro Pro Gly Thr Ser Asp Glu Phe Pro His Ser Asn
    1805                1810               1815

Gly Glu Ile Glu Asp Val Gln Thr Asp Ile Pro Ser Glu Pro Trp
    1820                1825               1830

Asn Thr Gly His Asp Trp Ile Leu Ala Asp Lys Arg Pro Thr Ala
    1835                1840               1845

Trp Phe Leu Pro Ser Ile Arg Ala Ala Asn Val Met Ala Ala Ser
    1850                1855               1860

Leu Arg Lys Ala Gly Lys Ser Val Val Val Leu Asn Arg Lys Thr
    1865                1870               1875

Phe Glu Arg Glu Tyr Pro Thr Ile Lys Gln Lys Lys Pro Asp Phe
    1880                1885               1890

Ile Leu Ala Thr Asp Ile Ala Glu Met Gly Ala Asn Leu Cys Val
    1895                1900               1905

Glu Arg Val Leu Asp Cys Arg Thr Ala Phe Lys Pro Val Leu Val
    1910                1915               1920

Asp Glu Gly Arg Lys Val Ala Ile Lys Gly Pro Leu Arg Ile Ser
    1925                1930               1935

Ala Ser Ser Ala Ala Gln Arg Arg Gly Arg Ile Gly Arg Asn Pro
    1940                1945               1950

Asn Arg Asp Gly Asp Ser Tyr Tyr Tyr Ser Glu Pro Thr Ser Glu
    1955                1960               1965

Asn Asn Ala His His Val Cys Trp Leu Glu Ala Ser Met Leu Leu
    1970                1975               1980

Asp Asn Met Glu Val Arg Gly Gly Met Val Ala Pro Leu Tyr Gly
    1985                1990               1995

Val Glu Gly Thr Lys Thr Pro Val Ser Pro Gly Glu Met Arg Leu
    2000                2005               2010
```

-continued

```
Arg  Asp  Asp  Gln  Arg  Lys  Val  Phe  Arg  Glu  Leu  Val  Arg  Asn  Cys
     2015                2020                     2025

Asp  Leu  Pro  Val  Trp  Leu  Ser  Trp  Gln  Val  Ala  Lys  Ala  Gly  Leu
     2030                2035                     2040

Lys  Thr  Asn  Asp  Arg  Lys  Trp  Cys  Phe  Glu  Gly  Pro  Glu  Glu  His
     2045                2050                     2055

Glu  Ile  Leu  Asn  Asp  Ser  Gly  Glu  Thr  Val  Lys  Cys  Arg  Ala  Pro
     2060                2065                     2070

Gly  Gly  Ala  Lys  Lys  Pro  Leu  Arg  Pro  Arg  Trp  Cys  Asp  Glu  Arg
     2075                2080                     2085

Val  Ser  Ser  Asp  Gln  Ser  Ala  Leu  Ser  Glu  Phe  Ile  Lys  Phe  Ala
     2090                2095                     2100

Glu  Gly  Arg  Arg  Gly  Ala  Ala  Glu  Val  Leu  Val  Val  Leu  Ser  Glu
     2105                2110                     2115

Leu  Pro  Asp  Phe  Leu  Ala  Lys  Lys  Gly  Gly  Glu  Ala  Met  Asp  Thr
     2120                2125                     2130

Ile  Ser  Val  Phe  Leu  His  Ser  Glu  Glu  Gly  Ser  Arg  Ala  Tyr  Arg
     2135                2140                     2145

Asn  Ala  Leu  Ser  Met  Met  Pro  Glu  Ala  Met  Thr  Ile  Val  Met  Leu
     2150                2155                     2160

Phe  Ile  Leu  Ala  Gly  Leu  Leu  Thr  Ser  Gly  Met  Val  Ile  Phe  Phe
     2165                2170                     2175

Met  Ser  Pro  Lys  Gly  Ile  Ser  Arg  Met  Ser  Met  Ala  Met  Gly  Thr
     2180                2185                     2190

Met  Ala  Gly  Cys  Gly  Tyr  Leu  Met  Phe  Leu  Gly  Gly  Val  Lys  Pro
     2195                2200                     2205

Thr  His  Ile  Ser  Tyr  Ile  Met  Leu  Ile  Phe  Phe  Val  Leu  Met  Val
     2210                2215                     2220

Val  Val  Ile  Pro  Glu  Pro  Gly  Gln  Gln  Arg  Ser  Ile  Gln  Asp  Asn
     2225                2230                     2235

Gln  Val  Ala  Tyr  Leu  Ile  Ile  Gly  Ile  Leu  Thr  Leu  Val  Ser  Ala
     2240                2245                     2250

Val  Ala  Ala  Asn  Glu  Leu  Gly  Met  Leu  Glu  Lys  Thr  Lys  Glu  Asp
     2255                2260                     2265

Leu  Phe  Gly  Lys  Lys  Asn  Leu  Ile  Pro  Ser  Ser  Ala  Ser  Pro  Trp
     2270                2275                     2280

Ser  Trp  Pro  Asp  Leu  Asp  Leu  Lys  Pro  Gly  Ala  Ala  Trp  Thr  Val
     2285                2290                     2295

Tyr  Val  Gly  Ile  Val  Thr  Met  Leu  Ser  Pro  Met  Leu  His  His  Trp
     2300                2305                     2310

Ile  Lys  Val  Glu  Tyr  Gly  Asn  Leu  Ser  Leu  Ser  Gly  Ile  Ala  Gln
     2315                2320                     2325

Ser  Ala  Ser  Val  Leu  Ser  Phe  Met  Asp  Lys  Gly  Ile  Pro  Phe  Met
     2330                2335                     2340

Lys  Met  Asn  Ile  Ser  Val  Ile  Met  Leu  Leu  Val  Ser  Gly  Trp  Asn
     2345                2350                     2355

Ser  Ile  Thr  Val  Met  Pro  Leu  Leu  Cys  Gly  Ile  Gly  Cys  Ala  Met
     2360                2365                     2370

Leu  His  Trp  Ser  Leu  Ile  Leu  Pro  Gly  Ile  Lys  Ala  Gln  Gln  Ser
     2375                2380                     2385

Lys  Leu  Ala  Gln  Arg  Arg  Val  Phe  His  Gly  Val  Ala  Lys  Asn  Pro
     2390                2395                     2400
```

```
Val Val Asp Gly Asn Pro Thr Val Asp Ile Glu Glu Ala Pro Glu
2405                    2410                2415

Met Pro Ala Leu Tyr Glu Lys Lys Leu Ala Leu Tyr Leu Leu Leu
2420                    2425                2430

Ala Leu Ser Leu Ala Ser Val Ala Met Cys Arg Thr Pro Phe Ser
2435                    2440                2445

Leu Ala Glu Gly Ile Val Leu Ala Ser Ala Ala Leu Gly Pro Leu
2450                    2455                2460

Ile Glu Gly Asn Thr Ser Leu Leu Trp Asn Gly Pro Met Ala Val
2465                    2470                2475

Ser Met Thr Gly Val Met Arg Gly Asn His Tyr Ala Phe Val Gly
2480                    2485                2490

Val Met Tyr Asn Leu Trp Lys Met Lys Thr Gly Arg Arg Gly Ser
2495                    2500                2505

Ala Asn Gly Lys Thr Leu Gly Glu Val Trp Lys Arg Glu Leu Asn
2510                    2515                2520

Leu Leu Asp Lys Arg Gln Phe Glu Leu Tyr Lys Arg Thr Asp Ile
2525                    2530                2535

Val Glu Val Asp Arg Asp Thr Ala Arg Arg His Leu Ala Glu Gly
2540                    2545                2550

Lys Val Asp Thr Gly Val Ala Val Ser Arg Gly Thr Ala Lys Leu
2555                    2560                2565

Arg Trp Phe His Glu Arg Gly Tyr Val Lys Leu Glu Gly Arg Val
2570                    2575                2580

Ile Asp Leu Gly Cys Gly Arg Gly Gly Trp Cys Tyr Tyr Ala Ala
2585                    2590                2595

Ala Gln Lys Glu Val Ser Gly Val Lys Gly Phe Thr Leu Gly Arg
2600                    2605                2610

Asp Gly His Glu Lys Pro Met Asn Val Gln Ser Leu Gly Trp Asn
2615                    2620                2625

Ile Ile Thr Phe Lys Asp Lys Thr Asp Ile His Arg Leu Glu Pro
2630                    2635                2640

Val Lys Cys Asp Thr Leu Leu Cys Asp Ile Gly Glu Ser Ser Ser
2645                    2650                2655

Ser Ser Val Thr Glu Gly Glu Arg Thr Val Arg Val Leu Asp Thr
2660                    2665                2670

Val Glu Lys Trp Leu Ala Cys Gly Val Asp Asn Phe Cys Val Lys
2675                    2680                2685

Val Leu Ala Pro Tyr Met Pro Asp Val Leu Glu Lys Leu Glu Leu
2690                    2695                2700

Leu Gln Arg Arg Phe Gly Gly Thr Val Ile Arg Asn Pro Leu Ser
2705                    2710                2715

Arg Asn Ser Thr His Glu Met Tyr Tyr Val Ser Gly Ala Arg Ser
2720                    2725                2730

Asn Val Thr Phe Thr Val Asn Gln Thr Ser Arg Leu Leu Met Arg
2735                    2740                2745

Arg Met Arg Arg Pro Thr Gly Lys Val Thr Leu Glu Ala Asp Val
2750                    2755                2760

Ile Leu Pro Ile Gly Thr Arg Ser Val Glu Thr Asp Lys Gly Pro
2765                    2770                2775

Leu Asp Lys Glu Ala Ile Glu Glu Arg Val Glu Arg Ile Lys Ser
2780                    2785                2790

Glu Tyr Met Thr Ser Trp Phe Tyr Asp Asn Asp Asn Pro Tyr Arg
```

-continued

```
              2795                2800                2805

Thr Trp His Tyr Cys Gly Ser Tyr Val Thr Lys Thr Ser Gly Ser
    2810                2815                2820

Ala Ala Ser Met Val Asn Gly Val Ile Lys Ile Leu Thr Tyr Pro
    2825                2830                2835

Trp Asp Arg Ile Glu Glu Val Thr Arg Met Ala Met Thr Asp Thr
    2840                2845                2850

Thr Pro Phe Gly Gln Gln Arg Val Phe Lys Glu Lys Val Asp Thr
    2855                2860                2865

Arg Ala Lys Asp Pro Pro Ala Gly Thr Arg Lys Ile Met Lys Val
    2870                2875                2880

Val Asn Arg Trp Leu Phe Arg His Leu Ala Arg Glu Lys Asn Pro
    2885                2890                2895

Arg Leu Cys Thr Lys Glu Glu Phe Ile Ala Lys Val Arg Ser His
    2900                2905                2910

Ala Ala Ile Gly Ala Tyr Leu Glu Glu Gln Glu Gln Trp Lys Thr
    2915                2920                2925

Ala Asn Glu Ala Val Gln Asp Pro Lys Phe Trp Glu Leu Val Asp
    2930                2935                2940

Glu Glu Arg Lys Leu His Gln Gln Gly Arg Cys Arg Thr Cys Val
    2945                2950                2955

Tyr Asn Met Met Gly Lys Arg Glu Lys Lys Leu Ser Glu Phe Gly
    2960                2965                2970

Lys Ala Lys Gly Ser Arg Ala Ile Trp Tyr Met Trp Leu Gly Ala
    2975                2980                2985

Arg Tyr Leu Glu Phe Glu Ala Leu Gly Phe Leu Asn Glu Asp His
    2990                2995                3000

Trp Ala Ser Arg Glu Asn Ser Gly Gly Gly Val Glu Gly Ile Gly
    3005                3010                3015

Leu Gln Tyr Leu Gly Tyr Val Ile Arg Asp Leu Ala Ala Met Asp
    3020                3025                3030

Gly Gly Gly Phe Tyr Ala Asp Asp Thr Ala Gly Trp Asp Thr Arg
    3035                3040                3045

Ile Thr Glu Ala Asp Leu Asp Asp Glu Gln Glu Ile Leu Asn Tyr
    3050                3055                3060

Met Ser Pro His His Lys Lys Leu Ala Gln Ala Val Met Glu Met
    3065                3070                3075

Thr Tyr Lys Asn Lys Val Val Lys Val Leu Arg Pro Ala Pro Gly
    3080                3085                3090

Gly Lys Ala Tyr Met Asp Val Ile Ser Arg Arg Asp Gln Arg Gly
    3095                3100                3105

Ser Gly Gln Val Val Thr Tyr Ala Leu Asn Thr Ile Thr Asn Leu
    3110                3115                3120

Lys Val Gln Leu Ile Arg Met Ala Glu Ala Glu Met Val Ile His
    3125                3130                3135

His Gln His Val Gln Asp Cys Asp Glu Ser Val Leu Thr Arg Leu
    3140                3145                3150

Glu Ala Trp Leu Thr Glu His Gly Cys Asn Arg Leu Lys Arg Met
    3155                3160                3165

Ala Val Ser Gly Asp Asp Cys Val Val Arg Pro Ile Asp Asp Arg
    3170                3175                3180

Phe Gly Leu Ala Leu Ser His Leu Asn Ala Met Ser Lys Val Arg
    3185                3190                3195
```

Lys Asp Ile Ser Glu Trp Gln Pro Ser Lys Gly Trp Asn Asp Trp
3200                3205                3210

Glu Asn Val Pro Phe Cys Ser His His Phe His Glu Leu Gln Leu
3215                3220                3225

Lys Asp Gly Arg Arg Ile Val Val Pro Cys Arg Glu Gln Asp Glu
3230                3235                3240

Leu Ile Gly Arg Gly Arg Val Ser Pro Gly Asn Gly Trp Met Ile
3245                3250                3255

Lys Glu Thr Ala Cys Leu Ser Lys Ala Tyr Ala Asn Met Trp Ser
3260                3265                3270

Leu Met Tyr Phe His Lys Arg Asp Met Arg Leu Leu Ser Leu Ala
3275                3280                3285

Val Ser Ser Ala Val Pro Thr Ser Trp Val Pro Gln Gly Arg Thr
3290                3295                3300

Thr Trp Ser Ile His Gly Lys Gly Glu Trp Met Thr Thr Glu Asp
3305                3310                3315

Met Leu Glu Val Trp Asn Arg Val Trp Ile Thr Asn Asn Pro His
3320                3325                3330

Met Gln Asp Lys Thr Met Val Lys Lys Trp Arg Asp Val Pro Tyr
3335                3340                3345

Leu Thr Lys Arg Gln Asp Lys Leu Cys Gly Ser Leu Ile Gly Met
3350                3355                3360

Thr Asn Arg Ala Thr Trp Ala Ser His Ile His Leu Val Ile His
3365                3370                3375

Arg Ile Arg Thr Leu Ile Gly Gln Glu Lys Tyr Thr Asp Tyr Leu
3380                3385                3390

Thr Val Met Asp Arg Tyr Ser Val Asp Ala Asp Leu Gln Leu Gly
3395                3400                3405

Glu Leu Ile
3410

<210> SEQ ID NO 8
<211> LENGTH: 3411
<212> TYPE: PRT
<213> ORGANISM: Artificial Sequence
<220> FEATURE:
<223> OTHER INFORMATION: Flaviviridae Flavivirus Yellow Fever Virus

<400> SEQUENCE: 8

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
                20                  25                  30

Gln Ile Gly Asn Arg Pro Gly Pro Ser Arg Gly Val Gln Gly Phe Ile
            35                  40                  45

Phe Phe Phe Leu Phe Asn Ile Leu Thr Gly Lys Lys Ile Thr Ala His
        50                  55                  60

Leu Lys Arg Leu Trp Lys Met Leu Asp Pro Arg Gln Gly Leu Ala Val
65                  70                  75                  80

Leu Arg Lys Val Lys Arg Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

```
Arg Trp Leu Leu Leu Asn Val Thr Ser Glu Asp Leu Gly Lys Thr Phe
130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
            165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
            195                 200                 205

Arg Arg Ala Ile Asp Leu Pro Thr His Glu Asn His Gly Leu Lys Thr
210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
            275                 280                 285

Ile Gly Ile Thr Asp Arg Asp Phe Ile Glu Gly Val His Gly Gly Thr
            290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
            325                 330                 335

Arg Pro Ala Glu Val Arg Lys Val Cys Tyr Asn Ala Val Leu Thr His
            340                 345                 350

Val Lys Ile Asn Asp Lys Cys Pro Ser Thr Gly Glu Ala His Leu Ala
            355                 360                 365

Glu Glu Asn Glu Gly Asp Asn Ala Cys Lys Arg Thr Tyr Ser Asp Arg
            370                 375                 380

Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
            405                 410                 415

Gln Thr Lys Ile Gln Tyr Val Ile Arg Ala Gln Leu His Val Gly Ala
            420                 425                 430

Lys Gln Glu Asn Trp Thr Thr Asp Ile Lys Thr Leu Lys Phe Asp Ala
            435                 440                 445

Leu Ser Gly Ser Gln Glu Val Glu Phe Ile Gly Tyr Gly Lys Ala Thr
450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
            485                 490                 495

Asp Leu Thr Leu Pro Trp Gln Ser Gly Ser Gly Gly Val Trp Arg Glu
            500                 505                 510

Met His His Leu Val Glu Phe Glu Pro Pro His Ala Ala Thr Ile Arg
            515                 520                 525

Val Leu Ala Leu Gly Asn Gln Glu Gly Ser Leu Lys Thr Ala Leu Thr
530                 535                 540
```

-continued

```
Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
        595                 600                 605

Val Ser Lys Gly Ala Pro Cys Arg Ile Pro Val Ile Val Ala Asp Asp
        610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
        675                 680                 685

Met Lys Gly Val Glu Arg Leu Ala Val Met Gly Asp Thr Ala Trp Asp
        690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
        740                 745                 750

Thr Arg Asn Met Thr Met Ser Met Ser Met Ile Leu Val Gly Val Ile
        755                 760                 765

Met Met Phe Leu Ser Leu Gly Val Gly Ala Asp Gln Gly Cys Ala Ile
770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Tyr Pro Glu Asp
                805                 810                 815

Pro Val Lys Leu Ala Ser Ile Val Lys Ala Ser Phe Glu Glu Gly Lys
        820                 825                 830

Cys Gly Leu Asn Ser Val Asp Ser Leu Glu His Glu Met Trp Arg Ser
        835                 840                 845

Arg Ala Asp Glu Ile Asn Ala Ile Phe Glu Glu Asn Glu Val Asp Ile
850                 855                 860

Ser Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                885                 890                 895

Gly Lys Asn Leu Val Phe Ser Pro Gly Arg Lys Asn Gly Ser Phe Ile
        900                 905                 910

Ile Asp Gly Lys Ser Arg Lys Glu Cys Pro Phe Ser Asn Arg Val Trp
        915                 920                 925

Asn Ser Phe Gln Ile Glu Glu Phe Gly Thr Gly Val Phe Thr Thr Arg
        930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
```

-continued

```
                965                 970                 975
Thr Phe Trp Met Gly Ser His Glu Val Asn Gly Thr Trp Met Ile His
            980                 985                 990
Thr Leu Glu Ala Leu Asp Tyr Lys Glu Cys Glu Trp Pro Leu Thr His
            995                 1000                1005
Thr Ile Gly Thr Ser Val Glu Glu Ser Glu Met Phe Met Pro Arg
            1010                1015                1020
Ser Ile Gly Gly Pro Val Ser Ser His Asn His Ile Pro Gly Tyr
            1025                1030                1035
Lys Val Gln Thr Asn Gly Pro Trp Met Gln Val Pro Leu Glu Val
            1040                1045                1050
Lys Arg Glu Ala Cys Pro Gly Thr Ser Val Ile Ile Asp Gly Asn
            1055                1060                1065
Cys Asp Gly Arg Gly Lys Ser Thr Arg Ser Thr Thr Asp Ser Gly
            1070                1075                1080
Lys Val Ile Pro Glu Trp Cys Cys Arg Ser Cys Thr Met Pro Pro
            1085                1090                1095
Val Ser Phe His Gly Ser Asp Gly Cys Trp Tyr Pro Met Glu Ile
            1100                1105                1110
Arg Pro Arg Lys Thr His Glu Ser His Leu Val Arg Ser Trp Val
            1115                1120                1125
Thr Ala Gly Glu Ile His Ala Val Pro Phe Gly Leu Val Ser Met
            1130                1135                1140
Met Ile Ala Met Glu Val Val Leu Arg Lys Arg Gln Gly Pro Lys
            1145                1150                1155
Gln Met Leu Val Gly Gly Val Val Leu Leu Gly Ala Met Leu Val
            1160                1165                1170
Gly Gln Val Thr Leu Leu Asp Leu Leu Lys Leu Thr Val Ala Val
            1175                1180                1185
Gly Leu His Phe His Glu Met Asn Asn Gly Gly Asp Ala Met Tyr
            1190                1195                1200
Met Ala Leu Ile Ala Ala Phe Ser Ile Arg Pro Gly Leu Leu Ile
            1205                1210                1215
Gly Phe Gly Leu Arg Thr Leu Trp Ser Pro Arg Glu Arg Leu Val
            1220                1225                1230
Leu Thr Leu Gly Ala Ala Met Val Glu Ile Ala Leu Gly Gly Val
            1235                1240                1245
Met Gly Gly Leu Trp Lys Tyr Leu Asn Ala Val Ser Leu Cys Ile
            1250                1255                1260
Leu Thr Ile Asn Ala Val Ala Ser Arg Lys Ala Ser Asn Thr Ile
            1265                1270                1275
Leu Pro Leu Met Ala Leu Leu Thr Pro Val Thr Met Ala Glu Val
            1280                1285                1290
Arg Leu Ala Ala Met Phe Phe Cys Ala Val Val Ile Ile Gly Val
            1295                1300                1305
Leu His Gln Asn Phe Lys Asp Thr Ser Met Gln Lys Thr Ile Pro
            1310                1315                1320
Leu Val Ala Leu Thr Leu Thr Ser Tyr Leu Gly Leu Thr Gln Pro
            1325                1330                1335
Phe Leu Gly Leu Cys Ala Phe Leu Ala Thr Arg Ile Phe Gly Arg
            1340                1345                1350
Arg Ser Ile Pro Val Asn Glu Ala Leu Ala Ala Ala Gly Leu Val
            1355                1360                1365
```

```
Gly Val Leu Ala Gly Leu Ala Phe Gln Glu Met Glu Asn Phe Leu
    1370            1375            1380

Gly Pro Ile Ala Val Gly Gly Leu Leu Met Met Leu Val Ser Val
    1385            1390            1395

Ala Gly Arg Val Asp Gly Leu Glu Leu Lys Lys Leu Gly Glu Val
    1400            1405            1410

Ser Trp Glu Glu Ala Glu Ile Ser Gly Ser Ser Ala Arg Tyr
    1415            1420            1425

Asp Val Ala Leu Ser Glu Gln Gly Phe Lys Leu Leu Ser Glu
    1430            1435            1440

Glu Lys Val Pro Trp Asp Gln Val Val Met Thr Ser Leu Ala Leu
    1445            1450            1455

Val Gly Ala Ala Leu His Pro Phe Ala Leu Leu Val Leu Ala
    1460            1465            1470

Gly Trp Leu Phe His Val Arg Gly Ala Arg Arg Ser Gly Asp Val
    1475            1480            1485

Leu Trp Asp Ile Pro Thr Pro Lys Ile Ile Glu Glu Cys Glu His
    1490            1495            1500

Leu Glu Asp Gly Ile Tyr Gly Ile Phe Gln Ser Thr Phe Leu Gly
    1505            1510            1515

Ala Ser Gln Arg Gly Val Gly Val Ala Gln Gly Gly Val Phe His
    1520            1525            1530

Thr Met Trp His Val Thr Arg Gly Ala Phe Leu Val Arg Asn Gly
    1535            1540            1545

Lys Lys Leu Ile Pro Ser Trp Ala Ser Val Lys Glu Asp Leu Val
    1550            1555            1560

Ala Tyr Gly Gly Ser Trp Lys Leu Glu Gly Arg Trp Asp Gly Glu
    1565            1570            1575

Glu Glu Val Gln Leu Ile Ala Ala Val Pro Gly Lys Asn Val Val
    1580            1585            1590

Asn Val Gln Thr Lys Pro Ser Leu Phe Lys Val Arg Asn Gly Gly
    1595            1600            1605

Glu Ile Gly Ala Val Ala Leu Asp Tyr Pro Ser Gly Thr Ser Gly
    1610            1615            1620

Ser Pro Ile Val Asn Arg Asn Gly Glu Val Ile Gly Leu Tyr Gly
    1625            1630            1635

Asn Gly Ile Leu Val Gly Asp Asn Ser Phe Val Ser Ala Ile Ser
    1640            1645            1650

Gln Thr Glu Val Lys Glu Glu Gly Lys Glu Glu Leu Gln Glu Ile
    1655            1660            1665

Pro Thr Met Leu Lys Lys Gly Met Thr Thr Val Leu Asp Phe His
    1670            1675            1680

Pro Gly Ala Gly Lys Thr Arg Arg Phe Leu Pro Gln Ile Leu Ala
    1685            1690            1695

Glu Cys Ala Arg Arg Arg Leu Arg Thr Leu Val Leu Ala Pro Thr
    1700            1705            1710

Arg Val Val Leu Ser Glu Met Lys Glu Ala Phe His Gly Leu Asp
    1715            1720            1725

Val Lys Phe His Thr Gln Ala Phe Ser Ala His Gly Ser Gly Arg
    1730            1735            1740

Glu Val Ile Asp Ala Met Cys His Ala Thr Leu Thr Tyr Arg Met
    1745            1750            1755
```

-continued

Leu Glu Pro Thr Arg Val Val Asn Trp Glu Val Ile Ile Met Asp
1760              1765              1770

Glu Ala His Phe Leu Asp Pro Ala Ser Ile Ala Ala Arg Gly Trp
1775              1780              1785

Ala Ala His Arg Ala Arg Ala Asn Glu Ser Ala Thr Ile Leu Met
1790              1795              1800

Thr Ala Thr Pro Pro Gly Thr Ser Asp Glu Phe Pro His Ser Asn
1805              1810              1815

Gly Glu Ile Glu Asp Val Gln Thr Asp Ile Pro Ser Glu Pro Trp
1820              1825              1830

Asn Thr Gly His Asp Trp Ile Leu Ala Asp Lys Arg Pro Thr Ala
1835              1840              1845

Trp Phe Leu Pro Ser Ile Arg Ala Ala Asn Val Met Ala Ala Ser
1850              1855              1860

Leu Arg Lys Ala Gly Lys Ser Val Val Leu Asn Arg Lys Thr
1865              1870              1875

Phe Glu Arg Glu Tyr Pro Thr Ile Lys Gln Lys Lys Pro Asp Phe
1880              1885              1890

Ile Leu Ala Thr Asp Ile Ala Glu Met Gly Ala Asn Leu Cys Val
1895              1900              1905

Glu Arg Val Leu Asp Cys Arg Thr Ala Phe Lys Pro Val Leu Val
1910              1915              1920

Asp Glu Gly Arg Lys Val Ala Ile Lys Gly Pro Leu Arg Ile Ser
1925              1930              1935

Ala Ser Ser Ala Ala Gln Arg Arg Gly Arg Ile Gly Arg Asn Pro
1940              1945              1950

Asn Arg Asp Gly Asp Ser Tyr Tyr Tyr Ser Glu Pro Thr Ser Glu
1955              1960              1965

Asn Asn Ala His His Val Cys Trp Leu Glu Ala Ser Met Leu Leu
1970              1975              1980

Asp Asn Met Glu Val Arg Gly Gly Met Val Ala Pro Leu Tyr Gly
1985              1990              1995

Val Glu Gly Thr Lys Thr Pro Val Ser Pro Gly Glu Met Arg Leu
2000              2005              2010

Arg Asp Asp Gln Arg Lys Val Phe Arg Glu Leu Val Arg Asn Cys
2015              2020              2025

Asp Leu Pro Val Trp Leu Ser Trp Gln Val Ala Lys Ala Gly Leu
2030              2035              2040

Lys Thr Asn Asp Arg Lys Trp Cys Phe Glu Gly Pro Glu Glu His
2045              2050              2055

Glu Ile Leu Asn Asp Ser Gly Glu Thr Val Lys Cys Arg Ala Pro
2060              2065              2070

Gly Gly Ala Lys Lys Pro Leu Arg Pro Arg Trp Cys Asp Glu Arg
2075              2080              2085

Val Ser Ser Asp Gln Ser Ala Leu Ser Glu Phe Ile Lys Phe Ala
2090              2095              2100

Glu Gly Arg Arg Gly Ala Ala Glu Val Leu Val Val Leu Ser Glu
2105              2110              2115

Leu Pro Asp Phe Leu Ala Lys Lys Gly Gly Glu Ala Met Asp Thr
2120              2125              2130

Ile Ser Val Phe Leu His Ser Glu Glu Gly Ser Arg Ala Tyr Arg
2135              2140              2145

Asn Ala Leu Ser Met Met Pro Glu Ala Met Thr Ile Val Met Leu

```
                      2150                2155                2160
      Phe Ile Leu Ala Gly Leu Leu Thr Ser Gly Met Val Ile Phe Phe
                      2165                2170                2175
      Met Ser Pro Lys Gly Ile Ser Arg Met Ser Met Ala Met Gly Thr
                      2180                2185                2190
      Met Ala Gly Cys Gly Tyr Leu Met Phe Leu Gly Gly Val Lys Pro
                      2195                2200                2205
      Thr His Ile Ser Tyr Ile Met Leu Ile Phe Phe Val Leu Met Val
                      2210                2215                2220
      Val Val Ile Pro Glu Pro Gly Gln Gln Arg Ser Ile Gln Asp Asn
                      2225                2230                2235
      Gln Val Ala Tyr Leu Ile Ile Gly Ile Leu Thr Leu Val Ser Ala
                      2240                2245                2250
      Val Ala Ala Asn Glu Leu Gly Met Leu Glu Lys Thr Lys Glu Asp
                      2255                2260                2265
      Leu Phe Gly Lys Lys Asn Leu Ile Pro Ser Ser Ala Ser Pro Trp
                      2270                2275                2280
      Ser Trp Pro Asp Leu Asp Leu Lys Pro Gly Ala Ala Trp Thr Val
                      2285                2290                2295
      Tyr Val Gly Ile Val Thr Met Leu Ser Pro Met Leu His His Trp
                      2300                2305                2310
      Ile Lys Val Glu Tyr Gly Asn Leu Ser Leu Ser Gly Ile Ala Gln
                      2315                2320                2325
      Ser Ala Ser Val Leu Ser Phe Met Asp Lys Gly Ile Pro Phe Met
                      2330                2335                2340
      Lys Met Asn Ile Ser Val Ile Met Leu Leu Val Ser Gly Trp Asn
                      2345                2350                2355
      Ser Ile Thr Val Met Pro Leu Leu Cys Gly Met Gly Cys Ala Met
                      2360                2365                2370
      Leu His Trp Ser Leu Ile Leu Pro Gly Ile Lys Ala Gln Gln Ser
                      2375                2380                2385
      Lys Leu Ala Gln Arg Arg Val Phe His Gly Val Ala Lys Asn Pro
                      2390                2395                2400
      Val Val Asp Gly Asn Pro Thr Val Asp Ile Glu Glu Ala Pro Glu
                      2405                2410                2415
      Met Pro Ala Leu Tyr Glu Lys Lys Leu Ala Leu Tyr Leu Leu Leu
                      2420                2425                2430
      Ala Leu Ser Leu Ala Ser Val Ala Met Cys Arg Thr Pro Phe Ser
                      2435                2440                2445
      Leu Ala Glu Gly Ile Val Leu Ala Ser Ala Ala Leu Gly Pro Leu
                      2450                2455                2460
      Ile Glu Gly Asn Thr Ser Leu Leu Trp Asn Gly Pro Met Ala Val
                      2465                2470                2475
      Ser Met Thr Gly Val Met Arg Gly Asn His Tyr Ala Phe Val Gly
                      2480                2485                2490
      Val Met Tyr Asn Leu Trp Lys Met Lys Thr Gly Arg Arg Gly Ser
                      2495                2500                2505
      Ala Asn Gly Lys Thr Leu Gly Glu Val Trp Lys Arg Glu Leu Asn
                      2510                2515                2520
      Leu Leu Asp Lys Arg Gln Phe Glu Leu Tyr Lys Arg Thr Asp Ile
                      2525                2530                2535
      Val Glu Val Asp Arg Asp Thr Ala Arg Arg His Leu Ala Glu Gly
                      2540                2545                2550
```

-continued

```
Lys Val Asp Thr Gly Val Ala Val Ser Arg Gly Thr Ala Lys Leu
2555                2560                2565

Arg Trp Phe His Glu Arg Gly Tyr Val Lys Leu Glu Gly Arg Val
2570                2575                2580

Ile Asp Leu Gly Cys Gly Arg Gly Gly Trp Cys Tyr Tyr Ala Ala
2585                2590                2595

Ala Gln Lys Glu Val Ser Gly Val Lys Gly Phe Thr Leu Gly Arg
2600                2605                2610

Asp Gly His Glu Lys Pro Met Asn Val Gln Ser Leu Gly Trp Asn
2615                2620                2625

Ile Ile Thr Phe Lys Asp Lys Thr Asp Ile His Arg Leu Glu Pro
2630                2635                2640

Val Lys Cys Asp Thr Leu Leu Cys Asp Ile Gly Glu Ser Ser Ser
2645                2650                2655

Ser Ser Val Thr Glu Gly Glu Arg Thr Val Arg Val Leu Asp Thr
2660                2665                2670

Val Glu Lys Trp Leu Ala Cys Gly Val Asp Asn Phe Cys Val Lys
2675                2680                2685

Val Leu Ala Pro Tyr Met Pro Asp Val Leu Glu Lys Leu Glu Leu
2690                2695                2700

Leu Gln Arg Arg Phe Gly Gly Thr Val Ile Arg Asn Pro Leu Ser
2705                2710                2715

Arg Asn Ser Thr His Glu Met Tyr Tyr Val Ser Gly Ala Arg Ser
2720                2725                2730

Asn Val Thr Phe Thr Val Asn Gln Thr Ser Arg Leu Leu Met Arg
2735                2740                2745

Arg Met Arg Arg Pro Thr Gly Lys Val Thr Leu Glu Ala Asp Val
2750                2755                2760

Ile Leu Pro Ile Gly Thr Arg Ser Val Glu Thr Asp Lys Gly Pro
2765                2770                2775

Leu Asp Lys Glu Ala Ile Glu Glu Arg Val Glu Arg Ile Lys Ser
2780                2785                2790

Glu Tyr Met Thr Ser Trp Phe Tyr Asp Asn Asp Asn Pro Tyr Arg
2795                2800                2805

Thr Trp His Tyr Cys Gly Ser Tyr Val Thr Lys Thr Ser Gly Ser
2810                2815                2820

Ala Ala Ser Met Val Asn Gly Val Ile Lys Ile Leu Thr Tyr Pro
2825                2830                2835

Trp Asp Arg Ile Glu Glu Val Thr Arg Met Ala Met Thr Asp Thr
2840                2845                2850

Thr Pro Phe Gly Gln Gln Arg Val Phe Lys Glu Lys Val Asp Thr
2855                2860                2865

Arg Ala Lys Asp Pro Pro Ala Gly Thr Arg Lys Ile Met Lys Val
2870                2875                2880

Val Asn Arg Trp Leu Phe Arg His Leu Ala Arg Glu Lys Asn Pro
2885                2890                2895

Arg Leu Cys Thr Lys Glu Glu Phe Ile Ala Lys Val Arg Ser His
2900                2905                2910

Ala Ala Ile Gly Ala Tyr Leu Glu Glu Gln Glu Gln Trp Lys Thr
2915                2920                2925

Ala Asn Glu Ala Val Gln Asp Pro Lys Phe Trp Glu Leu Val Asp
2930                2935                2940
```

-continued

```
Glu Glu Arg Lys Leu His Gln Gln Gly Arg Cys Arg Thr Cys Val
2945                2950                2955

Tyr Asn Met Met Gly Lys Arg Glu Lys Lys Leu Ser Glu Phe Gly
    2960                2965                2970

Lys Ala Lys Gly Ser Arg Ala Ile Trp Tyr Met Trp Leu Gly Ala
    2975                2980                2985

Arg Tyr Leu Glu Phe Glu Ala Leu Gly Phe Leu Asn Glu Asp His
    2990                2995                3000

Trp Ala Ser Arg Glu Asn Ser Gly Gly Gly Val Glu Gly Ile Gly
    3005                3010                3015

Leu Gln Tyr Leu Gly Tyr Val Ile Arg Asp Leu Ala Ala Met Asp
    3020                3025                3030

Gly Gly Gly Phe Tyr Ala Asp Asp Thr Ala Gly Trp Asp Thr Arg
    3035                3040                3045

Ile Thr Glu Ala Asp Leu Asp Asp Glu Gln Glu Ile Leu Asn Tyr
    3050                3055                3060

Met Ser Pro His His Lys Lys Leu Ala Gln Ala Val Met Glu Met
    3065                3070                3075

Thr Tyr Lys Asn Lys Val Val Lys Val Leu Arg Pro Ala Pro Gly
    3080                3085                3090

Gly Lys Ala Tyr Met Asp Val Ile Ser Arg Arg Asp Gln Arg Gly
    3095                3100                3105

Ser Gly Gln Val Val Thr Tyr Ala Leu Asn Thr Ile Thr Asn Leu
    3110                3115                3120

Lys Val Gln Leu Ile Arg Met Ala Glu Ala Glu Met Val Ile His
    3125                3130                3135

His Gln His Val Gln Asp Cys Asp Glu Ser Val Leu Thr Arg Leu
    3140                3145                3150

Glu Ala Trp Leu Thr Glu His Gly Cys Asn Arg Leu Lys Arg Met
    3155                3160                3165

Ala Val Ser Gly Asp Asp Cys Val Val Arg Pro Ile Asp Asp Arg
    3170                3175                3180

Phe Gly Leu Ala Leu Ser His Leu Asn Ala Met Ser Lys Val Arg
    3185                3190                3195

Lys Asp Ile Ser Glu Trp Gln Pro Ser Lys Gly Trp Asn Asp Trp
    3200                3205                3210

Glu Asn Val Pro Phe Cys Ser His His Phe His Glu Leu Gln Leu
    3215                3220                3225

Lys Asp Gly Arg Arg Ile Val Val Pro Cys Arg Glu Gln Asp Glu
    3230                3235                3240

Leu Ile Gly Arg Gly Arg Val Ser Pro Gly Asn Gly Trp Met Ile
    3245                3250                3255

Lys Glu Thr Ala Cys Leu Ser Lys Ala Tyr Ala Asn Met Trp Ser
    3260                3265                3270

Leu Met Tyr Phe His Lys Arg Asp Met Arg Leu Leu Ser Leu Ala
    3275                3280                3285

Val Ser Ser Ala Val Pro Thr Ser Trp Val Pro Gln Gly Arg Thr
    3290                3295                3300

Thr Trp Ser Ile His Gly Lys Gly Glu Trp Met Thr Thr Glu Asp
    3305                3310                3315

Met Leu Glu Val Trp Asn Arg Val Trp Ile Thr Asn Asn Pro His
    3320                3325                3330

Met Gln Asp Lys Thr Met Val Lys Lys Trp Arg Asp Val Pro Tyr
```

-continued

```
                    3335                3340                3345

Leu Thr Lys Arg Gln Asp Lys Leu Cys Gly Ser Leu Ile Gly Met
    3350                3355                3360

Thr Asn Arg Ala Thr Trp Ala Ser His Ile His Leu Val Ile His
    3365                3370                3375

Arg Ile Arg Thr Leu Ile Gly Gln Glu Lys Tyr Thr Asp Tyr Leu
    3380                3385                3390

Thr Val Met Asp Arg Tyr Ser Val Asp Ala Asp Leu Gln Leu Gly
    3395                3400                3405

Glu Leu Ile
    3410

<210> SEQ ID NO 9
<211> LENGTH: 10776
<212> TYPE: DNA
<213> ORGANISM: Artificial Sequence
<220> FEATURE:
<223> OTHER INFORMATION: Flaviviridae Flavivirus Yellow Fever Virus

<400> SEQUENCE: 9
aatcgagttg ctaggcaata aacacatttg gattaatttt aatcgttcgt tgagcgatta      60
gcagagaact gaccagaaca tgtctggtcg taaagctcag ggaaaaaccc tgggcgtcaa     120
tatggtacga cgaggagttc gctccttgtc aaacaaaata aaacaaaaaa caaaacaaat     180
tggaaacaga cctggacctt caagaggtgt tcaaggattt atctttttct ttttgttcaa     240 catttttgact ggaaaaaaga tcacagccca cctaaagagg ttgtggaaaa tgctggaccc     300
aagacaaggc ttggctgttc taaggaaagt caagagagtg gtggccagtt tgatgagagg     360
attgtcctca aggaaacgcc gttcccatga tgttctgact gtgcaattcc taattttggg     420
aatgctgttg atgacgggtg gagtgacctt ggtgcggaaa acagatggt tgctcctaaa     480 tgtgacatct gaggacctcg ggaaaacatt ctctgtgggc acaggcaact gcacaacaaa     540 catttttggaa gccaagtact ggtgcccaga ctcaatggaa tacaactgtc ccaatctcag     600
tccaagagag gagccagatg acattgattg ctggtgctat ggggtggaaa acgttagagt     660
cgcatatggt aagtgtgact cagcaggcag gtctaggagg tcaagaaggg ccattgactt     720
gcctacgcat gaaaaccatg gttgaagac ccggcaagaa aaatggatga ctggaagaat     780
gggtgaaagg caactccaaa agattgagag atggttcgtg aggaacccct ttttgcagt      840 gacggctctg accattgcct accttgtggg aagcaacatg acgcaacgag tcgtgattgc     900
cctactggtc ttggctgttg gtccggccta ctcagctcac tgcattggaa ttactgacag     960 ggattttcatt gagggggtgc atggaggaac ttgggttca gctaccctgg agcaagacaa     1020
gtgtgtcact gttatggccc ctgacaagcc ttcattggac atctcactag agacagtagc     1080
cattgataga cctgctgagg tgaggaaagt gtgttacaat gcagttctca ctcatgtgaa     1140
gattaatgac aagtgcccca gcactggaga ggcccaccta gctgaagaga cgaaggggga     1200
caatgcgtgc aagcgcactt attctgatag aggctggggc aatggctgtg gcctatttgg     1260
gaaagggagc attgtggcat gcgccaaatt cacttgtgcc aaatccatga gtttgtttga     1320
ggttgatcag accaaaaattc agtatgtcat cagagcacaa ttgcatgtag ggccaagca     1380 ggaaaattgg actaccgaca ttaagactct caagtttgat gccctgtcag gctcccagga     1440
agtcgagttc attgggtatg aaaagctac actggaatgc caggtgcaaa ctgcggtgga     1500
ctttggtaac agttacatcg ctgagatgga aacagagagc tggatagtgg acagacagtg     1560
```

```
ggcccaggac ttgaccctgc catggcagag tggaagtggc ggggtgtgga gagagatgca    1620
tcatcttgtc gaatttgaac ctccgcatgc cgccactatc agagtactgg ccctgggaaa    1680
ccaggaaggc tccttgaaaa cagctcttac tggcgcaatg agggttacaa aggacacaaa    1740
tgacaacaac ctttacaaac tacatggtgg acatgtttct tgcagagtga aattgtcagc    1800
tttgacactc aaggggacat cctacaaaat atgcactgac aaaatgtttt ttgtcaagaa    1860
cccaactgac actggccatg gcactgttgt gatgcaggtg aaagtgtcaa aaggagcccc    1920
ctgcaggatt ccagtgatag tagctgatga tcttacagcg gcaatcaata aaggcatttt    1980
ggttacagtt aacccatcg cctcaaccaa tgatgatgaa gtgctgattg aggtgaaccc    2040
accttttgga gacagctaca ttatcgttgg gagaggagat tcacgtctca cttaccagtg    2100
gcacaaagag ggaagctcaa taggaaagtt gttcactcag accatgaaag cgtggaacg    2160 cctggccgtc atgggagaca ccgcctggga tttcagctcc gctggagggt tcttcacttc    2220
ggttgggaaa ggaattcata cggtgtttgg ctctgccttt caggggctat ttggcggctt    2280
gaactggata acaaaggtca tcatgggggc ggtacttata tgggttggca tcaacacaag    2340
aaacatgaca atgtccatga gcatgatctt ggtaggagtg atcatgatgt ttttgtctct    2400
aggagttggg gcggatcaag gatgcgccat caactttggc aagagagagc tcaagtgcgg    2460
agatggtatc ttcatattta gagactctga tgactggctg aacaagtact catactatcc    2520
agaagatcct gtgaagcttg catcaatagt gaaagcctct tttgaagaag ggaagtgtgg    2580
cctaaattca gttgactccc ttgagcatga gatgtggaga agcagggcag atgagatcaa    2640 tgccatttt gaggaaaacg aggtggacat ttctgttgtc gtgcaggatc aaagaatgt    2700 ttaccagaga ggaactcatc cattttccag aattcgggat ggtctgcagt atggttggaa    2760 gacttgggt aagaaccttg tgttctcccc agggaggaag aatggaagct tcatcataga    2820
tggaaagtcc aggaaagaat gcccgttttc aaaccgggtc tggaattctt tccagataga    2880
ggagtttggg acgggagtgt tcaccacacg cgtgtacatg gacgcagtct ttgaatacac    2940
catagactgc gatggatcta tcttgggtgc agcggtgaac ggaaaaaga gtgcccatgg    3000 ctctccaaca ttttggatgg gaagtcatga agtaaatggg acatggatga tccacacctt    3060
ggaggcatta gattacaagg agtgtgagtg gccactgaca catacgattg gaacatcagt    3120
tgaagagagt gaaatgttca tgccgagatc aatcggaggc ccagttagct ctcacaatca    3180
tatccctgga tacaaggttc agacgaacgg accttggatg caggtaccac tagaagtgaa    3240
gagagaagct tgcccaggga ctagcgtgat cattgatggc aactgtgatg gacggggaaa    3300
atcaaccaga tccaccacgg atagcgggaa agttattcct gaatggtgtt gccgctcctg    3360
cacaatgccg cctgtgagct tccatggtag tgatgggtgt tggtatccca tggaaattag    3420
gccaaggaaa acgcatgaaa gccatctggt gcgctcctgg gttacagctg gagaaataca    3480
tgctgtccct tttggtttgg tgagcatgat gatagcaatg gaagtggtcc taaggaaaag    3540
acagggacca aagcaaatgt tggttggagg agtagtgctc ttgggagcaa tgctggtcgg    3600
gcaagtaact ctccttgatt tgctgaaact cacagtggct gtgggattgc atttccatga    3660
gatgaacaat ggaggagacg ccatgtatat ggcgttgatt gctgccttt caatcagacc    3720 agggctgctc atcggctttg gctcaggac cctatggagc cctcgggaac gccttgtgct    3780
gacccctagg gcagccatgg tggagattgc cttgggtggc gtgatgggcg gcctgtggaa    3840
gtatctaaat gcagtttctc tctgcatcct gacaataaat gctgttgctt ctaggaaagc    3900
atcaaatacc atcttgcccc tcatggctct gttgacacct gtcactatgg ctgaggtgag    3960
```

```
acttgccgca atgttctttt gtgccgtggt tatcataggg gtccttcacc agaatttcaa    4020
ggacacctcc atgcagaaga ctatacctct ggtggccctc acactcacat cttacctggg    4080
cttgacacaa ccttttttgg gcctgtgtgc atttctggca acccgcatat ttgggcgaag    4140
gagtatccca gtgaatgagg cactcgcagc agctggtcta gtgggagtgc tggcaggact    4200
ggcttttcag gagatggaga acttccttgg tccgattgca gttggaggac tcctgatgat    4260
gctggttagc gtggctggga gggtggatgg gctagagctc aagaagcttg gtgaagtttc    4320
atgggaagag gaggcggaga tcagcgggag ttccgcccgc tatgatgtgg cactcagtga    4380 acaagggag ttcaagctgc tttctgaaga gaaagtgcca tgggaccagg ttgtgatgac    4440
ctcgctggcc ttggttgggg ctgccctcca tccatttgct cttctgctgg tccttgctgg    4500
gtggctgttt catgtcaggg gagctaggag aagtggggat gtcttgtggg atattcccac    4560
tcctaagatc atcgaggaat gtgaacatct ggaggatggg atttatggca tattccagtc    4620
aaccttcttg ggggcctccc agcgaggagt gggagtggca cagggagggg tgttccacac    4680
aatgtggcat gtcacaagag gagctttcct tgtcaggaat ggcaagaagt tgattccatc    4740
ttgggcttca gtaaaggaag accttgtcgc ctatggtggc tcatggaagt tggaaggcag    4800
atgggatgga gaggaagagg tccagttgat cgcggctgtt ccaggaaaga acgtggtcaa    4860
cgtccagaca aaaccgagct tgttcaaagt gaggaatggg ggagaaatcg gggctgtcgc    4920
tcttgactat ccgagtggca cttcaggatc tcctattgtt aacaggaacg gagaggtgat    4980
tgggctgtac ggcaatggca tccttgtcgg tgacaactcc ttcgtgtccg ccatatccca    5040
gactgaggtg aaggaagaag gaaaggagga gctccaagag atcccgacaa tgctaaagaa    5100
aggaatgaca actgtccttg attttcatcc tggagctggg aagacaagac gtttcctccc    5160
acagatcttg gccgagtgcg cacggagacg cttgcgcact cttgtgttgg cccccaccag    5220
ggttgttctt tctgaaatga aggaggcttt tcacggcctg gacgtgaaat tccacacaca    5280 ggcttttttcc gctcacggca gcgggagaga agtcattgat gctatgtgcc atgccaccct    5340
aacttacagg atgttggaac caactagggt tgttaactgg gaagtgatca ttatggatga    5400
agcccatttt ttggatccag ctagcatagc cgctagaggt tgggcagcgc acagagctag    5460
ggcaaatgaa agtgcaacaa tcttgatgac agccacaccg cctgggacta gtgatgaatt    5520
tccacattca aatggtgaaa tagaagatgt tcaaacggac atacccagtg agccctggaa    5580
cacagggcat gactggatcc tggctgacaa aaggcccacg gcatggttcc ttccatccat    5640
cagagctgca aatgtcatgg ctgcctcttt gcgtaaggct ggaaagagtg tggtggtcct    5700
gaacaggaaa acctttgaga gagaataccc cacgataaag cagaagaaac ctgactttat    5760
attggccact gacatagctg aaatgggagc caacctttgc gtggagcgag tgctggattg    5820
caggacggct tttaagcctg tgcttgtgga tgaagggagg aaggtggcaa taaaagggcc    5880
acttcgtatc tccgcatcct ctgctgctca aaggaggggg cgcattggga gaaatcccaa    5940
cagagatgga gactcatact actattctga gcctacaagt gaaaataatg cccaccacgt    6000
ctgctggttg gaggcctcaa tgctcttgga caacatggag gtgaggggtg aatggtcgc    6060 cccactctat ggcgttgaag gaactaaaac accagtttcc cctggtgaaa tgagactgag    6120
ggatgaccag aggaaagtct tcagagaact agtgaggaat tgtgacctgc ccgtttggct    6180
ttcgtggcaa gtgccaaggc tggtttgaa gacgaatgat cgtaagtggt gttttgaagg    6240
ccctgaggaa catgagatct tgaatgacag cggtgaaaca gtgaagtgca gggctcctgg    6300
```

```
aggagcaaag aagcctctgc gcccaaggtg gtgtgatgaa agggtgtcat ctgaccagag   6360
tgcgctgtct gaatttatta agtttgctga aggtaggagg ggagctgctg aagtgctagt   6420
tgtgctgagt gaactccctg atttcctggc taaaaaaggt ggagaggcaa tggataccat   6480
cagtgtgttt ctccactctg aggaaggctc tagggcttac cgcaatgcac tatcaatgat   6540
gcctgaggca atgacaatag tcatgctgtt tatactggct ggactactga catcgggaat   6600
ggtcatcttt ttcatgtctc ccaaaggcat cagtagaatg tctatggcga tgggcacaat   6660
ggccggctgt ggatatctca tgttccttgg aggcgtcaaa cccactcaca tctcctatat   6720
catgctcata ttctttgtcc tgatggtggt tgtgatcccc gagccagggc aacaaaggtc   6780
catccaagac aaccaagtgg catacctcat tattggcatc ctgacgctgg tttcagcggt   6840
ggcagccaac gagctaggca tgctggagaa aaccaaagag gacctctttg gaagaagaa    6900 cttaattcca tctagtgctt caccctggag ttggccggat cttgacctga agccaggagc   6960
tgcctggaca gtgtacgttg gcattgttac aatgctctct ccaatgttgc accactggat   7020
caaagtcgaa tatggcaacc tgtctctgtc tggaatagcc cagtcagcct cagtcctttc   7080
tttcatggac aaggggatac cattcatgaa gatgaatatc tcggtcataa tgctgctggt   7140
cagtggctgg aattcaataa cagtgatgcc tctgctctgt ggcataggt gcgccatgct   7200 ccactggtct ctcattttac ctggaatcaa agcgcagcag tcaaagcttg cacagagaag   7260
ggtgttccat ggcgttgcca agaaccctgt ggttgatggg aatccaacag ttgacattga   7320
ggaagctcct gaaatgcctg ccctttatga gaagaaactg gctctatatc tccttcttgc   7380
tctcagccta gcttctgttg ccatgtgcag aacgccctt tcattggctg aaggcattgt   7440
cctagcatca gctgccctag gccgctcat agagggaaac accagccttc tttggaatgg   7500
acccatggct gtctccatga caggagtcat gaggggaat cactatgctt ttgtgggagt   7560
catgtacaat ctatggaaga tgaaaactgg acgccggggg agcgcgaatg gaaaaacttt   7620
gggtgaagtc tggaagaggg aactgaatct gttggacaag cgacagtttg agttgtataa   7680
aaggaccgac attgtggagg tggatcgtga tacggcacgc aggcatttgg ccgaagggaa   7740
ggtggacacc ggggtggcgg tctccagggg gaccgcaaag ttaaggtggt tccatgagcg   7800
tggctatgtc aagctggaag gtagggtgat tgacctgggg tgtggccgcg gaggctggtg   7860
ttactacgct gctgcgcaaa aggaagtgag tggggtcaaa ggatttactc ttggaagaga   7920
cggccatgag aaacccatga atgtgcaaag tctgggatgg aacatcatca ccttcaagga   7980
caaaactgat atccaccgcc tagaaccagt gaaatgtgac acccttttgt gtgacattgg   8040
agagtcatca tcgtcatcgg tcacagaggg ggaaaggacc gtgagagttc ttgatactgt   8100
agaaaaatgg ctggcttgtg gggttgacaa cttctgtgtg aaggtgttag ctccatacat   8160
gccagatgtt ctcgagaaac tggaattgct ccaaaggagg tttggcggaa cagtgatcag   8220
gaaccctctc tccaggaatt ccactcatga aatgtactac gtgtctggag cccgcagcaa   8280
tgtcacattt actgtgaacc aaacatcccg cctcctgatg aggagaatga ggcgtccaac   8340
tggaaaagtg accctggagg ctgacgtcat cctcccaatt gggacacgca gtgttgagac   8400
agacaaggga cccctggaca agaggccat agaagaaagg gttgagagga taaaatctga   8460
gtacatgacc tcttggtttt atgacaatga caaccctac aggacctggc actactgtgg   8520
ctcctatgtc acaaaaacct caggaagtgc ggcgagcatg gtaaatggtg ttattaaaat   8580
tctgacatat ccatgggaca ggatagagga ggtcacaaga atggcaatga ctgacacaac   8640
cccttttgga cagcaaagag tgtttaaaga aaaagttgac accagagcaa aggatccacc   8700
```

```
agcgggaact aggaagatca tgaaagttgt caacaggtgg ctgttccgcc acctggccag   8760
agaaaagaac cccagactgt gcacaaagga agaatttatt gcaaaagtcc gaagtcatgc   8820
agccattgga gcttacctgg aagaacaaga acagtggaag actgccaatg aggctgtcca   8880
agacccaaag ttctgggaac tggtggatga agaaggaag ctgcaccaac aaggcaggtg    8940
tcggacttgt gtgtacaaca tgatgggaa aagagagaag aagctgtcag agtttgggaa    9000
agcaaaggga agccgtgcca tatggtatat gtggctggga gcgcggtatc ttgagtttga   9060
ggccctggga ttcctgaatg aggaccattg ggcttccagg gaaaactcag gaggaggagt   9120
ggaaggcatt ggcttacaat acctaggata tgtgatcaga gacctggctg caatggatgg   9180
tggtggattc tacgcggatg acaccgctgg atgggacacg cgcatcacag aggcagacct   9240
tgatgatgaa caggagatct tgaactacat gagcccacat cacaaaaaac tggcacaagc   9300
agtgatggaa atgacataca agaacaaagt ggtgaaagtg ttgagaccag ccccaggagg   9360
gaaagcctac atggatgtca taagtcgacg agaccagaga ggatccgggc aggtagtgac   9420
ttatgctctg aacaccatca ccaacttgaa agtccaattg atcagaatgg cagaagcaga   9480
gatggtgata catcaccaac atgttcaaga ttgtgatgaa tcagttctga ccaggctgga   9540
ggcatggctc actgagcacg gatgtaacag actgaagagg atggcggtga gtggagacga   9600
ctgtgtggtc cggcccatcg atgacaggtt cggcctggcc ctgtcccatc tcaacgccat   9660
gtccaaggtt agaaaggaca tatctgaatg gcagccatca aaagggtgga atgattggga   9720
gaatgtgccc ttctgttccc accacttcca tgaactacag ctgaaggatg caggaggat    9780 tgtggtgcct tgccgagaac aggacgagct cattgggaga ggaagggtgt ctccaggaaa   9840
cggctgaatg atcaaggaaa cagcttgcct cagcaaagcc tatgccaaca tgtggtcact   9900
gatgtatttt cacaaaaggg acatgaggct actgtcattg ctgtttcct cagctgttcc    9960 cacctcatgg gttccacaag gacgcacaac atggtcgatt catgggaaag gggagtggat  10020
gaccacggaa gacatgcttg aggtgtggaa cagagtatgg ataaccaaca cccacacat   10080 gcaggacaag acaatggtga aaaaatggag agatgtccct tatctaacca agagacaaga  10140
caagctgtgc ggatcactga ttggaatgac caatagggcc acctgggcct cccacatcca  10200
tttggtcatc catcgtatcc gaacgctgat tggacaggag aaatacactg actacctaac  10260
agtcatggac aggtattctg tggatgctga cctgcaactg ggtgagctta tctgaaacac  10320
catctaacag gaataaccgg gatacaaacc acgggtggag aaccggactc cccacaacct  10380
gaaaccggga tataaaccac ggctggagaa ccggactccg cacttaaaat gaaacagaaa  10440
ccgggataaa aactacggat ggagaaccgg actccacaca ttgagacaga agaagttgtc  10500
agcccagaac cccacacgag ttttgccact gctaagctgt gaggcagtgc aggctgggac  10560
agccgacctc caggttgcga aaaacctggt ttctgggacc tcccacccca gagtaaaaag  10620
aacggagcct ccgctaccac cctcccacgt ggtggtagaa agacgggtc tagaggttag  10680 aggagaccct ccagggaaca aatagtggga ccatattgac gccagggaaa gaccggagtg  10740
gttctctgct tttcctccag aggtctgtga gcacag                            10776
```

<210> SEQ ID NO 10
<211> LENGTH: 10788
<212> TYPE: DNA
<213> ORGANISM: Artificial Sequence
<220> FEATURE:
<223> OTHER INFORMATION: Flaviviridae Flavivirus Yellow Fever Virus

```
<400> SEQUENCE: 10
aatcgagttg ctaggcaata aacacatttg gattaatttt aatcgttcgt tgagcgatta      60
gcagagaact gaccagaaca tgtctggtcg taaagctcag ggaaaaaccc tgggcgtcaa     120
tatggtacga cgaggagttc gctccttgtc aaacaaaata aaacaaaaaa caaaacaaat     180
tggaaacaga cctggacctt caagaggtgt tcaaggattt atcttttttct ttttgttcaa     240
cattttgact ggaaaaaaga tcacagccca cctaaagagg ttgtggaaaa tgctggaccc     300
aagacaaggc ttggctgttc taaggaaagt caagagagtg gtggccagtt tgatgagagg     360
attgtcctca aggaaacgcc gttcccatga tgttctgact gtgcaattcc taattttggg     420
aatgctgttg atgacgggtg gagtgacctt ggtgcggaaa acagatggt tgctcctaaa     480
tgtgacatct gaggacctcg ggaaaacatt ctctgtgggc acaggcaact gcacaacaaa     540
cattttggaa gccaagtact ggtgcccaga ctcaatggaa tacaactgtc ccaatctcag     600
tccaagagag gagccagatg acattgattg ctggtgctat ggggtggaaa acgttagagt     660
cgcatatggt aagtgtgact cagcaggcag gtctaggagg tcaagaaggg ccattgactt     720
gcctacgcat gaaaaccatg gtttgaagac ccggcaagaa aaatggatga ctggaagaat     780
gggtgaaagg caactccaaa agattgagag atggttcgtg aggaacccct tttttgcagt     840
gacggctctg accattgcct accttgtggg aagcaacatg acgcaacgag tcgtgattgc     900
cctactggtc ttggctgttg gtccggccta ctcagctcac tgcattggaa ttactgacag     960
ggatttcatt gagggggtgc atggaggaac ttgggtttca gctaccctgg agcaagacaa    1020
gtgtgtcact gttatggccc ctgacaagcc ttcattggac atctcactag agacagtagc    1080
cattgataga cctgctgagg tgaggaaagt gtgttacaat gcagttctca ctcatgtgaa    1140
gattaatgac aagtgcccca gcactggaga ggcccaccta gctgaagaga acgaagggga    1200
caatgcgtgc aagcgcactt attctgatag aggctggggc aatggctgtg gcctatttgg    1260
gaaagggagc attgtggcat cgccaaaatt cacttgtgcc aaatccatga gtttgtttga    1320
ggttgatcag accaaaattc agtatgtcat cagagcacaa ttgcatgtag ggccaagca    1380
ggaaaattgg actaccgaca ttaagactct caagtttgat gccctgtcag gctcccagga    1440
agtcgagttc attgggtatg aaaagctac actggaatgc caggtgcaaa ctgcggtgga    1500
ctttggtaac agttacatcg ctgagatgga aacagagagc tggatagtgg acagacagtg    1560
ggcccaggac ttgaccctgc catggcagag tggaagtggc ggggtgtgga gagagatgca    1620
tcatcttgtc gaatttgaac ctccgcatgc cgccactatc agagtactgg ccctgggaaa    1680
ccaggaaggc tccttgaaaa cagctcttac tggcgcaatg agggttacaa aggacacaaa    1740
tgacaacaac ctttacaaac tacatggtgg acatgtttct tgcagagtga aattgtcagc    1800
tttgacactc aagggacat cctacaaaat atgcactgac aaaatgtttt ttgtcaagaa    1860
cccaactgac actggccatg gcactgttgt gatgcaggtg aaagtgtcaa aggagcccc    1920
ctgcaggatt ccagtgatag tagctgatga tcttacagcg gcaatcaata aaggcatttt    1980
ggttacagtt aaccccatcg cctcaaccaa tgatgatgaa gtgctgattg aggtgaaccc    2040
acctttggga gacagctaca ttatcgtttgg gagaggagat tcacgtctca cttaccagtg    2100
gcacaaagag ggaagctcaa taggaaagtt gttcactcag accatgaaag gcgtggaacg    2160
cctggccgtc atgggagaca ccgcctggga tttcagctcc gctggagggt tcttcacttc    2220
ggttgggaaa ggaattcata cggtgtttgg ctctgccttt cagggggctat ttggcggctt    2280
gaactggata acaaaggtca tcatggggggc ggtacttata tgggttggca tcaacacaag    2340
```

```
aaacatgaca atgtccatga gcatgatctt ggtaggagtg atcatgatgt ttttgtctct   2400
aggagttggg gcggatcaag gatgcgccat caactttggc aagagagagc tcaagtgcgg   2460
agatggtatc ttcatattta gagactctga tgactggctg aacaagtact catactatcc   2520
agaagatcct gtgaagcttg catcaatagt gaaagcctct tttgaagaag ggaagtgtgg   2580
cctaaattca gttgactccc ttgagcatga gatgtggaga agcagggcag atgagatcaa   2640
tgccattttt gaggaaaacg aggtggacat ttctgttgtc gtgcaggatc caagaatgt    2700
ttaccagaga ggaactcatc cattttccag aattcgggat ggtctgcagt atggttggaa   2760
gacttggggt aagaaccttg tgttctcccc agggaggaag aatggaagct tcatcataga   2820
tggaaagtcc aggaaagaat gcccgttttc aaaccgggtc tggaattctt tccagataga   2880
ggagtttggg acgggagtgt tcaccacacg cgtgtacatg gacgcagtct ttgaatacac   2940
catagactgc gatggatcta tcttgggtgc agcggtgaac ggaaaaaaga gtgcccatgg   3000
ctctccaaca ttttggatgg gaagtcatga agtaaatggg acatggatga tccacacctt   3060
ggaggcatta gattacaagg agtgtgagtg gccactgaca catacgattg gaacatcagt   3120
tgaagagagt gaaatgttca tgccgagatc aatcggaggc ccagttagct ctcacaatca   3180
tatccctgga tacaaggttc agacgaacgg accttggatg caggtaccac tagaagtgaa   3240
gagagaagct tgcccaggga ctagcgtgat cattgatggc aactgtgatg gacggggaaa   3300
atcaaccaga tccaccacgg atagcgggaa agttattcct gaatggtgtt gccgctcctg   3360
cacaatgccg cctgtgagct tccatggtag tgatgggtgt tggtatccca tggaaattag   3420
gccaaggaaa acgcatgaaa gccatctggt gcgctcctgg gttacagctg gagaaataca   3480
tgctgtccct tttggtttgg tgagcatgat gatagcaatg gaagtggtcc taaggaaaag   3540
acagggacca aagcaaatgt tggttggagg agtagtgctc ttgggagcaa tgctggtcgg   3600
gcaagtaact ctccttgatt tgctgaaaact cacagtggct gtgggattgc atttccatga   3660
gatgaacaat ggaggagacg ccatgtatat ggcgttgatt gctgccttt caatcagacc    3720
agggctgctc atcggctttg ggctcaggac cctatggagc cctcgggaac gccttgtgct   3780
gaccctagga gcagccatgg tggagattgc cttgggtggc gtgatgggcg gcctgtggaa   3840
gtatctaaat gcagtttctc tctgcatcct gacaataaat gctgttgctt ctaggaaagc   3900
atcaaatacc atcttgcccc tcatggctct gttgacacct gtcactatgg ctgaggtgag   3960
acttgccgca atgttctttt gtgccgtggt tatcataggg gtccttcacc agaatttcaa   4020
ggacacctcc atgcagaaga ctatacctct ggtggccctc acactcacat cttacctggg   4080
cttgacacaa cctttttgg gcctgtgtgc atttctggca acccgcatat ttgggcgaag   4140
gagtatccca gtgaatgagg cactcgcagc agctggtcta gtgggagtgc tggcaggact   4200
ggcttttcag gagatggaga acttccttgg tccgattgca gttggaggac tcctgatgat   4260
gctggttagc gtggctggga gggtggatgg gctagcctc aagaagcttg tgaagtttc    4320
atgggaagag gaggcggaga tcagcgggag ttccgcccgc tatgatgtgg cactcagtga   4380
acaagggag ttcaagctgc tttctgaaga gaaagtgcca tgggaccagg ttgtgatgac    4440
ctcgctggcc ttggttgggg ctgccctcca tccatttgct cttctgctgg tccttgctgg   4500
gtggctgttt catgtcaggg gagctaggag aagtgggat gtcttgtggg atattcccac    4560
tcctaagatc atcgaggaat gtgaacatct ggaggatggg atttatggca tattccagtc   4620
aaccttcttg ggggcctccc agcgaggagt gggagtggca cagggagggg tgttccacac   4680
```

```
aatgtggcat gtcacaagag gagctttcct tgtcaggaat ggcaagaagt tgattccatc    4740
ttgggcttca gtaaaggaag accttgtcgc ctatggtggc tcatggaagt tggaaggcag    4800
atgggatgga gaggaagagg tccagttgat cgcggctgtt ccaggaaaga acgtggtcaa    4860
cgtccagaca aaaccgagct tgttcaaagt gaggaatggg ggagaaatcg gggctgtcgc    4920
tcttgactat ccgagtggca cttcaggatc tcctattgtt aacaggaacg gagaggtgat    4980
tgggctgtac ggcaatggca tccttgtcgg tgacaactcc ttcgtgtccg ccatatccca    5040
gactgaggtg aaggaagaag gaaggagga gctccaagag atcccgacaa tgctaaagaa    5100
aggaatgaca actgtccttg attttcatcc tggagctggg aagacaagac gtttcctccc    5160
acagatcttg gccgagtgcg cacggagacg cttgcgcact cttgtgttgg cccccaccag    5220
ggttgttctt tctgaaatga aggaggcttt tcacggcctg gacgtgaaat tccacacaca    5280 ggcttttttcc gctcacggca gcgggagaga agtcattgat gctatgtgcc atgccaccct    5340
aacttacagg atgttggaac caactagggt tgttaactgg gaagtgatca ttatggatga    5400
agcccatttt ttggatccag ctagcatagc cgctagaggt tgggcagcgc acagagctag    5460
ggcaaatgaa agtgcaacaa tcttgatgac agccacaccg cctgggacta gtgatgaatt    5520
tccacattca aatggtgaaa tagaagatgt tcaaacggac atacccagtg agccctggaa    5580
cacagggcat gactggatcc tggctgacaa aaggcccacg gcatggttcc ttccatccat    5640
cagagctgca aatgtcatgg ctgcctcttt gcgtaaggct ggaaagagtg tggtggtcct    5700
gaacaggaaa acctttgaga gagaataccc cacgataaag cagaagaaac ctgactttat    5760
attggccact gacatagctg aaatgggagc caacctttgc gtggagcgag tgctggattg    5820
caggacggct tttaagcctg tgcttgtgga tgaagggagg aaggtggcaa taaaagggcc    5880
acttcgtatc tccgcatcct ctgctgctca aaggagggg cgcattggga gaaatcccaa    5940
cagagatgga gactcatact actattctga gcctacaagt gaaaataatg cccaccacgt    6000
ctgctgggtt gaggcctcaa tgcttcttga acacatggag gtgaggggtg aatggtcgc    6060 cccactctat ggcgttgaag gaactaaaac accagtttcc cctggtgaaa tgagactgag    6120
ggatgaccag aggaaagtct tcagagaact agtgaggaat tgtgacctgc cgtttggct    6180 ttcgtggcaa gtggccaagg ctggtttgaa gacgaatgat cgtaagtggt gttttgaagg    6240
ccctgaggaa catgagatct tgaatgacag cggtgaaaca gtgaagtgca gggctcctgg    6300
aggagcaaag aagcctctgc gcccaaggtg gtgtgatgaa agggtgtcat ctgaccagag    6360
tgcgctgtct gaattttatta agtttgctga aggtaggagg ggagctgctg aagtgctagt    6420
tgtgctgagt gaactccctg atttcctggc taaaaaaggt ggagaggcaa tggataccat    6480
cagtgtgttt ctccactctg aggaaggctc tagggcttac cgcaatgcac tatcaatgat    6540
gcctgaggca atgacaatag tcatgctgtt tatactggct ggactactga catcgggaat    6600
ggtcatcttt ttcatgtctc ccaaaggcat cagtagaatg tctatggcga tgggcacaat    6660
ggccggctgt ggatatctca tgttccttgg aggcgtcaaa cccactcaca tctcctatat    6720
catgctcata ttctttgtcc tgatggtggt tgtgatcccc gagccagggc aacaaaggtc    6780
catccaagac aaccaagtgg catacctcat tattggcatc ctgacgctgg tttcagcggt    6840
ggcagccaac gagctaggca tgctggagaa aaccaaagag gacctctttg ggaagaagaa    6900
cttaattcca tctagtgctt caccctggag ttggccggat cttgacctga gccaggagc    6960 tgcctggaca gtgtacgttg gcattgttac aatgctctct ccaatgttgc accactggat    7020
caaagtcgaa tatggcaacc tgtctctgtc tggaatagcc cagtcagcct cagtcctttc    7080
```

```
tttcatggac aagggatac cattcatgaa gatgaatatc tcggtcataa tgctgctggt   7140
cagtggctgg aattcaataa cagtgatgcc tctgctctgt ggcataggt gcgccatgct   7200 ccactggtct ctcattttac ctggaatcaa agcgcagcag tcaaagcttg cacagagaag   7260
ggtgttccat ggcgttgcca agaaccctgt ggttgatggg aatccaacag ttgacattga   7320
ggaagctcct gaaatgcctg ccctttatga aagaaactg gctctatatc tccttcttgc   7380
tctcagccta gcttctgttg ccatgtgcag aacgcccttt tcattggctg aaggcattgt   7440
cctagcatca gctgccctag gccgctcat agagggaaac accagccttc tttggaatgg   7500
acccatggct gtctccatga caggagtcat gaggggaat cactatgctt ttgtgggagt   7560
catgtacaat ctatggaaga tgaaaactgg acgccggggg agcgcgaatg gaaaaacttt   7620
gggtgaagtc tggaagaggg aactgaatct gttggacaag cgacagtttg agttgtataa   7680
aaggaccgac attgtggagg tggatcgtga tacggcacgc aggcatttgg ccgaagggaa   7740
ggtggacacc ggggtggcgg tctccagggg gaccgcaaag ttaaggtggt tccatgagcg   7800
tggctatgtc aagctggaag gtagggtgat tgacctgggg tgtggccgcg gaggctggtg   7860
ttactacgct gctgcgcaaa aggaagtgag tggggtcaaa ggatttactc ttggaagaga   7920
cggccatgag aaacccatga atgtgcaaag tctgggatgg aacatcatca ccttcaagga   7980
caaaactgat atccaccgcc tagaaccagt gaaatgtgac acctttgt gtgacattgg   8040 agagtcatca tcgtcatcgg tcacagaggg ggaaaggacc gtgagagttc ttgatactgt   8100
agaaaaatgg ctggcttgtg gggttgacaa cttctgtgtg aaggtgttag ctccatacat   8160
gccagatgtt ctcgagaaac tggaattgct ccaaggagg tttggcggaa cagtgatcag   8220
gaaccctctc tccaggaatt ccactcatga aatgtactac gtgtctggag cccgcagcaa   8280
tgtcacattt actgtgaacc aaacatcccg cctcctgatg aggagaatga ggcgtccaac   8340
tggaaaagtg accctggagg ctgacgtcat cctcccaatt gggacacgca gtgttgagac   8400
agacaaggga ccctggaca agaggccat agaagaaagg gttgagagga taaaatctga   8460
gtacatgacc tcttggtttt atgacaatga caacccctac aggacctggc actactgtgg   8520
ctcctatgtc acaaaaacct caggaagtgc ggcgagcatg gtaaatggtg ttattaaaat   8580
tctgacatat ccatgggaca ggatagagga ggtcacaaga atggcaatga ctgacacaac   8640
ccctttggga cagcaaagag tgtttaaaga aaaagttgac accagagcaa aggatccacc   8700
agcgggaact aggaagatca tgaaagttgt caacaggtgg ctgttccgcc acctggccag   8760 agaaagaac cccagactgt gcacaaagga agaatttatt gcaaagtcc gaagtcatgc   8820 agccattgga gcttacctgg aagaacaaga acagtggaag actgccaatg aggctgtcca   8880
agacccaaag ttctgggaac tggtggatga agaaggaag ctgcaccaac aaggcaggtg   8940
tcggacttgt gtgtacaaca tgatgggaa aagagagaag aagctgtcag agtttgggaa   9000
agcaaaggga agccgtgcca tatggtatat gtggctggga gcgcggtatc ttgagtttga   9060
ggccctggga ttcctgaatg aggaccattg ggcttccagg gaaaactcag gaggaggagt   9120
ggaaggcatt ggcttacaat acctaggata tgtgatcaga gacctggctg caatggatgg   9180
tggtggattc tacgcggatg acaccgctgg atggacacg cgcatcacag aggcagacct   9240
tgatgatgaa caggagatct tgaactacat gagcccacat cacaaaaaac tggcacaagc   9300
agtgatggaa atgacataca gaacaaagt ggtgaaagtg ttgagaccag ccccaggagg   9360
gaaagcctac atggatgtca taagtcgacg agaccagaga ggatccgggc aggtagtgac   9420
```

```
ttatgctctg aacaccatca ccaacttgaa agtccaattg atcagaatgg cagaagcaga      9480
gatggtgata catcaccaac atgttcaaga ttgtgatgaa tcagttctga ccaggctgga      9540
ggcatggctc actgagcacg gatgtaacag actgaagagg atggcggtga gtggagacga      9600
ctgtgtggtc cggcccatcg atgacaggtt cggcctggcc ctgtcccatc tcaacgccat      9660
gtccaaggtt agaaaggaca tatctgaatg gcagccatca aagggtgga atgattggga       9720 gaatgtgccc ttctgttccc accacttcca tgaactacag ctgaaggatg caggaggat       9780 tgtggtgcct tgccgagaac aggacgagct cattgggaga ggaagggtgt ctccaggaaa      9840
cggctggatg atcaaggaaa cagcttgcct cagcaaagcc tatgccaaca tgtggtcact      9900
gatgtatttt cacaaaaggg acatgaggct actgtcattg gctgtttcct cagctgttcc      9960
cacctcatgg gttccacaag gacgcacaac atggtcgatt catggaaagg ggagtggat      10020 gaccacggaa gacatgcttg aggtgtggaa cagagtatgg ataaccaaca cccacacat      10080 gcaggacaag acaatggtga aaaatggag agatgtccct tatctaacca agagacaaga     10140
caagctgtgc ggatcactga ttggaatgac caataggggcc acctgggcct cccacatcca    10200
tttggtcatc catcgtatcc gaacgctgat tggacaggag aaatacactg actacctaac     10260
agtcatggac aggtattctg tggatgctga cctgcaactg ggtgagctta tctgaaacac     10320
catctaacag gaataaccgg gatacaaacc acgggtggag aaccggactc cccacaacct     10380
gaaaccggga tataaaccac ggctggaaga ccggactccg cacttaaaat gaaacagaaa     10440
ccgggataaa aactacggat ggagaaccgg actccacaca ttgagacaga agaagttgtc    10500
agcccagaac cccacgagt tttgccact gctaagctgt gaggcagtgc aggctgggac      10560
agccgacctc caggttgcga aaacctggt ttctgggacc tcccacccca gagtaaaaag     10620 aacgagcct ccgctaccac cctcccacgt ggtggtagaa agacggggtc tagaggttag     10680
aggagaccct ccagggaaca aatagtggga ccatattgac gccagggaaa gaccggagtg    10740
gttctctgct tttcctccag aggtctgtga gcacagtttg ctcaagaa                  10788

<210> SEQ ID NO 11
<211> LENGTH: 10811
<212> TYPE: DNA
<213> ORGANISM: Artificial Sequence
<220> FEATURE:
<223> OTHER INFORMATION: Flaviviridae Flavivirus Yellow Fever Virus

<400> SEQUENCE: 11
tgcattggtc tgcaaatcga gttgctaggc aataaacaca tttggattaa ttttaatcgt        60
tcgttgagcg attagcagag aactgaccag aacatgtctg gtcgtaaagc tcagggaaaa       120
accctgggcg tcaatatggt acgacgagga gttcgctcct tgtcaaacaa aataaaacaa      180
aaaacgaaac aaattggaaa cagacctgga ccttcaagag gtgttcaagg atttatcttt      240
ttctttttgt tcaacatttt gactggaaaa aagatcacag cccacctaaa gaggttgtgg      300
aaaatgctgg acccaagaca aggcttggct gttctaagga aagtcaagag agtggtggcc      360
agtttgatga gaggattgtc ctcaaggaaa cgccgttccc atgatgttct gactgtgcaa      420
ttcctaattt tgggaatgct gttgatgacg ggtggagtga ccttggtgcg gaaaaacaga      480
tggttgctcc taaatgtgac atctgaggac ctcgggaaaa cattctctgt gggcacaggc      540
aactgcacaa caacattttt ggaagccaag tactggtgcc cagactcaat ggaatacaac      600
tgtcccaatc tcagtccaag agaggagcca gatgacattg attgctggtg ctatgggtg      660 gaaaacgtta gagtcgcata tggtaagtgt gactcagcag gcaggtctag gaggtcaaga     720
```

```
agggccattg acttgcctac gcatgaaaac catggtttga agacccggca agaaaaatgg      780
atgactggaa gaatgggtga aaggcaactc caaaagattg agagatggtt cgtgaggaac      840
cccttttttg cagtgacggc tctgaccatt gcctaccttg tgggaagcaa catgacgcaa      900
cgagtcgtga ttgccctact ggtcttggct gttggtccgg cctactcagc tcactgcatt      960
ggaattactg acagggattt cattgagggg gtgcatggag gaacttgggt ttcagctacc     1020
ctggagcaag acaagtgtgt cactgttatg gcccctgaca agccttcatt ggacatctca     1080
ctagagacag tagccattga tagacctgct gaggtgagga aagtgtgtta caatgcagtt     1140
ctcactcatg tgaagattaa tgacaagtgc cccagcactg gagaggccca cctagctgaa     1200
gagaacgaag gggacaatgc cgtgcaagcg acttattctg atagaggctg gggcaatggc     1260
tgtggcctat ttgggaaagg gagcattgtg gcatgcgcca aattcacttg tgccaaatcc     1320
atgagtttgt ttgaggttga tcagaccaaa attcagtatg tcatcagagc acaattgcat     1380
gtaggggcca gcaggaaaaa ttggactacc gacattaaga ctctcaggtt tgatgccctg     1440
tcaggctccc aggaagtcga gttcattggg tatggaaaag ccacactgga atgccaggtg     1500
caaactgcgg tggactttgg taacagttac atcgctgaga tggaaacaga gagctggata     1560
gtggacagac agtgggccca ggacttgacc ctgccatggc agagtggaag tggcgggggtg     1620 tggagagaga tgcatcatct tgtcgaattt gaacctccgc atgccgccac tatcagagta     1680
ctggccctgg gaaaccagga aggctccttg aaaacagctc ttactggcgc aatgagggtt     1740
acaaaggaca caaatgacaa caaccttac aaactacatg gtggacatgt ttcttgcaga     1800
gtgaaattgt cagctttgac actcaagggg acatcctaca aaatatgcac tgacaaaatg     1860 tttttttgtca agaacccaac tgacactggc catggcactg ttgtgatgca ggtgaaagtg     1920
tcaaaaggag cccctgcag gattccagtg atagtagctg atgatcttac agcggcaatc     1980
aataaaggca ttttggttac agttaacccc atcgcctcaa ccaatgatga tgaagtgctg     2040
attgaggtga acccacctt tggagacagc tacattatcg ttgggagagg agattcacgt     2100
ctcacttacc agtggcacaa agagggaagc tcaataggaa agttgttcac tcagaccatg     2160
aaaggcgtgg aacgcctggc cgtcatggga gacaccgcct gggatttcag ctccgctgga     2220
gggttcttca cttcggttgg gaaaggaatt catacggtgt tggctctgc ctttcagggg     2280 ctatttggcg gcttgaactg gataacaaag gtcatcatgg gggcggtact tatatgggtt     2340
ggcatcaaca caagaaacat gacaatgtcc atgagcatga tcttggtagg agtgatcatg     2400
atgtttttgt ctctaggagt tggggcggat caaggatgcg ccatcaactt ggcaagagga     2460
gagctcaagt gcggagatgg tatcttcata tttagagact ctgatgactg gctgaacaag     2520
tactcatact atccagaaga tcctgtgaag cttgcatcaa tagtgaaagc ctcttttgaa     2580
gaagggaagt gtggcctaaa ttcagttgac tcccttgagc atgagatgtg gagaagcagg     2640
gcagatgaga tcaatgccat ttttgaggaa aacgaggtgg acatttctgt tgtcgtgcag     2700
gatccaaaga atgtttacca gagaggaact catccatttt ccagaattcg ggatggtctg     2760
cagtatggtt ggaagacttg gggtaagaac cttgtgttct ccccagggag gaagaatgga     2820
agcttcatca tagatggaaa gtccaggaaa gaatgcccgt tttcaaaccg ggtctggaat     2880 tcttccccaga tagaggagtt tgggacggga gtgttcacca cacgcgtgta catggacgca     2940
gtctttgaat acaccataga ctgcgatgga tctatcttgg gtgcagcggt gaacggaaaa     3000
aagagtgccc atggctctcc aacatttttgg atgggaagtc atgaagtaaa tgggacatgg     3060
```

```
atgatccaca ccttggaggc attagattac aaggagtgtg agtggccact gacacatacg    3120
attggaacat cagttgaaga gagtgaaatg ttcatgccga gatcaatcgg aggcccagtt    3180
agctctcaca atcatatccc tggatacaag gttcagacga acggaccttg gatgcaggta    3240
ccactagaag tgaagagaga agcttgccca gggactagcg tgatcattga tggcaactgt    3300
gatggacggg gaaaatcaac cagatccacc acggatagcg ggaaagttat tcctgaatgg    3360
tgttgccgct cctgcataat gccgcctgtg agcttccatg gtagtgatgg gtgttggtat    3420
cccatggaaa ttaggccaag gaaaacgcat gaaagccatc tggtgcgctc ctgggttaca    3480
gctggagaaa tacatgctgt ccctttggt ttggtgagca tgatgatagc aatgaagtg     3540 gtcctaagga aaagacaggg accaaagcaa atgttggttg gaggagtagt gctcttggga    3600
gcaatgctgg tcgggcaagt aactctcctt gatttgctga aactcacagt ggctgtggga    3660
ttgcatttcc atgagatgaa caatggagga gacgccatgt atatggcgtt gattgctgcc    3720
ttttcaatca gaccagggct gctcatcggc tttgggctca ggaccctatg gagccctcgg    3780
gaacgccttg tgctgacccc taggagcagc catggtggaga ttgccttggg tggcgtgatg    3840
ggcggcctgt ggaagtatct aaatgcagtt tctctctgca tcctgacaat aaatgctgtt    3900
gcttctagga aagcatcaaa taccatcttg cccctcatgg ctctgttgac acctgtcact    3960
atggctgagg tgagacttgc cgcaatgttc ctttgtgccg tggttatcat aggggtcctt    4020
caccagaatt tcaaggacac ctccatgcag aagactatac ctctggtggc cctcacactc    4080
acatcttacc tgggcttgac acaaccttt ttgggcctgt gtgcatttct ggcaacccgc    4140
atatttgggc gaaggagtat cccagtgaat gaggcactcg cagcagctgg tctagtggga    4200
gtgctggcag gactggcttt tcaggagatg gagaacttcc ttggtccgat gcagttgga     4260 ggactcctga tgatgctggt tagcgtggct gggagggtgg atgggctaga gctcaagaag    4320
cttggtgaag tttcatggga agaggaggcg gagatcagcg ggagttccgc ccgctatgat    4380
gtggcactca gtgaacaagg ggagttcaag ctgctttctg aagagaaagt gccatgggac    4440
caggttgtga tgacctcgct ggccttggtt ggggctgccc tccatccatt tgctcttctg    4500
ctggtccttg ctgggtggct gtttcatgtc agggagcta ggagaagtgg ggatgtcttg    4560
tgggatattc ccactcctaa gatcatcgag gaatgtgaac atctggagga tgggatttat    4620
ggcatattcc agtcaacctt cttgggggcc tcccagcgag gagtgggagt ggcacaggga    4680
ggggtgttcc acacaatgtg gcatgtcaca agaggagctt tccttgtcag gaatggcaag    4740
aagttgattc catcttgggc ttcagtaaag gaagaccttg tcgcctatgg tggctcatgg    4800
aagttggaag gcagatggga tggagaggaa gaggtccagt tgatcgcggc tgttccagga    4860
aagaacgtgg tcaacgtcca gacaaaaccg agcttgttca aagtgaggaa tggggagaa    4920 atcggggctg tcgctcttga ctatccgagt ggcacttcag gatctcctat tgttaacagg    4980 aacgagagg tgattgggct gtacggcaat ggcatccttg tcggtgacaa ctccttcgtg    5040
tccgccatat cccagactga ggtgaaggaa gaaggaaagg aggagctcca agagatcccg    5100
acaatgctaa agaaaggaat gacaactgtc cttgatttc atcctggagc tgggaagaca    5160 agacgttttcc tcccacagat cttggccgag tgcgcacgga gacgcttgcg cactcttgtg    5220
ttggccccca ccagggttgt tctttctgaa atgaaggagg cttttcacgg cctggacgtg    5280
aaattccaca cacaggcttt ttccgctcac ggcagcggga gagaagtcat tgatgctatg    5340
tgccatgcca ccctaactta caggatgttg gaaccaacta gggttgttaa ctgggaagtg    5400
atcattatgg atgaagccca ttttttggat ccagctagca tagccgctag aggttgggca    5460
```

```
gcgcacagag ctagggcaaa tgaaagtgca acaatcttga tgacagccac accgcctggg   5520
actagtgatg aatttccaca ttcaaatggt gaaatagaag atgttcaaac ggacataccc   5580
agtgagccct ggaacacagg gcatgactgg atcctggctg acaaaaggcc cacggcatgg   5640
ttccttccat ccatcagagc tgcaaatgtc atggctgcct ctttgcgtaa ggctggaaag   5700
agtgtggtgg tcctgaacag gaaaaccttt gagagagaat accccacgat aaagcagaag   5760
aaacctgact ttatattggc cactgacata gctgaaatgg agccaacct ttgcgtggag    5820 cgagtgctgg attgcaggac ggcttttaag cctgtgcttg tggatgaagg gaggaaggtg   5880
gcaataaaag ggccacttcg tatctccgca tcctctgctg ctcaaaggag ggggcgcatt   5940
gggagaaatc ccaacagaga tggagactca tactactatt ctgagcctac aagtgaaaat   6000
aatgcccacc acgtctgctg gttggaggcc tcaatgctct tggacaacat ggaggtgagg   6060
ggtggaatgg tcgccccact ctatggcgtt gaaggaacta aaacaccagt tccccctggt   6120
gaaatgagac tgagggatga ccagaggaaa gtcttcagag aactagtgag gaattgtgac   6180
ctgcccgttt ggctttcgtg gcaagtggcc aaggctggtt tgaagacgaa tgatcgtaag   6240
tggtgttttg aaggccctga ggaacatgag atcttgaatg acagcggtga acagtgaag    6300 tgcagggctc ctggaggagc aaagaagcct ctgcgcccaa ggtggtgtga tgaaagggtg   6360
tcatctgacc agagtgcgct gtctgaattt attaagtttg ctgaaggtag gaggggagct   6420
gctgaagtgc tagttgtgct gagtgaactc cctgatttcc tggctaaaaa aggtggagag   6480
gcaatggata ccatcagtgt gtttctccac tctgaggaag gctctagggc ttaccgcaat   6540
gcactatcaa tgatgcctga ggcaatgaca atagtcatgc tgtttatact ggctggacta   6600
ctgacatcgg gaatggtcat cttttttcatg tctcccaaag gcatcagtag aatgtctatg   6660
gcgatgggca caatggccgg ctgtggatat ctcatgttcc ttggaggcgt caaacccact   6720
cacatctcct atatcatgct catattcttt gtcctgatgg tggttgtgat ccccgagcca   6780
gggcaacaaa ggtccatcca agacaaccaa gtggcatacc tcattattgg catcctgacg   6840
ctggtttcag cggtggcagc caacgagcta ggcatgctgg agaaaaccaa agaggacctc   6900
tttgggaaga agaacttaat tccatctagt gcttcaccct ggagttggcc ggatcttgac   6960
ctgaagccag gagctgcctg gacagtgtac gttggcattg ttacaatgct ctctccaatg   7020
ttgcaccact ggatcaaagt cgaatatggc aacctgtctc tgtctggaat agcccagtca   7080
gcctcagtcc tttctttcat ggacaagggg ataccattca tgaagatgaa tatctcggtc   7140
ataatgctgc tggtcagtgg ctggaattca ataacagtga tgcctctgct ctgtggcata   7200
gggtgcgcca tgctccactg gtctctcatt ttacctggaa tcaaagcgca gcagtcaaag   7260
cttgcacaga gaaagggtgtt ccatggcgtt gccaagaacc ctgtggttga tgggaatcca   7320
acagttgaca ttgaggaagc tcctgaaatg cctgcccttt atgagaagaa actggctcta   7380
tatctccttc ttgctctcag cctagcttct gttgccatgt gcagaacgcc cttttcattg   7440
gctgaaggca ttgtcctagc atcagctgcc ctagggccgc tcatagaggg aaacaccagc   7500
cttctttgga atggaccat ggctgtctcc atgacaggag tcatgagggg gaatcactat    7560
gcttttgtgg gagtcatgta caatctatgg aagatgaaaa ctggacgccg ggggagcgcg   7620
aatgaaaaaa ctttgggtga agtctggaag agggaactga atctgttgga caagcgacag   7680
tttgagttgt ataaaaggac cgacattgtg gaggtggatc gtgataccgc acgcaggcat   7740
ttggccgaag ggaaggtgga caccgggggtg gcggtctcca gggggaccgc aaagttaagg   7800
```

```
tggttccatg agcgtggcta tgtcaagctg aaggtaggg tgattgacct ggggtgtggc    7860
cgcggaggct ggtgttacta cgctgctgcg caaaaggaag tgagtggggt caaaggattt    7920
actcttggaa gagacggcca tgagaaaccc atgaatgtgc aaagtctggg atggaacatc    7980
atcaccttca aggacaaaac tgatatccac cgcctagaac cagtgaaatg tgacacccct    8040
ttgtgtgaca ttggagagtc atcatcgtca tcggtcacag agggggaaag gaccgtgaga    8100
gttcttgata ctgtagaaaa atggctggct tgtggggttg acaacttctg tgtgaaggtg    8160
ttagctccat acatgccaga tgttctcgag aaactggaat tgctccaaag gaggtttggc    8220
ggaacagtga tcaggaaccc tctctccagg aattccactc atgaaatgta ctacgtgtct    8280
ggagcccgca gcaatgtcac atttactgtg aaccaaacat cccgcctcct gatgaggaga    8340
atgaggcgtc caactggaaa agtgaccctg gaggctgacg tcatcctccc aattgggaca    8400
cgcagtgttg agacagacaa gggacccctg gacaagagg ccatagaaga aagggttgag    8460
aggataaaat ctgagtacat gacctcttgg ttttatgaca atgacaaccc ctacaggacc    8520
tggcactact gtgctccta tgtcacaaaa acctcaggaa gtgcggcgag catggtaaat    8580
ggtgttatta aaattctgac atatccatgg gacaggatag aggaggtcac aagaatggca    8640
atgactgaca caacccctt tggacagcaa agagtgttta agaaaaagt tgacaccaga    8700
gcaaaggatc caccagcggg aactaggaag atcatgaaag ttgtcaacag gtggctgttc    8760
cgccacctgg ccagagaaaa gaaccccaga ctgtgcacaa ggaagaatt tattgcaaaa    8820
gtccgaagtc atgcagccat tggagcttac ctggaagaac aagaacagtg gaagactgcc    8880
aatgaggctg tccaagaccc aaagttctgg gaactggtgg atgaagaaag gaagctgcac    8940
caacaaggca ggtgtcggac ttgtgtgtac aacatgatgg ggaaaagaga gaagaagctg    9000
tcagagtttg gaaagcaaa gggaagccgt gccatatggt atatgtggct gggagcgcgg    9060
tatcttgagt ttgaggccct gggattcctg aatgaggacc attgggcttc cagggaaaac    9120
tcaggaggag gagtggaagg cattggctta caataccag gatatgtgat cagagacctg    9180
gctgcaatgg atggtggtgg attctacgcg gatgacaccg ctggatggga cacgcgcatc    9240
acagaggcag accttgatga tgaacaggag atcttgaact acatgagccc acatcacaaa    9300
aaactggcac aagcagtaat ggaaatgaca tacaagaaca aagtggtgaa agtgttgaga    9360
ccagccccag gagggaaagc ctacatggat gtcataagtc gacgagacca gagaggatcc    9420
gggcaggtag tgacttatgc tctgaacacc atcaccaact tgaaagtcca attgatcaga    9480
atggcagaag cagagatggt gatacatcac caacatgttc aagattgtga tgaatcagtt    9540
ctgaccaggc tggaggcatg gctcactgag cacggatgta acagactgaa gaggatggcg    9600
gtgagtggag acgactgtgt ggtccggccc atcgatgaca ggttcggcct ggccctgtcc    9660
catctcaacg ccatgtccaa ggttagaaag gacatatctg aatggcagcc atcaaaaggg    9720
tggaatgatt gggagaatgt gcccttctgt tcccaccact tccatgaact acagctgaag    9780
gatggcagga ggattgtggt gccttgccga gaacaggacg agctcattgg gagaggaagg    9840
gtgtctccag gaaacggctg gatgatcaag gaaacagctt gcctcagcaa agcctatgcc    9900
aacatgtggt cactgatgta ttttcacaaa agggacatga ggctactgtc attggctgtt    9960
tcctcagctg ttcccaccctc atgggttcca caaggacgca caacatggtc gattcatggg    10020
aaagggagt ggatgaccac ggaagacatg cttgaggtgt ggaacagagt atggataacc    10080
aacaacccac acatgcagga caagacaatg gtgaaaaaat ggagagatgt cccttatcta    10140
accaagagac aagacaagct gtgcggatca ctgattggaa tgaccaatag ggccacctgg    10200
```

-continued

| | | |
|---|---|---|
| gcctcccaca tccatttggt catccatcgt atccgaacgc tgattggaca ggagaaatac | 10260 |
| actgactacc taacagtcat ggacaggtat tctgtggatg ctgacctgca actgggtgag | 10320 |
| cttatctgaa acaccatcta acaggaataa ccgggataca aaccacgggt ggagaaccgg | 10380 |
| actcccaca acctgaaacc gggatataaa ccacggctgg agaacggac tccgcactta | 10440 |
| aaatgaaaca gaaaccggga taaaaactac ggatggagaa ccggactcca cacattgaga | 10500 |
| cagaagaagt tgtcagccca gaaccccaca cgagttttgc cactgctaag ctgtgaggca | 10560 |
| gtgcaggctg gacagccga cctccaggtt gcgaaaaacc tggtttctgg acctcccac | 10620 |
| cccagagtaa aaagaacgga gcctccgcta ccacccctccc acgtggtggt agaaagacgg | 10680 |
| ggtctagagg ttagaggaga ccctccaggg aacaaatagt gggaccatat tgacgccagg | 10740 |
| gaaagaccgg agtggttctc tgcttttcct ccagaggtct gtgagcacag tttgctcaag | 10800 |
| aataagcaga c | 10811 |

<210> SEQ ID NO 12
<211> LENGTH: 10785
<212> TYPE: DNA
<213> ORGANISM: Artificial Sequence
<220> FEATURE:
<223> OTHER INFORMATION: Flaviviridae Flavivirus Yellow Fever Virus

<400> SEQUENCE: 12

| | | |
|---|---|---|
| tcgagttgct aggcaataaa cacatttgga ttaattttaa tcgttcgttg agcgattagc | 60 |
| agagaactga ccagaacatg tctggtcgta aagctcaggg aaaaaccctg ggcgtcaata | 120 |
| tggtacgacg aggagttcgc tccttgtcaa acaaaataaa acaaaaaaca aacaaattg | 180 |
| gaaacagacc tggaccttca agaggtgttc aaggatttat ctttttcttt ttgttcaaca | 240 |
| ttttgactgg aaaaaagatc acagcccacc taaagaggtt gtggaaaatg ctggacccaa | 300 |
| gacaaggctt ggctgttcta aggaaagtca agagagtgg ggccagtttg atgagaggat | 360 |
| tgtcctcaag gaaacgccgt tcccatgatg ttctgactgt gcaattccta attttgggaa | 420 |
| tgctgttgat gacgggtgga gtgacctgg tgcggaaaaa cagatggttg ctcctaaatg | 480 |
| tgacatctga ggacctcggg aaaacattct ctgtgggcac aggcaactgc acaacaaaca | 540 |
| ttttggaagc caagtactgg tgcccagact caatggaata caactgtccc aatctcagtc | 600 |
| caagagagga gccagatgac attgattgct ggtgctatgg ggtggaaaac gttagagtcg | 660 |
| catatggtaa gtgtgactca gcaggcaggt ctaggaggtc aagaagggcc attgacttgc | 720 |
| ctacgcatga aaaccatggt ttgaagaccc ggcaagaaaa atggatgact ggaagaatgg | 780 |
| gtgaaaggca actccaaaag attgagagat ggttcgtgag gaaccccttt tttgcagtga | 840 |
| cggctctgac cattgcctac cttgtgggaa gcaacatgac gcaacgagtc gtgattgccc | 900 |
| tactggtctt ggctgttggt ccggcctact cagctcactg cattggaatt actgacaggg | 960 |
| atttcattga gggggtgcat ggaggaactt gggtttcagc tacccctggag caagacaagt | 1020 |
| gtgtcactgt tatggcccct gacaagcctt cattggacat ctcactagag acagtagcca | 1080 |
| ttgatagacc tgctgaggtg aggaaagtgt gttacaatgc agttctcact catgtgaaga | 1140 |
| ttaatgacaa gtgccccagc actggagagg cccacctagc tgaagagaac gaagggggaca | 1200 |
| atgcgtgcaa gcgcacttat tctgatagag ctggggcaa tggctgtggc ctatttggga | 1260 |
| aaggagcat tgtggcatgc gccaaattca cttgtgccaa atccatgagt ttgtttgagg | 1320 |
| ttgatcagac caaaattcag tatgtcatca gagcacaatt gcatgtaggg gccaagcagg | 1380 |

```
aaaattggac taccgacatt aagactctca agtttgatgc cctgtcaggc tcccaggaag    1440
tcgagttcat tgggtatgga aaagctacac tggaatgcca ggtgcaaact gcggtggact    1500
ttggtaacag ttacatcgct gagatggaaa cagagagctg atagtggac agacagtggg     1560 cccaggactt gaccctgcca tggcagagtg gaagtggcgg ggtgtggaga gagatgcatc    1620
atcttgtcga atttgaacct ccgcatgccg ccactatcag agtactggcc ctgggaaacc    1680
aggaaggctc cttgaaaaca gctcttactg gcgcaatgag ggttacaaag gacacaaatg    1740
acaacaacct ttacaaacta catggtggac atgtttcttg cagagtgaaa ttgtcagctt    1800
tgacactcaa ggggacatcc tacaaaatat gcactgacaa aatgtttttt gtcaaaaacc    1860
caactgacac tggccatggc actgttgtga tgcaggtgaa agtgtcaaaa ggagcccct    1920 gcaggattcc agtgatagta gctgatgatc ttacagcggc aatcaataaa ggcatttttgg   1980 ttacagttaa ccccatcgcc tcaaccaatg atgatgaagt gctgattgag gtgaacccac    2040
cttttggaga cagctacatt atcgttggga gaggagattc acgtctcact taccagtggc    2100
acaaagaggg aagctcaata ggaaagttgt tcactcagac catgaaaggc gtggaacgcc    2160
tggccgtcat gggagacacc gcctgggatt tcagctccgc tggagggttc ttcacttcgg    2220
ttgggaaagg aattcatacg tgtttggct ctgcctttca ggggctattt ggcggcttga     2280
actggataac aaaggtcatc atggggggcgg tacttatatg ggttggcatc aacacaagaa    2340
acatgacaat gtccatgagc atgatcttgg taggagtgat catgatgttt ttgtctctag    2400 gagttgggc ggatcaagga tgcgccatca actttggcaa gagagagctc aagtgcggag      2460
atggtatctt catatttaga gactctgatg actggctgaa caagtactca tactatccag    2520
aagatcctgt gaagcttgca tcaatagtga aagcctcttt tgaagaaggg aagtgtggcc    2580
taaattcagt tgactccctt gagcatgaga tgtggagaag cagggcagat gagatcaatg    2640
ccatttttga ggaaaacgag gtggacattt ctgttgtcgt gcaggatcca aagaatgttt    2700
accagagagg aactcatcca tttttccaga attcgggatgg tctgcagtat ggttggaaga    2760
cttggggtaa gaaccttgtg ttctccccag ggaggaagaa tggaagcttc atcatagatg    2820
gaaagtccag gaaagaatgc ccgttttcaa accgggtctg gaattctttc cagatagagg    2880
agtttgggac gggagtgttc accacacgcg tgtacatgga cgcagtcttt gaatacacca    2940
tagactgcga tggatctatc ttgggtgcag cggtgaacgg aaaaaagagt gcccatggct    3000
ctccaacatt ttgatggga agtcatgaag taaatgggac atggatgatc cacaccttgg      3060
aggcattaga ttacaaggag tgtgagtggc cactgacaca tacgattgga acatcagttg    3120
aagagagtga aatgttcatg ccgagatcaa tcggaggccc agttagctct cacaatcata    3180 tccctgata caaggttcag acgaacggac cttggatgca ggtaccacta gaagtgaaga    3240
gagaagcttg cccagggact agcgtgatca ttgatggcaa ctgtgatgga cggggaaaat    3300
caaccagatc caccacggat agcgggaaag ttattcctga atggtgttgc cgctcctgca    3360
caatgccgcc tgtgagcttc catggtagtg atgggtgttg gtatcccatg gaaattaggc    3420
caaggaaaac gcatgaaagc catctggtgc gctcctgggt tacagctgga gaaatacatg    3480
ctgtcccttt tggtttggtg agcatgatga tagcaatgga agtggtccta aggaaaagac    3540
agggaccaaa gcaaatgttg gttggaggag tagtgctctt gggagcaatg ctggtcgggc    3600
aagtaactct ccttgatttg ctgaaactca gtggctgt gggattgcat ttccatgaga      3660
tgaacaatgg aggagacgcc atgtatatgg cgttgattgc tgcctttca atcagaccag    3720 ggctgctcat cggctttggg ctcaggaccc tatggagccc tcgggaacgc cttgtgctga    3780
```

-continued

```
ccctaggagc agccatggtg gagattgcct tgggtggcgt gatgggcggc ctgtggaagt    3840
atctaaatgc agtttctctc tgcatcctga caataaatgc tgttgcttct aggaaagcat    3900
caaataccat cttgcccctc atggctctgt tgacacctgt cactatggct gaggtgagac    3960
ttgccgcaat gttcttttgt gccgtggtta tcatagggga ccttcaccag aatttcaagg    4020
acacctccat gcagaagact atacctctgg tggccctcac actcacatct tacctgggct    4080
tgacacaacc ttttttgggc ctgtgtgcat ttctggcaac ccgcatattt gggcgaagga    4140
gtatcccagt gaatgaggca ctcgcagcag ctggtctagt gggagtgctg caggactgg     4200
cttttcagga gatggagaac ttccttggtc cgattgcagt tggaggactc ctgatgatgc    4260
tggttagcgt ggctgggagg gtggatgggc tagagctcaa gaagcttggt gaagtttcat    4320
gggaagagga ggcggagatc agcgggagtt ccgcccgcta tgatgtggca ctcagtgaac    4380
aaggggagtt caagctgctt tctgaagaga aagtgccatg ggaccaggtt gtgatgacct    4440
cgctggcctt ggttggggct gccctccatc catttgctct tctgctggtc cttgctgggt    4500
ggctgtttca tgtcagggga ctaggagaa gtggggatgt cttgtgggat attcccactc     4560
ctaagatcat cgaggaatgt gaacatctgg aggatgggga ttatggcata ttccagtcaa    4620
ccttcttggg ggcctcccag cgaggagtgg gagtggcaca gggagggtg ttccacacaa     4680
tgtggcatgt cacaagagga gctttccttg tcaggaatgg caagaagttg attccatctt    4740
gggcttcagt aaaggaagac cttgtcgcct atggtggctc atggaagttg gaaggcagat    4800
gggatggaga ggaagaggtc cagttgatcg cggctgttcc aggaaagaac gtggtcaacg    4860
tccagacaaa accgagcttg ttcaaagtga ggaatgggg agaaatcggg gctgtcgctc     4920
ttgactatcc gagtggcact tcaggatctc ctattgttaa caggaacgga gaggtgattg    4980
ggctgtacgg caatggcatc cttgtcggtg acaactcctt cgtgtccgcc atatcccaga    5040
ctgaggtgaa ggaagaagga aaggaggagc tccaagagat cccgacaatg ctaaagaaag    5100
gaatgacaac tgtccttgat tttcatcctg gagctgggaa gacaagacgt ttcctcccac    5160
agatcttggc cgagtgcgca cggagacgct tgcgcactct tgtgttggcc cccaccaggg    5220
ttgttctttc tgaaatgaag gaggcttttc acggcctgga cgtgaaattc cacacacagg    5280
cttttttccgc tcacggcagc gggagagaag tcattgatgc tatgtgccat gccaccctaa    5340
cttacaggat gttggaacca actagggttg ttaactggga agtgatcatt atggatgaag    5400
cccatttttt ggatccagct agcatagccg ctagaggttg ggcagcgcac agagctaggg    5460
caaatgaaag tgcaacaatc ttgatgacag ccacaccgcc tgggactagt gatgaatttc    5520
cacattcaaa tggtgaaata gaagatgttc aaacggacat acccagtgag ccctggaaca    5580
cagggcatga ctgatcctg gctgacaaaa ggcccacggc atggttcctt ccatccatca     5640
gagctgcaaa tgtcatggct gcctcttttgc gtaaggctgg aaagagtgtg gtggtcctga    5700
acaggaaaac ctttgagaga gaatacccca cgataaagca aagaaacct gactttatat      5760
tggccactga catagctgaa atgggagcca acctttgcgt ggagcgagtg ctggattgca    5820
ggacggcttt taagcctgtg cttgtggata agggaggaa ggtggcaata aaagggccac      5880
ttcgtatctc cgcatcctct gctgctcaaa ggagggggcg cattgggaga atcccaaca     5940
gagatggaga ctcatactac tattctgagc ctacaagtga aaataatgcc caccacgtct    6000
gctggtggaa ggcctcaatg ctcttggaca acatggaggt gaggggtgga atggtcgccc    6060
cactctatgg cgttgaagga actaaaacac cagtttcccc tggtgaaatg agactgaggg    6120
```

```
atgaccagag gaaagtcttc agagaactag tgaggaattg tgacctgccc gtttggcttt     6180
cgtggcaagt ggccaaggct ggtttgaaga cgaatgatcg taagtggtgt tttgaaggcc     6240
ctgaggaaca tgagatcttg aatgacagcg gtgaaacagt gaagtgcagg gctcctggag     6300
gagcaaagaa gcctctgcgc ccaaggtggt gtgatgaaag ggtgtcatct gaccagagtg     6360
cgctgtctga atttattaag tttgctgaag gtaggagggg agctgctgaa gtgctagttg     6420
tgctgagtga actccctgat ttcctggcta aaaaaggtgg agaggcaatg gataccatca     6480
gtgtgtttct ccactctgag gaaggctcta gggcttaccg caatgcacta tcaatgatgc     6540
ctgaggcaat gacaatagtc atgctgttta tactggctgg actactgaca tcggaatgg      6600
tcatcttttt catgtctccc aaaggcatca gtagaatgtc tatggcgatg ggcacaatgg     6660
ccggctgtgg atatctcatg ttccttggag gcgtcaaacc cactcacatc tcctatatca     6720
tgctcatatt ctttgtcctg atggtggttg tgatccccga gccagggcaa caaaggtcca     6780
tccaagacaa ccaagtggca tacctcatta ttggcatcct gacgctggtt tcagcggtgg     6840
cagccaacga gctaggcatg ctggagaaaa ccaaagagga cctctttggg aagaagaact     6900
taattccatc tagtgcttca ccctggagtt ggccggatct tgacctgaag ccaggagctg     6960
cctgacagt gtacgttggc attgttacaa tgctctctcc aatgttgcac cactggatca      7020
aagtcgaata tggcaacctg tctctgtctg aatagcccca gtcagcctca gtcctttctt     7080
tcatggacaa ggggatacca ttcatgaaga tgaatatctc ggtcataatg ctgctggtca     7140
gtggctggaa ttcaataaca gtgatgcctc tgctctgtgg catggggtgc gccatgctcc     7200
actggtctct cattttacct ggaatcaaag cgcagcagtc aaagcttgca cagagaaggg     7260
tgttccatgg cgttgccaag aaccctgtgg ttgatgggaa tccaacagtt gacattgagg     7320
aagctcctga aatgcctgcc ctttatgaga agaaactggc tctatatctc cttcttgctc     7380
tcagcctagc ttctgttgcc atgtgcagaa cgccctttc attggctgaa ggcattgtcc       7440
tagcatcagc tgcccctagg ccgctcatag agggaaacac cagccttctt tggaatggac     7500
ccatggctgt ctccatgaca ggagtcatga gggggaatca ctatgctttt gtgggagtca     7560
tgtacaatct atggaagatg aaaactggac gccgggggag cgcgaatgga aaaactttgg     7620
gtgaagtctg gaagagggaa ctgaatctgt tggacaagcg acagtttgag ttgtataaaa     7680
ggaccgacat tgtggaggtg gatcgtgata cggcacgcag gcatttggcc gaagggaagg     7740
tggacaccgg ggtggcggtc tccaggggga ccgcaaagtt aaggtggttc catgagcgtg     7800
gctatgtcaa gctggaaggt agggtgattg acctggggtg tggccgcgga ggctggtgtt     7860
actacgctgc tgcgcaaaag gaagtgagtg gggtcaaagg atttactctt ggaagagacg     7920
gccatgagaa acccatgaat gtgcaaagtc tgggatggaa catcatcacc ttcaaggaca     7980
aaactgatat ccaccgccta gaaccagtga atgtgacac cttttgtgt gacattggag        8040
agtcatcatc gtcatcggtc acagaggggg aaaggaccgt gagagttctt gatactgtag     8100
aaaaatggct ggcttgtggg gttgacaact tctgtgtgaa ggtgttagct ccatacatgc     8160
cagatgttct cgagaaactg gaattgctcc aaaggaggtt tggcggaaca gtgatcagga     8220
accctctctc caggaattcc actcatgaaa tgtactacgt gtctggagcc cgcagcaatg     8280
tcacatttac tgtgaaccaa acatcccgcc tcctgatgag gagaatgagg cgtccaactg     8340
gaaaagtgac cctggaggct gacgtcatcc tcccaattgg gacacgcagt gttgagacag     8400
acaagggacc cctggacaaa gaggcctag aagaaagggt tgagaggata aaatctgagt      8460
acatgaccct cttggttttat gacaatgaca ccccctacag gacctggcac tactgtggct     8520
```

```
cctatgtcac aaaaacctca ggaagtgcgg cgagcatggt aaatggtgtt attaaaattc   8580
tgacatatcc atgggacagg atagaggagg tcacaagaat ggcaatgact gacacaaccc   8640
cttttggaca gcaaagagtg tttaaagaaa aagttgacac cagagcaaag gatccaccag   8700
cgggaactag gaagatcatg aaagttgtca acaggtggcg gttccgccac ctggccagag   8760
aaaagaaccc cagactgtgc acaaaggaag aatttattgc aaaagtccga agtcatgcag   8820
ccattggagc ttacctggaa gaacaagaac agtggaagac tgccaatgag gctgtccaag   8880
acccaaagtt ctgggaactg gtggatgaag aaaggaagct gcaccaacaa ggcaggtgtc   8940
ggacttgtgt gtacaacatg atggggaaaa gagagaagaa gctgtcagag tttgggaaag   9000
caaagggaag ccgtgccata tggtatatgt ggctgggagc gcggtatctt gagtttgagg   9060
ccctgggatt cctgaatgag gaccattggg cttccaggga aaactcagga ggaggagtgg   9120
aaggcattgg cttacaatac ctaggatatg tgatcagaga cctggctgca atggatggtg   9180
gtggattcta cgcggatgac accgctggat gggacacgcg catcacagag gcagaccttg   9240
atgatgaaca ggagatcttg aactacatga gcccacatca caaaaaactg gcacaagcag   9300
tgatggaaat gacatacaag aacaaagtgg tgaaagtgtt gagaccagcc ccaggaggga   9360
aagcctacat ggatgtcata agtcgacgag accagagagg atccgggcag gtagtgactt   9420
atgctctgaa caccatcacc aacttgaaag tccaattgat cagaatggca gaagcagaga   9480
tggtgataca tcaccaacat gttcaagatt gtgatgaatc agttctgacc aggctggagg   9540
catggctcac tgagcacgga tgtaacagac tgaagaggat ggcggtgagt ggagacgact   9600
gtgtggtccg gcccatcgat gacaggtttg gcctggccct gtcccatctc aacgccatgt   9660
ccaaggttag aaaggacata tctgaatggc agccatcaaa agggtggaat gattgggaga   9720
atgtgccctt ctgttccccac cacttccatg aactacagct gaaggatggc aggaggattg   9780
tggtgccttg ccgagaacag gacgagctca ttgggagagg aagggtgtct ccaggaaacg   9840
gctggatgat caaggaaaca gcttgcctca gcaaagccta tgccaacatg tggtcactga   9900 tgtatttttca caaagggac atgaggctac tgtcattggc tgtttcctca gctgttccca   9960
cctcatgggt tccacaagga cgcacaacat ggtcgattca tgggaaaggg gagtggatga  10020
ccacggaaga catgcttgag gtgtggaaca gagtatggat aaccaacaac ccacacatgc  10080
aggacaagac aatggtgaaa aaatggagag atgtcccctta tctaaccaag agacaagaca  10140
agctgtgcgg atcactgatt ggaatgacca atagggccac ctgggcctcc cacatccatt  10200
tggtcatcca tcgtatccga acgctgattg acaggagaa atacactgac tacctaacag  10260
tcatggacag gtattctgtg gatgctgacc tgcaactggg tgagcttatc tgaaacacca  10320
tctaacagga ataaccggga tacaaaccac gggtggagaa ccggactccc cacaacctga  10380
aaccgggata taaccacgg ctggagaacc ggactccgca cttaaaatga aacagaaacc  10440
gggataaaaa ctacgatgg agaaccggac tccacacatt gagacagaag aagttgtcag  10500
cccagaaccc cacacgagtt ttgccactgc taagctgtga ggcagtgcag gctgggacag  10560
ccgacctcca ggttgcgaaa aacctggttt ctgggacctc ccaccccaga gtaaaaagaa  10620
cggagcctcc gctaccaccc tcccacgtgg tggtagaaag acgggtctaa gaggttagag  10680
gagaccctcc agggaacaaa tagtgggacc atattgacgc cagggaaaga ccggagtggt  10740
tctctgcttt tcctccagag gtctgtgagc acagtttgct caaga               10785
```

<210> SEQ ID NO 13

```
<211> LENGTH: 3411
<212> TYPE: PRT
<213> ORGANISM: Artificial Sequence
<220> FEATURE:
<223> OTHER INFORMATION: Flaviviridae Flavivirus Yellow Fever Virus

<400> SEQUENCE: 13
```

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Val Arg Lys Asn
        115                 120                 125

Arg Trp Leu Leu Leu Asn Val Thr Ser Glu Asp Leu Gly Lys Thr Phe
    130                 135                 140

Ser Val Gly Thr Gly Asn Cys Thr Thr Asn Ile Leu Glu Ala Lys Tyr
145                 150                 155                 160

Trp Cys Pro Asp Ser Met Glu Tyr Asn Cys Pro Asn Leu Ser Pro Arg
                165                 170                 175

Glu Glu Pro Asp Asp Ile Asp Cys Trp Cys Tyr Gly Val Glu Asn Val
            180                 185                 190

Arg Val Ala Tyr Gly Lys Cys Asp Ser Ala Gly Arg Ser Arg Arg Ser
        195                 200                 205

Arg Arg Ala Ile Asp Leu Pro Thr His Glu Asn His Gly Leu Lys Thr
    210                 215                 220

Arg Gln Glu Lys Trp Met Thr Gly Arg Met Gly Glu Arg Gln Leu Gln
225                 230                 235                 240

Lys Ile Glu Arg Trp Phe Val Arg Asn Pro Phe Phe Ala Val Thr Ala
                245                 250                 255

Leu Thr Ile Ala Tyr Leu Val Gly Ser Asn Met Thr Gln Arg Val Val
            260                 265                 270

Ile Ala Leu Leu Val Leu Ala Val Gly Pro Ala Tyr Ser Ala His Cys
        275                 280                 285

Ile Gly Ile Thr Asp Arg Asp Phe Ile Glu Gly Val His Gly Gly Thr
    290                 295                 300

Trp Val Ser Ala Thr Leu Glu Gln Asp Lys Cys Val Thr Val Met Ala
305                 310                 315                 320

Pro Asp Lys Pro Ser Leu Asp Ile Ser Leu Glu Thr Val Ala Ile Asp
                325                 330                 335

Arg Pro Ala Glu Val Arg Lys Val Cys Tyr Asn Ala Val Leu Thr His
            340                 345                 350

Val Lys Ile Asn Asp Lys Cys Pro Ser Thr Gly Glu Ala His Leu Ala
        355                 360                 365

Glu Glu Asn Glu Gly Asp Asn Ala Cys Lys Arg Thr Tyr Ser Asp Arg
    370                 375                 380

-continued

```
Gly Trp Gly Asn Gly Cys Gly Leu Phe Gly Lys Gly Ser Ile Val Ala
385                 390                 395                 400

Cys Ala Lys Phe Thr Cys Ala Lys Ser Met Ser Leu Phe Glu Val Asp
            405                 410                 415

Gln Thr Lys Ile Gln Tyr Val Ile Arg Ala Gln Leu His Val Gly Ala
        420                 425                 430

Lys Gln Glu Asn Trp Thr Thr Asp Ile Lys Thr Leu Lys Phe Asp Ala
            435                 440                 445

Leu Ser Gly Ser Gln Glu Val Glu Phe Ile Gly Tyr Gly Lys Ala Thr
450                 455                 460

Leu Glu Cys Gln Val Gln Thr Ala Val Asp Phe Gly Asn Ser Tyr Ile
465                 470                 475                 480

Ala Glu Met Glu Thr Glu Ser Trp Ile Val Asp Arg Gln Trp Ala Gln
                485                 490                 495

Asp Leu Thr Leu Pro Trp Gln Ser Gly Ser Gly Val Trp Arg Glu
            500                 505                 510

Met His His Leu Val Glu Phe Glu Pro Pro His Ala Ala Thr Ile Arg
        515                 520                 525

Val Leu Ala Leu Gly Asn Gln Glu Gly Ser Leu Lys Thr Ala Leu Thr
530                 535                 540

Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
            580                 585                 590

Lys Asn Pro Thr Asp Thr Gly His Gly Thr Val Val Met Gln Val Lys
        595                 600                 605

Val Ser Lys Gly Ala Pro Cys Arg Ile Pro Val Ile Val Ala Asp Asp
610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
            660                 665                 670

Gln Trp His Lys Glu Gly Ser Ser Ile Gly Lys Leu Phe Thr Gln Thr
        675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Leu Asn Trp
                725                 730                 735

Ile Thr Lys Val Ile Met Gly Ala Val Leu Ile Trp Val Gly Ile Asn
            740                 745                 750

Thr Arg Asn Met Thr Met Ser Met Ser Met Ile Leu Val Gly Val Ile
        755                 760                 765

Met Met Phe Leu Ser Leu Gly Val Gly Ala Asp Gln Gly Cys Ala Ile
        770                 775                 780

Asn Phe Gly Lys Arg Glu Leu Lys Cys Gly Asp Gly Ile Phe Ile Phe
785                 790                 795                 800
```

```
Arg Asp Ser Asp Asp Trp Leu Asn Lys Tyr Ser Tyr Tyr Pro Glu Asp
                805                 810                 815

Pro Val Lys Leu Ala Ser Ile Val Lys Ala Ser Phe Glu Glu Gly Lys
            820                 825                 830

Cys Gly Leu Asn Ser Val Asp Ser Leu Glu His Glu Met Trp Arg Ser
            835                 840                 845

Arg Ala Asp Glu Ile Asn Ala Ile Phe Glu Glu Asn Glu Val Asp Ile
850                 855                 860

Ser Val Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
            885                 890                 895

Gly Lys Asn Leu Val Phe Ser Pro Gly Arg Lys Asn Gly Ser Phe Ile
            900                 905                 910

Ile Asp Gly Lys Ser Arg Lys Glu Cys Pro Phe Ser Asn Arg Val Trp
            915                 920                 925

Asn Ser Phe Gln Ile Glu Glu Phe Gly Thr Gly Val Phe Thr Thr Arg
            930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
            965                 970                 975

Thr Phe Trp Met Gly Ser His Glu Val Asn Gly Thr Trp Met Ile His
            980                 985                 990

Thr Leu Glu Ala Leu Asp Tyr Lys Glu Cys Glu Trp Pro Leu Thr His
            995                 1000                1005

Thr Ile Gly Thr Ser Val Glu Glu Ser Glu Met Phe Met Pro Arg
            1010                1015                1020

Ser Ile Gly Gly Pro Val Ser Ser His Asn His Ile Pro Gly Tyr
            1025                1030                1035

Lys Val Gln Thr Asn Gly Pro Trp Met Gln Val Pro Leu Glu Val
            1040                1045                1050

Lys Arg Glu Ala Cys Pro Gly Thr Ser Val Ile Ile Asp Gly Asn
            1055                1060                1065

Cys Asp Gly Arg Gly Lys Ser Thr Arg Ser Thr Thr Asp Ser Gly
            1070                1075                1080

Lys Val Ile Pro Glu Trp Cys Cys Arg Ser Cys Thr Met Pro Pro
            1085                1090                1095

Val Ser Phe His Gly Ser Asp Gly Cys Trp Tyr Pro Met Glu Ile
            1100                1105                1110

Arg Pro Arg Lys Thr His Glu Ser His Leu Val Arg Ser Trp Val
            1115                1120                1125

Thr Ala Gly Glu Ile His Ala Val Pro Phe Gly Leu Val Ser Met
            1130                1135                1140

Met Ile Ala Met Glu Val Val Leu Arg Lys Arg Gln Gly Pro Lys
            1145                1150                1155

Gln Met Leu Val Gly Gly Val Val Leu Leu Gly Ala Met Leu Val
            1160                1165                1170

Gly Gln Val Thr Leu Leu Asp Leu Leu Lys Leu Thr Val Ala Val
            1175                1180                1185

Gly Leu His Phe His Glu Met Asn Asn Gly Gly Asp Ala Met Tyr
            1190                1195                1200

Met Ala Leu Ile Ala Ala Phe Ser Ile Arg Pro Gly Leu Leu Ile
```

```
            1205                1210                1215

Gly Phe Gly Leu Arg Thr Leu Trp Ser Pro Arg Glu Arg Leu Val
            1220                1225                1230

Leu Thr Leu Gly Ala Ala Met Val Glu Ile Ala Leu Gly Gly Val
            1235                1240                1245

Met Gly Gly Leu Trp Lys Tyr Leu Asn Ala Val Ser Leu Cys Ile
            1250                1255                1260

Leu Thr Ile Asn Ala Val Ala Ser Arg Lys Ala Ser Asn Thr Ile
            1265                1270                1275

Leu Pro Leu Met Ala Leu Leu Thr Pro Val Thr Met Ala Glu Val
            1280                1285                1290

Arg Leu Ala Ala Met Phe Phe Cys Ala Val Val Ile Ile Gly Val
            1295                1300                1305

Leu His Gln Asn Phe Lys Asp Thr Ser Met Gln Lys Thr Ile Pro
            1310                1315                1320

Leu Val Ala Leu Thr Leu Thr Ser Tyr Leu Gly Leu Thr Gln Pro
            1325                1330                1335

Phe Leu Gly Leu Cys Ala Phe Leu Ala Thr Arg Ile Phe Gly Arg
            1340                1345                1350

Arg Ser Ile Pro Val Asn Glu Ala Leu Ala Ala Gly Leu Val
            1355                1360                1365

Gly Val Leu Ala Gly Leu Ala Phe Gln Glu Met Glu Asn Phe Leu
            1370                1375                1380

Gly Pro Ile Ala Val Gly Gly Leu Leu Met Met Leu Val Ser Val
            1385                1390                1395

Ala Gly Arg Val Asp Gly Leu Glu Leu Lys Lys Leu Gly Glu Val
            1400                1405                1410

Ser Trp Glu Glu Glu Ala Glu Ile Ser Gly Ser Ser Ala Arg Tyr
            1415                1420                1425

Asp Val Ala Leu Ser Glu Gln Gly Glu Phe Lys Leu Leu Ser Glu
            1430                1435                1440

Glu Lys Val Pro Trp Asp Gln Val Val Met Thr Ser Leu Ala Leu
            1445                1450                1455

Val Gly Ala Ala Leu His Pro Phe Ala Leu Leu Leu Val Leu Ala
            1460                1465                1470

Gly Trp Leu Phe His Val Arg Gly Ala Arg Arg Ser Gly Asp Val
            1475                1480                1485

Leu Trp Asp Ile Pro Thr Pro Lys Ile Ile Glu Glu Cys Glu His
            1490                1495                1500

Leu Glu Asp Gly Ile Tyr Gly Ile Phe Gln Ser Thr Phe Leu Gly
            1505                1510                1515

Ala Ser Gln Arg Gly Val Gly Val Ala Gln Gly Gly Val Phe His
            1520                1525                1530

Thr Met Trp His Val Thr Arg Gly Ala Phe Leu Val Arg Asn Gly
            1535                1540                1545

Lys Lys Leu Ile Pro Ser Trp Ala Ser Val Lys Glu Asp Leu Val
            1550                1555                1560

Ala Tyr Gly Gly Ser Trp Lys Leu Glu Gly Arg Trp Asp Gly Glu
            1565                1570                1575

Glu Glu Val Gln Leu Ile Ala Ala Val Pro Gly Lys Asn Val Val
            1580                1585                1590

Asn Val Gln Thr Lys Pro Ser Leu Phe Lys Val Arg Asn Gly Gly
            1595                1600                1605
```

-continued

```
Glu Ile Gly Ala Val Ala Leu Asp Tyr Pro Ser Gly Thr Ser Gly
1610                1615                1620

Ser Pro Ile Val Asn Arg Asn Gly Glu Val Ile Gly Leu Tyr Gly
1625                1630                1635

Asn Gly Ile Leu Val Gly Asp Asn Ser Phe Val Ser Ala Ile Ser
1640                1645                1650

Gln Thr Glu Val Lys Glu Glu Gly Lys Glu Leu Gln Glu Ile
1655                1660                1665

Pro Thr Met Leu Lys Lys Gly Met Thr Thr Val Leu Asp Phe His
1670                1675                1680

Pro Gly Ala Gly Lys Thr Arg Arg Phe Leu Pro Gln Ile Leu Ala
1685                1690                1695

Glu Cys Ala Arg Arg Arg Leu Arg Thr Leu Val Leu Ala Pro Thr
1700                1705                1710

Arg Val Val Leu Ser Glu Met Lys Glu Ala Phe His Gly Leu Asp
1715                1720                1725

Val Lys Phe His Thr Gln Ala Phe Ser Ala His Gly Ser Gly Arg
1730                1735                1740

Glu Val Ile Asp Ala Met Cys His Ala Thr Leu Thr Tyr Arg Met
1745                1750                1755

Leu Glu Pro Thr Arg Val Val Asn Trp Glu Val Ile Ile Met Asp
1760                1765                1770

Glu Ala His Phe Leu Asp Pro Ala Ser Ile Ala Ala Arg Gly Trp
1775                1780                1785

Ala Ala His Arg Ala Arg Ala Asn Glu Ser Ala Thr Ile Leu Met
1790                1795                1800

Thr Ala Thr Pro Pro Gly Thr Ser Asp Glu Phe Pro His Ser Asn
1805                1810                1815

Gly Glu Ile Glu Asp Val Gln Thr Asp Ile Pro Ser Glu Pro Trp
1820                1825                1830

Asn Thr Gly His Asp Trp Ile Leu Ala Asp Lys Arg Pro Thr Ala
1835                1840                1845

Trp Phe Leu Pro Ser Ile Arg Ala Ala Asn Val Met Ala Ala Ser
1850                1855                1860

Leu Arg Lys Ala Gly Lys Ser Val Val Val Leu Asn Arg Lys Thr
1865                1870                1875

Phe Glu Arg Glu Tyr Pro Thr Ile Lys Gln Lys Lys Pro Asp Phe
1880                1885                1890

Ile Leu Ala Thr Asp Ile Ala Glu Met Gly Ala Asn Leu Cys Val
1895                1900                1905

Glu Arg Val Leu Asp Cys Arg Thr Ala Phe Lys Pro Val Leu Val
1910                1915                1920

Asp Glu Gly Arg Lys Val Ala Ile Lys Gly Pro Leu Arg Ile Ser
1925                1930                1935

Ala Ser Ser Ala Ala Gln Arg Arg Gly Arg Ile Gly Arg Asn Pro
1940                1945                1950

Asn Arg Asp Gly Asp Ser Tyr Tyr Tyr Ser Glu Pro Thr Ser Glu
1955                1960                1965

Asn Asn Ala His His Val Cys Trp Leu Glu Ala Ser Met Leu Leu
1970                1975                1980

Asp Asn Met Glu Val Arg Gly Gly Met Val Ala Pro Leu Tyr Gly
1985                1990                1995
```

-continued

Val Glu Gly Thr Lys Thr Pro Val Ser Pro Gly Glu Met Arg Leu
2000                2005                2010

Arg Asp Asp Gln Arg Lys Val Phe Arg Glu Leu Val Arg Asn Cys
2015                2020                2025

Asp Leu Pro Val Trp Leu Ser Trp Gln Val Ala Lys Ala Gly Leu
2030                2035                2040

Lys Thr Asn Asp Arg Lys Trp Cys Phe Glu Gly Pro Glu Glu His
2045                2050                2055

Glu Ile Leu Asn Asp Ser Gly Glu Thr Val Lys Cys Arg Ala Pro
2060                2065                2070

Gly Gly Ala Lys Lys Pro Leu Arg Pro Arg Trp Cys Asp Glu Arg
2075                2080                2085

Val Ser Ser Asp Gln Ser Ala Leu Ser Glu Phe Ile Lys Phe Ala
2090                2095                2100

Glu Gly Arg Arg Gly Ala Ala Glu Val Leu Val Val Leu Ser Glu
2105                2110                2115

Leu Pro Asp Phe Leu Ala Lys Lys Gly Gly Glu Ala Met Asp Thr
2120                2125                2130

Ile Ser Val Phe Leu His Ser Glu Glu Gly Ser Arg Ala Tyr Arg
2135                2140                2145

Asn Ala Leu Ser Met Met Pro Glu Ala Met Thr Ile Val Met Leu
2150                2155                2160

Phe Ile Leu Ala Gly Leu Leu Thr Ser Gly Met Val Ile Phe Phe
2165                2170                2175

Met Ser Pro Lys Gly Ile Ser Arg Met Ser Met Ala Met Gly Thr
2180                2185                2190

Met Ala Gly Cys Gly Tyr Leu Met Phe Leu Gly Gly Val Lys Pro
2195                2200                2205

Thr His Ile Ser Tyr Ile Met Leu Ile Phe Phe Val Leu Met Val
2210                2215                2220

Val Val Ile Pro Glu Pro Gly Gln Gln Arg Ser Ile Gln Asp Asn
2225                2230                2235

Gln Val Ala Tyr Leu Ile Ile Gly Ile Leu Thr Leu Val Ser Ala
2240                2245                2250

Val Ala Ala Asn Glu Leu Gly Met Leu Glu Lys Thr Lys Glu Asp
2255                2260                2265

Leu Phe Gly Lys Lys Asn Leu Ile Pro Ser Ser Ala Ser Pro Trp
2270                2275                2280

Ser Trp Pro Asp Leu Asp Leu Lys Pro Gly Ala Ala Trp Thr Val
2285                2290                2295

Tyr Val Gly Ile Val Thr Met Leu Ser Pro Met Leu His His Trp
2300                2305                2310

Ile Lys Val Glu Tyr Gly Asn Leu Ser Leu Ser Gly Ile Ala Gln
2315                2320                2325

Ser Ala Ser Val Leu Ser Phe Met Asp Lys Gly Ile Pro Phe Met
2330                2335                2340

Lys Met Asn Ile Ser Val Ile Met Leu Leu Val Ser Gly Trp Asn
2345                2350                2355

Ser Ile Thr Val Met Pro Leu Leu Cys Gly Ile Gly Cys Ala Met
2360                2365                2370

Leu His Trp Ser Leu Ile Leu Pro Gly Ile Lys Ala Gln Gln Ser
2375                2380                2385

Lys Leu Ala Gln Arg Arg Val Phe His Gly Val Ala Lys Asn Pro

-continued

```
            2390                2395                2400

Val Val Asp Gly Asn Pro Thr Val Asp Ile Glu Glu Ala Pro Glu
    2405                2410                2415

Met Pro Ala Leu Tyr Glu Lys Lys Leu Ala Leu Tyr Leu Leu Leu
    2420                2425                2430

Ala Leu Ser Leu Ala Ser Val Ala Met Cys Arg Thr Pro Phe Ser
    2435                2440                2445

Leu Ala Glu Gly Ile Val Leu Ala Ser Ala Ala Leu Gly Pro Leu
    2450                2455                2460

Ile Glu Gly Asn Thr Ser Leu Leu Trp Asn Gly Pro Met Ala Val
    2465                2470                2475

Ser Met Thr Gly Val Met Arg Gly Asn His Tyr Ala Phe Val Gly
    2480                2485                2490

Val Met Tyr Asn Leu Trp Lys Met Lys Thr Gly Arg Arg Gly Ser
    2495                2500                2505

Ala Asn Gly Lys Thr Leu Gly Glu Val Trp Lys Arg Glu Leu Asn
    2510                2515                2520

Leu Leu Asp Lys Arg Gln Phe Glu Leu Tyr Lys Arg Thr Asp Ile
    2525                2530                2535

Val Glu Val Asp Arg Asp Thr Ala Arg Arg His Leu Ala Glu Gly
    2540                2545                2550

Lys Val Asp Thr Gly Val Ala Val Ser Arg Gly Thr Ala Lys Leu
    2555                2560                2565

Arg Trp Phe His Glu Arg Gly Tyr Val Lys Leu Glu Gly Arg Val
    2570                2575                2580

Ile Asp Leu Gly Cys Gly Arg Gly Gly Trp Cys Tyr Tyr Ala Ala
    2585                2590                2595

Ala Gln Lys Glu Val Ser Gly Val Lys Gly Phe Thr Leu Gly Arg
    2600                2605                2610

Asp Gly His Glu Lys Pro Met Asn Val Gln Ser Leu Gly Trp Asn
    2615                2620                2625

Ile Ile Thr Phe Lys Asp Lys Thr Asp Ile His Arg Leu Glu Pro
    2630                2635                2640

Val Lys Cys Asp Thr Leu Leu Cys Asp Ile Gly Glu Ser Ser Ser
    2645                2650                2655

Ser Ser Val Thr Glu Gly Glu Arg Thr Val Arg Val Leu Asp Thr
    2660                2665                2670

Val Glu Lys Trp Leu Ala Cys Gly Val Asp Asn Phe Cys Val Lys
    2675                2680                2685

Val Leu Ala Pro Tyr Met Pro Asp Val Leu Glu Lys Leu Glu Leu
    2690                2695                2700

Leu Gln Arg Arg Phe Gly Gly Thr Val Ile Arg Asn Pro Leu Ser
    2705                2710                2715

Arg Asn Ser Thr His Glu Met Tyr Tyr Val Ser Gly Ala Arg Ser
    2720                2725                2730

Asn Val Thr Phe Thr Val Asn Gln Thr Ser Arg Leu Leu Met Arg
    2735                2740                2745

Arg Met Arg Arg Pro Thr Gly Lys Val Thr Leu Glu Ala Asp Val
    2750                2755                2760

Ile Leu Pro Ile Gly Thr Arg Ser Val Glu Thr Asp Lys Gly Pro
    2765                2770                2775

Leu Asp Lys Glu Ala Ile Glu Glu Arg Val Glu Arg Ile Lys Ser
    2780                2785                2790
```

```
Glu Tyr Met Thr Ser Trp Phe Tyr Asp Asn Asp Asn Pro Tyr Arg
2795                2800                2805

Thr Trp His Tyr Cys Gly Ser Tyr Val Thr Lys Thr Ser Gly Ser
2810                2815                2820

Ala Ala Ser Met Val Asn Gly Val Ile Lys Ile Leu Thr Tyr Pro
2825                2830                2835

Trp Asp Arg Ile Glu Glu Val Thr Arg Met Ala Met Thr Asp Thr
2840                2845                2850

Thr Pro Phe Gly Gln Gln Arg Val Phe Lys Glu Lys Val Asp Thr
2855                2860                2865

Arg Ala Lys Asp Pro Pro Ala Gly Thr Arg Lys Ile Met Lys Val
2870                2875                2880

Val Asn Arg Trp Leu Phe Arg His Leu Ala Arg Glu Lys Asn Pro
2885                2890                2895

Arg Leu Cys Thr Lys Glu Glu Phe Ile Ala Lys Val Arg Ser His
2900                2905                2910

Ala Ala Ile Gly Ala Tyr Leu Glu Glu Gln Glu Gln Trp Lys Thr
2915                2920                2925

Ala Asn Glu Ala Val Gln Asp Pro Lys Phe Trp Glu Leu Val Asp
2930                2935                2940

Glu Glu Arg Lys Leu His Gln Gln Gly Arg Cys Arg Thr Cys Val
2945                2950                2955

Tyr Asn Met Met Gly Lys Arg Glu Lys Lys Leu Ser Glu Phe Gly
2960                2965                2970

Lys Ala Lys Gly Ser Arg Ala Ile Trp Tyr Met Trp Leu Gly Ala
2975                2980                2985

Arg Tyr Leu Glu Phe Glu Ala Leu Gly Phe Leu Asn Glu Asp His
2990                2995                3000

Trp Ala Ser Arg Glu Asn Ser Gly Gly Gly Val Glu Gly Ile Gly
3005                3010                3015

Leu Gln Tyr Leu Gly Tyr Val Ile Arg Asp Leu Ala Ala Met Asp
3020                3025                3030

Gly Gly Gly Phe Tyr Ala Asp Asp Thr Ala Gly Trp Asp Thr Arg
3035                3040                3045

Ile Thr Glu Ala Asp Leu Asp Asp Glu Gln Glu Ile Leu Asn Tyr
3050                3055                3060

Met Ser Pro His His Lys Lys Leu Ala Gln Ala Val Met Glu Met
3065                3070                3075

Thr Tyr Lys Asn Lys Val Val Lys Val Leu Arg Pro Ala Pro Gly
3080                3085                3090

Gly Lys Ala Tyr Met Asp Val Ile Ser Arg Arg Asp Gln Arg Gly
3095                3100                3105

Ser Gly Gln Val Val Thr Tyr Ala Leu Asn Thr Ile Thr Asn Leu
3110                3115                3120

Lys Val Gln Leu Ile Arg Met Ala Glu Ala Glu Met Val Ile His
3125                3130                3135

His Gln His Val Gln Asp Cys Asp Glu Ser Val Leu Thr Arg Leu
3140                3145                3150

Glu Ala Trp Leu Thr Glu His Gly Cys Asn Arg Leu Lys Arg Met
3155                3160                3165

Ala Val Ser Gly Asp Asp Cys Val Val Arg Pro Ile Asp Asp Arg
3170                3175                3180
```

```
Phe Gly Leu Ala Leu Ser His Leu Asn Ala Met Ser Lys Val Arg
    3185                3190                3195

Lys Asp Ile Ser Glu Trp Gln Pro Ser Lys Gly Trp Asn Asp Trp
3200                3205                3210

Glu Asn Val Pro Phe Cys Ser His His Phe His Glu Leu Gln Leu
3215                3220                3225

Lys Asp Gly Arg Arg Ile Val Val Pro Cys Arg Glu Gln Asp Glu
3230                3235                3240

Leu Ile Gly Arg Gly Arg Val Ser Pro Gly Asn Gly Trp Met Ile
3245                3250                3255

Lys Glu Thr Ala Cys Leu Ser Lys Ala Tyr Ala Asn Met Trp Ser
3260                3265                3270

Leu Met Tyr Phe His Lys Arg Asp Met Arg Leu Leu Ser Leu Ala
3275                3280                3285

Val Ser Ser Ala Val Pro Thr Ser Trp Val Pro Gln Gly Arg Thr
3290                3295                3300

Thr Trp Ser Ile His Gly Lys Gly Glu Trp Met Thr Thr Glu Asp
3305                3310                3315

Met Leu Glu Val Trp Asn Arg Val Trp Ile Thr Asn Asn Pro His
3320                3325                3330

Met Gln Asp Lys Thr Met Val Lys Lys Trp Arg Asp Val Pro Tyr
3335                3340                3345

Leu Thr Lys Arg Gln Asp Lys Leu Cys Gly Ser Leu Ile Gly Met
3350                3355                3360

Thr Asn Arg Ala Thr Trp Ala Ser His Ile His Leu Val Ile His
3365                3370                3375

Arg Ile Arg Thr Leu Ile Gly Gln Glu Lys Tyr Thr Asp Tyr Leu
3380                3385                3390

Thr Val Met Asp Arg Tyr Ser Val Asp Ala Asp Leu Gln Leu Gly
3395                3400                3405

Glu Leu Ile
    3410

<210> SEQ ID NO 14
<211> LENGTH: 3411
<212> TYPE: PRT
<213> ORGANISM: Artificial Sequence
<220> FEATURE:
<223> OTHER INFORMATION: Flaviviridae Flavivirus Yellow Fever Virus

<400> SEQUENCE: 14

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110
```

-continued

```
Leu Gly Met Leu Leu Met Thr Gly Val Thr Leu Val Arg Lys Asn
            115                 120                 125
Arg Trp Leu Leu Leu Asn Val Thr Ser Glu Asp Leu Gly Lys Thr Phe
130                 135                 140
Ser Val Gly Thr Gly Asn Cys Thr Thr Asn Ile Leu Glu Ala Lys Tyr
145                 150                 155                 160
Trp Cys Pro Asp Ser Met Glu Tyr Asn Cys Pro Asn Leu Ser Pro Arg
                165                 170                 175
Glu Glu Pro Asp Asp Ile Asp Cys Trp Cys Tyr Gly Val Glu Asn Val
            180                 185                 190
Arg Val Ala Tyr Gly Lys Cys Asp Ser Ala Gly Arg Ser Arg Arg Ser
        195                 200                 205
Arg Arg Ala Ile Asp Leu Pro Thr His Glu Asn His Gly Leu Lys Thr
    210                 215                 220
Arg Gln Glu Lys Trp Met Thr Gly Arg Met Gly Glu Arg Gln Leu Gln
225                 230                 235                 240
Lys Ile Glu Arg Trp Phe Val Arg Asn Pro Phe Phe Ala Val Thr Ala
                245                 250                 255
Leu Thr Ile Ala Tyr Leu Val Gly Ser Asn Met Thr Gln Arg Val Val
            260                 265                 270
Ile Ala Leu Leu Val Leu Ala Val Gly Pro Ala Tyr Ser Ala His Cys
        275                 280                 285
Ile Gly Ile Thr Asp Arg Asp Phe Ile Glu Gly Val His Gly Gly Thr
    290                 295                 300
Trp Val Ser Ala Thr Leu Glu Gln Asp Lys Cys Val Thr Val Met Ala
305                 310                 315                 320
Pro Asp Lys Pro Ser Leu Asp Ile Ser Leu Glu Thr Val Ala Ile Asp
                325                 330                 335
Arg Pro Ala Glu Val Arg Lys Val Cys Tyr Asn Ala Val Leu Thr His
            340                 345                 350
Val Lys Ile Asn Asp Lys Cys Pro Ser Thr Gly Glu Ala His Leu Ala
        355                 360                 365
Glu Glu Asn Glu Gly Asp Asn Ala Cys Lys Arg Thr Tyr Ser Asp Arg
    370                 375                 380
Gly Trp Gly Asn Gly Cys Gly Leu Phe Gly Lys Gly Ser Ile Val Ala
385                 390                 395                 400
Cys Ala Lys Phe Thr Cys Ala Lys Ser Met Ser Leu Phe Glu Val Asp
                405                 410                 415
Gln Thr Lys Ile Gln Tyr Val Ile Arg Ala Gln Leu His Val Gly Ala
            420                 425                 430
Lys Gln Glu Asn Trp Thr Thr Asp Ile Lys Thr Leu Lys Phe Asp Ala
        435                 440                 445
Leu Ser Gly Ser Gln Glu Val Glu Phe Ile Gly Tyr Gly Lys Ala Thr
    450                 455                 460
Leu Glu Cys Gln Val Gln Thr Ala Val Asp Phe Gly Asn Ser Tyr Ile
465                 470                 475                 480
Ala Glu Met Glu Thr Glu Ser Trp Ile Val Asp Arg Gln Trp Ala Gln
                485                 490                 495
Asp Leu Thr Leu Pro Trp Gln Ser Gly Ser Gly Gly Val Trp Arg Glu
            500                 505                 510
Met His His Leu Val Glu Phe Glu Pro Pro His Ala Ala Thr Ile Arg
        515                 520                 525
Val Leu Ala Leu Gly Asn Gln Glu Gly Ser Leu Lys Thr Ala Leu Thr
```

```
                530             535             540
Gly Ala Met Arg Val Thr Lys Asp Thr Asn Asp Asn Leu Tyr Lys
545                 550                 555                 560

Leu His Gly Gly His Val Ser Cys Arg Val Lys Leu Ser Ala Leu Thr
                565                 570                 575

Leu Lys Gly Thr Ser Tyr Lys Ile Cys Thr Asp Lys Met Phe Phe Val
                580                 585                 590

Lys Asn Pro Thr Asp Thr Gly His Gly Thr Val Val Met Gln Val Lys
                595                 600                 605

Val Ser Lys Gly Ala Pro Cys Arg Ile Pro Val Ile Val Ala Asp Asp
610                 615                 620

Leu Thr Ala Ala Ile Asn Lys Gly Ile Leu Val Thr Val Asn Pro Ile
625                 630                 635                 640

Ala Ser Thr Asn Asp Asp Glu Val Leu Ile Glu Val Asn Pro Pro Phe
                645                 650                 655

Gly Asp Ser Tyr Ile Ile Val Gly Arg Gly Asp Ser Arg Leu Thr Tyr
                660                 665                 670

Gln Trp His Lys Glu Gly Ser Ser Ile Gly Lys Leu Phe Thr Gln Thr
                675                 680                 685

Met Lys Gly Val Glu Arg Leu Ala Val Met Gly Asp Thr Ala Trp Asp
690                 695                 700

Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
                725                 730                 735

Ile Thr Lys Val Ile Met Gly Ala Val Leu Ile Trp Val Gly Ile Asn
                740                 745                 750

Thr Arg Asn Met Thr Met Ser Met Ser Met Ile Leu Val Gly Val Ile
                755                 760                 765

Met Met Phe Leu Ser Leu Gly Val Gly Ala Asp Gln Gly Cys Ala Ile
770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Pro Glu Asp
                805                 810                 815

Pro Val Lys Leu Ala Ser Ile Val Lys Ala Ser Phe Glu Glu Gly Lys
                820                 825                 830

Cys Gly Leu Asn Ser Val Asp Ser Leu Glu His Glu Met Trp Arg Ser
                835                 840                 845

Arg Ala Asp Glu Ile Asn Ala Ile Phe Glu Glu Asn Glu Val Asp Ile
850                 855                 860

Ser Val Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                885                 890                 895

Gly Lys Asn Leu Val Phe Ser Pro Gly Arg Lys Asn Gly Ser Phe Ile
                900                 905                 910

Ile Asp Gly Lys Ser Arg Lys Glu Cys Pro Phe Ser Asn Arg Val Trp
                915                 920                 925

Asn Ser Phe Gln Ile Glu Glu Phe Gly Thr Gly Val Phe Thr Thr Arg
                930                 935                 940

Val Tyr Met Asp Ala Val Phe Glu Tyr Thr Ile Asp Cys Asp Gly Ser
945                 950                 955                 960
```

-continued

```
Ile Leu Gly Ala Ala Val Asn Gly Lys Lys Ser Ala His Gly Ser Pro
            965                 970                 975

Thr Phe Trp Met Gly Ser His Glu Val Asn Gly Thr Trp Met Ile His
            980                 985                 990

Thr Leu Glu Ala Leu Asp Tyr Lys Glu Cys Glu Trp Pro Leu Thr His
        995                 1000                1005

Thr Ile Gly Thr Ser Val Glu Glu Ser Glu Met Phe Met Pro Arg
    1010                1015                1020

Ser Ile Gly Gly Pro Val Ser Ser His Asn His Ile Pro Gly Tyr
    1025                1030                1035

Lys Val Gln Thr Asn Gly Pro Trp Met Gln Val Pro Leu Glu Val
    1040                1045                1050

Lys Arg Glu Ala Cys Pro Gly Thr Ser Val Ile Ile Asp Gly Asn
    1055                1060                1065

Cys Asp Gly Arg Gly Lys Ser Thr Arg Ser Thr Thr Asp Ser Gly
    1070                1075                1080

Lys Val Ile Pro Glu Trp Cys Cys Arg Ser Cys Thr Met Pro Pro
    1085                1090                1095

Val Ser Phe His Gly Ser Asp Gly Cys Trp Tyr Pro Met Glu Ile
    1100                1105                1110

Arg Pro Arg Lys Thr His Glu Ser His Leu Val Arg Ser Trp Val
    1115                1120                1125

Thr Ala Gly Glu Ile His Ala Val Pro Phe Gly Leu Val Ser Met
    1130                1135                1140

Met Ile Ala Met Glu Val Val Leu Arg Lys Arg Gln Gly Pro Lys
    1145                1150                1155

Gln Met Leu Val Gly Gly Val Val Leu Leu Gly Ala Met Leu Val
    1160                1165                1170

Gly Gln Val Thr Leu Leu Asp Leu Leu Lys Leu Thr Val Ala Val
    1175                1180                1185

Gly Leu His Phe His Glu Met Asn Asn Gly Gly Asp Ala Met Tyr
    1190                1195                1200

Met Ala Leu Ile Ala Ala Phe Ser Ile Arg Pro Gly Leu Leu Ile
    1205                1210                1215

Gly Phe Gly Leu Arg Thr Leu Trp Ser Pro Arg Glu Arg Leu Val
    1220                1225                1230

Leu Thr Leu Gly Ala Ala Met Val Glu Ile Ala Leu Gly Gly Val
    1235                1240                1245

Met Gly Gly Leu Trp Lys Tyr Leu Asn Ala Val Ser Leu Cys Ile
    1250                1255                1260

Leu Thr Ile Asn Ala Val Ala Ser Arg Lys Ala Ser Asn Thr Ile
    1265                1270                1275

Leu Pro Leu Met Ala Leu Leu Thr Pro Val Thr Met Ala Glu Val
    1280                1285                1290

Arg Leu Ala Ala Met Phe Phe Cys Ala Val Val Ile Ile Gly Val
    1295                1300                1305

Leu His Gln Asn Phe Lys Asp Thr Ser Met Gln Lys Thr Ile Pro
    1310                1315                1320

Leu Val Ala Leu Thr Leu Thr Ser Tyr Leu Gly Leu Thr Gln Pro
    1325                1330                1335

Phe Leu Gly Leu Cys Ala Phe Leu Ala Thr Arg Ile Phe Gly Arg
    1340                1345                1350
```

```
Arg Ser Ile Pro Val Asn Glu Ala Leu Ala Ala Gly Leu Val
    1355                1360                1365

Gly Val Leu Ala Gly Leu Ala Phe Gln Glu Met Glu Asn Phe Leu
    1370                1375                1380

Gly Pro Ile Ala Val Gly Gly Leu Leu Met Met Leu Val Ser Val
    1385                1390                1395

Ala Gly Arg Val Asp Gly Leu Glu Leu Lys Lys Leu Gly Glu Val
    1400                1405                1410

Ser Trp Glu Glu Glu Ala Glu Ile Ser Gly Ser Ser Ala Arg Tyr
    1415                1420                1425

Asp Val Ala Leu Ser Glu Gln Gly Glu Phe Lys Leu Leu Ser Glu
    1430                1435                1440

Glu Lys Val Pro Trp Asp Gln Val Val Met Thr Ser Leu Ala Leu
    1445                1450                1455

Val Gly Ala Ala Leu His Pro Phe Ala Leu Leu Leu Val Leu Ala
    1460                1465                1470

Gly Trp Leu Phe His Val Arg Gly Ala Arg Arg Ser Gly Asp Val
    1475                1480                1485

Leu Trp Asp Ile Pro Thr Pro Lys Ile Ile Glu Glu Cys Glu His
    1490                1495                1500

Leu Glu Asp Gly Ile Tyr Gly Ile Phe Gln Ser Thr Phe Leu Gly
    1505                1510                1515

Ala Ser Gln Arg Gly Val Gly Val Ala Gln Gly Gly Val Phe His
    1520                1525                1530

Thr Met Trp His Val Thr Arg Gly Ala Phe Leu Val Arg Asn Gly
    1535                1540                1545

Lys Lys Leu Ile Pro Ser Trp Ala Ser Val Lys Glu Asp Leu Val
    1550                1555                1560

Ala Tyr Gly Gly Ser Trp Lys Leu Glu Gly Arg Trp Asp Gly Glu
    1565                1570                1575

Glu Glu Val Gln Leu Ile Ala Ala Val Pro Gly Lys Asn Val Val
    1580                1585                1590

Asn Val Gln Thr Lys Pro Ser Leu Phe Lys Val Arg Asn Gly Gly
    1595                1600                1605

Glu Ile Gly Ala Val Ala Leu Asp Tyr Pro Ser Gly Thr Ser Gly
    1610                1615                1620

Ser Pro Ile Val Asn Arg Asn Gly Glu Val Ile Gly Leu Tyr Gly
    1625                1630                1635

Asn Gly Ile Leu Val Gly Asp Asn Ser Phe Val Ser Ala Ile Ser
    1640                1645                1650

Gln Thr Glu Val Lys Glu Glu Gly Lys Glu Glu Leu Gln Glu Ile
    1655                1660                1665

Pro Thr Met Leu Lys Lys Gly Met Thr Thr Val Leu Asp Phe His
    1670                1675                1680

Pro Gly Ala Gly Lys Thr Arg Arg Phe Leu Pro Gln Ile Leu Ala
    1685                1690                1695

Glu Cys Ala Arg Arg Arg Leu Arg Thr Leu Val Leu Ala Pro Thr
    1700                1705                1710

Arg Val Val Leu Ser Glu Met Lys Glu Ala Phe His Gly Leu Asp
    1715                1720                1725

Val Lys Phe His Thr Gln Ala Phe Ser Ala His Gly Ser Gly Arg
    1730                1735                1740

Glu Val Ile Asp Ala Met Cys His Ala Thr Leu Thr Tyr Arg Met
```

-continued

```
               1745                1750                1755
Leu Glu Pro Thr Arg Val Val Asn Trp Glu Val Ile Ile Met Asp
        1760                1765                1770
Glu Ala His Phe Leu Asp Pro Ala Ser Ile Ala Ala Arg Gly Trp
        1775                1780                1785
Ala Ala His Arg Ala Arg Ala Asn Glu Ser Ala Thr Ile Leu Met
        1790                1795                1800
Thr Ala Thr Pro Pro Gly Thr Ser Asp Glu Phe Pro His Ser Asn
        1805                1810                1815
Gly Glu Ile Glu Asp Val Gln Thr Asp Ile Pro Ser Glu Pro Trp
        1820                1825                1830
Asn Thr Gly His Asp Trp Ile Leu Ala Asp Lys Arg Pro Thr Ala
        1835                1840                1845
Trp Phe Leu Pro Ser Ile Arg Ala Ala Asn Val Met Ala Ala Ser
        1850                1855                1860
Leu Arg Lys Ala Gly Lys Ser Val Val Val Leu Asn Arg Lys Thr
        1865                1870                1875
Phe Glu Arg Glu Tyr Pro Thr Ile Lys Gln Lys Lys Pro Asp Phe
        1880                1885                1890
Ile Leu Ala Thr Asp Ile Ala Glu Met Gly Ala Asn Leu Cys Val
        1895                1900                1905
Glu Arg Val Leu Asp Cys Arg Thr Ala Phe Lys Pro Val Leu Val
        1910                1915                1920
Asp Glu Gly Arg Lys Val Ala Ile Lys Gly Pro Leu Arg Ile Ser
        1925                1930                1935
Ala Ser Ser Ala Ala Gln Arg Arg Gly Arg Ile Gly Arg Asn Pro
        1940                1945                1950
Asn Arg Asp Gly Asp Ser Tyr Tyr Tyr Ser Glu Pro Thr Ser Glu
        1955                1960                1965
Asn Asn Ala His His Val Cys Trp Leu Glu Ala Ser Met Leu Leu
        1970                1975                1980
Asp Asn Met Glu Val Arg Gly Gly Met Val Ala Pro Leu Tyr Gly
        1985                1990                1995
Val Glu Gly Thr Lys Thr Pro Val Ser Pro Gly Glu Met Arg Leu
        2000                2005                2010
Arg Asp Asp Gln Arg Lys Val Phe Arg Glu Leu Val Arg Asn Cys
        2015                2020                2025
Asp Leu Pro Val Trp Leu Ser Trp Gln Val Ala Lys Ala Gly Leu
        2030                2035                2040
Lys Thr Asn Asp Arg Lys Trp Cys Phe Glu Gly Pro Glu Glu His
        2045                2050                2055
Glu Ile Leu Asn Asp Ser Gly Glu Thr Val Lys Cys Arg Ala Pro
        2060                2065                2070
Gly Gly Ala Lys Lys Pro Leu Arg Pro Arg Trp Cys Asp Glu Arg
        2075                2080                2085
Val Ser Ser Asp Gln Ser Ala Leu Ser Glu Phe Ile Lys Phe Ala
        2090                2095                2100
Glu Gly Arg Arg Gly Ala Ala Glu Val Leu Val Val Leu Ser Glu
        2105                2110                2115
Leu Pro Asp Phe Leu Ala Lys Lys Gly Gly Glu Ala Met Asp Thr
        2120                2125                2130
Ile Ser Val Phe Leu His Ser Glu Glu Gly Ser Arg Ala Tyr Arg
        2135                2140                2145
```

-continued

```
Asn Ala Leu Ser Met Met Pro Glu Ala Met Thr Ile Val Met Leu
    2150                2155                2160
Phe Ile Leu Ala Gly Leu Leu Thr Ser Gly Met Val Ile Phe Phe
    2165                2170                2175
Met Ser Pro Lys Gly Ile Ser Arg Met Ser Met Ala Met Gly Thr
    2180                2185                2190
Met Ala Gly Cys Gly Tyr Leu Met Phe Leu Gly Gly Val Lys Pro
    2195                2200                2205
Thr His Ile Ser Tyr Ile Met Leu Ile Phe Phe Val Leu Met Val
    2210                2215                2220
Val Val Ile Pro Glu Pro Gly Gln Gln Arg Ser Ile Gln Asp Asn
    2225                2230                2235
Gln Val Ala Tyr Leu Ile Ile Gly Ile Leu Thr Leu Val Ser Ala
    2240                2245                2250
Val Ala Ala Asn Glu Leu Gly Met Leu Glu Lys Thr Lys Glu Asp
    2255                2260                2265
Leu Phe Gly Lys Lys Asn Leu Ile Pro Ser Ser Ala Ser Pro Trp
    2270                2275                2280
Ser Trp Pro Asp Leu Asp Leu Lys Pro Gly Ala Ala Trp Thr Val
    2285                2290                2295
Tyr Val Gly Ile Val Thr Met Leu Ser Pro Met Leu His His Trp
    2300                2305                2310
Ile Lys Val Glu Tyr Gly Asn Leu Ser Leu Ser Gly Ile Ala Gln
    2315                2320                2325
Ser Ala Ser Val Leu Ser Phe Met Asp Lys Gly Ile Pro Phe Met
    2330                2335                2340
Lys Met Asn Ile Ser Val Ile Met Leu Leu Val Ser Gly Trp Asn
    2345                2350                2355
Ser Ile Thr Val Met Pro Leu Leu Cys Gly Ile Gly Cys Ala Met
    2360                2365                2370
Leu His Trp Ser Leu Ile Leu Pro Gly Ile Lys Ala Gln Gln Ser
    2375                2380                2385
Lys Leu Ala Gln Arg Arg Val Phe His Gly Val Ala Lys Asn Pro
    2390                2395                2400
Val Val Asp Gly Asn Pro Thr Val Asp Ile Glu Glu Ala Pro Glu
    2405                2410                2415
Met Pro Ala Leu Tyr Glu Lys Lys Leu Ala Leu Tyr Leu Leu Leu
    2420                2425                2430
Ala Leu Ser Leu Ala Ser Val Ala Met Cys Arg Thr Pro Phe Ser
    2435                2440                2445
Leu Ala Glu Gly Ile Val Leu Ala Ser Ala Ala Leu Gly Pro Leu
    2450                2455                2460
Ile Glu Gly Asn Thr Ser Leu Leu Trp Asn Gly Pro Met Ala Val
    2465                2470                2475
Ser Met Thr Gly Val Met Arg Gly Asn His Tyr Ala Phe Val Gly
    2480                2485                2490
Val Met Tyr Asn Leu Trp Lys Met Lys Thr Gly Arg Arg Gly Ser
    2495                2500                2505
Ala Asn Gly Lys Thr Leu Gly Glu Val Trp Lys Arg Glu Leu Asn
    2510                2515                2520
Leu Leu Asp Lys Arg Gln Phe Glu Leu Tyr Lys Arg Thr Asp Ile
    2525                2530                2535
```

```
Val Glu Val Asp Arg Asp Thr Ala Arg Arg His Leu Ala Glu Gly
2540                2545                2550

Lys Val Asp Thr Gly Val Ala Val Ser Arg Gly Thr Ala Lys Leu
2555                2560                2565

Arg Trp Phe His Glu Arg Gly Tyr Val Lys Leu Glu Gly Arg Val
2570                2575                2580

Ile Asp Leu Gly Cys Gly Arg Gly Gly Trp Cys Tyr Tyr Ala Ala
2585                2590                2595

Ala Gln Lys Glu Val Ser Gly Val Lys Gly Phe Thr Leu Gly Arg
2600                2605                2610

Asp Gly His Glu Lys Pro Met Asn Val Gln Ser Leu Gly Trp Asn
2615                2620                2625

Ile Ile Thr Phe Lys Asp Lys Thr Asp Ile His Arg Leu Glu Pro
2630                2635                2640

Val Lys Cys Asp Thr Leu Leu Cys Asp Ile Gly Glu Ser Ser Ser
2645                2650                2655

Ser Ser Val Thr Glu Gly Glu Arg Thr Val Arg Val Leu Asp Thr
2660                2665                2670

Val Glu Lys Trp Leu Ala Cys Gly Val Asp Asn Phe Cys Val Lys
2675                2680                2685

Val Leu Ala Pro Tyr Met Pro Asp Val Leu Glu Lys Leu Glu Leu
2690                2695                2700

Leu Gln Arg Arg Phe Gly Gly Thr Val Ile Arg Asn Pro Leu Ser
2705                2710                2715

Arg Asn Ser Thr His Glu Met Tyr Tyr Val Ser Gly Ala Arg Ser
2720                2725                2730

Asn Val Thr Phe Thr Val Asn Gln Thr Ser Arg Leu Leu Met Arg
2735                2740                2745

Arg Met Arg Arg Pro Thr Gly Lys Val Thr Leu Glu Ala Asp Val
2750                2755                2760

Ile Leu Pro Ile Gly Thr Arg Ser Val Glu Thr Asp Lys Gly Pro
2765                2770                2775

Leu Asp Lys Glu Ala Ile Glu Glu Arg Val Glu Arg Ile Lys Ser
2780                2785                2790

Glu Tyr Met Thr Ser Trp Phe Tyr Asp Asn Asp Asn Pro Tyr Arg
2795                2800                2805

Thr Trp His Tyr Cys Gly Ser Tyr Val Thr Lys Thr Ser Gly Ser
2810                2815                2820

Ala Ala Ser Met Val Asn Gly Val Ile Lys Ile Leu Thr Tyr Pro
2825                2830                2835

Trp Asp Arg Ile Glu Glu Val Thr Arg Met Ala Met Thr Asp Thr
2840                2845                2850

Thr Pro Phe Gly Gln Gln Arg Val Phe Lys Glu Lys Val Asp Thr
2855                2860                2865

Arg Ala Lys Asp Pro Pro Ala Gly Thr Arg Lys Ile Met Lys Val
2870                2875                2880

Val Asn Arg Trp Leu Phe Arg His Leu Ala Arg Glu Lys Asn Pro
2885                2890                2895

Arg Leu Cys Thr Lys Glu Glu Phe Ile Ala Lys Val Arg Ser His
2900                2905                2910

Ala Ala Ile Gly Ala Tyr Leu Glu Glu Gln Glu Gln Trp Lys Thr
2915                2920                2925

Ala Asn Glu Ala Val Gln Asp Pro Lys Phe Trp Glu Leu Val Asp
```

```
            2930                2935                2940
Glu  Glu  Arg  Lys  Leu  His  Gln  Gln  Gly  Arg  Cys  Arg  Thr  Cys  Val
         2945                2950                2955

Tyr  Asn  Met  Met  Gly  Lys  Arg  Glu  Lys  Lys  Leu  Ser  Glu  Phe  Gly
         2960                2965                2970

Lys  Ala  Lys  Gly  Ser  Arg  Ala  Ile  Trp  Tyr  Met  Trp  Leu  Gly  Ala
         2975                2980                2985

Arg  Tyr  Leu  Glu  Phe  Glu  Ala  Leu  Gly  Phe  Leu  Asn  Glu  Asp  His
         2990                2995                3000

Trp  Ala  Ser  Arg  Glu  Asn  Ser  Gly  Gly  Gly  Val  Glu  Gly  Ile  Gly
         3005                3010                3015

Leu  Gln  Tyr  Leu  Gly  Tyr  Val  Ile  Arg  Asp  Leu  Ala  Ala  Met  Asp
         3020                3025                3030

Gly  Gly  Gly  Phe  Tyr  Ala  Asp  Asp  Thr  Ala  Gly  Trp  Asp  Thr  Arg
         3035                3040                3045

Ile  Thr  Glu  Ala  Asp  Leu  Asp  Asp  Glu  Gln  Glu  Ile  Leu  Asn  Tyr
         3050                3055                3060

Met  Ser  Pro  His  His  Lys  Lys  Leu  Ala  Gln  Ala  Val  Met  Glu  Met
         3065                3070                3075

Thr  Tyr  Lys  Asn  Lys  Val  Val  Lys  Val  Leu  Arg  Pro  Ala  Pro  Gly
         3080                3085                3090

Gly  Lys  Ala  Tyr  Met  Asp  Val  Ile  Ser  Arg  Arg  Asp  Gln  Arg  Gly
         3095                3100                3105

Ser  Gly  Gln  Val  Val  Thr  Tyr  Ala  Leu  Asn  Thr  Ile  Thr  Asn  Leu
         3110                3115                3120

Lys  Val  Gln  Leu  Ile  Arg  Met  Ala  Glu  Ala  Glu  Met  Val  Ile  His
         3125                3130                3135

His  Gln  His  Val  Gln  Asp  Cys  Asp  Glu  Ser  Val  Leu  Thr  Arg  Leu
         3140                3145                3150

Glu  Ala  Trp  Leu  Thr  Glu  His  Gly  Cys  Asn  Arg  Leu  Lys  Arg  Met
         3155                3160                3165

Ala  Val  Ser  Gly  Asp  Asp  Cys  Val  Val  Arg  Pro  Ile  Asp  Asp  Arg
         3170                3175                3180

Phe  Gly  Leu  Ala  Leu  Ser  His  Leu  Asn  Ala  Met  Ser  Lys  Val  Arg
         3185                3190                3195

Lys  Asp  Ile  Ser  Glu  Trp  Gln  Pro  Ser  Lys  Gly  Trp  Asn  Asp  Trp
         3200                3205                3210

Glu  Asn  Val  Pro  Phe  Cys  Ser  His  His  Phe  His  Glu  Leu  Gln  Leu
         3215                3220                3225

Lys  Asp  Gly  Arg  Arg  Ile  Val  Val  Pro  Cys  Arg  Glu  Gln  Asp  Glu
         3230                3235                3240

Leu  Ile  Gly  Arg  Gly  Arg  Val  Ser  Pro  Gly  Asn  Gly  Trp  Met  Ile
         3245                3250                3255

Lys  Glu  Thr  Ala  Cys  Leu  Ser  Lys  Ala  Tyr  Ala  Asn  Met  Trp  Ser
         3260                3265                3270

Leu  Met  Tyr  Phe  His  Lys  Arg  Asp  Met  Arg  Leu  Leu  Ser  Leu  Ala
         3275                3280                3285

Val  Ser  Ser  Ala  Val  Pro  Thr  Ser  Trp  Val  Pro  Gln  Gly  Arg  Thr
         3290                3295                3300

Thr  Trp  Ser  Ile  His  Gly  Lys  Gly  Glu  Trp  Met  Thr  Thr  Glu  Asp
         3305                3310                3315

Met  Leu  Glu  Val  Trp  Asn  Arg  Val  Trp  Ile  Thr  Asn  Asn  Pro  His
         3320                3325                3330
```

```
Met Gln Asp Lys Thr Met Val Lys Lys Trp Arg Asp Val Pro Tyr
    3335            3340                3345
Leu Thr Lys Arg Gln Asp Lys Leu Cys Gly Ser Leu Ile Gly Met
    3350            3355                3360
Thr Asn Arg Ala Thr Trp Ala Ser His Ile His Leu Val Ile His
    3365            3370                3375
Arg Ile Arg Thr Leu Ile Gly Gln Glu Lys Tyr Thr Asp Tyr Leu
    3380            3385                3390
Thr Val Met Asp Arg Tyr Ser Val Asp Ala Asp Leu Gln Leu Gly
    3395            3400                3405
Glu Leu Ile
    3410

<210> SEQ ID NO 15
<211> LENGTH: 10862
<212> TYPE: DNA
<213> ORGANISM: Artificial Sequence
<220> FEATURE:
<223> OTHER INFORMATION: Flaviviridae Flavivirus Yellow Fever Virus

<400> SEQUENCE: 15
agtaaatcct gtgtgctaat tgaggtgcat tggtctgcaa atcgagttgc taggcaataa      60
acacatttgg attaattta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa aacaaaaaac aaaacaaatt ggaaacagac ctggaccttc     240
aagaggtgtt caaggattta tcttttttctt tttgttcaac attttgactg gaaaaaagat     300
cacagcccac ctaaagaggt tgtggaaaat gctggaccca agacaaggct tggctgttct     360
aaggaaagtc aagagagtgg tggccagttt gatgagagga ttgtcctcaa ggaaacgccg     420
ttcccatgat gttctgactg tgcaattcct aatttttggga atgctgttga tgacgggtgg     480
agtgaccttg gtgcggaaaa acagatggtt gctcctaaat gtgacatctg aggacctcgg     540
gaaaacattc tctgtgggca caggcaactg cacaacaaac atttggaag ccaagtactg     600 gtgcccagac tcaatggaat acaactgtcc caatctcagt ccaagagagg agccagatga     660
cattgattgc tggtgctatg gggtggaaaa cgttagagtc gcatatggta agtgtgactc     720
agcaggcagg tctaggaggt caagaagggc cattgacttg cctacgcatg aaaaccatgg     780
tttgaagacc cggcaagaaa aatggatgac tggaagaatg ggtgaaaggc aactccaaaa     840
gattgagaga tggttcgtga ggaaccccct ttttgcagtg acggctctga ccattgccta     900
ccttgtggga agcaacatga cgcaacgagt cgtgattgcc ctactggtct tggctgttgg     960
tccggcctac tcagctcact gcattggaat tactgacagg gatttcattg agggggtgca    1020
tggaggaact tgggtttcag ctaccctgga gcaagacaag tgtgtcactg ttatggcccc    1080
tgacaagcct tcattggaca tctcactaga gacagtagcc attgatagac tgctgaggt     1140 gaggaaagtg tgttacaatg cagttctcac tcatgtgaag attaatgaca gtgccccag    1200 cactggagag gcccacctag ctgaagagaa cgaaggggac aatgcgtgca agcgcactta    1260
ttctgataga ggctggggca atggctgtgg cctatttggg aaaggagca ttgtggcatg    1320 cgccaaattc acttgtgcca aatccatgag tttgtttgag gttgatcaga ccaaaattca    1380
gtatgtcatc agagcacaat tgcatgtagg ggccaagcag gaaaattgga ctaccgacat    1440
taagactctc aagtttgatg ccctgtcagg ctcccaggaa gtcgagttca ttgggtatgg    1500
```

-continued

```
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
agctgatgat cttacagcgg caatcaataa aggcattttg gttacagtta accccatcgc    2040
ctcaaccaat gatgatgaag tgctgattga ggtgaaccca cctttggag acagctacat     2100 tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
ggtgtttggc tctgccttc aggggctatt tggcggcttg aactggataa caaaggtcat     2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga acaagtactc atactatcca gaagatcctg tgaagcttgc    2580
atcaatagtg aaagcctctt ttgaagaagg gaagtgtggc ctaaattcag ttgactccct    2640
tgagcatgag atgtggagaa gcagggcaga tgagatcaat gccattttg aggaaaacga     2700 ggtggacatt tctgttgtcg tgcaggatcc aaagaatgtt taccagagag gaactcatcc    2760
attttccaga attcgggatg gtctgcagta tggttggaag acttggggta agaaccttgt    2820
gttctcccca gggaggaaga atggaagctt catcatagat ggaaagtcca ggaaagaatg    2880
cccgttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acgggaaaa tcaaccagat ccaccacgga     3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct gggagcaat gctggtcggg caagtaactc tccttgattt     3660
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
```

```
ctgcatcctg acaataaatg ctgttgcttc taggaaagca tcaaatacca tcttgcccct   3960
catggctctg ttgacacctg tcactatggc tgaggtgaga cttgccgcaa tgttcttttg   4020
tgccgtggtt atcatagggg tccttcacca gaatttcaag gacacctcca tgcagaagac   4080
tatacctctg gtggccctca cactcacatc ttacctgggc ttgacacaac cttttttggg   4140
cctgtgtgca tttctggcaa cccgcatatt tgggcgaagg agtatcccag tgaatgaggc   4200
actcgcagca gctggtctag tgggagtgct ggcaggactg gcttttcagg agatggagaa   4260
cttccttggt ccgattgcag ttggaggact cctgatgatg ctggttagcg tggctgggag   4320
ggtggatggg ctagagctca agaagcttgg tgaagtttca tgggaagagg aggcggagat   4380
cagcgggagt tccgcccgct atgatgtggc actcagtgaa caaggggagt tcaagctgct   4440
ttctgaagag aaagtgccat gggaccaggt tgtgatgacc tcgctggcct tggttggggc   4500
tgccctccat ccatttgctc ttctgctggt ccttgctggg tggctgtttc atgtcagggg   4560
agctaggaga agtggggatg tcttgtggga tattcccact cctaagatca tcgaggaatg   4620
tgaacatctg gaggatggga tttatggcat attccagtca accttcttgg gggcctccca   4680
gcgaggagtg ggagtggcac agggagggt gttccacaca atgtggcatg tcacaagagg   4740
agcttttcctt gtcaggaatg gcaagaagtt gattccatct tgggcttcag taaaggaaga   4800
ccttgtcgcc tatggtggct catggaagtt ggaaggcaga tgggatggag aggaagaggt   4860
ccagttgatc gcggctgttc caggaaagaa cgtggtcaac gtccagacaa aaccgagctt   4920
gttcaaagtg aggaatgggg gagaaatcgg ggctgtcgct cttgactatc cgagtggcac   4980
ttcaggatct cctattgtta acaggaacgg agaggtgatt gggctgtacg gcaatggcat   5040
ccttgtcggt gacaactcct tcgtgtccgc catatcccag actgaggtga aggaagaagg   5100
aaaggaggag ctccaagaga tcccgacaat gctaaagaaa ggaatgacaa ctgtccttga   5160
ttttcatcct ggagctggga agacaagacg tttcctccca cagatcttgg ccgagtgcgc   5220
acggagacgt ttgcgcactc ttgtgttggc ccccaccagg gttgttcttt ctgaaatgaa   5280
ggaggctttt cacggcctgg acgtgaaatt ccacacacag gctttttccg ctcacggcag   5340
cgggagagaa gtcattgatg ctatgtgcca tgccacccta acttacagga tgttggaacc   5400
aactagggtt gttaactggg aagtgatcat tatggatgaa gcccattttt tggatccagc   5460
tagcatagcc gctagaggtt gggcagcgca cagagctagg gcaaatgaaa gtgcaacaat   5520
cttgatgaca gccacaccgc ctgggactag tgatgaattt ccacattcaa atggtgaaat   5580
agaagatgtt caaacggaca tacccagtga gccctggaac acagggcatg actggatcct   5640
ggctgacaaa aggcccacgg catggttcct tccatccatc agagctgcaa atgtcatggc   5700
tgcctctttg cgtaaggctg aaagagtgt ggtggtcctg aacaggaaaa ccttttgagag   5760
agaataccccc acgataaagc agaagaaacc tgactttata ttggccactg acatagctga   5820
aatgggagcc aaccttttcg tggagcgagt gctggattgc aggacggctt ttaagcctgt   5880
gcttgtggat gaagggagga aggtggcaat aaaagggcca cttcgtatct ccgcatcctc   5940
tgctgctcaa aggaggggc gcattgggag aaatcccaac agagatggag actcatacta   6000
ctattctgag cctacaagtg aaaataatgc ccaccacgtc tgctggttgg aggcctcaat   6060
gctcttggac aacatggagg tgaggggtgg aatggtcgcc ccactctatg gcgttgaagg   6120
aactaaaaca ccagttcccc ctggtgaaat gagactgagg gatgaccaga ggaaagtctt   6180
cagagaacta gtgaggaatt gtgacctgcc cgtttggctt tcgtggcaag tggccaaggc   6240
tggtttgaag acgaatgatc gtaagtggtg ttttgaaggc cctgaggaac atgagatctt   6300
```

```
gaatgacagc ggtgaaacag tgaagtgcag ggctcctgga ggagcaaaga agcctctgcg   6360
cccaaggtgg tgtgatgaaa gggtgtcatc tgaccagagt gcgctgtctg aatttattaa   6420
gtttgctgaa ggtaggaggg gagctgctga agtgctagtt gtgctgagtg aactccctga   6480
tttcctggct aaaaaggtg gagaggcaat ggataccatc agtgtgtttc tccactctga    6540
ggaaggctct agggcttacc gcaatgcact atcaatgatg cctgaggcaa tgacaatagt   6600
catgctgttt atactggctg gactactgac atcgggaatg gtcatctttt tcatgtctcc   6660
caaaggcatc agtagaatgt ctatggcgat gggcacaatg gccggctgtg gatatctcat   6720
gttccttgga ggcgtcaaac ccactcacat ctcctatatc atgctcatat tctttgtcct   6780
gatggtggtt gtgatccccg agccagggca acaaaggtcc atccaagaca accaagtggc   6840
atacctcatt attggcatcc tgacgctggt ttcagcggtg gcagccaacg agctaggcat   6900
gctggagaaa accaaagagg acctcttttg gaagaagaac ttaattccat ctagtgcttc   6960
accctggagt tggccggatc ttgacctgaa gccaggagct gcctggacag tgtacgttgg   7020
cattgttaca atgctctctc caatgttgca ccactgatc aaagtcgaat atggcaacct    7080
gtctctgtct ggaatagccc agtcagcctc agtcctttct ttcatggaca aggggatacc   7140
attcatgaag atgaatatct cggtcataat gctgctggtc agtggctgga attcaataac   7200
agtgatgcct ctgctctgtg catagggtg cgccatgctc cactggtctc tcattttacc    7260
tggaatcaaa gcgcagcagt caaagcttgc acagagaagg gtgttccatg gcgttgccaa   7320
gaaccctgtg gttgatggga atccaacagt tgacattgag gaagctcctg aaatgcctgc   7380
cctttatgag aagaaactgg ctctatatct ccttcttgct ctcagcctag cttctgttgc   7440
catgtgcaga acgcccttt cattggctga aggcattgtc ctagcatcag ctgccctagg    7500
gccgctcata gagggaaaca ccagccttct ttggaatgga cccatggctg tctccatgac   7560
aggagtcatg aggggaatc actatgcttt tgtgggagtc atgtacaatc tatggaagat    7620
gaaaactgga cgccggggga gcgcgaatgg aaaaactttg ggtgaagtct ggaagaggga   7680
actgaatctg ttggacaagc gacagtttga gttgtataaa aggaccgaca ttgtggaggt   7740
ggatcgtgat acggcacgca ggcatttggc cgaagggaag gtggacaccg gggtggcggt   7800 ctccagggg accgcaaagt taaggtggtt ccatgagcgt ggctatgtca agctggaagg   7860
tagggtgatt gacctggggt gtggccgcgg aggctggtgt tactacgctg ctgcgcaaaa   7920
ggaagtgagt ggggtcaaag gatttactct tggaagagac ggccatgaga acccatgaa    7980 tgtgcaaagt ctgggatgga acatcatcac cttcaaggac aaaactgata tccaccgcct   8040
agaaccagtg aaatgtgaca ccctttttgtg tgacattgga gagtcatcat cgtcatcggt   8100
cacagagggg gaaaggaccg tgagagttct tgatactgta gaaaaatggc tggcttgtgg   8160
ggttgacaac ttctgtgtga aggtgttagc tccatacatg ccagatgttc tcgagaaact   8220
ggaattgctc caaaggaggt ttggcggaac agtgatcagg aaccctctct ccaggaattc   8280
cactcatgaa atgtactacg tgtctggagc ccgcagcaat gtcacattta ctgtgaacca   8340
aacatcccgc ctcctgatga ggagaatgag gcgtccaact ggaaaagtga ccctggaggc   8400
tgacgtcatc ctcccaattg ggacacgcag tgttgagaca gacaagggac ccctggacaa   8460
agaggccata gaagaagggg ttgagaggat aaaatctgag tacatgacct cttggttta    8520 tgacaatgac aaccccctaca ggacctggca ctactgtggc tcctatgtca caaaaacctc   8580
aggaagtgcg gcgagcatgg taaatggtgt tattaaaatt ctgacatatc catgggacag   8640
gatagaggag gtcacaagaa tggcaatgac tgacacaacc cccttttgga agcaaagagt   8700
```

```
gtttaaagaa aaagttgaca ccagagcaaa ggatccacca gcgggaacta ggaagatcat    8760
gaaagttgtc aacaggtggc tgttccgcca cctggccaga gaaaagaacc ccagactgtg    8820
cacaaaggaa gaatttattg caaaagtccg aagtcatgca gccattggag cttacctgga    8880
agaacaagaa cagtggaaga ctgccaatga ggctgtccaa gacccaaagt tctgggaact    8940
ggtggatgaa gaaaggaagc tgcaccaaca aggcaggtgt cggacttgtg tgtacaacat    9000
gatggggaaa agagagaaga agctgtcaga gtttgggaaa gcaaagggaa gccgtgccat    9060
atggtatatg tggctgggag cgcggtatct tgagtttgag gccctgggat tcctgaatga    9120
ggaccattgg gcttccaggg aaaactcagg aggaggagtg gaaggcattg gcttacaata    9180
cctaggatat gtgatcagag acctggctgc aatggatggt ggtggattct acgcggatga    9240
caccgctgga tgggacacgc gcatcacaga ggcagacctt gatgatgaac aggagatctt    9300
gaactacatg agcccacatc acaaaaaact ggcacaagca gtgatggaaa tgacatacaa    9360
gaacaaagtg gtgaaagtgt tgagaccagc cccaggaggg aaagcctaca tggatgtcat    9420
aagtcgacga gaccagagag gatccgggca ggtagtgact tatgctctga acaccatcac    9480
caacttgaaa gtccaattga tcagaatggc agaagcagag atggtgatac atcaccaaca    9540
tgttcaagat tgtgatgaat cagttctgac caggctggag gcatggctca ctgagcacgg    9600
atgtaacaga ctgaagagga tggcggtgag tggagacgac tgtgtggtcc ggcccatcga    9660
tgacaggttc ggcctggccc tgtcccatct caacgccatg tccaaggtta aaaggacat    9720
atctgaatgg cagccatcaa aagggtggaa tgattgggag aatgtgccct tctgttccca    9780
ccacttccat gaactacagc tgaaggatgg caggaggatt gtggtgcctt gccgagaaca    9840
ggacgagctc attgggagag aagggtgtc tccaggaaac ggctggatga tcaaggaaac    9900
agcttgcctc agcaaagcct atgccaacat gtggtcactg atgtatttc acaaaaggga    9960
catgaggcta ctgtcattgg ctgtttcctc agctgttccc acctcatggg ttccacaagg   10020
acgcacaaca tggtcgattc atgggaaagg ggagtggatg accacggaag acatgcttga   10080
ggtgtggaac agagtatgga taaccaacaa cccacacatg caggacaaga caatggtgaa   10140
aaaatggaga gatgtccctt atctaaccaa gagacaagac aagctgtgcg gatcactgat   10200
tggaatgacc aatagggcca cctgggcctc ccacatccat ttggtcatcc atcgtatccg   10260
aacgctgatt ggacaggaga aatacactga ctacctaaca gtcatggaca ggtattctgt   10320
ggatgctgac ctgcaactgg gtgagcttat ctgaaacacc atctaacagg aataaccggg   10380
atacaaacca cgggtggaga accggactcc ccacaacctg aaaccgggat ataaaccacg   10440
gctggagaac cggactccgc acttaaaatg aaacagaaac cgggataaaa actacggatg   10500
gagaaccgga ctccacacat tgagacagaa gaagttgtca gcccagaacc ccacacgagt   10560
tttgccactg ctaagctgtg aggcagtgca ggctgggaca gccgacctcc aggttgcgaa   10620
aaacctggtt tctgggacct cccacccag agtaaaaga acggagcctc cgctaccacc   10680
ctcccacgtg gtggtagaaa gacggggtct agaggttaga ggagaccctc cagggaacaa   10740
atagtgggac catattgacg ccagggaaag accggagtgg ttctctgctt ttcctccaga   10800
ggtctgtgag cacagtttgc tcaagaataa gcagacctt ggatgacaaa cacaaaacca   10860
ct                                                                   10862
```

HIGH YIELD YELLOW FEVER VIRUS STRAIN WITH INCREASED PROPAGATION IN CELLS

RELATED APPLICATION

This application is a divisional of U.S. patent application Ser. No. 13/012,917 filed Jan. 25, 2011, now U.S. Pat. No. 8,741,312 issued on Jan. 3, 2014, which is a continuation-in-part of International Application No. PCT/US2010/043010, filed on Jul. 23, 2010, which claims the benefit of priority to U.S. Provisional Application No. 61/230,483, filed on Jul. 31, 2009. The entire teachings of the above applications are incorporated herein by reference.

BACKGROUND OF THE INVENTION

The Yellow Fever virus is endemic, that is, continuously present with low levels of infection in some tropical areas of Africa and the Americas, where it regularly amplifies into epidemics. Other parts of the world, including coastal regions of South America, the Caribbean islands, and Central and North America, are infested with the mosquito vector capable of transmitting the virus and are therefore considered at risk for yellow fever epidemics (World Health Organization Fact Sheet No. 100, revised December, 2001).

For example, in Africa alone, thirty-three countries with a combined population of 508 million, are at risk (Id.). Each year, the World Health Organization (WHO) estimates there are 200,000 cases of yellow fever, with 30,000 deaths (Id.). Travel to these tropical regions also is believed to result in a small number of imported cases in countries generally free of yellow fever. Although yellow fever cases have not been reported in Asia, "this region is at risk because the appropriate primates and mosquitoes are present" (Id.).

The Yellow Fever (YF) virus is in the genus Flavivirus, in the family Flaviviridae. In the so-called "jungle" or "sylvan cycle", the YF virus is enzootic, maintained and transmitted by canopy breeding mosquitoes to monkeys in the rainforests. The "urban cycle" begins when humans become infected by entering the rainforests and are bitten by YF-infected mosquitoes. The "urban cycle" continues with peridomestic transmission from humans to mosquitoes and thence to other humans, and can result in yellow fever epidemics in villages and cities Illness ranges in severity from a self-limited febrile illness to severe hepatitis and fatal hemorrhagic disease.

Unvaccinated humans, including both native people and travelers to YF endemic areas are at significant risk of YF infection when occupational and other activities bring them in contact with infected mosquitoes in the sylvan cycle or the urban cycle.

Patients with yellow fever may be viremic, i.e., have virus in their blood, for 3 to 6 days during the early phase of illness. This phase may be followed by a short period of symptom remission.

The toxic phase develops as the fever returns, with clinical symptoms including, for example, high fever and nausea, hemorrhagic symptoms, including hematemesis (black vomit), epistaxis (nose bleed), gum bleeding, and petechial and purpuric hemorrhages (bruising). Deepening jaundice and proteinuria frequently occur in severe cases.

In the late stages of disease, patients can develop hypotension, shock, metabolic acidosis, acute tubular necrosis, myocardial dysfunction, and cardiac arrhythmia. Confusion, seizures, and coma can also occur, as well as complications such as secondary bacterial infections and kidney failure.

There is no specific treatment for yellow fever. Steps to prevent yellow fever include use of insect repellent, protective clothing, and vaccination with the available, but risky attenuated vaccine.

Live, attenuated vaccines produced from the 17D substrain, are available, but adverse events associated with the attenuated vaccine can lead to a severe infection with the live 17D virus, and serious and fatal adverse neurotropic and viscerotropic events, the latter resembling the severe infection by the wild-type YF virus. Thus there is a need for a safer, inactivated, non-replicating vaccine that will elicit a neutralizing antibody response while eliminating the potential for neurotropic and viscerotropic adverse events.

Thus, there is an on-going need for an effective, inactivated, "killed" or non-replicating vaccine in order to avoid the potential for neurotropic and viscerotropic adverse events associated with the currently available attenuated YF 17D vaccine. Further, there is a need for an improved vaccine produced in Vero cells without animal-derived proteins, a vaccine that can be safely used for persons for whom the live vaccine is contraindicated or for whom warnings appear on the label. Such individuals include immunosuppressed persons, persons with thymic disease, egg-allergic, young infants, and the elderly.

A problem with any potential inactivated virus is that it may need to be delivered at a higher titer than the existing live attenuated vaccines, because the latter can expand antigenic mass during cycles of replication in the host whereas an inactivated vaccine contains a fixed dose of antigen. Therefore, in order to develop a sufficiently potent inactivated vaccine, it is desirable to modify the YF virus in order to produce a high yield of virus in the conditioned medium (also called supernatant fluid) of a cell culture. It is highly desirable to use the attenuated 17D vaccine strain for vaccine manufacturing, since the 17D strain can be manipulated at a lower level of biocontainment than the wild-type virulent YF virus. However, the attenuated 17D vaccine strain yields in cell culture are inherently lower than yields of wild-type virus. For these reasons, modifications of the 17D vaccine strain to achieve higher yields in cell culture used for vaccine production would be useful.

BRIEF SUMMARY OF THE INVENTION

The invention provides a vaccine comprising a strain or strains of Yellow Fever virus which have been adapted to propagate in Vero cells to higher yields than an unadapted virus. "Unadapted virus" is defined to mean that Yellow Fever virus vaccine known as 17D. Sequence analysis of examples of such strains demonstrates that an adapted virus possessing a mutation in the envelope (E) protein resulting in a lysine to arginine substitution in amino acid residue 160 has improved properties. The invention also provides for vaccines comprising a Yellow Fever virus containing one or more mutations in the E protein, that result in increased propagation in Vero cells and in higher yields when using serum free culture medium than the unadapted virus.

Additional examples of adapted Yellow Fever virus strains which propagate in Vero cells to higher yields than unadapted virus have been identified. These include modified Yellow Fever virus strains wherein the nucleic acid molecules of said modified Yellow Fever virus strains comprise at least one amino acid mutation selected from: an amino acid mutation in the NS1 protein, an amino acid mutation in the NS2A protein, and an amino acid mutation in the NS4B protein, optionally wherein said at least one amino acid mutation is in further combination with an amino acid mutation in the envelope protein. Preferred embodiments include 1) a strain having three mutations: a) a lysine to arginine substitution in amino acid residue 160 ($lys_{160}arg$) in the E protein, b) a threonine to isoleucine substitution in amino acid residue 317 ($thr_{317}ile$) in the non-structural protein 1 (NS1), and c) a phenylalanine to leucine substitution in amino acid residue 170 ($phe_{170}leu$) in the non-structural protein 2A (NS2A); and 2) a strain with a mutation in the non-structural protein 4B (NS4B), resulting in an isoleucine to methionine substitution at amino acid residue 113 ($ile_{113}met$).

The invention provides for vaccines comprising a Yellow Fever virus containing one or more mutations selected from: a mutation in the NS1 protein optionally combined with a mutation in the E protein; a mutation in the NS2A protein optionally combined with a mutation in the E protein; and a mutation in the NS4B protein optionally combined with a mutation in the E protein that result in increased propagation in Vero cells and in higher yields than the unadapted virus.

The Yellow Fever virus is the prototype species in the genus Flavivirus, in the family Flaviviridae. Structural and functional studies of the E protein of tick-borne encephalitis (TBE) virus, a fast-growing, virulent member of the flavivirus genus, indicate that Domains I and II in the E protein of TBE participate in an acidic pH-dependent conformational change that facilitates flavivirus membrane fusion with the host and subsequent infectivity. The junction of Domains I and II function as a 'molecular hinge' resulting in a major rearrangement of these domains from of the normal dimeric structure of the E protein at acid pH into a homotrimeric state. [Rey F A et al. The envelope glycoprotein from tick-borne encephalitis virus at 2 Å resolution. *Nature* 375: 291-298 (1995); Heinz F X et al. Structural changes and functional control of the tick-borne encephalitis virus glycoprotein E by the heterodimeric association with protein prM. *Virology* 198: 109-117 (1994); Mandl C W et al. Antigenic structure of the flavivirus envelope protein E at the molecular level, using tick-borne encephalitis virus as a model. *Journal of Virology* 63(2): 564-571 (1989); Harrison S C. Viral membrane fusion. *Nature structural and molecular biology* 15(7): 690-698 (2008); Stiasny K et al. Molecular mechanisms of flavivirus membrane fusion. *Amino acids* DOI 10.1007/s00726-009-0370-4, published on line 1 Nov. 2009.]

Lys 160 in the E protein of Yellow Fever virus is located in the molecular hinge region between Domains I and II. Mutations in this region could alter the acid-dependent conformational change in region Domain I of the E protein required for fusion and virus internalization into the cell cytoplasm. Without being bound by theory, higher yields seen with the lysine to arginine change at amino acid 160 in Domain I of the E protein of the adapted Yellow Fever virus strain may be due to an increased affinity for protons that arginine provides as compared with lysine, that results in enhanced membrane fusion with the host and more efficient infectivity. In regard to the invention, it is important to note that the side chains of lysine and arginine have pKa values of 10.53 and 12.48, respectively, indicating a one hundred fold greater affinity for protons in arginine than in lysine. The increased affinity for protons that the side chain of arginine shows relative to lysine's side chain may enhance the rate and efficiency of E protein conformational change at the molecular hinge, membrane fusion, and flavivirus infectivity, resulting in higher yields of virus in the adapted virus strain.

Other members within the genus Flavivirus include West Nile, dengue, and Japanese encephalitis viruses. The non-structural proteins found in West Nile Virus are known to be directly or indirectly involved in viral RNA synthesis. Amino acid substitutions in the non-structural proteins of these viruses have been shown to affect the yields of mutant viruses grown in Vero cells. For example, a proline to leucine substitution at amino acid 250 in the NS1 protein of the flavivirus Kunjin, a West Nile Virus subtype, grows at 100-fold lower titers than wild-type virus. Similarly, mutation of the C-terminal sites in the NS2A protein of yellow fever virus was shown to be lethal for virus replication. Brinton M A. The molecular biology of west nile virus: a new invader of the western hemisphere. *Annual Review of Microbiology* 56: 371-402 (2002).

In a first aspect, the invention provides a modified Yellow Fever virus strain that results in increased propagation in Vero cells and a higher yield in the conditioned medium of a cell culture relative to the unadapted virus comprising at least one mutation relative to the unadapted virus selected from: a mutation in the E protein, a mutation in the NS1 protein, a mutation in the NS2A protein, and a mutation in the NS4B protein, optionally wherein said at least one mutation in the NS1 protein, the NS2A protein, or the NS4B protein is in further combination with a mutation of the E protein.

Replacement of basic amino acids that are located within 20 amino acids, or within 10 Angstroms, of lysine 160 in the E protein of the Yellow Fever virus (including lysine 160 itself), with amino acids having higher side chain pKa values than the replaced basic amino acids, can result in strains of Yellow Fever virus that produce higher yields of virus than an unadapted Yellow Fever virus. The invention thus provides for Yellow Fever viruses, and vaccines containing them, comprising a modified nucleic acid molecule encoding an E protein, the virus being capable of propagating in Vero cells to higher yields than the unadapted virus. Preferred embodiments include viruses comprising a modified E protein with an increased pKa within 20 amino acids, or within 10 Angstroms, of lysine 160 in the E protein.

In a third aspect, the invention provides a nucleic acid molecule comprising a sequence encoding a modified envelope protein of the Yellow Fever virus, wherein said nucleic acid molecule comprises a nucleotide mutation in the codon for the amino acid at position 160 of the envelope protein. In an embodiment of this aspect, the invention provides a nucleic acid molecule comprising a sequence encoding at least one modified nucleic acid relative to the nucleic acid of the unadapted virus, wherein said at least one modified nucleic acid is selected from: a modified nucleic acid of the NS1 protein, a modified nucleic acid of the NS2A protein and a modified nucleic acid of the NSB4 protein, optionally wherein said at least one modified nucleic acid is in further combination with a modified nucleic acid of the envelope protein of the Yellow Fever virus, wherein said optional modified nucleic acid of the envelope protein comprises a nucleotide mutation in the codon for the amino acid at position 160 of the envelope protein. In a further embodiment of this aspect, the nucleotide mutation in the codon for the amino acid at position 160 of the envelope protein results in a change from AAG to AGG, AGA, CGC, CGA, CGG or CGU. Additionally, the invention provides for vectors, constructs, modified Yellow Fever virus strains, and cells comprising or containing such a nucleic acid molecule or a protein encoded thereby.

In a fourth aspect, the invention provides a modified Yellow Fever virus strain, wherein the nucleic acid molecule of said strain comprises a sequence encoding an envelope protein of the Yellow Fever virus, wherein said envelope protein comprises an amino acid mutation at position 160 of the envelope protein. In an embodiment of this aspect, the invention provides a modified Yellow Fever virus strain, wherein the nucleic acid molecule of said strain comprises a sequence encoding an envelope protein of the Yellow Fever virus, wherein said envelope protein optionally comprises an amino acid mutation at position 160 of the envelope protein.

In a fifth aspect, the invention provides a nucleic acid molecule comprising a sequence encoding an envelope protein of the Yellow Fever virus, wherein said envelope protein comprises an amino acid mutation at position 160 of the envelope protein. In an embodiment of this aspect, the invention optionally provides a nucleic acid molecule comprising a sequence encoding an envelope protein of the Yellow Fever virus, wherein said envelope protein comprises an amino acid mutation at position 160 of the envelope protein. Additionally, the invention provides for vectors, constructs, modified Yellow Fever virus strains, and cells comprising or containing such nucleic acid molecules or proteins encoded thereby. The nucleic acid molecules preferably comprise a sequence encoding a modified envelope protein of the Yellow Fever virus, wherein said nucleic acid molecule encodes the protein sequence in SEQ ID NO. 4, 6, or 7.

In a sixth aspect, the invention provides a method for enhancing the propagation of Yellow Fever virus in cells. In an embodiment of this aspect, the method comprises mutating a nucleic acid molecule comprising a sequence encoding the envelope protein of the Yellow Fever virus, wherein the mutation comprises a nucleotide mutation in the codon for the amino acid at position 160 of the envelope protein. In another embodiment of this aspect, the method optionally comprises mutating a nucleic acid molecule comprising a sequence encoding the envelope protein of the Yellow Fever virus, wherein the mutation comprises a nucleotide mutation in the codon for the amino acid at position 160 of the envelope protein. In a further embodiment, the method comprises mutating a nucleic acid molecule comprising a sequence encoding the envelope protein of the Yellow Fever virus, wherein said mutation comprises an amino acid mutation at position 160 of the envelope protein. In a final embodiment, the method optionally comprises mutating a nucleic acid molecule comprising a sequence encoding the envelope protein of the Yellow Fever virus, wherein said mutation comprises an amino acid mutation at position 160 of the envelope protein. The word "mutating" is intended to mean selecting for a mutation, or introducing a mutation. The relevant mutant viruses can be obtained by a method of selection and evolutionary pressure during passages in a specific host cell line (such as Vero cells) or by site-directed mutagenesis using infectious clone technology well known in the art. However, the former method is preferred because it identifies mutated viruses by virtue of the desired phenotypic characteristic (increased yields in Vero cell cultures).

In a seventh aspect, the invention provides a modified Yellow Fever virus strain, wherein the nucleic acid molecule of said strain comprises a nucleotide mutation in the codon for amino acids flanking the E160 codon selected from position 134, 137, 144, 148, 157, 160, 175, or 177 of the envelope protein of Yellow Fever virus. In an embodiment of this aspect, the invention provides a modified Yellow Fever virus strain, wherein the nucleic acid molecule of said strain optionally comprises a nucleotide mutation in the codon for amino acids flanking the E160 codon selected from position 134, 137, 144, 148, 157, 160, 175, or 177 of the envelope protein of Yellow Fever virus. In another embodiment of this aspect, the mutated codon within 20 amino acids flanking the E160 mutation results in an amino acid mutation in the envelope protein at that position, wherein the pKa value of the side chain of the mutated amino acid is higher than the pKa value of the side chain of the original amino acid at that position.

In an eighth aspect, the invention provides for Yellow Fever viruses, and vaccines containing them, comprising a modified nucleic acid molecule encoding an NS1 protein, the virus being capable of propagating in Vero cells to higher yields than the unadapted virus. Preferred embodiments include viruses comprising a modified NS1 protein and a modified E protein. A more preferred embodiment includes viruses comprising a modified NS1 protein and a modified E protein with an increased pKa within 20 amino acids, or within 10 Angstroms, of lysine 160 in the E protein.

In a ninth aspect, the invention provides for Yellow Fever viruses, and vaccines containing them, comprising a modified nucleic acid molecule encoding an NS2A protein, the virus being capable of propagating in Vero cells to higher yields than the unadapted virus. Preferred embodiments include viruses comprising a modified NS2A protein and a modified E protein. A more preferred embodiment includes viruses comprising a modified NS2A protein and a modified E protein with an increased pKa within 20 amino acids, or within 10 Angstroms, of lysine 160 in the E protein.

In a tenth aspect, the invention provides for Yellow Fever viruses, and vaccines containing them, comprising a modified nucleic acid molecule encoding an NS1 protein and an NS2A protein, the virus being capable of propagating in Vero cells to higher yields than the unadapted virus. Preferred embodiments include viruses comprising a modified NS1 protein, a modified NS2 protein, and a modified E protein. A more preferred embodiment includes viruses comprising a modified NS1 protein, a modified NS2 protein, and a modified E protein with an increased pKa within 20 amino acids, or within 10 Angstroms, of lysine 160 in the E protein.

In an eleventh aspect, the invention provides for Yellow Fever viruses, and vaccines containing them, comprising a modified nucleic acid molecule encoding an NS4B protein, the virus being capable of propagating in Vero cells to higher yields than the unadapted virus.

In a twelfth aspect, the invention provides a nucleic acid molecule comprising a sequence encoding a modified non-structural protein 1 of the Yellow Fever virus, wherein said nucleic acid molecule comprises a nucleotide mutation in the codon for the amino acid at position 317 of the non-structural protein 1. In an embodiment of this aspect, the nucleotide mutation in the codon for the amino acid at position 317 of the non-structural protein 1 results in a change from ACA to AUA. Additionally, the invention provides for vectors, constructs, modified Yellow Fever virus strains, and cells comprising or containing such a nucleic acid molecule or a protein encoded thereby.

In a thirteenth aspect, the invention provides a nucleic acid molecule comprising a sequence encoding a modified non-structural protein 2A of the Yellow Fever virus, wherein said nucleic acid molecule comprises a nucleotide mutation in the codon for the amino acid at position 170 of the non-structural protein 2A. In an embodiment of this aspect, the nucleotide mutation in the codon for the amino acid at position 170 of the non-structural protein 2A results in a change from UUU to CUU. Additionally, the invention provides for vectors, constructs, modified Yellow Fever virus strains, and cells comprising or containing such a nucleic acid molecule or a protein encoded thereby.

In a fourteenth aspect, the invention provides a nucleic acid molecule comprising a sequence encoding a modified non-structural protein 4B of the Yellow Fever virus, wherein said nucleic acid molecule comprises a nucleotide mutation in the codon for the amino acid at position 113 of the non-structural protein 4B. In an embodiment of this aspect, the nucleotide mutation in the codon for the amino acid at position 113 of the non-structural protein 4B results in a change from AUA to AUG. Additionally, the invention provides for vectors, constructs, modified Yellow Fever virus strains, and cells comprising or containing such a nucleic acid molecule or a protein encoded thereby.

In a fifteenth aspect, the invention provides a modified Yellow Fever virus strain, wherein the nucleic acid molecule of said strain comprises a sequence encoding proteins of the Yellow Fever virus, wherein said proteins comprise an amino acid mutation at position 160 of the envelope protein, at position 317 of the NS1 protein, at position 170 of the NS2A protein, or at position 113 of the NS4B protein.

In a sixteenth aspect, the invention provides a nucleic acid molecule comprising a sequence encoding an envelope protein, an NS1 non-structural protein, an NS2A non-structural protein, or an NS4B non-structural protein of the Yellow Fever virus, wherein said proteins comprise an amino acid mutation at position 160 of the envelope protein, at position 317 of the NS1 protein, at position 170 of the NS2A protein, or at position 113 of the NS4B protein. Additionally, the invention provides for vectors, constructs, modified Yellow Fever virus strains, and cells comprising or containing such a nucleic acid molecule or proteins encoded thereby. The nucleic acid molecules preferably comprise a sequence encoding a modified protein of the Yellow Fever virus, wherein said nucleic acid molecule encodes the protein sequence in SEQ ID NO: 7 and SEQ ID NO: 8.

In a seventeenth aspect, the invention provides a method for enhancing the propagation of Yellow Fever virus in cells. In an embodiment of this aspect, the method comprises mutating a nucleic acid molecule comprising a sequence encoding the envelope protein, the NS1 non-structural protein, the NS2A non-structural protein, or the NS4B non-structural protein of the Yellow Fever virus, wherein said mutations comprise an amino acid mutation at position 160 of the envelope protein, at position 317 of the NS1 protein, at position 170 of the NS2A protein, or at position 113 of the NS4B protein. The word "mutating" is intended to mean selecting for a mutation, or introducing a mutation.

In an eighteenth aspect, the invention provides a modified Yellow Fever virus strain, wherein the nucleic acid molecule of said strain comprises a nucleotide mutation in the codon for amino acids 317 of the NS1 protein, 170 of the NS2A protein, or 113 of the NS4B protein, and wherein the nucleic acid molecule also comprises a nucleotide mutation in the codon for amino acids flanking the E160 codon selected from position 134, 137, 144, 148, 157, 160, 175, or 177 of the envelope protein of Yellow Fever virus. In an embodiment of this aspect, the mutated codon within 20 amino acids flanking the E160 mutation results in an amino acid mutation in the envelope protein at that position, wherein the pKa value of the side chain of the mutated amino acid is higher than the pKa value of the side chain of the original amino acid at that position.

The invention also provides methods of making and using the nucleic acid molecules, modified E proteins, modified NS1 proteins, modified NS2A proteins, modified NS4B proteins, modified Yellow Fever viruses, vectors, constructs and cells containing the same.

BRIEF DESCRIPTION OF THE DRAWINGS

FIG. 2 is a schematic representation of the preparation of the virus seeds.

FIG. 3A is a schematic of the process used for 10 serial passages (P1 through P10) to modify the nucleotide sequence of the viral genome virus to develop a seed virus with enhanced growth in Vero cells for preparation of an inactivated Yellow Fever virus candidate.

FIG. 3B is a graphical representation of the virus replication for passage one (P1) and passage 11 (P11) of the initial experiment, in which P11 virus differs from P1 by a single mutation at E160 (lys→arg)

FIG. 4A-L depicts the consensus alignment of the P1 and P11 nucleic acid sequences. The starting nucleic acid sequence, P1, is identified herein as SEQ ID NO: 1. A comparison of the P1 passage and the P11 passage revealed a genetic mutation at nucleotide residue #211 of SEQ ID NO: 1, and a second mutation at nucleotide residue #1452 of SEQ ID NO: 1. Thus, "P1 consensus" corresponds to SEQ ID NO.1; "P11 consensus" corresponds to SEQ ID NO. 2 having the codon mutation at envelope protein amino acid position 160.

FIG. 5A-J depicts the amino acid sequence of P1 and P11, with the Series B-P1 and Series B3-P11 amino acid sequences from the repeat passaging study. The amino acid sequence for P1 is identified herein as SEQ ID NO: 3. A comparison of the amino acid sequence for P1 and that of P11 (SEQ ID NO. 4) revealed a mutation at amino acid residue 160 of the envelope protein (E160) (amino acid 445 of the P1 amino acid sequence in FIG. 5B). Series B-P1 and Series B3-P11 present partial amino acid sequences from the repeat passaging study. The amino acid sequence for B-P1 is identified herein as SEQ ID NO: 5. A comparison of the amino acid sequence for B-P1 and that of B3-P11 (SEQ ID NO. 6) revealed a mutation at amino acid residue 160 of the envelope protein (E160) in B3-P11 (amino acid 445 of the P1 amino acid sequence).

Figure 8A:
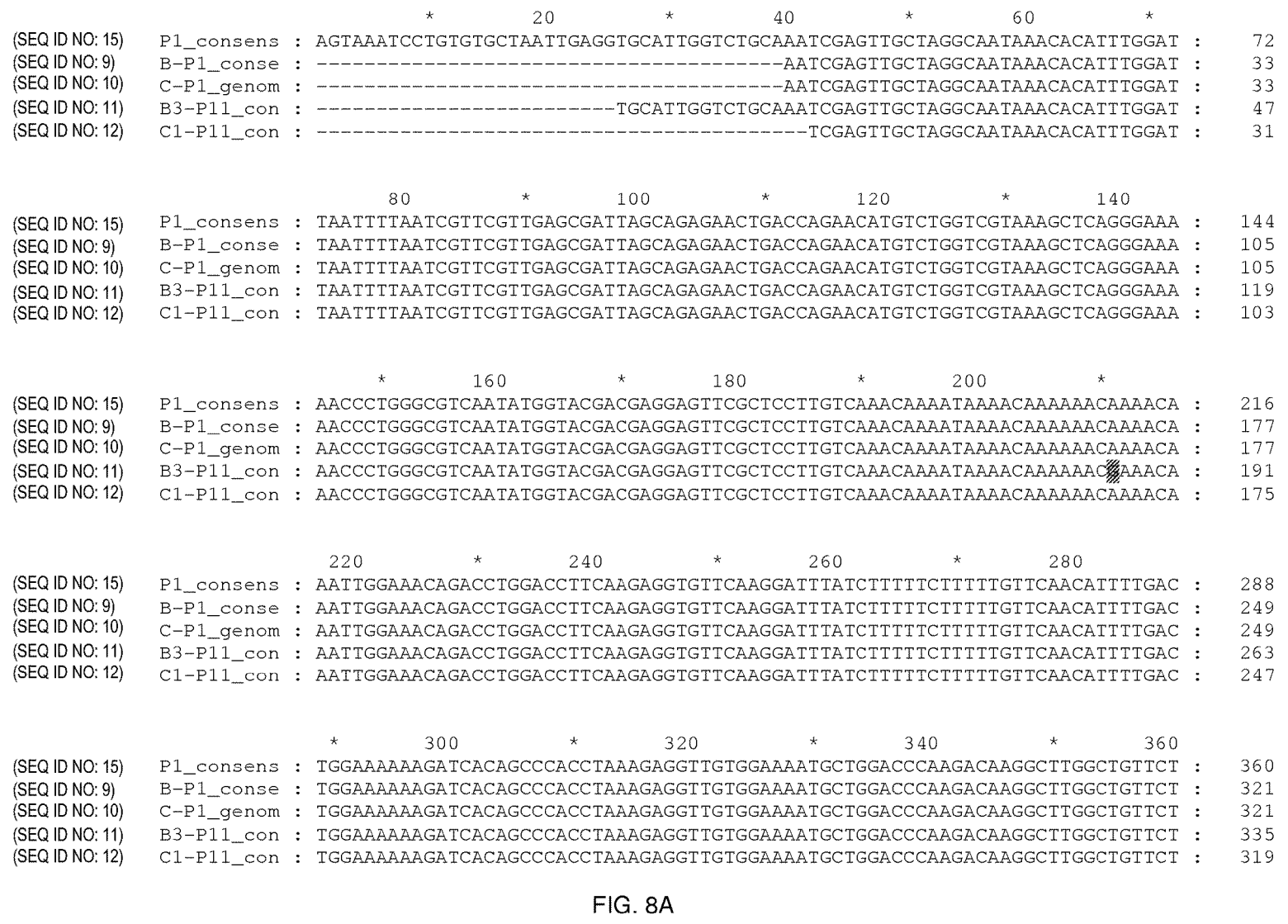
Figure 8B:
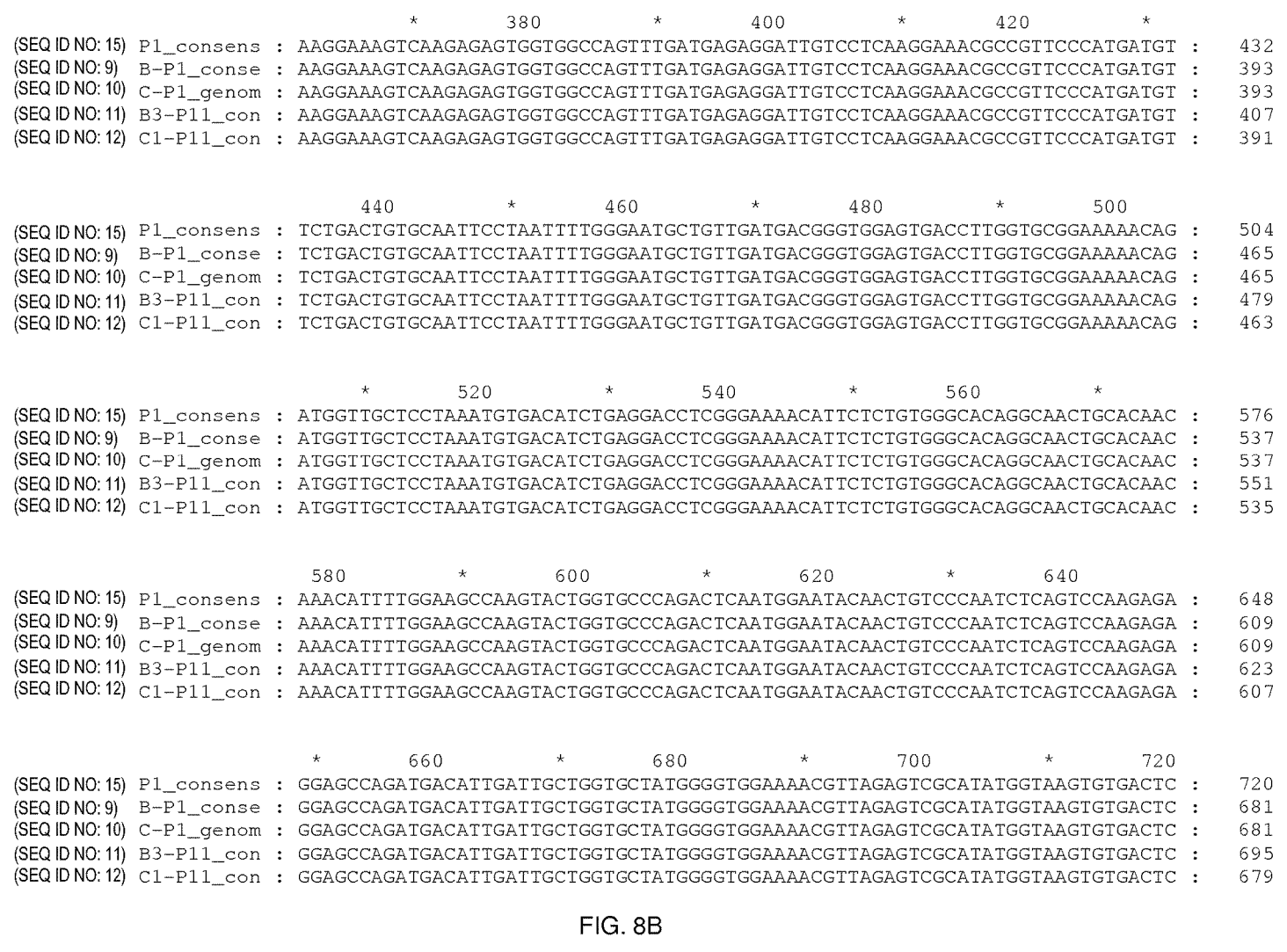
Figure 8C:
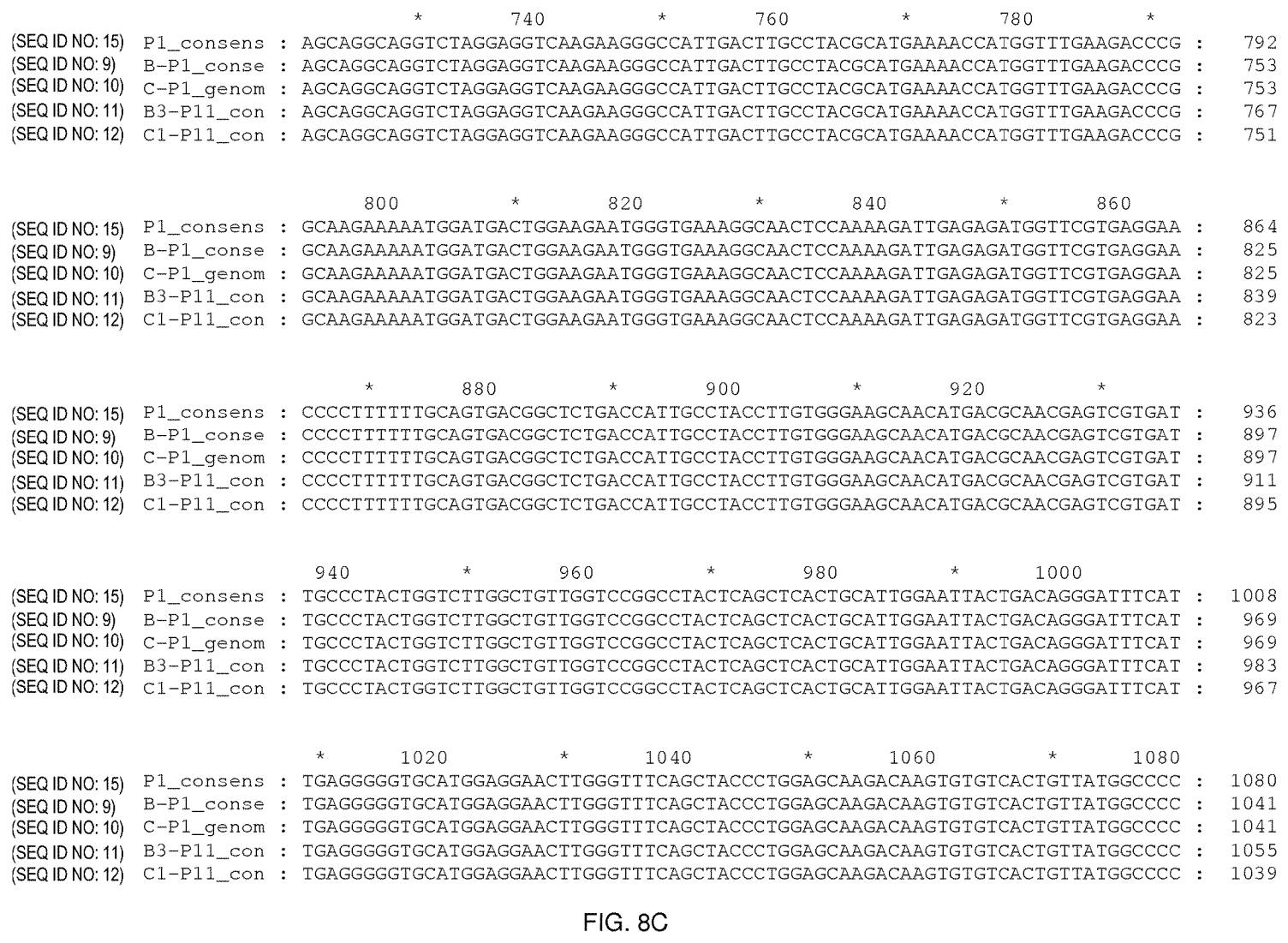
Figure 8I:
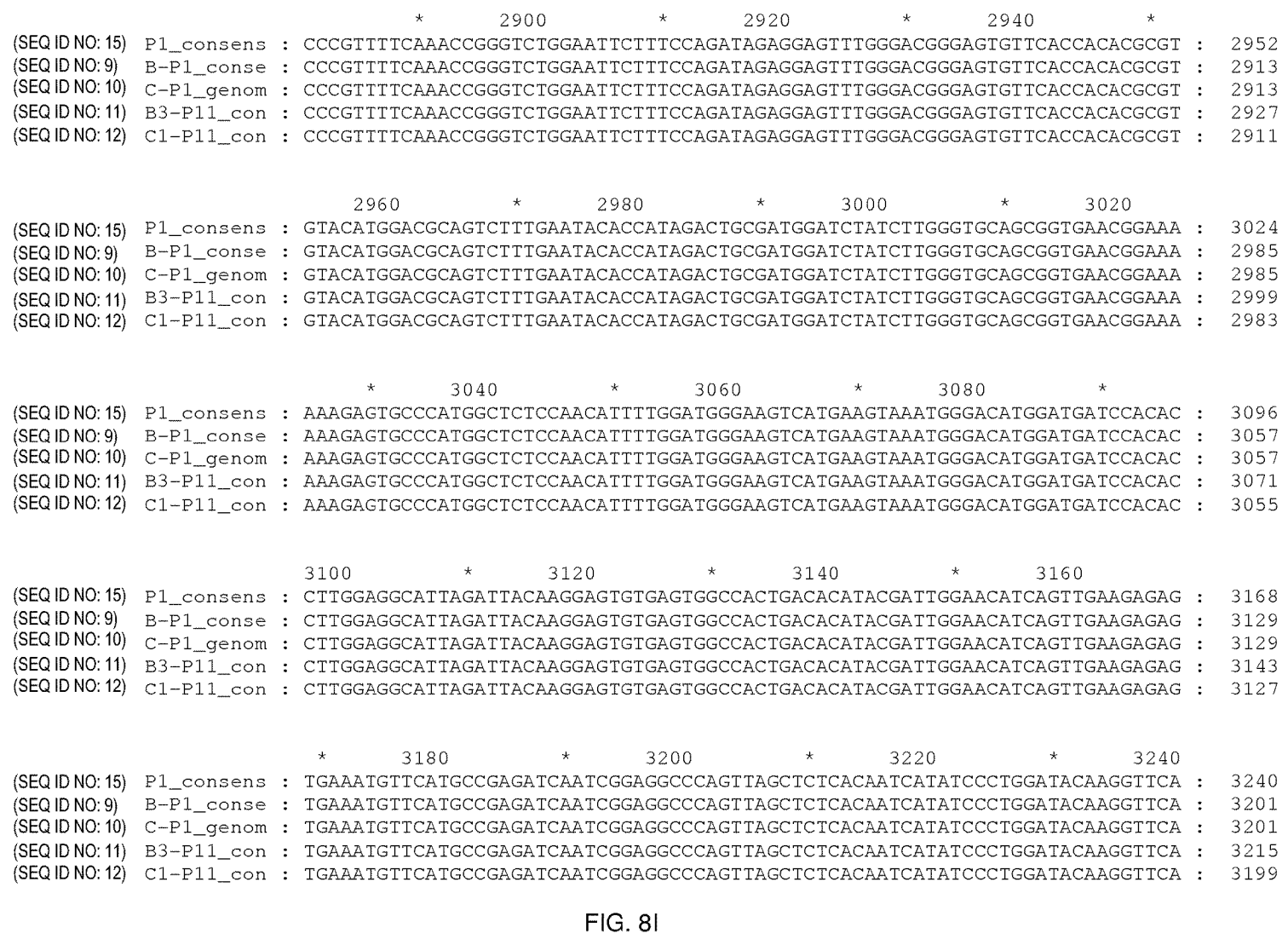
Figure 8K:
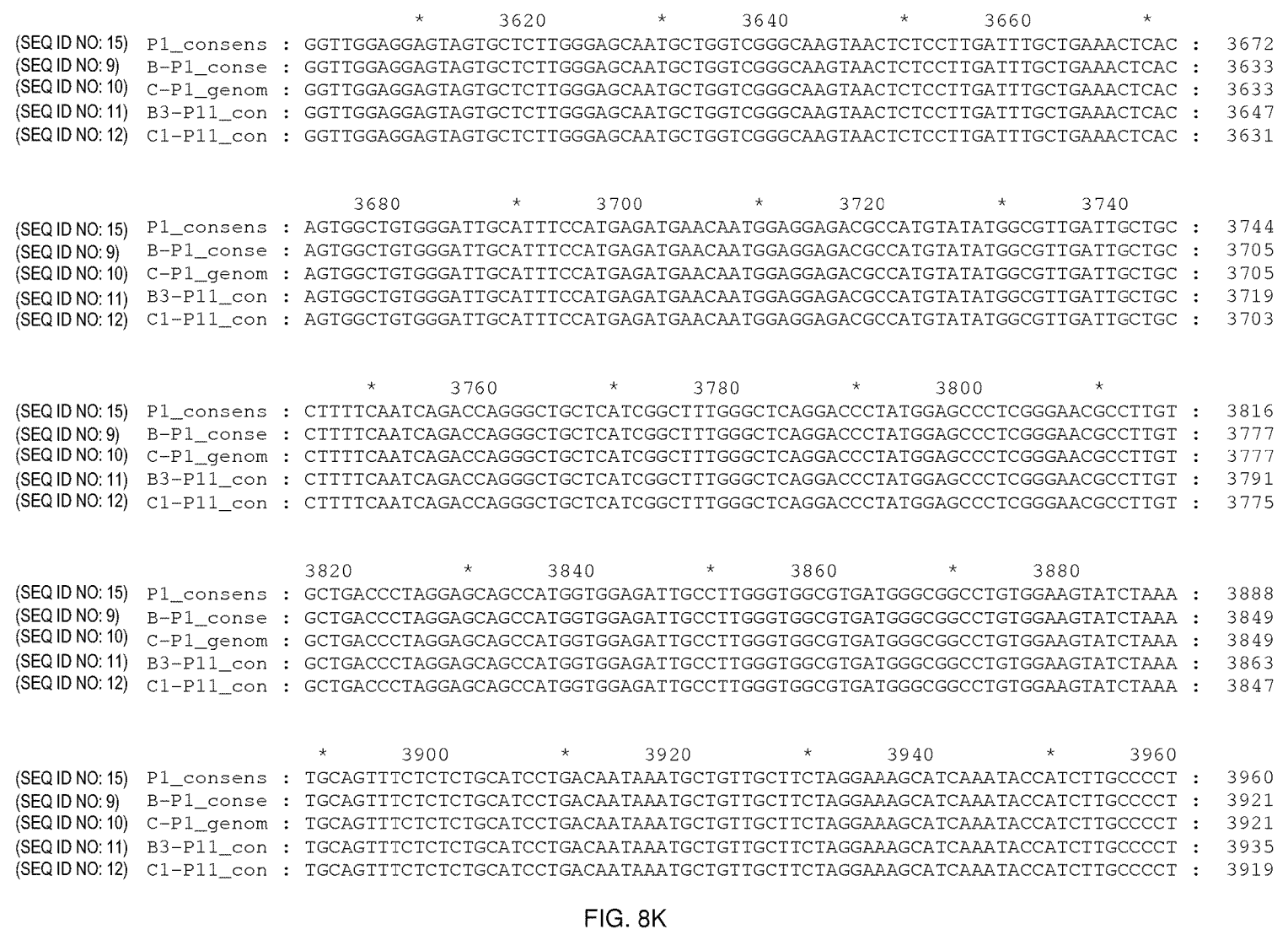
Figure 8M:
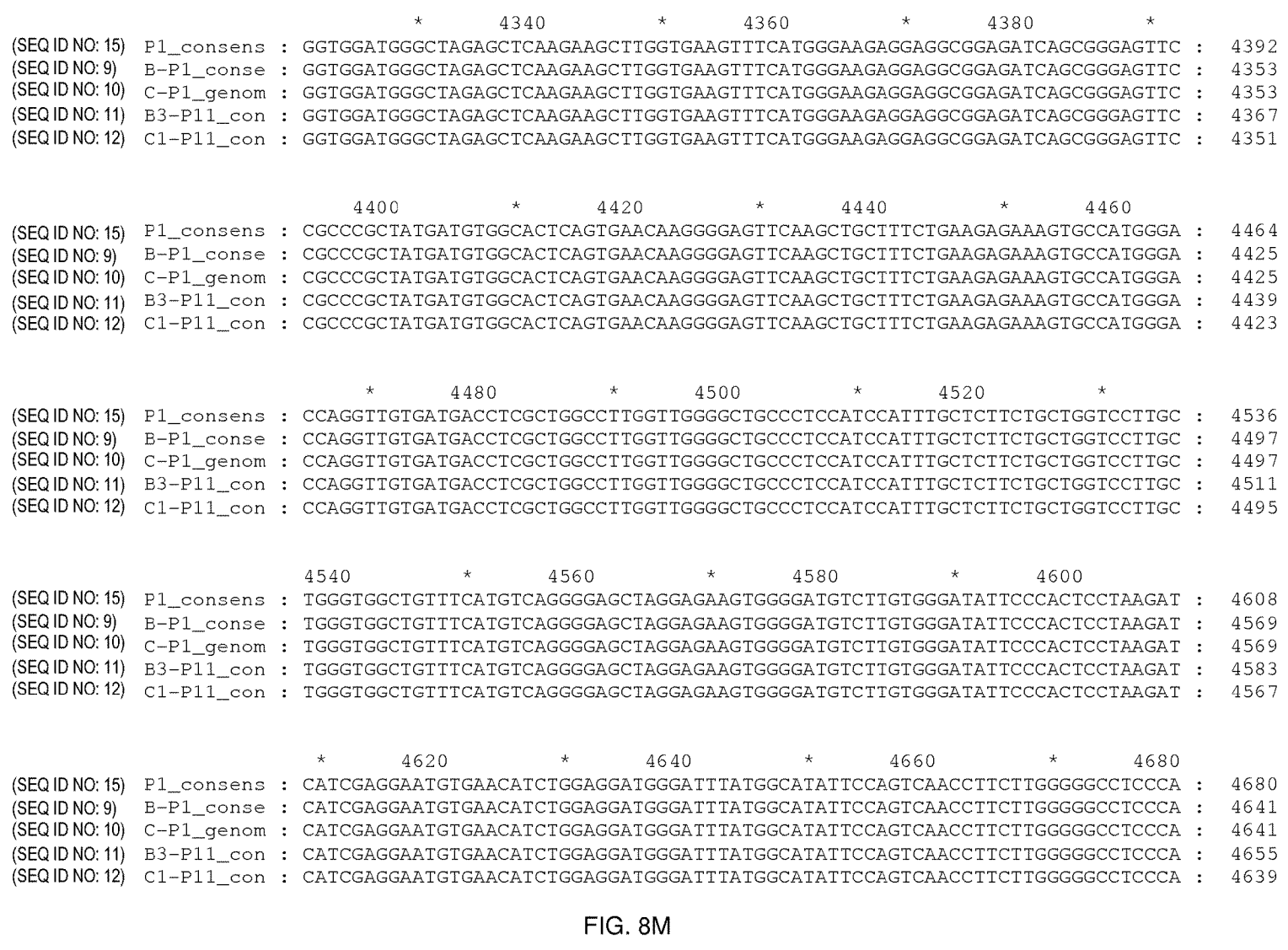
Figure 8W:
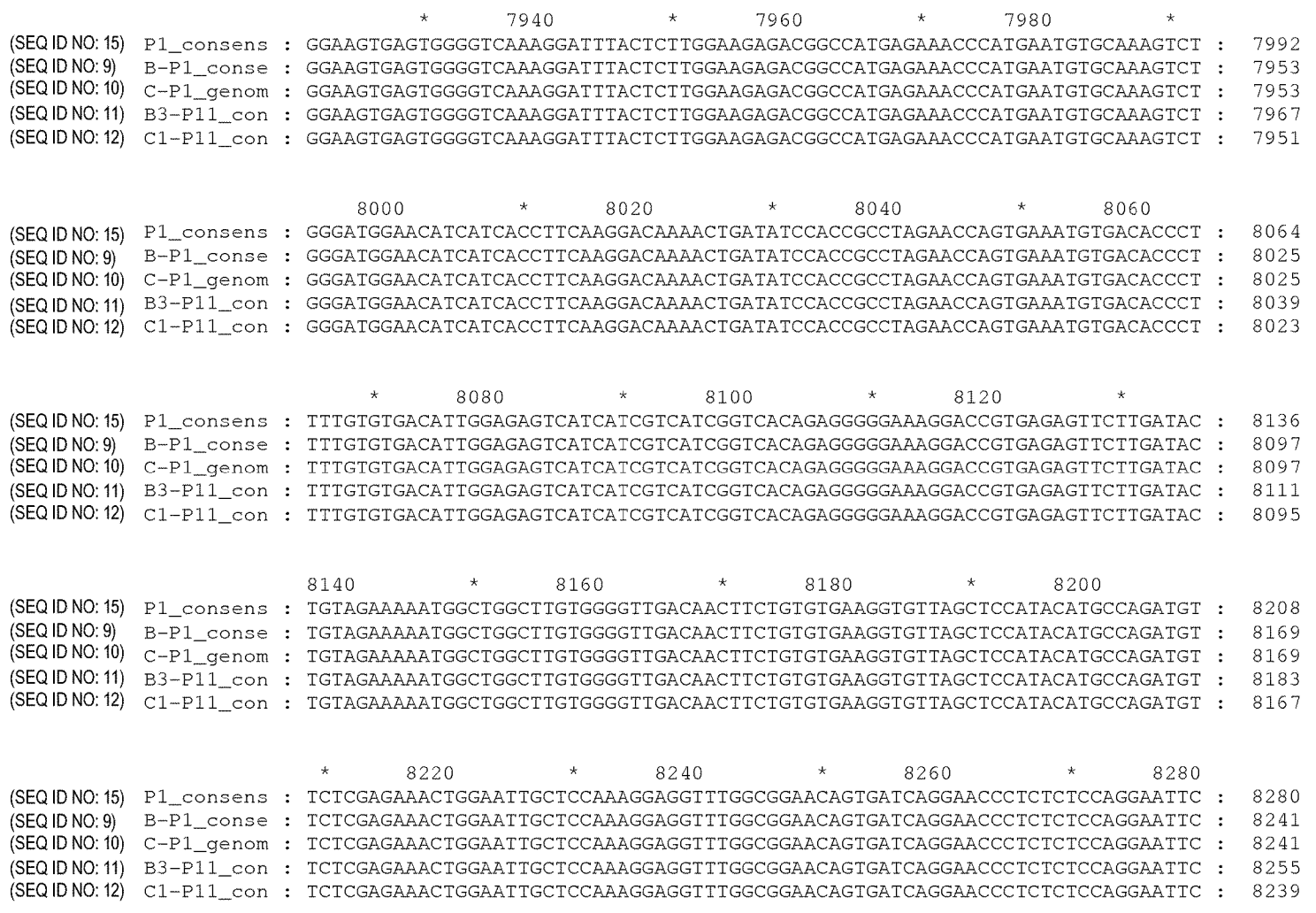
Figure 8X:
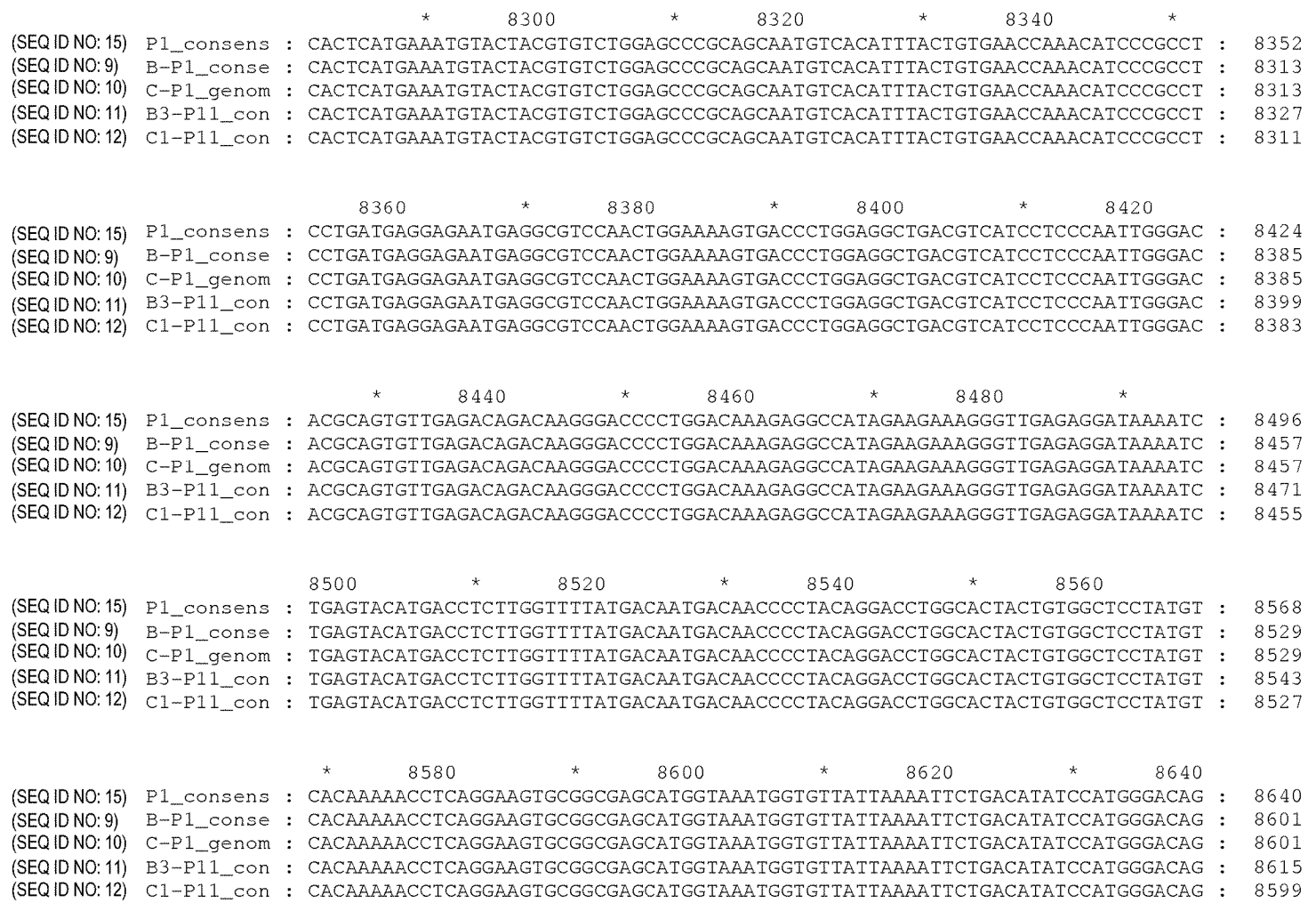

FIG. 8A-EE depicts the consensus alignment of the P1, B-P1, C-P1, B3-P11 and C1-P11 nucleic acid sequences. The nucleic acid sequence, P1, is identified herein as SEQ ID NO: 15. The nucleic acid sequence, B-P1, is identified herein as SEQ ID NO: 9. The nucleic acid sequence, B3-P11, is identified herein as SEQ ID NO: 11. The nucleic acid sequence, C-P1, is identified herein as SEQ ID NO: 10. The nucleic acid sequence, C1-P11, is identified herein as SEQ ID NO: 12. A comparison of the B-P1 passage and the B3-P11 passage revealed a genetic mutation in B3-P11 at nucleotide residue #1452 of SEQ ID NO: 15, a second mutation in B3-P11 at nucleotide residue #3402 of SEQ ID NO: 15, and a third mutation in B3-P11 at nucleotide residue #4016 of SEQ ID NO: 15. A comparison of the C-P1 passage and the C1-P11 passage revealed a genetic mutation in C1-P11 at nucleotide residue #7225 of SEQ ID NO: 15. SEQ ID NO: 11 corresponds to B3-P11, and has the codon mutations at envelope protein amino acid position 160, non-structural protein 1 amino acid position 317, and non-structural protein 2A amino acid position 170. SEQ ID NO.12 corresponds to C1-P11, and has the codon mutation at non-structural protein 4B amino acid position 113.

FIG. 9A-F depicts the amino acid sequence of B-P1 and B3-P11 from the repeat passaging study. The amino acid sequence for B-P1 is identified herein as SEQ ID NO: 13. A comparison of the amino acid sequence for B-P1 and that of B3-P11 (SEQ ID NO: 7) revealed a mutation at amino acid residue 160 of the envelope protein (E160) (amino acid 445 in FIG. 9A), a mutation at amino acid residue 317 of the non-structural protein 1 (NS1-317) (amino acid 1095 in FIG. 9B), and a mutation at amino acid residue 170 of the non-structural protein 2A (NS2A-170) (amino acid 1300 in FIG. 9C). Series B-P1 and Series B3-P11 present complete amino acid sequences from the repeat passaging study.

FIG. 10A-F depicts the amino acid sequence of C-P1 and C1-P11 from the repeat passaging study. The amino acid sequence for C-P1 is identified herein as SEQ ID NO: 14. A comparison of the amino acid sequence for C-P1 and that of C1-P11 (SEQ ID NO: 8) revealed a mutation at amino acid residue 113 of the non-structural protein 4B (NS4B-113) (amino acid 2369 in FIG. 10E). Series C-P1 and Series C1-P11 present complete amino acid sequences from the repeat passaging study.

DETAILED DESCRIPTION OF THE PREFERRED EMBODIMENTS

Figure 1:
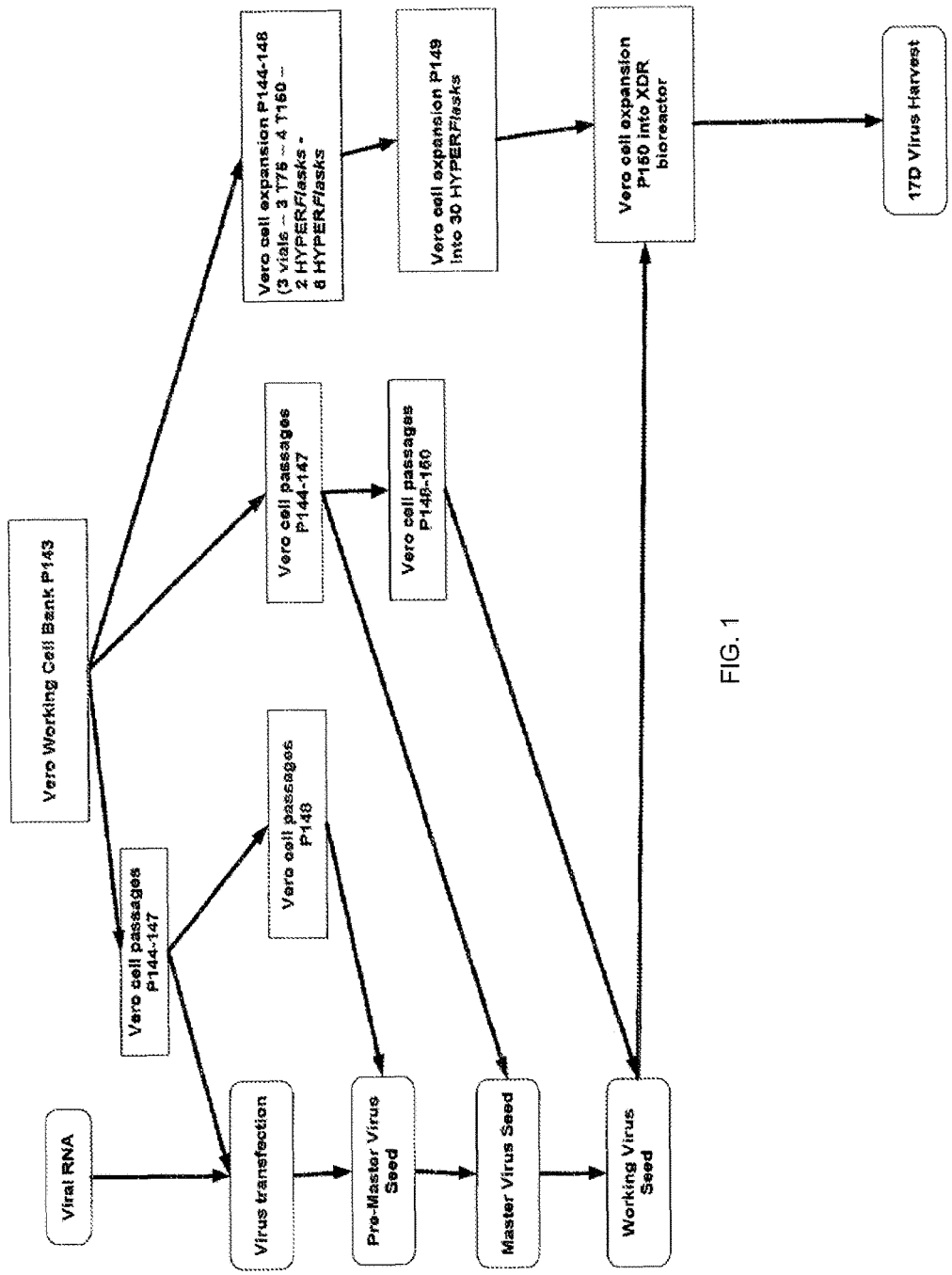
FIG. 1 is a schematic representation of the passage history of Vero cells during the manufacture of the disclosed yellow fever vaccine.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Overview of Approach and Benefits

The invention relates to compositions and methods for use in preventing Yellow Fever virus infection. Disclosed herein is a method of producing an inactivated Yellow Fever virus candidate, the method comprising the serial passage of the YF 17D virus (i.e., an "unadapted virus") in certified African green monkey kidney cells (VERO) to increase the titer to yield a sufficient antigenic mass to induce a protective immune response and/or modify the nucleotide sequence of the viral genome. This method has been repeated and shown to be reproducible.

One embodiment of the invention is a modified Yellow Fever (YF) virus that will grow to high titers in Vero cells. Another embodiment of the invention is a vaccine comprising a whole virion, chemically inactivated Yellow Fever (YF) virus prepared from serum-free conditioned medium from Vero cells infected with 17D virus. In one embodiment of the invention, the virus has been purified from host cell DNA and proteins by depth filtration, ultrafiltration, diafiltration, and chromatographic separation. The method is described in U.S. Application Ser. No. 61/228,026 filed on Jul. 23, 2009, and its corresponding International Application No. PCT/US2010/043013 filed on Jul. 23, 2010, which are each incorporated herein by reference. The purified virus may be inactivated by using a method that ensures preservation of critical, neutralizing epitopes. For example, the virus can be inactivated using formalin, heat, UV, gamma irradiation or beta-propiolactone. A purified, inactivated virus may be formulated with an adjuvant, such as adsorbed to aluminum hydroxide adjuvant, and stored as a liquid at temperatures of from about 2 degrees Celsius (2° C.) to about 8 degrees Celsius (8° C.).

A vaccine containing the purified, inactivated virus is believed to be safer than the currently available attenuated, live YF virus vaccine because the disclosed inactivated YF virus vaccine is non-replicating. The inventors of the present subject matter have now developed a safer, inactivated, non-replicating YF vaccine that will elicit a neutralizing antibody response while eliminating the potential for neurotropic and viscerotropic adverse events. In addition, the improved vaccine can be manufactured by modern methods in Vero cells without animal derived proteins, and therefore it can be used safely in persons (including egg-allergic persons) for whom the live vaccine (produced in hens' eggs) is contraindicated or for whom warnings appear in the label. Such warnings would include, for example warnings to immunosuppressed persons, persons with thymic disease, egg-allergic persons, infants <9 months, and the elderly.

Adaptation of Yellow Fever Virus for Robust Production in Vero Cells:

The Vero cells used in the virus development phase were obtained from the World Health Organization (W.H.O.) seed lot, WHO Vero 10-87 Cell Bank at Passage 134. The WHO Vero 10-87 Cell Bank was originally made by the Institut Merieux using the ATCC Vero cell line CCL81 at Passage 129. The cells were thawed into OptiPRO™ SFM (serum-free medium) supplemented with 5% fetal bovine serum which was removed 24 hours later and replaced with OptiPRO™ SFM medium without fetal bovine serum. The serum, certified as being of USA origin, was gamma irradiated and had been tested for adventitious agents by the manufacturer; additional testing for sterility, mycoplasma, and adventitious viruses was performed on this material by WuXi AppTec. All subsequent passages of Vero cells to make the cell banks, virus seeds, and vaccine were made in OptiPRO™ SFM without serum. No other animal derived materials or products were used in producing the cell banks or the final vaccine according to an embodiment of the invention.

Preparation of Vero Cell Banks:

Master and Working Cell banks were prepared according to cGMP and were tested and characterized according to FDA Points to Consider. The Vero cells had an established provenance and were free from regulatory concerns about Bovine spongiform encephalitis (BSE). Serum-free growth medium was employed in propagating cells.

Passage History of Vero Cells During Manufacture of Seed Viruses and Vaccine Lots:

The passage history of Vero cells during the manufacture of the disclosed yellow fever vaccine is shown schematically in FIG. 1. The WHO cells were received at Passage 134, the Master Cell Bank (MCB) and Working Cell bank (MWCB) were banked at Passages 139 and 143 respectively. The cells were further expanded a maximum of 11 passages to Passage 154 during cell expansion in stationary cultures prior to seeding of the bioreactor used for virus production. The estimated number of population doublings in the bioreactor is calculated to be 1 to 3.

Preparation of Master and Working Virus Seeds:

FIG. 2 is a schematic representation of the preparation of Virus seeds according to an embodiment of the invention.

An important safety factor for the disclosed vaccine is the use of the attenuated YF 17D vaccine for manufacture. The attenuated virus used as a starting material was a commercial vaccine, YF-VAX® (Sanofi Pasteur, Swiftwater Pa.) which had undergone various tests for adventitious agents. The original YF-VAX® material used to inoculate Vero cells was derived from embryonated hens' eggs, and contained hydrolyzed porcine gelatin as a stabilizer. However, the likelihood of carry-over of an adventitious agent from eggs was mitigated by use of RNA transfection to produce the Pre-Master Virus Seed.

The cells were propagated in OptiPro-SFM medium (Invitrogen, Grand Island, N.Y.). To develop the modified Yellow Fever (YF) virus that will grow to high titers in Vero cells, initially the YF-17D virus at a 0.01 multiplicity of infection (MOI) was used to infect a T-25 flask with a confluent layer of Vero cells. The cell culture was incubated at 37° C. and 5 percent $CO_2$.

Figure 3A:
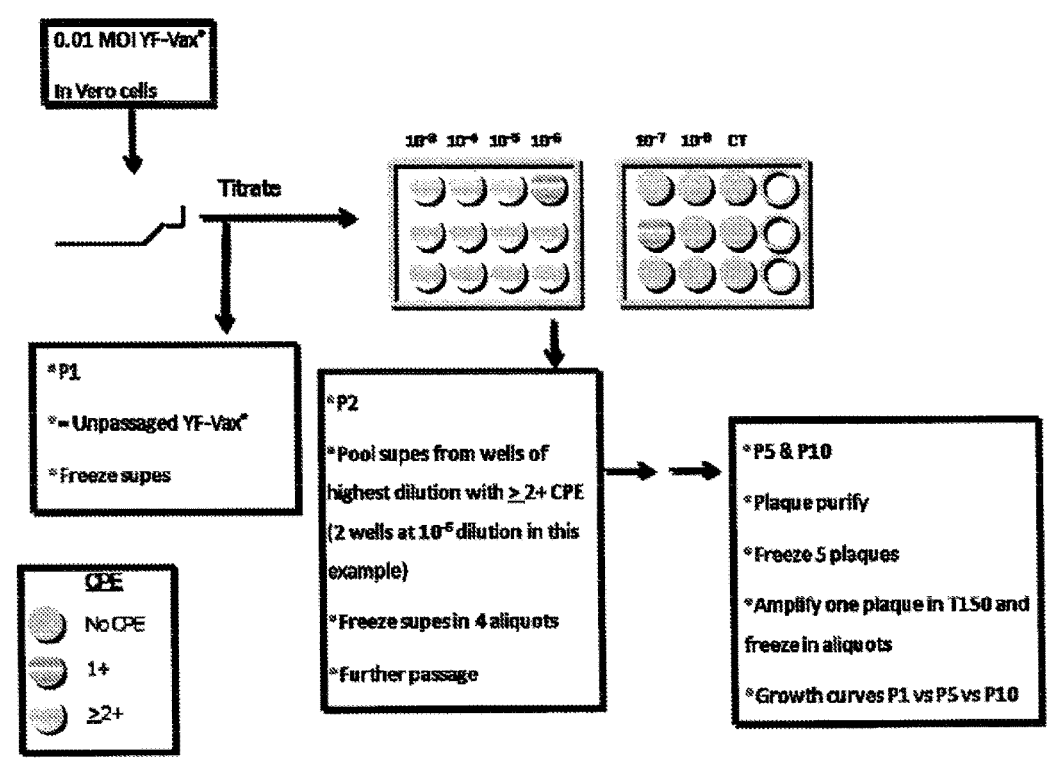
Figure 3C:
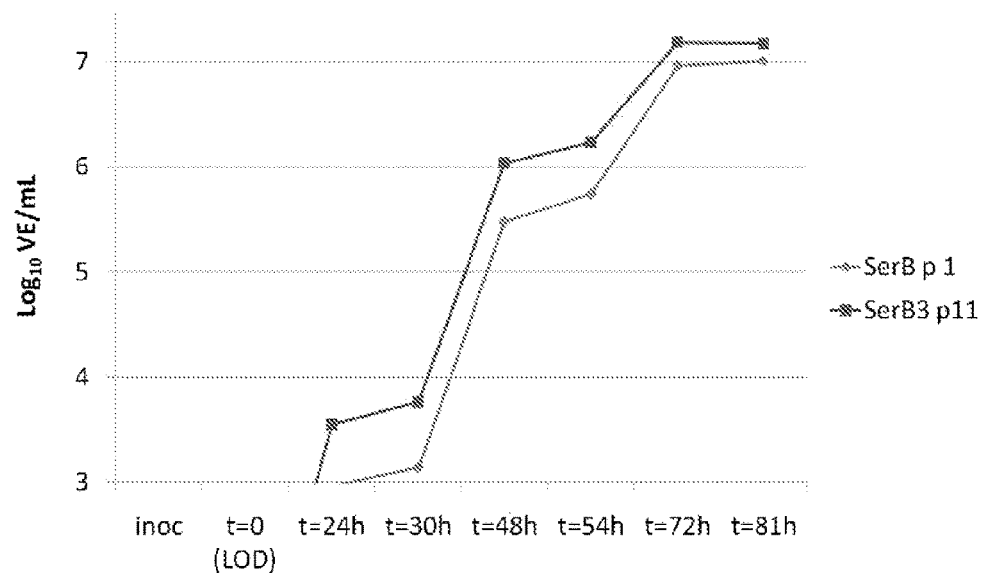
FIG. 3C is a graphical representation of a repeat passaging study of passage one (Bp1, Cp1) and passage 11 (B-p11, C-p11) virus performed in a series of experiments: Series B and C.
Figure 3C:
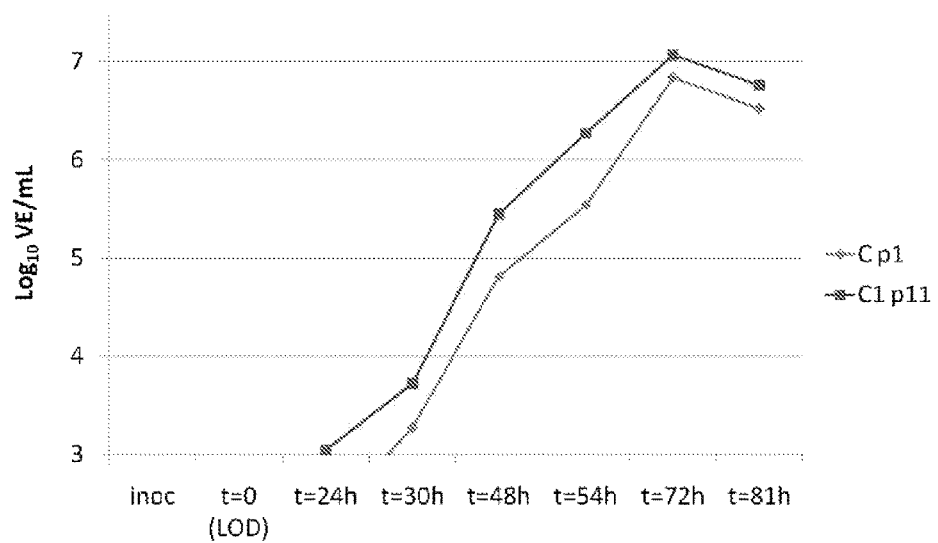

Once cytopathic effect (CPE) was observed in about 2+(50%) of the cells, aliquots of the culture were prepared, labeled as passage one (P1) and stored at −80° C. for use as the inoculum to continue the serial passages. A schematic of the procedure used to make P1 through P10 is shown in FIG. 3A.

An aliquot of the Passage 1 (P1) virus was diluted $10^{-1}$ through $10^{-8}$ and each dilution was inoculated onto confluent monolayers of three (3) Vero cell cultures propagated in sterile 12 well plates from which growth medium had been removed.

$Log_{10}$ dilutions were prepared by transferring 0.2 ml of virus to 1.8 ml of phosphate buffered saline (PBS) to equal a $10^{-1}$ dilution. The virus plus PBS was mixed and then a new pipette was used to transfer 0.2 ml to 1.8 ml of $PBS=10^{-2}$, and then repeated through $10^{-8}$ dilution. Twelve well confluent monolayers of Vero cell culture were labeled and $log_{10}$ dilutions of the P1 material (negative control, $10^{-1}$ (3 wells), $10^{-2}$ (3 wells), $10^{-3}$ (3 wells), $10^{-4}$ (3 wells), $10^{-5}$ (3 wells), $10^{-6}$ (3 wells), $10^{-7}$ (3 wells) and $10^{-8}$ (3 wells) were prepared and inoculated onto medium-free cultures using a new pipette for each dilution of inoculum. The negative control cultures were inoculated with a similar volume of PBS. After inoculating the cultures they were incubated at 37° C. for 1 hour with intermittent rocking and then 1.0 ml of maintenance medium was added per culture. Cells were observed each day for cytopathic effect (CPE) and recorded as 1+(25% of the cell monolayer effected), 2+(50% of the cell monolayer effected), 3+(75% of the cell monolayer effected) and 100% (all of the cell monolayer effected). Estimates of CPE were based on a comparison with the control cells. The plaque assay was also performed on the same dilutions of inoculum to verify that the CPE represented viral infectivity.

Once CPE (2+) developed in these cultures, five 0.5 ml aliquots of the medium were harvested from the cultures that received the highest dilution or next to the highest dilution of inoculum. The five aliquots were prepared and stored as passage 2 (P2) at −80° C. The strategy was to select the virus population that replicated at or near the highest $log_{10}$ dilution based on the appearance of CPE in the cells. As such, the virus population selected would be the population that was best adapted to replicate in the cells with possible genetic changes that will allow for an increase in viral titer.

Subsequently, $log_{10}$ dilutions were prepare of an aliquot of the P2 virus and used to infect cultures of Vero cell propagated in 12-well plates as described for passage one YF virus. Similar methods were employed to complete 10 serial passages of the virus.

P10 and P11:

At each serial passage, each of the aliquots used as the inoculum was also tested to determine the infectivity titers by plaque assay in Vero cells. At passage 10, five single, well isolated plaques, each representing progeny from a single infectious virus particle, were selected at the highest dilution that yielded plaques. Each plaque was suspended in 0.3 ml of medium containing Human Serum Albumin (HSA) to protect the virus infectivity during freezing and stored at −80° C.

The series of passages (P1 to P10) of the YF 17D virus in Vero static cultures at dilutions of $10^{-1}$ to $10^{-8}$ were performed at the University of Texas Medical Branch (Galveston, Tex.). The strategy was to select the virus population that replicated at or near the highest log 10 dilution based on the microscopic appearance of CPE in the Vero cells. The virus population that showed cytopathic effects at the highest dilution, the P10 harvest, was selected as the optimized, "high-yield" virus. The high yield virus population that showed CPE at the highest dilution was sequenced.

The High Yield Virus:

The "high yield" virus was adapted for increased replication in Vero cells by 10 serial virus passages at terminal dilution in Vero cells. At Virus Passage 10, a single plaque forming unit was picked and passed in fluid culture to produce a mini-seed stock at Virus Passage 11. The graph in FIG. 3B shows comparative growth curves of P1 and P11 viruses, that had been inoculated at high MOI; the data indicate that the P11 virus has a higher peak titer than the P1 virus. This virus (P11) showed a 3-7 fold increased replication capacity in in Vero cells compared to the YF 17D at Virus Passage 1. The Virus Passage 11 virus stock was used for RNA extraction and the RNA used to produce cGMP grade virus seeds.

RNA Sequence of the Vero Adapted 17D Virus (P11)

The full genomic consensus sequences of the viruses at P1 and P11 from the original YF-VAX® were determined Two genetic mutations or nucleotide differences were found, as shown in Table 1 below. One nucleotide difference lies in the capsid (C) gene and one in the envelope (E) gene. The term "capsid" as used herein, refers to the shell of protein that surrounds and protects the nucleic acid of a virus. The change in the C gene was silent (no amino acid change), whereas the E gene mutation resulted in an amino acid (Lys→Arg) mutation.

TABLE 1

RNA sequence and mutations in the YF 17D virus adapted to Vero cells

| NT residue # | Nucleotide Change | | Amino Acid Change | | Location | Codon | |
|---|---|---|---|---|---|---|---|
| | P1 | P11 | P1 | P11 | | P1 | P11 |
| 211 | A | G | Threonine | Threonine | C31 | ACA | ACG |
| 1452 | A | G | Lysine | Arginine | E160 | AAG | AGG |

The first mutation was an A to G conversion at nucleotide residue #211, according to SEQ ID NO: 1, which resulted in a change in the codon for the amino acid at position 31 of the capsid protein (C31) from ACA to ACG. This mutation, however, did not change the amino acid residue at this position. The second mutation was an A to G conversion at nucleotide residue #1452, according to SEQ ID NO: 1, which resulted in a change in the codon for the amino acid at position 160 of the envelope protein (E160) from AAG to AGG. This mutation resulted in a Lysine to Arginine substitution at this position. A consensus alignment of the nucleic acid and amino acid sequences for P1 and P11 are depicted in FIGS. 4 and 5.

Plaque Purification of P10 Harvest:

As described above, virus from P10 was purified by plaque formation. The virus isolated from one plaque was inoculated into a T 150 flask. The conditioned medium from this flask was harvested when 50 percent of the cells exhibited CPE. This material was aliquoted in one mL aliquots and designated P11. The P11 virus was then used as the source of RNA for transfection of Vero cells. The P11 titer of plaque forming units was determined to be $8.5 \times 10^7$ plaque forming units (PFU). The RNA isolated from the P 11 virus was used to transfect cells to produce a Pre-Master Seed. The Pre-Master Seed virus was passaged in additional cultures of Vero cells to produce a Master and Working Virus Seed stock.

Manufacture of Master Virus Seed:

The Master Virus Seed (MVS) was produced in Vero cells under serum-free conditions using a single vial of the Pre-Master Seed as the virus inoculum, as represented schematically in FIG. 2. Cells from the Manufacturer's Working Cell Bank (MWCB) of Vero cells at Passage 143 were expanded to eleven (11) 225 $cm^3$ T-flasks. Once the cells became confluent, one flask was trypsinized and used to determine cell number and also to seed additional flasks used to produce the Working Virus Seed. The OptiPRO™ SFM medium was removed from the remaining 10 T-flasks and the cells were inoculated with Pre-Master Seed virus at a multiplicity of infection (MOI) ~0.01 PFU/cell. The virus was allowed to adsorb for 60 (±5) minutes at 37°±2° C., after which pre-warmed OptiPRO™ SFM medium was added to the flasks. The infected culture was then incubated at 37°±2° C. with ~5% $CO_2$.

After 3 days, when CPE was observed in ≥80% of the cell population, the virus propagation process was terminated by harvesting the cell culture fluid. The virus-containing culture fluid was pooled from all flasks, centrifuged to remove cell debris, and mixed with sterile 70% sorbitol to a final sorbitol concentration of 7%. This mixture was filled into 4 mL cryovials at 2 mL per vial and frozen at ≤−60° C. The frozen virus stock constitutes the YF 17D MVS.

As shown in FIG. 2, the highest Vero cell passage level used for production of the MVS was 147.

Manufacture of Working Virus Seed:

The Working Virus Seed (WVS) was produced as shown in FIG. 2, from a single vial of the MVS under cGMP conditions. Starting with cells in the 11th T225 flask used to determine the cell density in the production of MVS, four T225 flasks were seeded at a cell density $1 \times 10^6$ viable cells per flasks, Passage 147. The cells were passaged into 4 new T225 flasks to allow time for the production of the Master Seed Stock. Cells at Passage 148 were then seeded into eleven T225 flasks for the production of the WVS.

When the cells were greater than 80% confluent, the cell density in one flask was determined. This cell density was used to estimate the cell density in the remaining ten flasks and the cells in the 10 flasks were infected with virus from the MVS at a MOI of 0.01 PFU/cell. To perform the infection, the medium was removed from the flasks and then diluted virus was added in phosphate buffered saline. After one hour fresh medium was added to each flask and the cells were returned to the incubator. The cells were observed microscopically for CPE. When CPE was greater than 80% the virus was harvested. The medium from the 10 flasks was centrifuged to remove cellular debris and the clarified supernatant was pooled into one vessel. Sorbitol (final concentration 7%) was added to the virus-containing supernatant as a cryo-preservative. The pooled virus was aliquoted into 4 mL cryovials, two mL per vial. The filled vials were stored at ≤−60° C. Once frozen, one vial from the end of the bank was tested in a plaque assay in Vero cells to determine the virus titer.

Increase in Titer Achieved in P11 Compared to P1:

The original YF virus and P11 harvest of YF virus were titrated by plaque assay in Vero cells to determine the infectivity titers expressed as plaque forming units (PFU) (Table 1). The original YF-VAX 17D vaccine contained $10^{3.7}$ $log_{10}$ per ml in Vero cells. The peak titer for passage one was 6.68 $log_{10}$ per ml and remained at about the same titer through P6 and then increased significantly to 7.67 $log_{10}$ by P10. Thus, in this experiment, there was a 1.0 $log_{10}$ (10-fold) increase in the titer of the passage 10 (7.67 $log_{10}$) over the titer (6.68 $log_{10}$) of the P1 virus (see Table 2).

Virus growth curves were also performed concurrently on the P1 and P11 viruses. Growth curves was performed by infecting duplicate 75 $cm^2$ flasks of Vero cells at high MOI of 1.0 and a second growth curve was performed using a low MOI of 0.001. At high MOI it is expected that all cells are infected at initiation of the culture, while at low MOI, virus released by a small number of cells initially infected would infect the remaining cells of the culture; thus, virus in a low-MOI growth curve would be expected to be somewhat delayed compared to a high-MOI culture. At times 0, 6, 18, 24, 30, 48, 54 and 72 hr post inoculation, conditioned medium (2 mL) was removed from the cultures, stabilized with 2% HSA and frozen (duplicate one ml samples) at −80° C. $Log_{10}$ dilutions of each sample were tested in Vero cells to determine the infectivity titer and the growth curves were plotted over time.

TABLE 2

Peak infectivity titer for each sequential passage of YF virus

| Passages of YF-VAX in Vero cells | Highest Dilutions yielding plaques | Average # of plaques | Peak infectivity titer (PFU/ml) | Conversion of plaque forming units to equal the infectivity titer in $log_{10}$ PFU per ml |
|---|---|---|---|---|
| 0 | $10^{-3}$ | 1 | $5 \times 10^3$ | 3.7 |
| 1 | $10^{-5}$ | 9.67 | $4.83 \times 10^6$ | 6.68 |
| 2 | $10^{-5}$ | 12.67 | $6.33 \times 10^6$ | 6.80 |
| 3 | $10^{-4}$ | 21.67 | $1.08 \times 10^6$ | 6.03 |
| 4 | $10^{-5}$ | 12.67 | $6.33 \times 10^6$ | 6.80 |
| 6 | $10^{-6}$ | 1.00 | $5.00 \times 10^6$ | 6.70 |
| 8 | $10^{-6}$ | 3.00 | $1.50 \times 10^7$ | 7.18 |
| 9 | $10^{-6}$ | 5.67 | $2.83 \times 10^7$ | 7.45 |
| 10 | $10^{-6}$ | 9.33 | $4.67 \times 10^7$ | 7.67 |

The growth curve results using an MOI of 1.0 indicated that the P1 YF virus increased from a titer of 4.09 $log_{10}$ at 0 hours; or at the time of inoculation to a maximum titer of 6.28 $log_{10}$ at 48 hours post inoculation (PI) and the titers showed a slight decrease of 6.21 and 6.18 $log_{10}$ at 60 and 72 hours PI, respectively. The results for passage 11 (P11) showed an increase in titers over the passage one virus (P1). At the time of inoculation, the titer was 4.15 $log_{10}$ and reached a maximum titer of 6.83 $log_{10}$ at 48 hours P.I. and had decreased to a titer of 6.54 $log_{10}$ at 72 hours P.I (see Table 3). The peak virus titer at approximately 48 hours for the P11 virus was 0.55 $log_{10}$ or 3.5 times higher than for the P1 virus.

TABLE 3

Growth curve of Yellow Fever 17D Passage 1 and Passage 11 virus at high MOI (1.0)

| | Time points (hr) | | | | | | | |
|---|---|---|---|---|---|---|---|---|
| | 0 | 6 | 18 | 24 | 30 | 48 | 54 | 72 |
| Passage 1 | 4.15 | 4.11 | 5.63 | 6.09 | 6.05 | 6.28 | 6.21 | 6.18 |
| Passage 11 | 4.09 | 4.22 | 5.60 | 6.27 | 6.63 | 6.83 | 6.68 | 6.54 |
| P1 STDEV | 0.11 | 0.02 | 0.17 | 0.08 | 0.05 | 0.03 | 0.05 | 0.04 |
| P11 STDEV | 0.04 | 0.08 | 0.21 | 0.02 | 0.10 | 0.14 | 0.18 | 0.10 |

As compared to the growth curve using high MOI, the pattern of the growth curve using an MOI of 0.001 showed a lag in replication but maximum titers were higher. At the time of inoculation, the titers were 1.7 and 0.57 $\log_{10}$ for the passage 1 and 11, respectively. There was a linear increase in titers and by 72 hours PI, maximum titers of 7.35 and 8.17 $\log_{10}$ had been attained by P1 and P11, respectively. The peak virus titer at approximately 72 hours for the P11 virus was 0.82 $\log_{10}$ or 6.6 times higher than for the P1 virus. These results indicated that the serial passage of YF-VAX produced a substantial increase in titer and that this approach appears to be promising for developing an inactivated YF vaccine (see Table 4).

TABLE 4

Growth curve of Yellow Fever 17D Passage 1 and Passage 11 virus at low MOI (0.001)

| | Time points (hr) | | | | | | | |
|---|---|---|---|---|---|---|---|---|
| | 0 | 6 | 18 | 24 | 30 | 48 | 54 | 72 |
| Passage 1 | 1.70 | 2.00 | 2.57 | 4.14 | 4.72 | 6.44 | 7.19 | 7.35 |
| Passage 11 | 0.57 | 0.67 | 3.01 | 4.44 | 5.18 | 7.04 | 7.38 | 8.17 |
| P1 STDEV | 0.00 | 0.30 | 0.19 | 0.07 | 0.06 | 0.04 | 0.02 | 0.03 |
| P11 STDEV | 0.98 | 1.15 | 0.14 | 0.05 | 0.05 | 0.02 | 0.10 | 0.10 |

These results indicated that the serial passage of the YF virus produced a substantial increase in titer. Next, as described above, the sequence analysis of P1 and P11 was performed, the comparative results of which show that the serial passages may have resulted in two genetic mutations in the YF virus, one of which resulted in an amino acid change.

The disclosed modified YF virus produced by the serial passage of the attenuated YF 17D virus vaccine in certified African green monkey kidney cells (Vero) showed enhanced productivity in cells. The methods of the invention involve vaccination of subjects with the modified, inactivated YF virus to produce immunity to Yellow Fever.

Vaccine Production in Bioreactors:

Bioreactors containing approximately 5 g/L of Cytodex 1 microcarriers were seeded with approximately $5 \times 10^5$ Vero cells/mL in OptiPRO™ SFM medium. The cells were allowed to propagate for 3 to 4 days until cells attached to the microcarriers achieved a density of $\geq 7 \times 10^5$ nuclei per mL. For virus inoculation, the agitation and parameter controls are turned off and the microcarriers and cells are allowed to settle. Approximately 75% of the medium volume was removed through a 90 μm sieve tube which is designed to retain microcarriers in the reactor. WVS virus is introduced at a MOI of ~0.01 PFU/cell. Low agitation was applied at this low volume for about 1 hour to allow virus to adsorb to and infect cells. Fresh medium was added to the full volume before agitation and parameter controls are returned to their original settings. On day 3 or 4 post infection, 75% of the conditioned medium was removed, and the reactor was re-fed with fresh medium. The culture was allowed to proceed for 2 or 3 more days and on Day 5, 6, or 7 post infection the conditioned medium was harvested. To ensure biosafety, harvest samples were taken from the bioreactor immediately before microcarrier removal and tested for sterility, mycoplasma, retroviruses and adventitious viruses (in vitro assay).

The reactor mixing was stopped to allow for settling of the microcarriers. The culture is transferred from the bioreactor through a 90 μm sieve tube into a bioprocess bag. The 90 μm sieve reduces the amount of microcarriers and large particulates from transferring into the harvest. This was the Virus Harvest. The Virus Harvest was sampled and tested for infectivity, potency, identity, endotoxin, sterility, residual Vero cell DNA, and residual Vero cell proteins.

Virus Purification and Inactivation:

The culture conditioned medium was harvested, clarified in two steps, digested with BENZONASE®, purified by ultrafiltration and diafiltration and then sterile filtered to generate the Live Virus Bulk. The Live Virus Bulk was then inactivated by treatment with β-propiolactone (BPL) which permeates the virus envelope and disrupts the viral RNA by alkylating purine residues, rendering the virus inactive. The inactivated virus is further purified by cellufine sulfate column chromatography and diluted to the desired viral concentration to form the Bulk Vaccine Drug Substance.

Repeat of YFV 17D Passaging Study:

Experiments were performed to repeat the passage of YF virus from unpassaged virus stock through P11 using similar techniques as in the original passage series.

Preparation of the Virus Stocks:

Vero cells were maintained under serum-free conditions throughout the study, using OptiPRO SFM.

The initial source of the YFV 17D virus was from a single vial of YF-VAX® (Sanofi Pasteur, Swiftwater Pa.). The vial was originally reconstituted and dispensed into aliquots. One of these aliquots was used for the repeat experiments. The repeat serial passaging was performed in duplicate such that there were two runs of the study, performed in parallel, referred to here as series B and C.

At each passage of the virus, the virus sample was diluted in serial 10-fold dilutions, and the diluted virus was used to inoculate Vero cells seeded in 12 well plates. The serial dilutions performed at each passage were inoculated in duplicate such that one set of plates was used for the preparing the next passage of virus, inoculating 4 wells per dilution, and the other set of plates was used to determine the titer of the passaged virus, inoculating 2 wells per dilution.

For the serial passages of the virus, the dilution selected for passaging the virus was the last dilution where generalized cytopathic effect (CPE) was observed, three to four days after infection. The media from the four wells was pooled for the next passage. The titer of the virus was determined by plaque assay using an immunostain to visualize and count the plaques. The immunostain method allowed for determining the titer after 3 days of infection.

For the initial passage of the virus, 0.3 ml of the YF-VAX aliquot was diluted into 3 mL final, using OptiPRO SFM, for a $10^{-1}$ dilution. The diluted virus was divided equally into three aliquots. From each of these aliquots, serial 10-fold dilutions were made to $10^{-5}$, making two dilution series (B and C). This is referred to here as the P0→P1 passage. From the plaque assay inoculated using the dilution series, of the P0 virus was determined, and for the plates inoculated for passage, the P1 virus was generated. Each round of the passaging is summarized in the Table 5.

TABLE 5

Serial Passages of YFV 17D (Results same for series B and C)

| Passage | Dilutions plated | Dilution harvested for next passage |
|---|---|---|
| P0 (initial vial) | N/A | N/A |
| P0 → P1 | $10^{-1}$ to $10^{-5}$ | $10^{-3}$ |
| P1 → P2 | $10^{-2}$ to $10^{-7}$ | $10^{-5}$ |
| P2 → P3 | $10^{-3}$ to $10^{-8}$ | $10^{-5}$ |
| P3 → P4 | $10^{-3}$ to $10^{-9}$ | $10^{-5}$ |
| P4 → P5 | $10^{-3}$ to $10^{-9}$ | $10^{-5}$ |
| P5 → P6 | $10^{-3}$ to $10^{-9}$ | $10^{-4}$ |
| P6 → P7 | $10^{-3}$ to $10^{-9}$ | $10^{-5}$ |
| P7 → P8 | $10^{-3}$ to $10^{-7}$ | $10^{-4}$ |
| P8 → P9 | $10^{-3}$ to $10^{-7}$ | $10^{-5}$ |
| P9 → P10 | $10^{-3}$ to $10^{-7}$ | $10^{-5}$ |

The passaging was repeated for 10 serial passages of the virus. Once the virus was harvested from the last passage, the titers were generated for the P10 virus from each series. The P10 viruses were then diluted for inoculating cells such that only one plaque per well would develop after inoculation. Well-isolated plaques could then be picked from the wells. From the B series, six well-isolated plaques were picked, and from C, two were picked. The picked plaques were used to inoculate T25 flasks to generate the P11 virus stocks for growth curve studies.

Growth Curve Analysis:

For the growth curve studies, the P1 stock virus from each series was compared to the P11 stocks for each series. Since the volume of the P1 stocks would have been limiting for this, an aliquot of P1 virus from each series was diluted three-fold, then aliquots made from the diluted virus to generate P1 stocks for the growth curve. For the P11 stocks, three stocks from the B series were analyzed, and the two from the C series. Prior to the growth curve studies, aliquots of the virus stocks were assayed to confirm the level of infectivity.

The growth curve analysis was performed by infecting Vero cells in T25 flasks, at low MOI of 0.001 PFU/cell. The study was conducted under serum free conditions using OptiPRO SFM as the culture medium. After diluting the virus stocks to achieve the target 0.001 MOI, a sample was reserved to confirm the titer of the inoculum. The virus inocula were allowed to adsorb to the cells for approximately one hour. After adsorption, the monolayers were washed three times then the cultures were fed with 8 ml of medium. At each time point, 1 mL was removed from each culture, and 1 mL fresh media was added back. The reserved one mL of medium was clarified by centrifugation and stored at −80° C. in the presence of sorbitol, until ready to assay. The time points for which samples were taken were 0, 24, 30, 48, 54, 72, and 81 hours after infection. A plaque assay was performed on all samples. The results of the study are detailed in FIG. 3C.

For both the B and C series, there was one P11 virus stock that was shown to replicate to higher titers than the P1 virus stock from the series. The P1 stocks for both B and C, and the B3-P11 stock and the C1-P11 stock were selected for sequence analysis. The sequence analysis illustrates that the B3 stock enjoys the same Lys→Arg mutation at E160 as was observed in the original passage series, as well as a Threonine (Thr)→Isoleucine (Ile) mutation at amino acid position 317 in non-structural protein 1 (NS1-317), and a Phenylalanine (Phe)→Leucine (Leu) mutation at amino acid position 170 in non-structural protein 2A (NS2A-170). While, the C1 stock did not carry the same mutation in the E gene, further study of the C1 stock genome is ongoing, and has revealed a mutation at amino acid position 113 in non-structural protein NS4B (NS4B-113).

Table 6 summarizes the nucleotide and amino acid changes found in the modified Yellow Fever viruses obtained from the original and repeat passage studies.

TABLE 6

Nucleotide and amino acid changes in the consensus sequence between passage 1 (P1) and P11 in three separate passage series of yellow fever 17D vaccine (YF-VAX®) in Vero cells. The position of the altered nucleotide or amino acid in the designated viral protein (or non-coding region, NCR) is shown. Some nucleotide changes were silent (did not result in corresponding amino acid mutations).

| Protein | Original passage series | | Repeat Series B | | Repeat Series C | |
|---|---|---|---|---|---|---|
| | Nucleotide | Amino acid | Nucleotide | Amino acid | Nucleotide | Amino acid |
| 5'NCR | | | | | | |
| prM | | | | | | |
| E | 211 A→G | | 211 A→G | | | |
| | 1452 A→G | 160 K→R | 1452 A→G | 160 K→R | | |
| | | | 1507 T→C | | | |
| | | | | | 1897 G→A | |
| NS1 | | | 3402 C→T | 317 T→I | | |
| NS2a | | | 4016 T→C | 170 F→L | | |
| NS2b | | | | | | |
| NS3 | | | | | | |
| NS4a | | | | | | |
| NS4b | | | | | 7225 A→G | 113 I→M |
| NS5 | | | | | | |
| 3'NCR | | | 9343 G→A | | | |
| | | | | | 9670 C→T | |

Non-Limiting Aspects of the Invention:

A Yellow Fever viral strain was produced to develop a safer, inactivated, non-replicating vaccine that will elicit a neutralizing antibody response while eliminating the potential for neurotropic and viscerotropic adverse events for the prevention of human disease. Additional Yellow Fever virus strains are produced to develop safer, inactivated, non-replicating vaccines that will elicit a neutralizing antibody response while eliminating the potential for neurotropic and viscerotropic adverse events for the prevention of human disease. These embodiments of the invention are set forth above in the Summary.

The invention provides a modified Yellow Fever virus strain, wherein the nucleic acid molecule of said strain comprises an amino acid mutation at one or more positions flanking the 160 mutation, for example residues 134, 137, 144, 148, 157, 160, 175, 177 of the envelope protein. In an embodiment of this aspect, the invention provides a modified Yellow Fever virus strain, wherein the nucleic acid molecule of said strain comprises at least one amino acid mutation selected from: an amino acid mutation in the NS1 protein, an amino acid mutation in the NS2A protein, an amino acid mutation in the NS4B protein, optionally wherein said at least one amino acid mutation is in further combination with an amino acid mutation at one or more positions 134, 137, 144, 148, 157, 160, 175, 177 of the envelope protein. In a further embodiment of this aspect, the amino acid mutation(s) at position 157 is lysine to arginine; at position 148 is lysine to arginine; at position 144 is histidine to arginine, tyrosine or lysine; at position 137 is tyrosine to arginine or lysine, at position 175 is tyrosine to arginine or lysine; and/or at position 177 is lysine to arginine.

The invention also provides a modified Yellow Fever virus strain, wherein the nucleic acid molecule of said strain comprises an amino acid mutation at one or more positions flanking the 160 mutation, for example residues 134, 137, 144, 148, 157, 160, 175, 177 of the envelope protein, in combination with mutations at one or more positions 317 of NS1, 170 of NS2A, 113 of NS4B. In an embodiment of this aspect, the amino acid mutation(s) in the envelope protein at position 157 is lysine to arginine; at position 148 is lysine to arginine; at position 144 is histidine to arginine, tyrosine or lysine; at position 137 is tyrosine to arginine or lysine; at position 175 is tyrosine to arginine or lysine; and/or at position 177 is lysine to arginine; and the amino acid mutation in NS1 at position 317 is threonine to isoleucine, in NS2A at position 170 is phenylalanine to leucine, in NS4B at position 113 is isoleucine to methionine.

In embodiments according to certain aspects of the invention, the cells are selected from Vero cells. Other cells suitable for propagation of the Yellow Fever virus may utilized, including but not limited to, primary chick embryo, primary duck embryo, primary dog kidney, primary rabbit kidney, WI-38, MRC-5, or fetal rhesus lung.

In some embodiments of these aspects, the nucleotide mutation in the codon for the amino acid at position 160 of the envelope protein results in a change from AAG to AGG, AGA, CGC, CGA, CGG or CGU. In other embodiments of these aspects, the amino acid mutation at position 160 is lysine to arginine.

In still other embodiments of these aspects, the nucleotide mutation in the codon for the amino acid at position 317 of NS1 results in a change from ACA to AUA, the nucleotide mutation in the codon for the amino acid at position 170 of NS2A results in a change from UUU to CUU, the nucleotide mutation in the codon for the amino acid at position 113 of NS4B results in a change from AUA to AUG. In other embodiments of these aspects, the amino acid mutation at position 317 of NS1 is threonine to isoleucine, at position 170 of NS2A is phenylalanine to leucine, at position 113 of NS4B is isoleucine to methionine.

In the methods according to the various aspects of the invention, the Yellow Fever virus or vaccines of the invention can be administered in amounts and by using methods that can readily be determined by persons of ordinary skill in this art. The chemically inactivated viral vaccines can be administered and formulated, for example, as a sterile aqueous solution containing between $10^2$ and $10^8$, e.g., or between $10^6$ and $10^7$, inactivated equivalents of infectious units (e.g., plaque-forming units (PFU) or tissue culture infectious doses) in a dose volume of from about 0.1 to about 1.0 ml, or about 0.5 ml. to be administered by, for example, subcutaneous, intramuscular, epidermal, or intradermal routes. In addition, in an appropriate formulation, a mucosal route, such as the intranasal oral route, can be selected. Selection of an appropriate amount of virus to administer can be determined by those of skill in this art, and this amount can vary due to numerous factors, e.g., the size and general health of the subject to whom the virus is to be administered. The subject can be vaccinated a single time or, if necessary, follow-up immunization can take place.

As is noted above, the vaccines can be administered as primary prophylactic agents to a subject that is at risk of Yellow Fever virus infection. Also, although not required, adjuvants can be used to enhance the immunogenicity of the Yellow Fever virus vaccines. Selection of appropriate adjuvants can readily be carried out by those of skill in this art.

Also as is noted above, the live virus can be inactivated by treatment with β-propiolactone (BPL), rendering the virus inactive. Other suitable methods of virus inactivation include, but are not limited to, formalin, ultraviolet radiation, ethylenimine, acetylethylenimine, and binary ethylenimine

EXEMPLIFICATION

The examples below are intended to further illustrate certain preferred embodiments of the invention, and are not intended to limit the scope of the invention.

Antibody Responses in Mice:

The neutralizing antibody responses in female, outbred BALB/c and CD-1 mice after immunization with inactivated yellow fever vaccine compared to live virus was assessed. Yellow fever (YF) virus was inactivated with beta propiolactone (BPL), formulated with alum adjuvant and injected by the intramuscular route as two or three doses, each separated by 14 days. Two dose levels of virus were tested in BALB/c mice, the high dose level only was tested in CD1 mice. Sera taken at 14 days after the last immunization were tested for neutralizing antibody activity.

Preimmunization Procedures:

Female BALB/c and CD-1 strain mice (6 weeks of age) were acclimated in designated isolators in a restricted virus animal facility. Serum sample were collected Study Day 28 or 42 upon sacrifice. Mice were housed at 5 mice per cage and each animal was uniquely identified on the cage cards, and by ear notch. Mice were acclimated for a week prior to the initiation of any treatments. Mice received sterilized food and water and were housed in sterilized polycarbonate cages with sterilized bedding with a 12-hour light cycle (on at 6 am and off at 6 pm). General health was evaluated by technical staff daily and by a veterinarian weekly and as needed for health issues. Body weights were collected on Day 0 prior to immunization and on Day 28 and 42.

Immunization Procedure:

Body weight was determined on Day 0 prior to immunization Immunization was given by either the i.m. (alum formulations) or s.c. (live virus or inactivated vaccine with Freund's adjuvant) route. Injections were given with mice under light anesthesia with suboptimal dose of ketamine/xylazine mixture. For s.c. route with live virus, a volume of 100 μl of vaccine in a 1 ml syringe fitted with a 27 gauge needle is injected between the skin and underlying layers of tissue in the scapular region on the backs of mice. For i.m. administration, a volume of 100 μl of vaccine in a 0.5 ml insulin syringe is injected into the muscle bundles of 2 rear upper legs of mice (50 μl/leg).

(approximately 8 to 10 minutes). A 0.5 ml volume was delivered s.c. between the skin and underlying layers of tissue in the scapular region on the backs of mice (Formulation with Freund's adjuvant).

Live Yellow Fever (YF Vax™) vaccine was reconstituted with 0.6 ml of supplied saline to a virus concentration of approximately $1.1 \times 10^5$ PFU/ml.

The inactivated whole virion vaccine adsorbed to 0.2% aluminum hydroxide ("alum") adjuvant was prepared no more than 2 weeks prior to day of dosing.

Preliminary Mouse Studies

Groups of 5 mice each were dosed with as outlined in Table 7. Serum samples were collected by cardiac puncture 14 or 28 days post last vaccination.

TABLE 7

| Group | # Mice | Strain | Vaccine (Volume = 0.1 ml) | Route | Vaccination schedule | Neut. Ab |
|---|---|---|---|---|---|---|
| 1 | 5 | BALB/c | $10^8$ BPL-inactivated in 0.2% alum | IM | Day 0, 14 | Day 28 |
| 2 | 5 | BALB/c | $10^8$ BPL-inactivated in 0.2% alum | IM | Day 0, 14, 28 | Day 42 |
| 3 | 5 | BALB/c | $10^7$ BPL-inactivated in 0.2% alum | IM | Day 0, 14 | Day 28 |
| 4 | 5 | BALB/c | $10^7$ BPL-inactivated in 0.2% alum | IM | Day 0, 14, 28 | Day 42 |
| 5 | 5 | BALB/c | $10^8$ BPL-inactivated in Freund's complete/incomplete | SC | Day 0, 14, 28 | Day 42 |
| 6 | 5 | BALB/c | $10^7$ BPL-inactivated Freund's complete/incomplete | SC | Day 0, 14, 28 | Day 42 |
| 7 | 5 | BALB/c | $10^8$ BPL-inactivated no adjuvant | IM | Day 0, 14, 28 | Day 42 |
| 8 | 5 | BALB/c | Live YF Vax® | SC | Day 0 | Day 28 |
| 9 | 5 | CD1 | $10^8$ BPL-inactivated in 0.2% alum | IM | Day 0, 14 | Day 28 |
| 10 | 5 | CD1 | $10^8$ BPL-inactivated in 0.2% alum | IM | Day 0, 14, 28 | Day 42 |
| 11 | 5 | BALB/c | 0.2% alum | IM | Day 0, 14, 28 | Day 42 |

Sacrifice:

Mice were sacrificed 28 or 42 days after the first vaccination. Body weight was determined on all mice on Study Day 28 and prior to sacrifice. Blood was collected for neutralizing antibody testing. Blood (0.7-1.0 ml) was removed by cardiac puncture from mice anesthetized with light ketamine/xylazine treatment before they are humanely terminated by ketamine/xylazine overdose.

Experimental Design:

Alum-formulated vaccine prepared the day prior to immunization as a suspension and the vaccine was well mixed prior to filling each syringe. Alum-formulated preparations were administered by the i.m. route, a volume of 100 μl of vaccine in a 0.5 ml insulin syringe was injected into the muscle bundles of 2 rear upper legs of mice (50 μl/leg).

Live Yellow Fever (YF) vaccine was reconstituted with 0.6 ml of saline to a virus concentration of approximately $1.1 \times 10^5$ pfu/ml. A dose of $1 \times 10^4$ PFU (i.e. $1/10^{th}$ the human dose) was delivered in a volume of 100 μl of sterile saline administered on day 0 s.c.

Freund's adjuvanted vaccine was formulated the day of vaccination by placing 2 ml of antigen solution into a glass syringe, and 2 ml of the adjuvant into another glass syringe. The syringes were connected through the luer fitting to the 3-way valve. The plunger from the antigen solution was carefully depressed first, pushing the antigen into the oil of the adjuvant. The plungers were alternately pushed, to mix the adjuvant and the antigen solution into an emulsion Plaque Reduction Neutralization Activity in Mouse Sera Plaque reduction neutralization test was performed using a dilution of 17D virus which, in the absence of neutralization, produces 10-40 plaque forming units per well in 12 well plates. An equal volume of serially diluted mouse serum was incubated with virus for 16-20 h at 4° C. and then the inoculated into duplicate wells of Vero cells in 12 well plates. After virus absorption for 60 minutes at 37° C., the wells are overlaid with medium containing 0.75% methylcellulose, incubated for 4 days at 37° C., fixed and stained with crystal violet and plaques counted using a stereomicroscope over light box. The 50% plaque reduction titer represents the final mouse serum dilution resulting in less than 50% of the average plaque counts when no serum is added.

Figure 6:
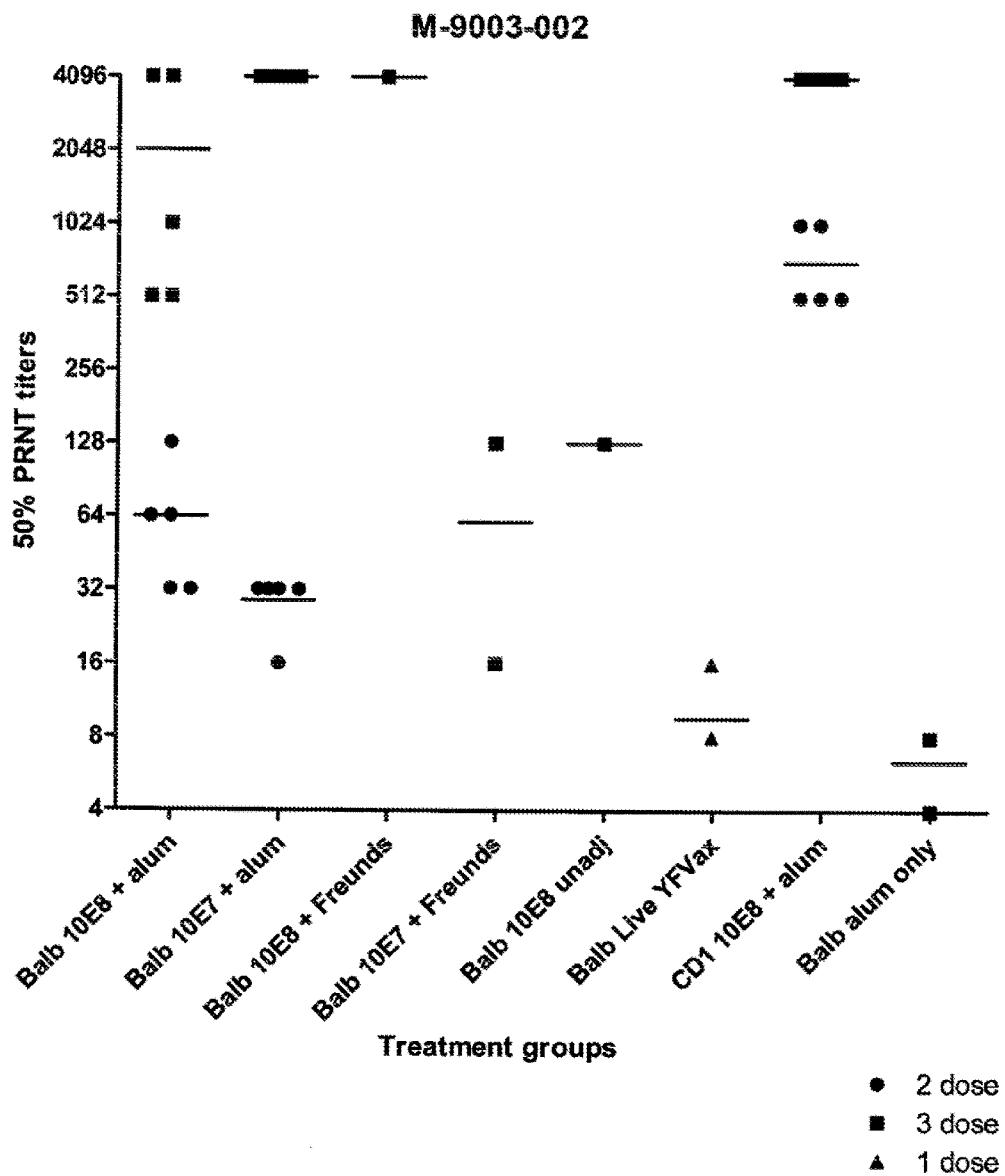
FIG. 6 depicts the comparative 50% plaque reduction neutralization test (PRNT50) titers between treatment groups of BALB/c and CD-1 strain mice in a preliminary mouse study (M-9003-002) of the efficacy of inactivated Yellow Fever vaccine.
Figure 7:
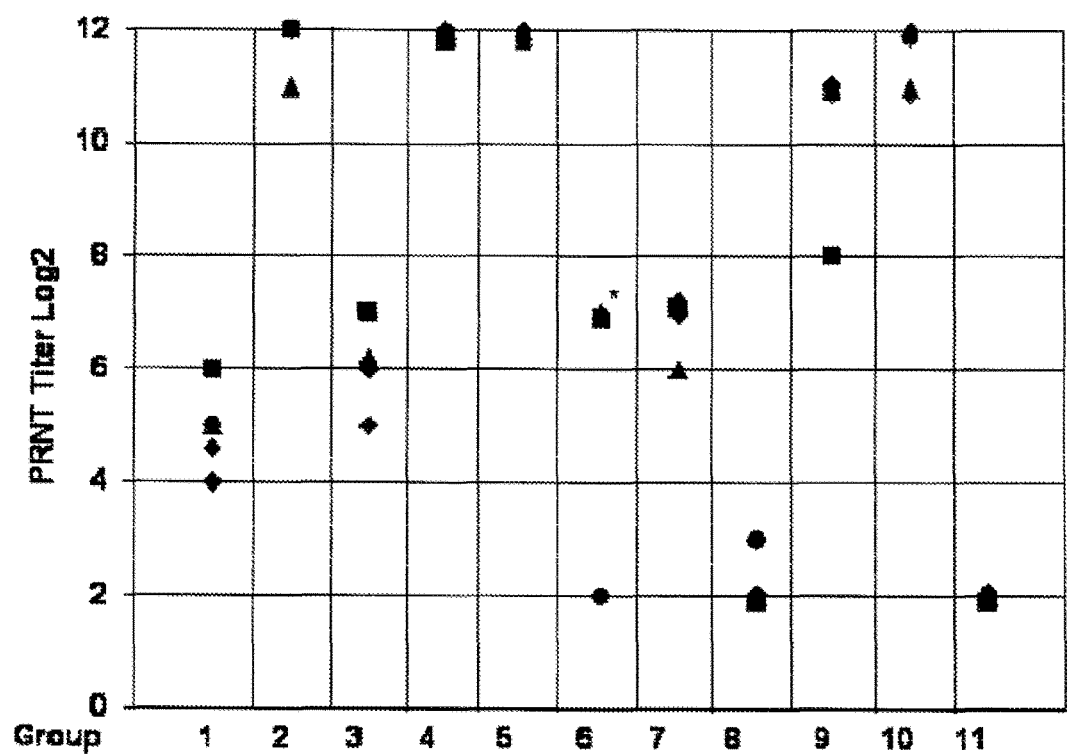
FIG. 7 is a graphical representation of PRNT50 antibody titers for the preliminary mouse study (M-9003-002).

The plaque reduction neutralization test (PRNT) responses and titers are shown in Table 8 and FIGS. 6 and 7. The PRNT test is currently the generally accepted standard for antibodies against Yellow Fever virus. All mice, regardless of strain, receiving 2 or 3 doses of inactivated vaccine given either without adjuvant (Group 7), with alum (Groups 1, 2, 3, 4, 9, 10, 11), or with Freund's adjuvant (Groups 5, 6) developed neutralizing antibody responses. Titers of greater than 4096 were found in 5 of 5 BALB/c mice immunized with 3 doses of alum bound inactivated virus at the $10^7$ EU/dose. These titers were higher than BALB/c mice immunized with 3 doses of inactivated virus delivered with Freund's adjuvant (Group 6, titers 16-128).

CD1 mice immunized with 2 doses of alum bound inactivated virus at the $10^8$ EU/dose level achieved higher titers (Group 9; titers 512-1024) than did similarly immunized BALB/c mice (Group 3; titers of 32-64). Only 1 in 5 mice receiving live YF Vax® (Group 8) mounted a neutralizing antibody response that was above the baseline levels in the mice receiving alum only (Groups 11).

In FIG. 7, each symbol represents an individual mouse. Treatment groups are shown in Tables 7 and 8. For Group 6 (*) the highest dilution of serum tested was 1:128. For Group 9 (**) the highest dilution of serum tested was 1:2048.

This study demonstrates that robust neutralizing antibody titers can be achieved in mice immunized with 2 or more inoculations of the disclosed inactivated YF virus delivered with alum. Outbred CD1 mice had higher antibody responses than an inbred strain (BALB/c). Alum was a superior adjuvant to Freund's, but this result could also be related to the route of immunization (SC for Freund's vs. IM for alum). Additional studies will be performed to determine if immunogenicity can be achieved with a single dose of vaccine.

TABLE 8

Mice with plaque reduction neutralization activity

| Group | Strain of mice | Vaccine | Schedule Vaccination | Sacrifice | % Positive (+/total) |
|---|---|---|---|---|---|
| 1 | BALB/c | $10^8$ BPL-inactivated in 0.2% alum | Day 0, 14 | Day 28 | 100% (5/5) |
| 2 | BALB/c | $10^8$ BPL-inactivated in 0.2% alum | Day 0, 14, 28 | Day 42 | 100% (5/5) |

TABLE 8-continued

Mice with plaque reduction neutralization activity

| Group | Strain of mice | Vaccine | Schedule Vaccination | Sacrifice | % Positive (+/total) |
|---|---|---|---|---|---|
| 3 | BALB/c | $10^7$ BPL-inactivated in 0.2% alum | Day 0, 14 | Day 28 | 100% (5/5) |
| 4 | BALB/c | $10^7$ BPL-inactivated in 0.2% alum | Day 0, 14, 28 | Day 42 | 100% (5/5) |
| 5 | BALB/c | $10^8$ BPL-inactivated in Freund's complete/incomplete | Day 0, 14, 28 | Day 42 | 100% (5/5) |
| 6 | BALB/c | $10^7$ BPL-inactivated in Freund's complete/incomplete | Day 0, 14, 28 | Day 42 | 100% (5/5) |
| 7 | BALB/c | $10^8$ BPL-inactivated no adjuvant | Day 0, 14, 28 | Day 42 | 100% (5/5) |
| 8 | BALB/c | Live YF Vax ® | Day 0 | Day 28 | 20% (1/5) |
| 9 | CD1 | $10^8$ BPL-inactivated in 0.2% alum | Day 0, 14 | Day 28 | 100% (5/5) |
| 10 | CD1 | $10^8$ BPL-inactivated in 0.2% alum | Day 0, 14, 28 | Day 42 | 100% (5/5) |
| 11 | BALB/c | 0.2% alum | Day 0, 14, 28 | Day 42 | 0% (0/5) |

EQUIVALENTS

While this invention has been particularly shown and described with references to preferred embodiments thereof, it will be understood by those skilled in the art that various changes in form and details may be made therein without departing from the scope of the invention encompassed by the appended claims. Additionally, the references, patents and patent publications cited herein are incorporated by reference in their entirety.

What is claimed is:

1. A modified Yellow Fever virus strain comprising a nucleic acid sequence having mutations relative to the nucleic acid sequence of unmodified Yellow Fever virus, wherein said mutations comprise: a mutation in the nucleic acid sequence encoding the NS1 protein of the virus in the codon for the amino acid at position 317 wherein the mutation results in a codon change from threonine to isoleucine; a mutation in the nucleic acid sequence encoding the NS2A protein of the virus in the codon for the amino acid position 170 wherein the mutation results in a codon change from phenylalanine to leucine, and optionally a mutation in the nucleic acid sequence encoding the NS4B protein of the virus in the codon for the amino acid at position 113 wherein the mutation results in a codon change from isoleucine to methionine, and said mutations are in further combination with a mutation of the nucleic acid sequence encoding the envelope protein of the virus in the codon for the amino acid at position 160 wherein the mutation results in a codon change from lysine to arginine, wherein said modified Yellow Fever virus strain has increased propagation in Vero cells and a higher yield in the conditioned medium of a Vero cell culture relative to unmodified Yellow Fever virus.

2. An inactivated Yellow Fever virus comprising the modified Yellow Fever virus of claim 1.

3. A vaccine comprising the inactivated virus of claim 2.

4. A method for inducing an immune response to Yellow Fever virus in a subject, the method comprising administering the vaccine of claim 3 to the subject.

5. The method according to claim 4, wherein the subject is at risk of developing, but does not have, Yellow Fever virus infection.

6. A method for making a vaccine comprising culturing cells infected with a modified Yellow Fever virus strain of claim 1, purifying the virus to generate a live virus bulk, and inactivating said virus live bulk.

\* \* \* \* \*